United States Patent
Geleziunas et al.

(10) Patent No.: US 11,116,774 B2
(45) Date of Patent: Sep. 14, 2021

(54) MODULATORS OF TOLL-LIKE RECEPTORS FOR THE TREATMENT OF HIV

(71) Applicant: Gilead Sciences, Inc., Foster City, CA (US)

(72) Inventors: Romas Geleziunas, Belmont, CA (US); Joseph E. Hesselgesser, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 169 days.

(21) Appl. No.: 14/795,676

(22) Filed: Jul. 9, 2015

(65) Prior Publication Data
US 2016/0008374 A1 Jan. 14, 2016

Related U.S. Application Data

(60) Provisional application No. 62/118,377, filed on Feb. 19, 2015, provisional application No. 62/058,569, (Continued)

(51) Int. Cl.
*A61K 31/551* (2006.01)
*A61K 39/39* (2006.01)
(Continued)

(52) U.S. Cl.
CPC .......... *A61K 31/551* (2013.01); *A61K 31/437* (2013.01); *A61K 31/4985* (2013.01);
(Continued)

(58) Field of Classification Search
None
See application file for complete search history.

(56) References Cited

U.S. PATENT DOCUMENTS 3,798,209 A 3/1974 Witkowski et al.
3,950,351 A 4/1976 Rossignol et al.
(Continued)

FOREIGN PATENT DOCUMENTS

CA 2772253 A1 3/2011
CN 101284810 A1 10/2008
(Continued)

OTHER PUBLICATIONS

Chang et al., "Immune Activation and the Role of TLRs and TLR Agonists in the Pathogenesis of HIV-1 Infection in the Humanized Mouse Model," The Journal of Infectious Diseases 208 (S2): S145-9 (Year: 2013).*
(Continued)

*Primary Examiner* — M Franco G Salvoza
(74) *Attorney, Agent, or Firm* — Mintz, Levin, Cohn, Ferris, Glovsky and Popeo, P.C.

(57) ABSTRACT

Provided are methods, uses, pharmaceutical regimens, pharmaceutical compositions, and kits comprising modulators of TLR7, including those of Formula II:

Formula II (Continued)

and pharmaceutically acceptable salts thereof, useful in treating HIV infections.

9 Claims, 14 Drawing Sheets

Related U.S. Application Data filed on Oct. 1, 2014, provisional application No. 62/023,692, filed on Jul. 11, 2014.

(51) Int. Cl.

| | |
|---|---|
| *A61K 45/06* | (2006.01) |
| *A61K 31/437* | (2006.01) |
| *A61K 31/4985* | (2006.01) |
| *A61K 31/513* | (2006.01) |
| *A61K 31/519* | (2006.01) |
| *A61K 31/52* | (2006.01) |
| *A61K 31/527* | (2006.01) |
| *A61K 31/5365* | (2006.01) |
| *A61K 31/5377* | (2006.01) |
| *A61K 31/675* | (2006.01) |
| *A61K 39/00* | (2006.01) |

(52) U.S. Cl.
CPC .......... *A61K 31/513* (2013.01); *A61K 31/519* (2013.01); *A61K 31/52* (2013.01); *A61K 31/527* (2013.01); *A61K 31/5365* (2013.01); *A61K 31/5377* (2013.01); *A61K 31/675* (2013.01); *A61K 39/39* (2013.01); *A61K 45/06* (2013.01); *A61K 2039/55511* (2013.01)

(56) References Cited

U.S. PATENT DOCUMENTS

| | | | |
|---|---|---|---|
| 4,539,205 A | 9/1985 | Goodman et al. | |
| 4,639,436 A | 1/1987 | Junge et al. | |
| 4,643,992 A | 2/1987 | Goodman et al. | |
| 4,880,784 A | 11/1989 | Robins et al. | |
| 5,011,828 A | 4/1991 | Goodman et al. | |
| 5,041,426 A | 8/1991 | Robins et al. | |
| 5,057,540 A | 10/1991 | Kensil et al. | |
| 5,395,937 A | 3/1995 | Nikolaides et al. | |
| 5,397,781 A | 3/1995 | Yanagibashi et al. | |
| 5,424,311 A | 6/1995 | Billhardt-Troughton et al. | |
| 5,620,978 A | 4/1997 | Cai et al. | |
| 5,681,835 A | 10/1997 | Willson | |
| 5,693,641 A | 12/1997 | Van Nest et al. | |
| 6,028,076 A | 2/2000 | Hirota et al. | |
| 6,268,391 B1 | 7/2001 | Dickerson | |
| 6,299,884 B1 | 10/2001 | Van Nest et al. | |
| 6,329,381 B1 | 12/2001 | Kurimoto et al. | |
| 6,376,501 B1 | 4/2002 | Isobe et al. | |
| 6,452,325 B1 | 9/2002 | Dupont | |
| 6,552,192 B1 | 4/2003 | Hanus et al. | |
| 6,629,831 B2 | 10/2003 | Wei | |
| 7,157,465 B2 | 1/2007 | Isobe et al. | |
| 7,521,454 B2 | 4/2009 | Isobe et al. | |
| 7,592,326 B2 | 9/2009 | Karaolis | |
| 7,642,350 B2 | 1/2010 | Pryde | |
| 7,968,544 B2 | 6/2011 | Graupe et al. | |
| 8,067,411 B2 | 11/2011 | Bonnert et al. | |
| 8,067,426 B2 | 11/2011 | Biggadike et al. | |
| 8,138,172 B2 | 3/2012 | Cook et al. | |
| 8,148,374 B2 | 4/2012 | Desai et al. | |
| 8,217,069 B2 | 7/2012 | Yonekubo et al. | |
| 8,367,670 B2 | 2/2013 | Desai et al. | |
| 8,476,270 B2 | 7/2013 | Halcomb | |
| 8,507,507 B2 | 8/2013 | Halcomb et al. | |
| 8,629,142 B2 | 1/2014 | Desai et al. | |
| 8,637,036 B2 * | 1/2014 | Mascola ............ C07K 16/1063 424/160.1 | |
| 8,728,465 B2 | 5/2014 | Black et al. | |
| 8,728,486 B2 | 5/2014 | David et al. | |
| 8,729,088 B2 | 5/2014 | Carson et al. | |
| 8,809,527 B2 | 8/2014 | Desai et al. | |
| 8,962,652 B2 | 2/2015 | Halcomb et al. | |
| 8,993,755 B2 | 3/2015 | Graupe et al. | |
| 9,127,006 B2 | 9/2015 | Desai et al. | |
| 9,161,934 B2 | 10/2015 | Halcomb et al. | |
| 9,452,154 B2 | 9/2016 | Delaney, IV et al. | |
| 9,452,166 B2 | 9/2016 | Desai et al. | |
| 9,573,952 B2 | 2/2017 | Allen et al. | |
| 9,611,268 B2 | 4/2017 | Graupe et al. | |
| 9,738,646 B2 | 8/2017 | Brown et al. | |
| 9,988,425 B2 | 6/2018 | Brander et al. | |
| 10,172,860 B2 | 1/2019 | Desai et al. | |
| 10,202,384 B2 | 2/2019 | Brown et al. | |
| 10,508,117 B2 | 12/2019 | Andres et al. | |
| 2002/0173655 A1 | 11/2002 | Dellaria et al. | |
| 2003/0044428 A1* | 3/2003 | Moss ................ A61K 39/21 424/208.1 | |
| 2003/0065005 A1 | 4/2003 | Charles et al. | |
| 2003/0100764 A1 | 5/2003 | Bonk et al. | |
| 2003/0162806 A1 | 8/2003 | Dellaria et al. | |
| 2003/0176458 A1 | 9/2003 | Dellaria et al. | |
| 2003/0186949 A1 | 10/2003 | Dellaria et al. | |
| 2003/0195209 A1 | 10/2003 | Dellaria et al. | |
| 2004/0029885 A1 | 2/2004 | Bauer et al. | |
| 2004/0116362 A1 | 6/2004 | Sartorelli et al. | |
| 2004/0132748 A1 | 7/2004 | Isobe et al. | |
| 2005/0043239 A1 | 2/2005 | Douangpanya et al. | |
| 2006/0052403 A1 | 3/2006 | Isobe et al. | |
| 2006/0269936 A1 | 11/2006 | Vlach et al. | |
| 2007/0190071 A1 | 8/2007 | Kurimoto et al. | |
| 2007/0197478 A1 | 8/2007 | Jones et al. | |
| 2007/0197558 A1 | 8/2007 | Betebenner et al. | |
| 2008/0008682 A1 | 1/2008 | Chong et al. | |
| 2008/0026924 A1 | 1/2008 | Konzal | |
| 2008/0047249 A1 | 2/2008 | Davis et al. | |
| 2008/0167289 A1 | 7/2008 | Kay et al. | |
| 2008/0182863 A1 | 7/2008 | Simmen et al. | |
| 2008/0234255 A1 | 9/2008 | Chen | |
| 2008/0269240 A1 | 10/2008 | Hashimoto et al. | |
| 2008/0300244 A1 | 12/2008 | Bonnert et al. | |
| 2009/0005560 A1 | 1/2009 | Oka et al. | |
| 2009/0082332 A1 | 3/2009 | Abbot et al. | |
| 2009/0099216 A1 | 4/2009 | Millichip et al. | |
| 2009/0105212 A1 | 4/2009 | Isobe et al. | |
| 2009/0118263 A1 | 5/2009 | Hashimoto et al. | |
| 2009/0131458 A1 | 5/2009 | Lazarides et al. | |
| 2009/0143400 A1 | 6/2009 | McInally et al. | |
| 2009/0192153 A1 | 7/2009 | Hashimoto et al. | |
| 2009/0202484 A1 | 8/2009 | Chong et al. | |
| 2009/0209524 A1 | 8/2009 | Bennett et al. | |
| 2009/0221551 A1 | 9/2009 | Kshirsagar et al. | |
| 2009/0221556 A1 | 9/2009 | Kshirsagar et al. | |
| 2009/0221631 A1 | 9/2009 | Jones et al. | |
| 2009/0263470 A1 | 10/2009 | Coller et al. | |
| 2009/0291938 A1 | 11/2009 | Cao et al. | |
| 2009/0324551 A1 | 12/2009 | Carson et al. | |
| 2009/0325877 A1 | 12/2009 | Grunt et al. | |
| 2010/0029585 A1 | 2/2010 | Howbert et al. | |
| 2010/0075995 A1 | 3/2010 | Biggadike et al. | |
| 2010/0087443 A1 | 4/2010 | Bonnert et al. | |
| 2010/0093998 A1 | 4/2010 | Isobe et al. | |
| 2010/0099870 A1 | 4/2010 | Isobe et al. | |
| 2010/0120799 A1 | 5/2010 | Lazarides et al. | |
| 2010/0130491 A1 | 5/2010 | Bonnert et al. | |
| 2010/0015230 A1 | 6/2010 | Dellaria et al. | |
| 2010/0143301 A1 | 6/2010 | Desai et al. | |
| 2010/0210598 A1 | 8/2010 | Carson et al. | |
| 2010/0215642 A1 | 8/2010 | Lan et al. | |
| 2010/0240623 A1 | 9/2010 | Cook et al. | |
| 2010/0256169 A1 | 10/2010 | Averett | |
| 2010/0280001 A1 | 11/2010 | Bonnert et al. | |
| 2010/0298364 A1 | 11/2010 | Bennett et al. | |
| 2011/0028715 A1 | 2/2011 | Isobe et al. | |
| 2011/0053893 A1 | 3/2011 | Wu et al. | |
| 2011/0282061 A1 | 11/2011 | Johnson | |
| 2012/0035193 A1 | 2/2012 | Biggadike et al. | |

(56) References Cited

U.S. PATENT DOCUMENTS

| | | | |
|---|---|---|---|
| 2013/0018042 A1 | 1/2013 | Howbert et al. | |
| 2013/0109647 A1 | 5/2013 | Berrey et al. | |
| 2013/0136776 A1 | 5/2013 | Cleary et al. | |
| 2013/0236492 A1 | 9/2013 | Baudner et al. | |
| 2013/0243726 A1 | 9/2013 | Ray et al. | |
| 2014/0024664 A1 | 1/2014 | Bazin-Lee et al. | |
| 2014/0045837 A1 | 2/2014 | Kurimoto et al. | |
| 2014/0134132 A1 | 5/2014 | Fu et al. | |
| 2014/0142086 A1 | 5/2014 | Howbert et al. | |
| 2014/0170221 A1* | 6/2014 | Irvine | A61K 35/17 424/489 |
| 2014/0220107 A1* | 8/2014 | Kalyanaraman | A61K 39/12 424/450 |
| 2015/0105350 A1* | 4/2015 | Ramanathan | A61K 31/35 514/81 |
| 2016/0008374 A1 | 1/2016 | Geleziunas et al. | |

FOREIGN PATENT DOCUMENTS

| | | |
|---|---|---|
| CN | 101663302 | 3/2010 |
| DE | 2220246 | 12/1972 |
| DE | 2438037 | 2/1975 |
| DE | 2758025 | 7/1979 |
| EP | 1035123 | 9/2000 |
| EP | 1147108 | 10/2001 |
| EP | 01550662 | 7/2005 |
| EP | 1939201 | 7/2008 |
| EP | 2132209 | 12/2009 |
| EP | 2133353 | 12/2009 |
| EP | 2138497 | 12/2009 |
| EP | 2143724 A1 | 1/2010 |
| EP | 2364314 | 9/2011 |
| EP | 2143724 B1 | 12/2013 |
| EP | 3166607 A1 | 5/2017 |
| EP | 2477987 A1 | 1/2018 |
| JP | 49001576 | 1/1974 |
| JP | 55111420 | 8/1980 |
| JP | H 05320143 A | 12/1993 |
| JP | 1995330770 | 6/1997 |
| JP | 2886570 | 4/1999 |
| JP | 1999180982 | 1/2001 |
| JP | 2005089334 | 4/2005 |
| JP | 2009-007273 | 1/2009 |
| JP | 2014505045 A | 2/2014 |
| PT | 2364314 | 6/2014 |
| TW | 200813057 | 3/2008 |
| TW | 1401084 B | 7/2013 |
| WO | WO-1990014837 | 12/1990 |
| WO | WO-1993019785 | 10/1993 |
| WO | WO-1997044038 | 11/1997 |
| WO | WO-1998001448 | 1/1998 |
| WO | WO-1998005661 | 2/1998 |
| WO | WO-1999028321 | 6/1999 |
| WO | WO-1999032122 | 7/1999 |
| WO | WO-1999032477 | 7/1999 |
| WO | WO-200000478 | 1/2000 |
| WO | WO-200119825 | 3/2001 |
| WO | WO-2002076954 | 10/2002 |
| WO | WO-2003020722 | 3/2003 |
| WO | WO-2004029054 | 4/2004 |
| WO | WO-2004076454 | 9/2004 |
| WO | WO-2005016348 | 2/2005 |
| WO | WO-2005016349 | 2/2005 |
| WO | WO-2005067901 | 7/2005 |
| WO | WO-2005112935 | 12/2005 |
| WO | WO-2005117889 | 12/2005 |
| WO | WO-2005120511 | 12/2005 |
| WO | WO-2005123736 | 12/2005 |
| WO | WO-2006034001 A2 | 3/2006 |
| WO | WO-2006089106 | 8/2006 |
| WO | 2006/117670 A1 | 11/2006 |
| WO | WO-2007014838 | 2/2007 |
| WO | WO-2007024707 | 3/2007 |
| WO | WO-2007034817 | 3/2007 |
| WO | WO-2007034882 | 3/2007 |
| WO | WO-2007034917 | 3/2007 |
| WO | WO2007049771 A1 | 5/2007 |
| WO | WO-2007089334 | 8/2007 |
| WO | WO-2007103554 A1 | 9/2007 |
| WO | WO-2007108968 | 9/2007 |
| WO | WO-2007142755 | 12/2007 |
| WO | WO-2007148064 | 12/2007 |
| WO | WO-2008004948 | 1/2008 |
| WO | WO-2008005555 A1 | 1/2008 |
| WO | WO-2008051493 | 5/2008 |
| WO | WO-2008055870 A1 | 5/2008 |
| WO | WO-2008101867 | 8/2008 |
| WO | WO-2008113711 | 9/2008 |
| WO | WO2008124575 | 10/2008 |
| WO | WO-2008124703 A2 | 10/2008 |
| WO | WO-2008129994 A1 | 10/2008 |
| WO | 2008/135791 A1 | 11/2008 |
| WO | 2009/005687 A1 | 1/2009 |
| WO | WO-2009005687 A1 | 1/2009 |
| WO | WO-2009019553 A2 | 2/2009 |
| WO | WO-2009022185 | 2/2009 |
| WO | WO-2009023269 | 2/2009 |
| WO | WO-2009/062285 A1 | 5/2009 |
| WO | WO-2009067547 | 5/2009 |
| WO | WO-2009132135 A1 | 10/2009 |
| WO | WO-2010018130 | 2/2010 |
| WO | WO-2010018131 | 2/2010 |
| WO | WO-2010018132 | 2/2010 |
| WO | WO-2010018134 | 2/2010 |
| WO | 2010/077613 A1 | 7/2010 |
| WO | WO-2010/107939 A2 | 9/2010 |
| WO | WO-2010/130034 A1 | 11/2010 |
| WO | 2011/031965 A1 | 3/2011 |
| WO | 2011/049825 A1 | 4/2011 |
| WO | WO-2012/003497 A1 | 1/2012 |
| WO | WO-2012/003498 A1 | 1/2012 |
| WO | WO-2012/030904 A2 | 3/2012 |
| WO | 2012/087596 A1 | 6/2012 |
| WO | WO-2012/145728 A1 | 10/2012 |
| WO | WO-2013/068438 A1 | 5/2013 |
| WO | WO-2013/159064 A1 | 10/2013 |
| WO | WO-2014063059 | 4/2014 |
| WO | WO-2015048770 A2 | 4/2015 |
| WO | 2016/007765 A1 | 1/2016 |
| WO | 2016/044182 A1 | 3/2016 |
| WO | 2016/044183 | 4/2016 |
| WO | WO-2020237027 A1 | 11/2020 |

OTHER PUBLICATIONS

Smith et al., "Developments in HIV-1 immunotherapy and therapeutic vaccination," F100Prime Reports 6:43 (Year: 2014).*
Charpentier et al., "Persistent low-level HIV-1 RNA between 20 and 50 copies/mL in antiretroviral-treated patients: associated factors and virological outcome," J Antimicrob Chemother 67: 2231-2235 (Year: 2012).*
Denton et al., "Humanized Mouse Models of HIV Infection," AIDS Rev. 13(3):135-148 (Year: 2011).*
Malbec et al., "Broadly neutralizing antibodies that inhibit HIV-1 cell to cell transmission," Journal of Experimental Medicine vol. 210, No. 13: 2813-2821 (Year: 2013).*
Horwitz et al., "Broadly neutralizing antibodies that inhibit HIV-1 cell to cell transmission," Journal of Experimental Medicine vol. 210, No. 13: 2813-2821 (Year: 2013).*
Barouch, D. et al. (2013) "Therapeutic efficacy of potent neutralizing HIV-1-specific monoclonal antibodies in SHIV-infected rhesus monkeys" *Nature* 503:224-239.
Barton, et al. (2013) "Prospects for Treatment of Latent HIV" Nature.com 93(1):46-56.
Battistini et al. (2014) "*HIV-1 Latency: An Update of Molecular Mechanisms and Therapeutic Strategies*" Viruses 6:1715-1758.
Buffa, V. et al. (2012) "Evaluaton of TLR Agonists as Potential Mucosal Adjuvants for HIV gp140 and Tetanus Toxoid in Mice" *PLOS ONE* 7(12):e50529 pp. 1-10.
Chang, J. et al. (2009) "TLR-mediated immune activation in HIV" *Blood* 113(2):269-270.

(56) References Cited

OTHER PUBLICATIONS

Chang, J. et al. (2012) "TLR7/9 antagonist reduces HIV-1-induced immune activation" *Retrovirology* 9(Supp12):172.
Cillo, A. et al. (2014) "Quantification of HIV-1 latency reversal in resting CD4+ T cells from patients on suppressive antiretroviral therapy" *PNAS* 111(19):7078-7083.
Coiras, M. (2010) "HIV-1 Latency and Eradication of Long-term Viral Reservoirs" http://www.discoverymedicine.com/Mayte-Coiras/2010/030/03/hiv-1-latency-and-eradication Mar. 13, 2014 12 pgs.
Eriksson, S. et al. (2013) "Comparative Analyss of Measures of Viral Reservoirs in HIV-1 Eradication Studies" *PLOS Pathogens* 9(2):e1003174 1-17.
Gunthard, H. et al. (2001) "Residual Human Immunodeficiency Virus (HIV) Type 1 RNA and DNA in Lymph Nodes and HIV RNA in Genital Secretions and in Cerebrospinal Fluid after Suppression of Viremia for 2 Years" *The Journal of Infectious Diseases* 183:1318-27.
Hubert, J. et al. (2000) "Natural history of serum HIV-1 RNA levels in 330 patients with a known date of infection" *AIDS* 14:123-131.
International Search Report and Written Opinion dated Sep. 8, 2015 for PCT/US2015/039776.
Jiang, G. et al. (2015) "Targeting NF-$_\kappa$B Signaling with Protein Kinase C Agonists as an Emerging Strategy for Combating HIV Latency" *AIDS Research and Human Retroviruses* 31(1):4-12.
Julien,J. et al. (2013) "Broadly Neutralizing Antibody PGT121 Allosterically Modulates CD4 Binding via Recognition of the HIV-gp120 V3 Base and Multiple Surrounding Glycans" *PLOS Pathogens* 9(5):1-15.
Kwong, P. et al. (2012) "Human Antibodies that Neutralize HIV-1: Identification, Structures, and B Cell Ontogenies" *Immunity* 37:412-425.
Lanford, R. et al. (2013) "GS-9620, an Oral Agonist of Toll-Like Receptor-7, Induces Prolonged Suppression of Hepatitis B Virus in Chronically Infected Chimpanzees" *Gastroenterology* 144:1508-1517.
Loveday, C. (1995) "Prediction of progression to AIDS with serum HIV-1 RNA and CD4 count" *The Lancet* 345:790-791.
Marsden, M. et al. (2014) "Neutralizing the HIV Reservoir" *Cell* 158:971-972.
Mofenson, L. et al. (1997) "The Relationship betwee Serum Human Immunodeficiency Virus Type 1 (HIV-1) RNA Level, CD4 Lymphocyte Percent, and Long-Term Mortality Risk in HIV-1-Infected Children" *The Journal of Infectious Diseases* 175:1029-38.
Moody, M. et al. (2014) "TLR-7/8 and 9 Agonists Cooperate to Enthance HIV-1 Envelope Antibody Responses in Rhesus Macaques" *J. Virol.* 1-42.
Office Action dated Aug. 2, 2016 for Pakistan Patent Appl. No. 451/2015.
Ostrowski, S. et al. (2008) "Residual Virae,ia in HIV-1-Infected Patients with Plasma Viral Load £20 copies/ml is Associated with Increased Blood Levels of Soluble Immune Activation Markers" *Scandinavian Journal of Immunology* 68:652-660.
Persaud, D. (2000) "A stable latent reservoir for HIV-1 in resting CD4+ T lymphocytes in infected children" *The Journal of Clinical Investigation* 105(7):995-1003.
Picker, L. et al. (2013) "Antibodies advance the search fora cure" *Nature* 503:207-208.
Rasmussen, T. (2013) "Eliminating the latent HIV reservoir by reactivation strategies" *Human Vaccines & Immunotherapeutics* 9(4):790-799.
Roethle, P. et al. (2013) "Identification and Optimization of Pteridinone Toll-like Receptor 7 (TLR7) Agonists for the Oral Treatment of Viral Hepatitis" *Journal of Medicinal Chemistry* 56:7324-7333.
Shingai, M. et al. (2013) "Antibody-mediated immunotherapy of macaques chronically infected with SHIV suppresses viraemia" *Nature* 503:277-291.
Siliciano, R. et al. (2011) "HIV Latency" *Cold Spring Harb Perspect Med* 1:a007096, pp. 1-20.
Van Der Sluis, R. et al (2013) "Dendritic Cell-induced Activation of Latent HIV-1 Provirus in Actively Proliferating Primary T Lymphocytes" *PLOS Pathogens* 9(3) e1003259 pp. 1-15.
Walker, L. et al. (2011) "Broad neutralization coverage of HIV by multiple highly potent antibodies" *Nature* 477:466-471.
Whitney (2014) "Rapid seeding of the viral reservoir prior to SIV viraemia in rhesus monkeys" *Nature* 512:74-77.
Buitendijk, Gardiquimond: A Toll-Like Receptor-7 Agonist That Inhibits HIV Type 1 Infection of Human Macrophages and Activated T cells, Nov. 6, 2013, AIDS Research and Human Retroviruses, vol. 29, No. 6, 12 pages.
European Patent Office, Examination Report for EP 10760831.7, dated Oct. 12, 2015, 4 pages.
Meyer, Clinical Investigations of Toll-Like Receptor Agonists, Jul. 2008, pp. 1051-1065, vol. 17, No. 7.
Cabeza, et al., Antiproliferative effects of palladium(II) complexes of 5-nitrosopyrimidines and interactions with the proteolytic regulatory enzymes of the renin-angiotensin system in tumoral brain c, Journal of Inorganic Biochemistry Jun. 18, 2013, pp. 118-127, vol. 126.
Moye, The synthesis of 4,6-Dihydroxy-2-methoxypyrimidine and derived pyrimidine intermediates, Australian Journal of Chemistry, Jan. 1, 1964, pp. 1309-1310, vol. 17, No. 11.
European Patent Office, International Preliminary Report on Patentability and Written Opinion for PCT International Application No. PCT/US2008/007955, dated Dec. 29, 2009, 11 pages.
European Patent Office, International Preliminary Report on Patentability and Written Opinion for PCT International Application No. PCT/US2009/041432, dated Oct. 26, 2010, 7 pages.
European Patent Office, International Preliminary Report on Patentability and Written Opinion for PCT International Application No. PCT/US2010/049471, dated Mar. 27, 2012, 7 pages.
European Patent Office, International Preliminary Report on Patentability and Written Opinion for PCT International Application No. PCT/US2015/057932, dated May 6, 2016, 21 pages.
European Patent Office, International Preliminary Report on Patentability and Written Opinion for PCT International Application No. PCT/US2015/057933, dated May 2, 2017, 7 pages.
European Patent Office, International Preliminary Report and Written Opinion on Patentability for PCT International Application No. PCT/US2009/067002, dated Feb. 22, 2010, 10 pages.
European Patent Office, International Search Report and Written Opinion for PCT International Application No. PCT/US2015/050037, dated Dec. 3, 2015, 10 pages.
European Patent Office, International Search Report and Written Opinion for PCT International Application No. PCT/US2017/028251, dated Nov. 16, 2017, 22 pages.
European Patent Office, International Search Report and Written Opinion for PCT International Application No. PCT/US2018/029974, dated Sep. 18, 2018, 21 pages.
European Patent Office, International Search Report and Written Opinion for PCT International Application No. PCT/US2016/052092, dated Nov. 10, 2016, 11 pages.
Gibson, Pharmaceutical Preformulation and Formulation, 2009, pp. 334-335.
Ashizawa et al., Iyakuhin no Takeigensho to Shoseki no Kagaku [Science of crystallization and polymorph phenomenon of pharmaceutical product], Maruzen Planet Co., Ltd, Sep. 20, 2002, pp. 305-317. [No English Translation].
Barr, et al., ISCOMSs and Other Saponin Based Adjuvants, Advanced Drug Delivery Reviews, 1998, pp. 247-271, vol. 32.
Boyer, et al., Pathogenesis, Diagnosis, and Management of Hepatitis C, J. of Hepatology, Supp. 1, 2000, pp. 98-112.
Boyle, et al., Synthesis of a 2,4-Diaminodihydrohomopteridine, 6-Acetyl-2,4-Diamino-7,8-Dihydro-9H-Pyrimido[4,5-b][1,4]Diazepine, Using a Furazano[3,4-d]Pyrimidine Precursor, Tetrahedron, 1991, pp. 5259-5268, vol. 28.
Breault, et al., Exploring 8-benzyl pteridine-6,7-diones as inhibitors of glutamate recemase (Mur1) in Gram-positive bacteria, Bioorganic & Medicinal Chemistry Letters, Dec. 1, 2008, p. 6101; figure 2; compound 2; p. 6102; tables 2-3; compounds 0-12, 14-16; p. 6103; table 4; compound 25.

(56) References Cited

OTHER PUBLICATIONS

Caira, Crystalline Polymorphism of Organic Compounds, Topics in Current Chemistry, Jan. 1, 1998, pp. 163-208 and 177-180, vol. 198.
Calisher, et al., Antigenic relationships between Flaviviruses as determined by cross-neutralization tests with polyclonal antisera, J. Gen. Virology, 1989, pp. 37-43, vol. 70.
Di Bisceglie, et al., The unmet challenges of hepatitis C, Scientific American, Inc., 1999, pp. 80-85.
Dustin, Flying under the radar: The immunbiology of Hepatitis C, Annu. Rev. Immunol. 2007, pp. 71-99, vol. 25.
Dymock, Novel approaches to the treatment of hepatitis C virus infection, Antivirial Chemistry & Chemotherapy, 2000, pp. 79-96, vol. 11.
Dzierba, et al., Dihydropyridopyrazinones and Dihydripterdinones as Corticotropin-Releasing Factor-a receptor antagonists: Structure—Activity Relationships and Computational Modeling, J. Med. Chem. 2007, pp. 5569-5572, vol. 50.
European Patent Office, Examination Report for European Patent Application No. EP 10760831.7, dated Mar. 20, 2015, 4 pages.
Farumashia, Jun. 2014, p. 575, vol. 50, No. 6 [No English Translation].
Gluck, et al., New technology platforms in the development of vaccines for the future, 2002, B10-B6, vol. 5.
Goodchild, et al., Primary leukocyte screens for innate immune agonists, Journal of Biomolecular Screening, 2009, pp. 723-730, vol. 14.
Gordon, et al., Control of hepatitis C: A medicinal chemistry perspective, Journal of Medicinal Chemistry, 2005, pp. 1-20, vol. 48.
Guillory, Generation of Polymorphs, Hydrates, Solvates, and Amorphous Solids, Polymorphism in Pharmaceutical Solids, 1999, pp. 184-227.
Horowitz, et al., HIV-1 suppression and durable control by combining single broadly neutralizing antibodies and antiretroviral drugs in humanized mice, PNAS USA pp. 16538-16543.
Horsmans, et al., Isatoribine, an agonist of TLR7, reduces plasma virus concentration in chronic hepatitis C infection, Hepatology, 2005, pp. 724-731, vol. 42.
International Searching Authority at the European Patent Office, International Search Report and Written Opinion for PCT International Patent Application No. PCT/US2009/067002, dated Feb. 22, 2010, 10 pages.
International Searching Authority at the European Patent Office, International Search Report and Written Opinion for PCT International Patent Application No. PCT/US2015/050039, dated Apr. 3, 2016, 16 pages.
Isobe, et al., Synthesis and biological evaluation of novel-9-substituted-8-hydroxyadenine derivatives as potent interferon inducers, Journal of Medicinal Chemistry, 2006, pp. 2088-2095, vol. 49, No. 6.
Jin, et al., Synthesis and Immunostimulatory activity of 8-substituted amino 9-benzyladenines as potent Toll-like receptor 7 agonists, Bioorg. Med. Chem. Lett, 2006, pp. 4559-4563, vol. 16.
Jurocova, et al., Synthesis of Base-Modified 'Abbreviated' NAD Analogues, Collection of Czechoslovak Chemical Communications, 1995, pp. 237-250, vol. 60, No. 2.
Kelly, Synthesis and antirhinovirus activity of 6-(dimethylamino)-2-(trifluoromethyl)-9-(substituted benzyl)-9H-purines, Journal of Medicinal Chemistry, Aug. 1989, pp. 1757-1763, vol. 32, No. 8 [in U.S. Appl. No. 12/215,598].
Korba, et al., Treatment of chronic woodchuck hepatitis virus infection in the Eastern Wookdchuck (*Marnota monax*) with nucleoside analgoues is predictive of therapy for chronic hepatitis B virus infection in humans, Hepatology, 2000, pp. 1165-1175, vol. 31.
Lee, et al., Activation of anti-hepatitis C virus responses via Toll-like receptor 7, 2006, Proc. Natl. Acad. Sci., pp. 1828-1833, vol. 103.
Matsuoka, Kesshotake no Kiso to Oyo [Fundamentals and application of crystalline polymorphs], CMC Publishing CO., LTD, Oct. 22, 2010, pp. 105-117 and 181-191.

Menne, et al., The woodchuck as an animal model for pathogenesis and therapy of chronic hepatitis B virus infection, World J. Gastroenterol, 2007, pp. 104-24, vol. 13.
Moenning, et al., The pestiviruses, Advances in Virus Research, 1992, pp. 53-98, vol. 41.
Moradpour, et al., Replication of hepatitisc C virus, Nature Reviews, Microbiology, 2007, pp. 453-463, vol. 5.
Nagashima, et al., Solution-Phase parallel synthesis of a N-Alkylated dihydropteridinone library from fluorous-amino acids, J. Comb. Chem., 2004, pp. 942-949, vol. 6.
Prince, et al., Common Antiviral Agents, Contract Pharma, 2014, 9 pages.
Scott, et al., Interferon-alpha-2b plus ribavirin: a review of its use in the management of chronic hepatitis C, Drugs, 2002, pp. 507-556, vol. 62.
Stahly, Diversity in Single-and Multiple-Component Crystals. The Search for and Prevalence of Polymorphs and Cocrystals, Crystal Growth & Design, 2007, pp. 1007-1026, vol. 7.
Sun, et al., Functional characterization of ex vivo blood myeloid and plasmacytoid dendritic cells after infection with dengue virus, Virology, 2009, pp. 207-215, vol. 383.
Susvilo, et al., Study on the reaction of methy N-Methyl-N-(6-substituted-5-nitropyrimidine-4-yl) glycinates with sodium alkoxides, J. Heterocyclic Chem., 2006, pp. 267-276, vol. 43.
Tennant, Animal models of hepatitis B virus infection, Clinics in Liver Disease, 1999, pp. 241-266, vol. 3.
Thomas, et al., Investigating toll-like receptor agonists for potential to treat hepatitis C virus infection, Antimicrobial Agents and Chemotherapy, 2007, pp. 2969-2978, vol. 51.
Borducchi, et al., Antibody and TLR7 Agonist Delay Viral Rebound in SHIV-Infected Monkeys, Nature, Oct. 3, 2018, 21 pages, vol. 564.
Brittain, Polymorphism in Pharmaceutical Solids, 1999, 25 pages.
Lewin, HIV Rebound Prevented in Monkeys, Nature, 2018, 2 pages.
Schlaepfer, TLR7/8 Triggering Exerts Opposing Effects in Acute versus Latent HIV Infection, Journal of Immunology, 2006, pp. 2888-2895, vol. 176.
Zhang, et al., Structural analysis reveals that Toll-like Receptor 7 is a dual receptor for Guanosine and single-stranded RNA, Immunity, Oct. 18, 2016, pp. 737-748, vol. 45.
Zhang, et al., Structural analysis of Toll-like Receptor 7 reveal detailed RNA sequence specificity and recognition mechanism of agonistic ligands, Cell Reports, Dec. 18, 2016, pp. 3371-3381, vol. 25.
Borducchi et al., Ad26/MVA therapeutic vaccination with TLR7 stimulation in SIV-infected rhesus monkeys, Nature, Dec. 8, 2016, vol 540, pp. 284-287.
Chilean Patent Office, Office Action for CL Application No. 1392-2011 (2013) with English Translation, 16 pages.
Colombian Patent Office, Office Action for CO Application No. 11.067.510 (2012) with English Translation, 12 pages.
Eurasian Patent Office, Office Action for EA Application No. 201190021/28 with English Translation, dated Mar. 2013, 9 pages.
Eurasian Patent Office, Office Action for EA Application No. 201190021/28 with English Translation, dated May 28, 2013, 2 pages.
European Patent Office, International Search Report and Written Opinion for PCT/US2020/033959, dated Sep. 16, 2020, 11 pages.
European Patent Office, Extended European Search Report for EP Application No. 14158708.9, dated Dec. 1, 2014, 8 pages.
Japanese Patent Office, Office Action for JP Application No. 2011-540807 with English Translation, dated Jan. 6, 2014, 5 pages.
Japanese Patent Office, Office Action for JP Application No. 2014-139372 with English Translation, dated Oct. 28, 2015, 10 pages.
Taiwan Patent Office, Office Action for TW Application No. 104102090 with English Translation, dated Sep. 9, 2015, 13 pages.
Taiwan Patent Office, Office Action for TW Application No. 098141711 with English Translation, dated Aug. 19, 2013, 16 pages.
Ukraine Patent Office, Office Action for UA Application No. 201108585 with English Translation, dated Jan. 28, 2014, 4 pages.
Vietnam Patent Office, Office Action for VN Application No. 1201101604 with English Translation, dated Sep. 30, 2013, 2 pages.

(56) References Cited

OTHER PUBLICATIONS

European Patent Office, International Preliminary Report on Patentability for International Application No. PCT/US2015/050039, dated Mar. 21, 2017, 10 pages.

European Patent Office, International Preliminary Report on Patentability for International Application No. PCT/US2015/057933, dated Apr. 11, 2017 7 pages.

European Patent Office, International Search Report and Written Opinion for PCT International Application No. PCT/US2015/050039, dated Mar. 4, 2016, 16 pages.

Illan-Cabeza, et al., Antiproliferatvie effects of palladium(II) complexes of 5-nitrosopyrimidines and interactions with the proteolytic regulatory enzymes of the renin-angiotensin system in tumoral brain cells, J. Inorg. Biochem., 2013, pp. 118-127, vol. 126.

Chinese Patent Office, CN201310465647 First Office Action dated Nov. 12, 2014, 13 pages.

Chinese Patent Office, CN201310465647 Second Office Action dated Mar. 24, 2015, 8 pages.

European Patent Office, International Search Report and Written Opinion for PCT International Application No. PCTUS2015057933, dated Jan. 21, 2016, 9 pages.

European Patent Office, International Search Report and Written Opinion for PCT International Application No. PCT/US2015/057934, dated Mar. 18, 2016, 20 pages.

European Patent Office, International Preliminary Report on Patentability and Written Opinion for PCT/US2008/007955, dated Sep. 15, 2009, 32 pages.

European Patent Office, International Search Report and Written Opinion for PCT International Application No. PCT/US2015/057932, dated Apr. 15, 2016, 17 pages.

European Patent Office, International Preliminary Report on Patentability and Written Opinion for PCT International Application No. PCT/US2015/057934, dated May 2, 2017, 14 pages.

\* cited by examiner

MODULATORS OF TOLL-LIKE RECEPTORS FOR THE TREATMENT OF HIV

CROSS REFERENCE TO RELATED APPLICATIONS

This application claims the benefit of U.S. Provisional Application No. 62/023,692, filed on Jul. 11, 2014, U.S. Provisional Application No. 62/058,569, filed on Oct. 1, 2014, and U.S. Provisional Application No. 62/118,377 filed on Feb. 19, 2015, which is hereby incorporated by reference in their entirety.

FIELD OF THE INVENTION

This application relates generally to compounds and pharmaceutical compositions which selectively modulate toll-like receptors (such as TLR7) and methods of using such compounds in the treatment of Human Immunodeficiency Virus (HIV) infections.

BACKGROUND OF THE INVENTION

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines. Agonists of TLR7 are immunostimulants and induce the production of endogenous interferon-α in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections.

TLR7 modulating compounds include the TLR7 agonist compounds of U.S. Pat. Nos. 8,367,670; 8,629,142; and 8,809,527, demonstrated through IFN-α Minimum Effective Concentration (MEC). The activity of TLR7 agonist GS-9620 has been discussed in the articles by Lanford et al., Gastroenterology 2013 June; 144(7):1508-17 and the article by Roethle et al., *Journal of Medicinal Chemistry*, Volume 56, Issue 18, Pages 7324-7333, discusses the TLR7 agonist activity of compounds of in U.S. Pat. Nos. 8,367,670; 8,629,142; and 8,809,527, including those of Examples 4, 49, 89, 99, and 105.

U.S. Pat. No. 8,507,507 discloses TLR7 agonist compounds, including 4-amino-6-(2-methoxyethoxy)-1-((4'-(pyrrolidin-1-ylmethyl)-[1,1'-biphenyl]-4-yl)methyl)-1H-imidazo[4,5-c]pyridin-2(3H)-one. U.S. Pat. No. 7,968,544 teaches TLR7 agonist compounds, including 6-amino-2-butoxy-9-(3-(pyrrolidin-1-ylmethyl)benzyl)-9H-purin-8-ol.

Around the world more than thirty million people are infected by the HIV virus. Numerous drugs and combination therapies have been developed for the treatment of HIV infections in humans. While combination antiretroviral therapies (cART) and highly active antiretroviral therapies (HAART) have been able to reduce HIV viral activation, often below 50 copies of HIV RNA/ml of plasma, no therapy has provided elimination of HIV infected cells which are not actively replicating HIV, commonly referred to as a patient's latent reservoir of HIV. Strategies have been sought for "kick and kill" methods of treating HIV in which the cells of the latent reservoir are to "kick" the HIV-infected cells into inducing transcription of the quiescent, replication-competent HIV proviruses, creating a state of transient viremia and making the activated cells susceptible to the "kill" from antiretroviral therapies. "Kick" programs have tested various agents, including histone deacetylase inhibitors, disulfiram, PD-1 antibodies, and HIV vaccines, as noted in *Prospects for Treatment of Latent HIV*, Barton et al., Clin. Pharm. & Therap., Vol. 93, Issue 1, pp. 46-56; *Neutralizing the HIV Reservoir*, Marsden et al., Cell, 158, Aug. 28, 2014, pp. 971-972; *HIV-1 Latency: An Update of Molecular Mechanisms and Therapeutic Strategies*, Battistini et al., Viruses 2014, 6, 1715-1758; and Quantification of HIV-1 latency reversal in resting CD4+ T cells from patients on suppressive antiretroviral therapy, Cillo et al., PNAS, May 13 2014, Vol. 111, No. 19, pp. 7078-7083.

There remains a need for new agents and therapies capable of assisting in the activation of the latent HIV-infected cells to enhance the activity of antiretroviral therapies and immune responses.

SUMMARY OF THE INVENTION

Provided herein are methods of treatment, regimens, pharmaceutical formulations, and kits which may be useful in treating HIV infections in a human, wherein each of the methods of treatment, regimens, pharmaceutical formulations, and kits comprise the use of a TLR7 modulating compound, including a compound of Formula II, or a pharmaceutically acceptable salt thereof:

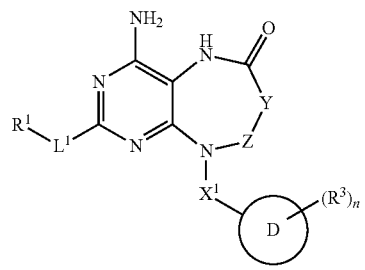

Formula II wherein:

Y—Z is —CR$^4$R$^5$—, —CR$^4$R$^5$—CR$^4$R$^5$—, —C(O)CR$^4$R$^5$—, —CR$^4$R$^5$C(O)—, —NR$^8$C(O)—, —C(O)NR$^8$—, —CR$^4$R$^5$S(O)$_2$—, or —CR$^5$=CR$^5$—;

L$^1$ is —NR$^8$—, —O—, —S—, —N(R$^8$)C(O)—, —S(O)$_2$—, —S(O)—, —C(O)N(R$^8$)—, —N(R$^8$)S(O)$_2$—, —S(O)$_2$N(R$^8$)— or a covalent bond;

R$^1$ is C$_1$-C$_8$ alkyl, C$_1$-C$_8$ substituted alkyl, haloalkyl, C$_2$-C$_8$ alkenyl, C$_2$-C$_8$ substituted alkenyl, C$_2$-C$_8$ alkynyl, C$_2$-C$_8$ substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl;

X$^1$ is C$_1$-C$_8$ alkylene, C$_1$-C$_8$ alkylene, heteroalkylene, substituted heteroalkylene, C$_2$-C$_8$ alkenylene, C$_2$-C$_8$ substituted alkenylene, C$_2$-C$_8$ alkynylene, C$_2$-C$_8$ substituted alkynylene, carbocyclylene, substituted carbocyclylene, heterocyclylene, substituted heterocyclylene, —NR$^8$—, —O—, —C(O)—, —S(O)—, S(O)$_2$—, or a bond;

D is carbocyclyl, substituted carbocyclyl, heterocyclyl or substituted heterocyclyl wherein said carbocyclyl, substituted carbocyclyl, heterocyclyl or substituted heterocyclyl is substituted with one or two -L$^2$-NR$^6$R$^7$; or D is a heterocyclyl, substituted heterocyclyl, heteroaryl or substituted heteroaryl wherein said heterocyclyl, substituted heterocyclyl, heteroaryl or substituted heteroaryl comprises one to four nitrogen atoms;

each L$^2$ is independently C$_1$-C$_8$ alkylene, C$_1$-C$_8$ substituted alkylene, heteroalkylene, substituted heteroalkylene, or a covalent bond;

each R$^3$ is independently halogen, cyano, azido, nitro, C$_1$-C$_8$ alkyl, C$_1$-C$_8$ substituted alkyl, hydroxyl, amino, heteroalkyl, substituted heteroalkyl, C$_1$-C$_8$ alkoxy, haloalkyl, haloalkoxy, —CHO, —C(O)OR$^8$, —S(O)R$^8$, —S(O)$_2$R$^8$; —C(O)NR$^9$R$^{10}$, —N(R$^9$)C(O)R$^8$, carbocyclyl, substituted carbocyclyl, carbocyclylalkyl, substituted carbocyclylalkyl, C$_2$-C$_8$ alkenyl, C$_2$-C$_8$ substituted alkenyl, C$_2$-C$_8$ alkynyl, C$_2$-C$_8$ substituted alkynyl, —S(O)$_2$NR$^9$R$^{10}$, —N(R$^9$)S(O)$_2$R$^8$, —N(R$^9$)S(O)$_2$OR$^{10}$, —OS(O)$_2$NR$^9$R$^{10}$;

n is 0, 1, 2, 3, 4 or 5;

R$^4$ and R$^5$ are each independently H, C$_1$-C$_8$ alkyl, C$_1$-C$_8$ substituted alkyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, cyano, azido, OR$^8$, —C(O)H, —C(O)R$^8$, —S(O)R$^8$, —S(O)$_2$R$^8$, —C(O)OR$^8$, or —C(O)NR$^9$R$^{10}$; or R$^4$ and R$^5$, taken together with the carbon to which they are both attached, form a carbocycle, substituted carbocycle, heterocycle or substituted heterocycle; or R$^4$ and R$^5$, when on the same carbon atom, taken together with the carbon to which they are attached are —C(O)— or —C(NR$^8$)—; or two R$^4$ or two R$^5$ on adjacent carbon atoms when taken together with the carbons to which they are attached form a 3 to 6 membered carbocycle, substituted carbocycle, heterocycle or substituted heterocycle;

R$^6$ and R$^7$ are each independently H, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, —C(O)H, —C(O)R$^8$, —S(O)R$^8$, —S(O)$_2$R$^8$, —C(O)OR$^8$, or —C(O)NR$^9$R$^{10}$, S(O)$_2$NR$^9$R$^{10}$; or R$^6$ and R$^7$, taken together with the nitrogen to which they are both attached, form a substituted or unsubstituted heterocycle, which may contain one or more additional heteroatoms selected from N, O, P, or S; or R$^7$ taken together with L$^2$, and the N to which they are both attached, forms a substituted or unsubstituted 3 to 8 membered heterocycle which may contain one or more additional heteroatoms selected from N, O, S, or P;

R$^8$ is H, C$_1$-C$_8$ alkyl, C$_1$-C$_8$ substituted alkyl, haloalkyl, C$_2$-C$_8$ alkenyl, C$_2$-C$_8$ substituted alkenyl, C$_2$-C$_8$ alkynyl, C$_2$-C$_8$ substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; and R$^9$ and R$^{10}$ are each independently H, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; or R$^9$ and R$^{10}$, taken together with the nitrogen to which they are both bonded, form a substituted or unsubstituted heterocycle;

wherein each substituted alkyl, substituted alkenyl, substituted alkynyl, substituted heteroalkyl, substituted carbocyclyl, substituted carbocyclylalkyl, substituted heterocyclyl, substituted heterocyclylalkyl, substituted arylalkyl, substituted heteroarylalkyl, substituted carbocyclylheteroalkyl, substituted heterocyclylheteroalkyl, substituted arylheteroalkyl, substituted heteroarylheteroalkyl, substituted alkylene, substituted heteroalkylene, substituted alkenylene, substituted alkynylene, substituted carbocyclylene, or substituted heterocyclylene is independently substituted with one to four substituents selected from the group consisting of -halogen, —R, —O⁻, =O, —OR, —SR, —S⁻, —NR$_2$, —N(+)R$_3$, =NR, —C(halogen)$_3$, —CR(halogen)$_2$, —CR$_2$(halogen), —CN, —OCN, —SCN, —N=C=O, —NCS, —NO, —NO$_2$, =N$_2$, —N$_3$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NR, —S(=O)R, —NRS(=O)$_2$R, —NRS(=O)$_2$NRR, —NRS(=O)$_2$OR, —OP(=O)(OR)$_2$, —P(=O)(OR)$_2$, —P(O)(OR)(O)R, —C(=O)R, —C(=S)R, —C(=O)OR, —C(=S)OR, —C(=O)SR, —C(=S)SR, —C(=O)NRR, —C(=S)NRR, —C(=NR)NRR, and —NRC(=NR)NRR; wherein each R is independently H, alkyl, cycloalkyl, aryl, arylalkyl, or heterocyclyl.

Compounds of Formula II, and pharmaceutically acceptable salts thereof, may be prepared by methods disclosed in U.S. 2010/014330, U.S. Pat. No. 8,367,670, and 8,629,142 (Desai et al.), which are incorporated by reference herein in their entirety, and by other methods known in the art.

While not wishing to be bound by theory, the inventors currently believe that the compounds of Formula II, and of Examples 119, 120, 121, 123, and 124 are agonists of TLR7 and may also be agonists of other TLRs.

Another aspect of the present invention includes a method for treating an HIV infection in a human, the method comprising administering to a human in need thereof a therapeutically effective amount of a compound of Formula II.

The present invention includes combinations of aspects and embodiments, as well as preferences, as herein described throughout the present specification.

DETAILED DESCRIPTION

Figure 1:
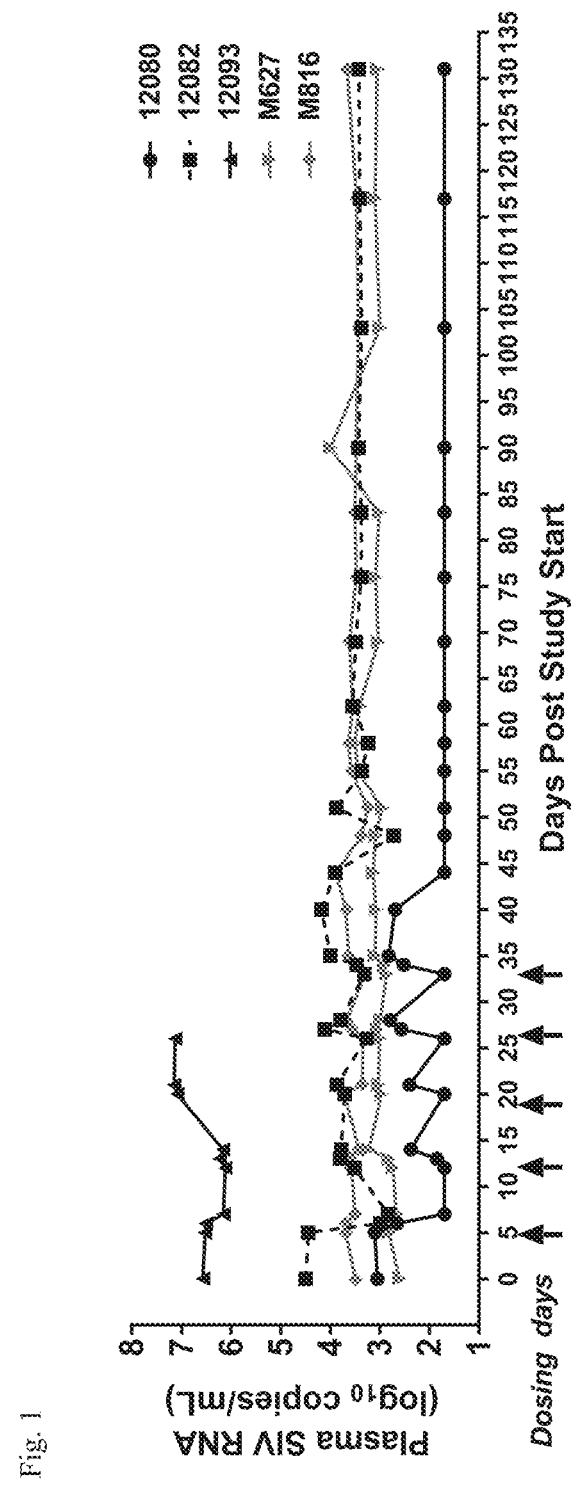
FIG. 1 depicts the absolute viral load for each animal for each study day in the SIV⁺ rhesus macaques study.

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents referenced herein are each incorporated by reference in their entirety for all purposes.

TLR7 modulating compounds (TLR7 modulating agents) which may be used in the methods, combinations, pharmaceutical compositions, uses, and regimens described herein include GSK2245035, Imiquimod, Resiquimod (R848), R-852 (PF-4878691), ANA773, 5-amino-7-hydroxy-3-((2R,3R,5S)-3-hydroxy-5-(hydroxymethyl)tetrahydrofuran-2-yl)thiazolo[4,5-d]pyrimidin-2(3H)-one (active metabolite of ANA773), AZD8848 (DSP3025), SM-360320, IMO-8400, CL097, CL075 (3M002), GARDIQUIMOD™ (1-(4-Amino-2-ethylaminomethylimidazo[4,5-c]quinolin-1-yl)-2-methylpropan-2-ol), Isatoribine, 6-amino-2-(butylamino)-7,9-dihydro-9-[(6-methyl-3-pyridinyl)methyl]-8H-purin-8-one (SM-276001), 852A (N-[4-(4-amino-2-ethyl-1H-imidazo[4,5-c]quinolin-1-yl)butyl] methanesulfonamide), 3M-854A and 3M-052, 5-(4-amino-2-methyl-1H-imidazo[4,5-c]quinolin-1-yl)-4,4-dimethylpentan-2-one (S-34240), loxoribine, as well as the TLR7 modulating compounds described in U.S. Pat. No. 8,729,088B2, U.S. Pat. No. 8,728,486B2, U.S. Pat. No. 8,728,465B2, US20140142086A1, US20140134132A1, US20110053893A1, WO2013068438A1, US20130109647A1, US20130136776A1, US20130243726A1, U.S. Pat. No. 7,968,544. U.S. Pat. No. 8,507,507, US 2010/0256169, U.S. Pat. Nos. 4,643,992, 4,539,205, 5,011,828, 5,041,426, 4,880,784, US 2003/0195209, US 2003/0186949, US 2003/0176458, US 2003/0162806, 2003/0100764, US 2003/0065005, US 2002/0173655, U.S. Pat. No. 5,395,937, US 2010/0215642, US 2010/0210598, US 2010/0256169, US 2009/0324551, US 2010/0029585, US20120035193, US20110282061, US20140024664, US20100240623, US2008026924, US20140045837, US20130236492, and US20130018042, the contents of each of which is incorporated herein in their entirety by reference.

Provided for each of the uses, methods, regimens, pharmaceutical formulations/compositions, and kits described herein there are separate embodiments comprising the use of a TLR7 modulating compound of Formula II wherein the compound is as described in the individual groups below:

(a) $L^1$ is —NR$^8$—;
(b) $L^1$ is —O—;
(c) $L^1$ is —S—;
(d) $L^1$ is —S(O)—;
(e) $L^1$ is a covalent bond;
(f) $L^1$ is —C(O)N(R$^8$)—;
(g) $L^1$ is —N(R$^8$)S(O)$_2$
(h) $L^1$ is —S(O)$_2$N(R$^8$)—.

(i) $R^1$ is alkyl;
(j) $R^1$ is substituted alkyl;
(k) $R^1$ is heteroalkyl;
(l) $R^1$ is substituted heteroalkyl;
(m) $X^1$ is alkylene
(n) $X^1$ is substituted alkylene;
(o) $X^1$ is heteroalkylene;
(p) $X^1$ is substituted heteroalkylene;
(q) $X^1$ is $C_1$-$C_6$ alkylene;
(r) $X^1$ is substituted $C_1$-$C_6$ alkylene;
(s) $X^1$ is $C_1$-$C_6$ heteroalkylene;
(t) $X^1$ is substituted $C_1$-$C_6$ heteroalkylene;
(u) $X^1$ is —$CH_2$—;
(v) D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$;
(w) D is a heterocyclyl or heteroaryl wherein said heterocyclyl or heteroaryl comprises one to four nitrogen atoms;
(x) D is a 3- to 12-membered carbocyclyl or 3- to 12-membered heterocyclyl wherein said carbocyclyl or heterocyclyl is substituted with -$L^2$-$NR^6R^7$;
(y) D is phenyl, biphenyl or pyridinyl wherein said phenyl, biphenyl or pyridinyl is substituted with -$L^2$-$NR^6R^7$;
(z) D is a heterocyclyl, substituted heterocyclyl, heteroaryl or substituted heteroaryl wherein said heterocyclyl, substituted heterocyclyl, heteroaryl or substituted heteroaryl comprises one to four nitrogen atoms;
(aa) D is a heterocyclyl, substituted heterocyclyl, heteroaryl or substituted heteroaryl wherein said heterocyclyl, substituted heterocyclyl, heteroaryl or substituted heteroaryl is optionally substituted pyridinyl, optionally substituted piperidinyl, optionally substituted piperazinyl or optionally substituted 1,2,3,4-tetrahydroisoquinolinyl;
(bb) D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^6$ and $R^7$ independently are H, alkyl, heteroalkyl, or, together with the nitrogen atom to which they are attached, form a substituted or unsubstituted heterocyclyl;
(cc) D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S;
(dd) D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^7$ taken together with $L^2$, and the N to which they are both attached, forms a substituted or unsubstituted 3 to 8 membered heterocycle which may contain one or more additional heteroatoms selected from N, O, S, or P;
(ee) —Y—Z— is —$CR^4R^5$—;
(ff) —Y—Z— is —$CR^4R^5$—$CR^4R^5$—;
(gg) —Y—Z— is —$CR^4R^5$— wherein each $R^4$ or $R^5$ is independently H or $C_1$-$C_6$ alkyl;
(hh) —Y—Z— is —$CH_2$—;
(ii) —Y—Z— is —$(CH_2)_2$—; and
(jj) —Y—Z— is —C(O)—.

In each of the embodiments listed from (a) to (jj), above, it is understood that, other than the definitions specified, all variable for the specific embodiment are otherwise as defined above for Formula II.

In one embodiment of Formula II, —Y—Z— is —$CR^4R^5$— or —$CR^4R^5$—$CR^4R^5$— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, $R^7$ taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— or —$CR^4R^5$—$CR^4R^5$— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— wherein each $R^4$ or $R^5$ is independently H or $CH_3$ and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, $R^7$ taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— wherein each $R^4$ or $R^5$ is independently H or $CH_3$ and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— wherein $R^4$ and $R^5$ taken together with the carbon to which they are attached is —C(O)— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, $R^7$ taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— wherein $R^4$ and $R^5$ taken together with the carbon to which they are attached is —C(O)— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CH_2CH_2$— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, $R^7$ taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CH_2CH_2$— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In separate embodiments of the uses, methods of treatment, regimens, pharmaceutical formulations, and kits described herein, the TLR7 modulating compound of Formula II is represented by Formula Ia:

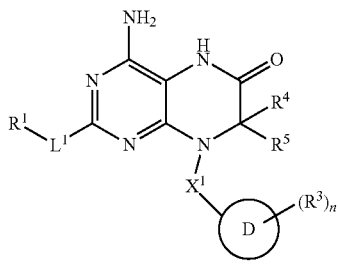

or a pharmaceutically acceptable salt thereof, wherein:
$L^1$ is —NH— or —O—;
$R^1$ is alkyl, substituted alkyl, heteroalkyl, substituted heteroalkyl, heterocyclylalkyl, substituted heterocyclylalkyl, carbocyclylalkyl or substituted carbocyclylalkyl;
each of $R^4$ and $R^5$ independently is H or $C_1$-$C_6$ alkyl or $R^4$ and $R^5$ taken together with the carbon to which they are attached is —C(O)—;
$X^1$ is $C_1$-$C_6$ alkylene, $C_1$-$C_6$ heteroalkylene or $C_1$-$C_6$ substituted heteroalkylene;
D is phenyl, biphenyl or pyridinyl, wherein said phenyl, biphenyl or pyridinyl is substituted with -$L^2$-$NR^6R^7$; or
D is pyridinyl, piperidinyl, piperazinyl or 1,2,3,4-tetrahydroisoquinolinyl;
n is 0 or 1;
$R^3$ is halogen, cyano, alkyl, carbocyclyl, carbocyclylalkyl, haloalkyl, —C(O)$OR^8$, —C(O)$NR^9R^{10}$ or —CHO;
$L^2$ is $C_1$-$C_6$ alkylene or a covalent bond;
each of $R^6$ and $R^7$ independently is H, alkyl, or heteroaryl; or
$R^6$ and $R^7$ taken together with the nitrogen to which they are attached form a substituted or unsubstituted 4-6 membered heterocycle comprising 0 to 2 heteroatoms selected from N, O or S.

In one embodiment of Formula Ia, each of $R^4$ and $R^5$ independently is H or $C_1$-$C_6$ alkyl. In another embodiment of Formula Ia, each of $R^4$ and $R^5$ is H. In another embodiment of Formula Ia, $R^4$ and $R^5$ taken together with the carbon to which they are attached is —C(O)—. In another embodiment of Formula Ia, $L^1$ is —O—. In another embodiment of Formula Ia, $L^1$ is —NH—. In another embodiment of Formula Ia, $X^1$ is $C_1$-$C_6$ alkylene. In another embodiment of Formula Ia, $X^1$ is $C_1$-$C_6$ heteroalkylene. In another embodiment of Formula Ia, $X^1$ is $C_1$-$C_6$ substituted heteroalkylene. In another embodiment of Formula Ia, $X^1$ is —$CH_2$—. In another embodiment of Formula Ia, D is phenyl, biphenyl or pyridinyl, wherein said phenyl, biphenyl or pyridinyl is substituted with -$L^2$-$NR^6R^7$. In another embodiment of Formula Ia, D is pyridinyl, piperidinyl, or piperazinyl. In another embodiment of Formula Ia, $L^2$ is —$CH_2$—. In another embodiment of Formula Ia, each of $R^6$ and $R^7$ independently is H, alkyl, or heteroaryl. In another embodiment of Formula Ia, $R^6$ and $R^7$ taken together with the nitrogen to which they are attached form a substituted or unsubstituted 4-6 membered heterocycle comprising 0 to 2 heteroatoms selected from N, O or S.

In one embodiment of Formula Ia, each of $R^4$ and $R^5$ independently is H or $CH_3$ and D is phenyl, biphenyl or pyridinyl, wherein said phenyl, biphenyl or pyridinyl is substituted with -$L^2$-$NR^6R^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is —$CH_2$—. In another aspect of this embodiment, $X^1$ is —$CH_2$—. In another aspect of this embodiment, $L^1$ is —O—. In another aspect of this embodiment, $L^1$ is —NH—.

In one embodiment of Formula Ia, each of $R^4$ and $R^5$ independently is H or $CH_3$ and D is pyridinyl, piperidinyl, or piperazinyl. In another aspect of this embodiment, $X^1$ is —$CH_2$—. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is —O—. In another aspect of this embodiment, $L^1$ is —NH—.

In one embodiment of Formula Ia, $R^4$ and $R^5$ taken together with the carbon to which they are attached is —C(O)— and D is phenyl, biphenyl or pyridinyl, wherein said phenyl, biphenyl or pyridinyl is substituted with -$L^2$-$NR^6R^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is —$CH_2$—. In another aspect of this embodiment, $X^1$ is —$CH_2$—. In another aspect of this embodiment, $L^1$ is —O—. In another aspect of this embodiment, $L^1$ is —NH—.

In one embodiment of Formula Ia, $R^4$ and $R^5$ taken together with the carbon to which they are attached is —C(O)— and D is pyridinyl, piperidinyl, piperazinyl or 1,2,3,4-tetrahydroisoquinolinyl. In another aspect of this embodiment, $X^1$ is —$CH_2$—. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is —O—. In another aspect of this embodiment, $L^1$ is —NH—.

In separate embodiments of the uses, methods of treatment, regimens, pharmaceutical formulations, and kits described herein, the TLR7 modulating compound of Formula II is represented by Formula IIa:

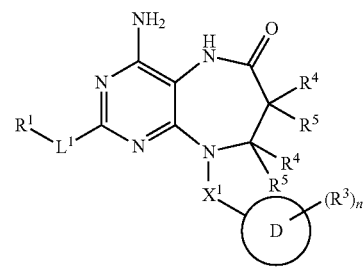

or a pharmaceutically acceptable salt thereof, wherein:
$L^1$ is —NH— or —O—;
$R^1$ is alkyl, substituted alkyl, heteroalkyl, substituted heteroalkyl, heterocyclylalkyl, substituted heterocyclylalkyl, carbocyclylalkyl or substituted carbocyclylalkyl;
each of $R^4$ and $R^5$ independently is H or $C_1$-$C_6$ alkyl or any $R^4$ and $R^5$ on the same carbon atom when taken together with the carbon to which they are attached is —C(O)—;

$X^1$ is $C_1$-$C_6$ alkylene, $C_1$-$C_6$ heteroalkylene or $C_1$-$C_6$ substituted heteroalkylene;

D is phenyl, biphenyl or pyridinyl, wherein said phenyl, biphenyl or pyridinyl is substituted with -$L^2$-$NR^6R^7$; or D is pyridinyl, piperidinyl, piperazinyl or 1,2,3,4-tetrahydroisoquinolinyl;

n is 0 or 1, $R^3$ is halogen, cyano, alkyl, carbocyclyl, carbocyclylalkyl, haloalkyl, —C(O)$OR^8$, —C(O)$NR^9R^{10}$ or —CHO;

$L^2$ is $C_1$-$C_6$ alkylene or a covalent bond;

each of $R^6$ and $R^7$ independently is H, alkyl, or heteroaryl; or $R^6$ and $R^7$ taken together with the nitrogen to which they are attached form a substituted or unsubstituted 4-6 membered heterocycle comprising 0 to 2 heteroatoms selected from N, O or S.

In one embodiment of Formula IIa, each of $R^4$ and $R^5$ independently is H or $C_1$-$C_6$ alkyl. In another embodiment of Formula IIa, each of $R^4$ and $R^5$ is H. In another embodiment of Formula IIa, $L^1$ is —O—. In another embodiment of Formula IIa, $L^1$ is —NH—. In another embodiment of Formula IIa, $X^1$ is $C_1$-$C_6$ alkylene. In another embodiment of Formula IIa, $X^1$ is $C_1$-$C_6$ heteroalkylene. In another embodiment of Formula IIa, $X^1$ is $C_1$-$C_6$ substituted heteroalkylene. In another embodiment of Formula IIa, $X^1$ is —$CH_2$—. In another embodiment of Formula IIa, D is phenyl, biphenyl or pyridinyl, wherein said phenyl, biphenyl or pyridinyl is substituted with -$L^2$-$NR^6R^7$. In another embodiment of Formula IIa, D is pyridinyl, piperidinyl, piperazinyl or 1,2,3,4-tetrahydroisoquinolinyl. In another embodiment of Formula IIa, $L^2$ is —$CH_2$—. In another embodiment of Formula IIa, each of $R^6$ and $R^7$ independently is H, alkyl, or heteroaryl. In another embodiment of Formula IIa, $R^6$ and $R^7$ taken together with the nitrogen to which they are attached form a substituted or unsubstituted 4-6 membered heterocycle comprising 0 to 2 heteroatoms selected from N, O or S.

In one embodiment of Formula IIa, each of $R^4$ and $R^5$ independently is H or $CH_3$ and D is phenyl, biphenyl or pyridinyl, wherein said phenyl, biphenyl or pyridinyl is substituted with -$L^2$-$NR^6R^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is —$CH_2$—. In another aspect of this embodiment, $X^1$ is —$CH_2$—. In another aspect of this embodiment, $L^1$ is —O—. In another aspect of this embodiment, $L^1$ is —NH—.

In one embodiment of Formula IIa, each of $R^4$ and $R^5$ independently is H or $CH_3$ and D is pyridinyl, piperidinyl, or piperazinyl. In another aspect of this embodiment, $X^1$ is —$CH_2$. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is —O—. In another aspect of this embodiment, $L^1$ is —NH—.

Each of the uses, methods, regimens, compositions, and kits described herein comprise a further embodiment wherein the TLR7 modulating compound is selected from a compound of Formula III, or a pharmaceutically acceptable salt thereof:

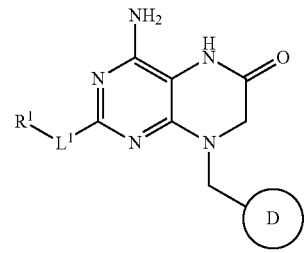

Formula III wherein:

the D ring represents a moiety selected from:

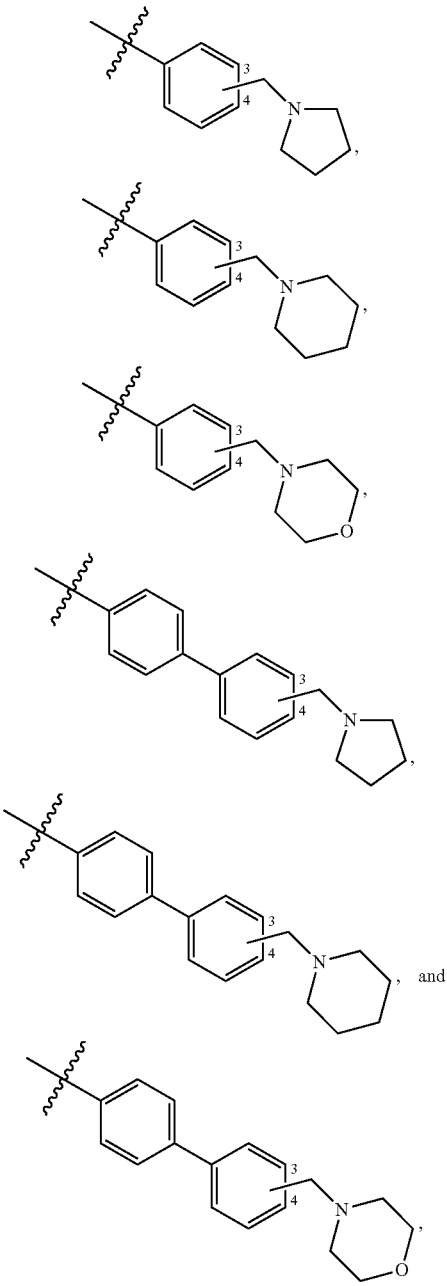

wherein, in each instance, the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, —S—, —$N(R^8)C(O)$—, —$S(O)_2$—, —$S(O)$—, —$C(O)N(R^8)$—, —$N(R^8)S(O)_2$—, —$S(O)_2N(R^8)$— or a covalent bond;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H, $C_1$-$C_8$ alkyl, substituted alkyl, $C_1$-$C_8$ haloalkyl, $C_2$-$C_8$ alkenyl, $C_2$-$C_8$ substituted alkenyl, $C_2$-$C_8$ alkynyl, and $C_2$-$C_8$ substituted alkynyl, wherein the substituted $C_1$-$C_8$ alkyl, substituted $C_2$-$C_8$ alkenyl, and substituted $C_2$-$C_8$ alkynyl groups are substituted by 1, 2, 3, or 4 substituents independently selected from F, Cl, Br, I, CN, OH, —O—$C_1$-$C_3$ alkyl, —S—$C_1$-$C_3$ alkyl, —C(O)—$C_1$-$C_3$ alkyl, —$CO_2H$, and —C(O)—O—$C_1$-$C_3$ alkyl.

Each of the uses, methods, regimens, compositions, and kits described herein comprise further separate embodiments wherein the TLR7 modulating compound is independently selected from a compound of Formula III(a), Formula III(b), Formula III(c), Formula III(d), Formula III(e), or Formula III(f), or a pharmaceutically acceptable salt thereof:

Formula III(a)

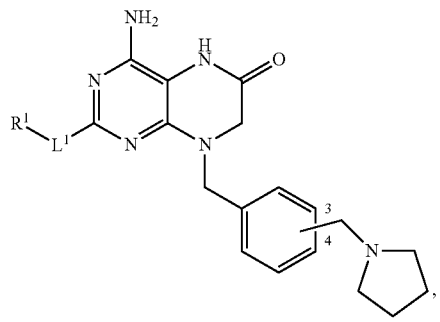

Formula III(b)

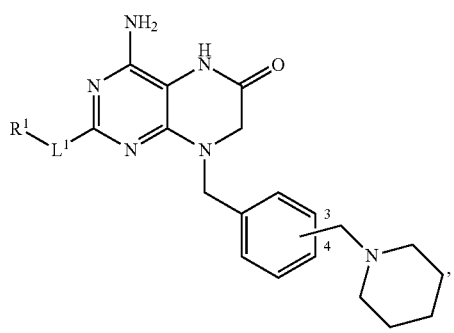

Formula III(c)

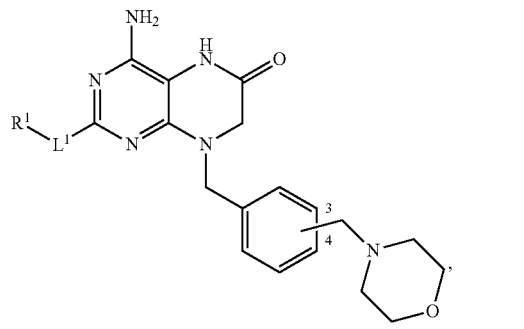

Formula III(d)

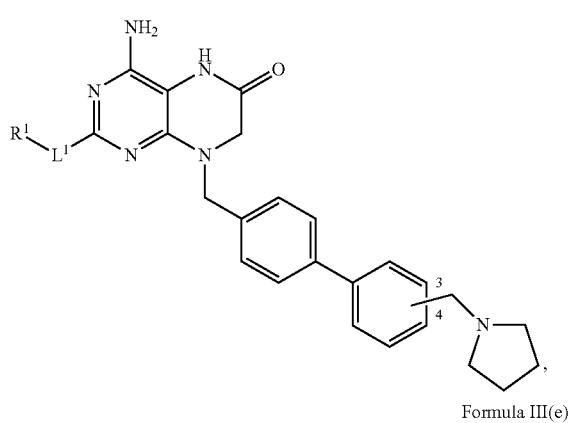

Formula III(e)

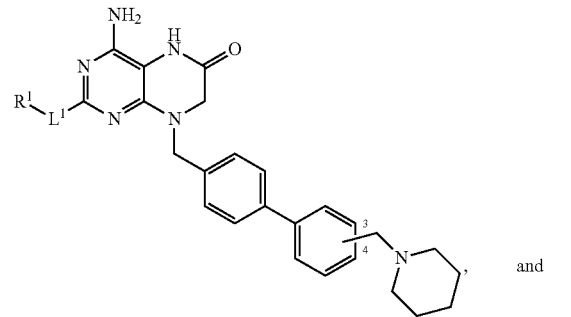

and

Formula III(f)

wherein, in each instance, the pyrrolidin-1-ylmethyl, piperidin-1-ylmethyl, or morpholinomethyl group is bound to the 3-position or 4-position of the phenyl ring to which it is bound, and $L^1$, $R^1$, and $R^8$ are each as defined above for Formula III.

Further separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, —S—, —$N(R^8)C(O)$—, —$S(O)_2$—, —$S(O)$—, —$C(O)N(R^8)$—, —$N(R^8)S(O)_2$—, —$S(O)_2N(R^8)$— or a covalent bond;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H, $C_1$-$C_6$ alkyl, or substituted alkyl, wherein the substituted $C_1$-$C_6$ alkyl is substituted by 1, 2, 3, or 4 substituents independently selected from F, Cl, Br, I, CN, OH, —O—$C_1$-$C_3$ alkyl, —S—$C_1$-$C_3$ alkyl, —C(O)—$C_1$-$C_3$ alkyl, —$CO_2H$, and —C(O)—O—$C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, —S—, —$N(R^8)C(O)$—, —$S(O)_2$—, —$S(O)$—, —$C(O)N(R^8)$—, —$N(R^8)S(O)_2$—, —$S(O)_2N(R^8)$— or a covalent bond;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H, $C_1$-$C_6$ alkyl, or substituted alkyl, wherein the substituted $C_1$-$C_6$ alkyl is substituted by 1, 2, 3, or 4 substituents independently selected from F, Cl, Br, I, CN, OH, —O—$C_1$-$C_3$ alkyl, —S—$C_1$-$C_3$ alkyl, —C(O)—$C_1$-$C_3$ alkyl, —$CO_2H$, and —C(O)—O—$C_1$-$C_3$ alkyl.

Further separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, or —S—;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H, $C_1$-$C_6$ alkyl, or substituted alkyl, wherein the substituted $C_1$-$C_6$ alkyl is substituted by 1, 2, 3, or 4 substituents independently selected from F, Cl, Br, I, CN, OH, —O—$C_1$-$C_3$ alkyl, —S—$C_1$-$C_3$ alkyl, —C(O)—$C_1$-$C_3$ alkyl, —$CO_2H$, and —C(O)—O—$C_1$-$C_3$ alkyl.

Still further separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, or —S—;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H, $C_1$-$C_3$ alkyl, or substituted alkyl, wherein the substituted $C_1$-$C_3$ alkyl is substituted by 1, 2, 3, or 4 substituents independently selected from F, Cl, Br, I, CN, OH, —O—$C_1$-$C_3$ alkyl, —S—$C_1$-$C_3$ alkyl, —C(O)—$C_1$-$C_3$ alkyl, —$CO_2H$, and —C(O)—O—$C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—, —O—, or —S—;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H and $C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —$NR^8$—;

$R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl; and $R^8$ is selected from the group of H and $C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —S—; and $R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —SO$_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —O—; and $R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —SO$_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —NR$^8$—;

$R^1$ is unsubstituted $C_1$-$C_6$ alkyl, or $C_1$-$C_6$ alkyl substituted by 1 substituent selected from fluoroalkyl, OH, and —O—$C_1$-$C_3$ alkyl; and $R^8$ is selected from the group of H and $C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —NR$^8$—;

$R^1$ is unsubstituted $C_1$-$C_6$ alkyl or $C_1$-$C_6$ alkyl substituted by 1-O—$C_1$-$C_3$ alkyl substituent; and $R^8$ is selected from the group of H and $C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —S—; and $R^1$ is unsubstituted $C_1$-$C_6$ alkyl, or $C_1$-$C_6$ alkyl substituted 1 substituent selected from fluoroalkyl, OH, and —O—$C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment, the pyrrolidin-1-ylmethyl, piperidin-1-ylmethyl, or morpholinomethyl group is bound to the 3-position or 4-position of the phenyl ring to which it is bound; $L^1$ is —S—; and $R^1$ is unsubstituted $C_1$-$C_6$ alkyl or $C_1$-$C_6$ alkyl substituted by 1-O—$C_1$-$C_3$ alkyl substituent.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment:

the pyrrolidin-1-ylmethyl, piperidin-1-ylmethyl, or morpholinomethyl group is bound to the 3-position or 4-position of the phenyl ring to which it is bound;

$L^1$ is —O—; and $R^1$ is unsubstituted $C_1$-$C_6$ alkyl, or $C_1$-$C_6$ alkyl substituted by 1 substituent selected from fluoroalkyl, OH, and —O—$C_1$-$C_3$ alkyl.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment, the pyrrolidin-1-ylmethyl, piperidin-1-ylmethyl, or morpholinomethyl group is bound to the 3-position or 4-position of the phenyl ring to which it is bound; $L^1$ is —O—; and $R^1$ is unsubstituted $C_1$-$C_6$ alkyl or $C_1$-$C_6$ alkyl substituted by 1-O—$C_1$-$C_3$ alkyl substituent.

Additional separate embodiments are provided for each of the uses, methods, regimens, compositions, and kits described herein wherein the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment, the pyrrolidin-1-ylmethyl, piperidin-1-ylmethyl, or morpholinomethyl group is bound to the 3-position or 4-position of the phenyl ring to which it is bound; $L^1$ is —O—; and $R^1$ is unsubstituted $C_1$-$C_6$ alkyl. In further additional embodiments the TLR7 modulating compound is independently selected from Formula III, Formula III(a), Formula III(b), Formula III(c), Formula III(d), Formula III(e), or Formula III(f), or a pharmaceutically acceptable salt thereof, wherein, in each embodiment, the pyrrolidin-1-ylmethyl, piperidin-1-ylmethyl, or morpholinomethyl group is bound to the 3-position or 4-position of the phenyl ring to which it is bound; $L^1$ is —O—; and $R^1$ is unsubstituted $C_3$-$C_6$ alkyl.

Each of the uses, methods, regimens, compositions, and kits described herein comprise further separate embodiments wherein the TLR7 modulating compound is independently selected from a compound of Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2), or a pharmaceutically acceptable salt thereof:

Formula III(a)(1)

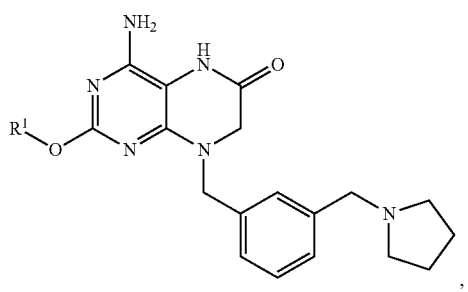

,

Formula III(a)(2)

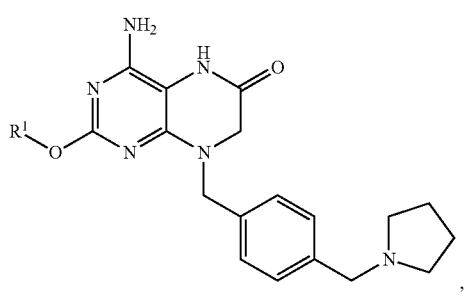

,

Formula III(b)(1)

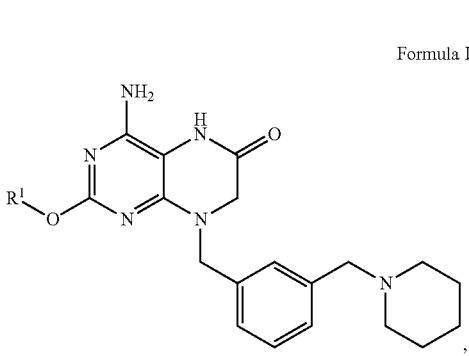

,

Formula III(b)(2)

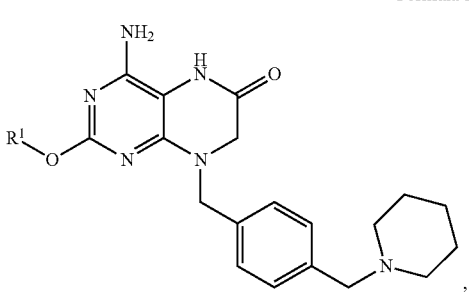

,

Formula III(c)(1)

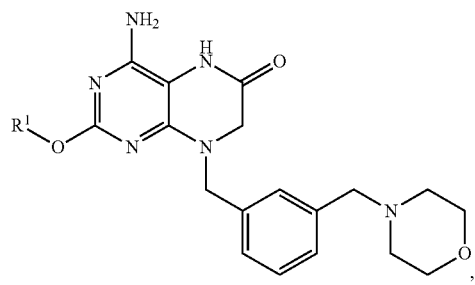

,

Formula III(c)(2)

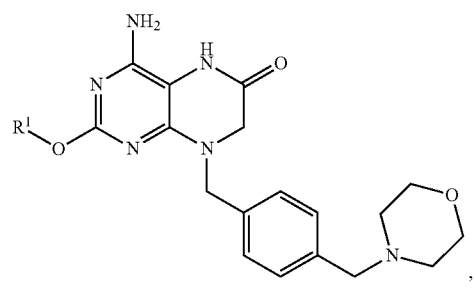

,

Formula III(d)(1)

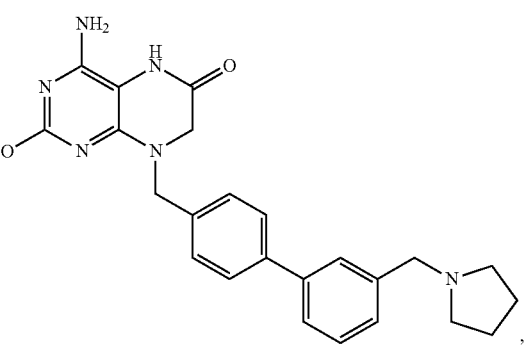

,

Formula III(d)(2)

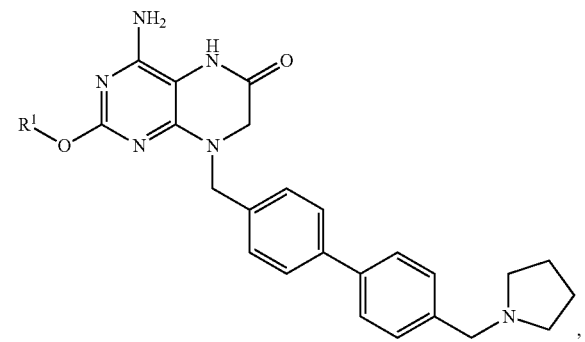

,

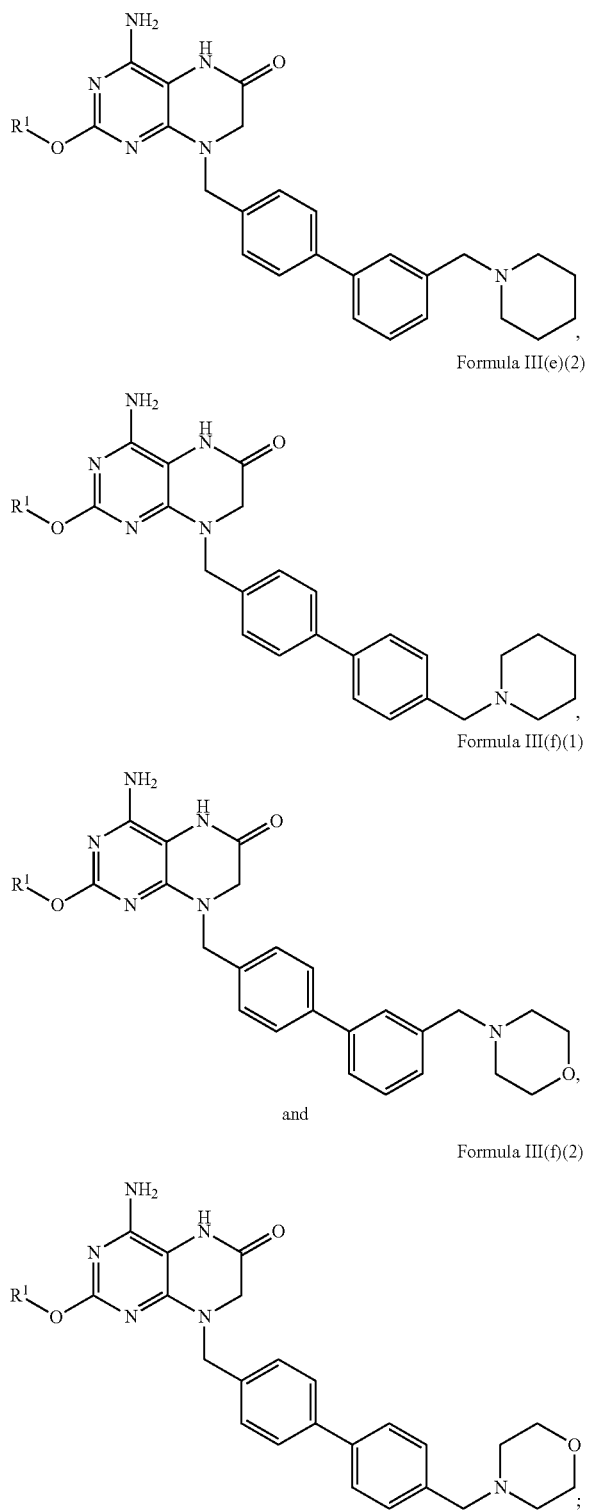

wherein, in each embodiment, $R^1$ is $C_3$-$C_6$ cycloalkyl, unsubstituted $C_1$-$C_8$ alkyl, or $C_1$-$C_8$ alkyl substituted by 1 substituent selected from haloalkyl, OH, —O—$C_1$-$C_6$ alkyl, —$SO_2$—$C_1$-$C_6$ alkyl, $C_3$-$C_6$ cycloalkyl, phenyl, pyridinyl, imidazolyl, furanyl, tetrahydrofuranyl, pyrrolidinyl, pyrrolidin-2-only, and tetrahydropyranyl.

Each of the uses, methods, regimens, compositions, and kits described herein comprise further separate embodiments wherein the TLR7 modulating compound is independently selected from a compound of Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2), or a pharmaceutically acceptable salt thereof, wherein $R^1$ is unsubstituted $C_1$-$C_6$ alkyl or $C_1$-$C_6$ alkyl substituted 1 substituent selected from fluoroalkyl, OH, and —O—$C_1$-$C_3$ alkyl.

Each of the uses, methods, regimens, compositions, and kits described herein comprise further separate embodiments wherein the TLR7 modulating compound is independently selected from a compound of Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2), or a pharmaceutically acceptable salt thereof, wherein $R^1$ is unsubstituted $C_1$-$C_6$ alkyl or $C_1$-$C_6$ alkyl substituted by 1-O—$C_1$-$C_3$ alkyl substituent.

Each of the uses, methods, regimens, compositions, and kits described herein comprise further separate embodiments wherein the TLR7 modulating compound is independently selected from a compound of Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2), or a pharmaceutically acceptable salt thereof, wherein $R^1$ is unsubstituted $C_1$-$C_6$ alkyl.

Each of the uses, methods, regimens, compositions, and kits described herein comprise further separate embodiments wherein the TLR7 modulating compound is independently selected from a compound of Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2), or a pharmaceutically acceptable salt thereof, wherein $R^1$ is $C_1$-$C_6$ alkyl substituted by 1-O—$C_1$-$C_3$ alkyl substituent.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The acronym "HIV" refers to the human immunodeficiency virus that causes acquired immunodeficiency syndrome, "AIDS".

The term "treating", and grammatical equivalents thereof, when used in the context of treating a disease, means slowing or stopping the progression of a disease, or ameliorating at least one symptom of a disease, more preferably ameliorating more than one symptom of a disease.

As used herein, "a compound of the invention". "a compound described herein", and "a compound of "Formula Ia" or "Formula II" or "Formula IIa", as well as reference to a compound of each of the other formulas herein, means a compound of the specified formula, structure, or chemical name, including alternative forms thereof such as, solvated forms, hydrated forms, esterified forms, or physiologically functional derivatives thereof. Compounds of the invention also include tautomeric forms thereof, e.g., tautomeric "enols" as described herein. Similarly, with respect to isolatable intermediates, the phrase "a compound of formula (number)" means a compound of that formula and alternative forms thereof.

The terms "combination antiretroviral therapy" ("cART") refers to combinations or "cocktails" of antiretroviral medications used to treat human viral infections, including HIV infections. As used herein, the terms "combination antiretroviral therapy" and "cART include combinations and regimens often referred to as Highly Active Antiretroviral Therapy (HAART). HAART and cART combinations and regimens commonly include multiple, often three or more, drugs such as nucleoside reverse transcriptase inhibitors (NRTIs), non-nucleoside reverse transcriptase inhibitors (NNRTIs), protease inhibitors (PIs), fusion inhibitors, CCR5 agonists, and/or integrase inhibitors.

The terms "chronic set point", "set point in chronic HIV infection", "viral load set point", and "viral set point in chronic HIV infection" refer to the HIV viral load established in a patient's blood after infection or following the introduction of antiretroviral therapy or treatment, including combination antiretroviral therapy or treatment.

The terms "viral load" and "HIV viral load" refer to the level of HIV detectable in a the blood of an HIV infected human after HIV infection or following treatment with antiretroviral therapy, such as with cART or HAART treatment regimens. can be calculated by estimating the amount of virus in an involved body fluid. For example, it can be given in HIV RNA copies per milliliter of blood or blood plasma. An "undetectable" HIV viral load comprises a condition in which HIV RNA copies cannot be detected by standard viral load tests. An undetectable HIV viral load as used herein refers to a viral load of fewer than 50 HIV RNA copies per milliliter of blood or blood plasma. The term "viremia" refers to the measurable presence of virus or viral particles in circulation in a virally infected human. The term "transient viremia" refers to a brief, transitory, or temporary increase in the measurable presence of virus or viral particles in circulation in a virally infected human. Examples of transient HIV viremia include a period in which the HIV-1 RNA level in the blood or plasma of an HIV infected human which has been maintained for a period of time at a concentration of less than 50 copies of HIV-1 RNA per mL briefly, transitorily, or temporarily rises to a concentration of greater than 50 copies/mL, such as from 50 to 2,000 copies/mL, or a period in which the HIV-1 RNA level in the blood or plasma of an HIV infected human which has been maintained for a period of time at a concentration of less than 40 copies of HIV-1 RNA per mL briefly, transitorily, or temporarily rises to a concentration of greater than 40 copies/mL, such as from 40 to 2,000 copies/mL. Transient, transitory, or temporary viremia may constitute a concentration of greater than 50 copies/mL after repeated testing of an "undetectable" HIV viral load of below 50 copies/mL for a designated period, such as one month, three months, six months, nine months, or one year. It may also constitute a concentration of greater than 50 copies/mL after repeated testing of an "undetectable" HIV viral load of below 50 copies/mL following a specified number or series of tested concentrations of less than 50 copies of HIV-1 RNA per mL, as determined by a health care provider. In separate embodiments the number of consecutive tested concentrations of less than 50 copies may be 1, 2, 3, 4, 5, 6, 7, 8, 9, 10, 11, 12, 13, 14, 15, 16, 17, 18, 19, 20, 21, 22, 23, 24, 24, 25, 26, 27, 28, 29, or 30 and may be for tests conducted, for instance, daily, weekly, biweekly, monthly, bimonthly, quarterly (every 3 months), biannually (twice per year), or annually (once per year).

The terms "virologic suppression" and "virologically suppressed" refer to a response to treatment in which the measurable level of viremia in a virally infected human is maintained at or below a desired level for a specified human or antiviral treatment or regimen. An example of HIV virologic suppression in an HIV-infected human may be the maintenance in the human of a measurable HIV viral load of less than 200 copies of HIV-1 RNA per mL of blood or plasma. Other examples of virologic suppression would be the maintenance in the human of a viral load of less than 100 copies/mL, less than 50 copies/ml, less than 40 copies/mL, less than 30 copies/mL, and less than 20 copies/mL.

The terms "latent HIV reservoir", "HIV latent reservoir", "HIV reservoir", "latent reservoir", and "latent HIV infection" refer to a condition in which resting CD4+ T lymphocytes or other cells are infected with HIV but are not actively producing HIV. The presently inactive HIV infected cells are referred to as "latently infected cells". Antiretroviral therapy (ART) can reduce the level of HIV in the blood to an undetectable level, while latent reservoirs of HIV continue to survive. When a latently infected cell is reactivated, the cell begins to produce HIV (HIV replication).

The term "regimen" refers to a systematic schedule of administering pharmaceutically effective agents to a patient in need thereof, such as a human in need thereof, to reach a therapeutic objective.

The terms "modulation", "modulating" and "modulator" refer to the actions of an agent to agonize (activate or enhance) or antagonize (inhibit or diminish) the function of a biological target. Agonists or enhancers include those modulators which increase the activity of TLR3, TLR4, TLR7, or TLR9 receptors. Within each method, combination, kit, use, composition, and regimen described herein utilizing or containing a TLR7 modulator or TLR7 modulating compound there is a separate embodiment in which the TLR7 modulator or TLR7 modulating compound is an agonist of TLR7. TLR7 agonism may be determined by the PBMC assay protocol in U.S. Pat. No. 8,367,670, the contents of which are incorporated herein by reference, as well as in Bioorg. Med. Chem. Lett. 16, 4559 (2006). Specifically, cryo-preserved PBMCs are thawed and seeded 96 well plates with 750,000 cells/well in 190 fJ. Liwell cell media. The PBMCs are then incubated for 1 hour at 37° C. at 5% CO2. Then, the compounds to be tested are added in 10 f.LL cell 55 media at 8 point, half-log dilution titration. The plates are incubated at 37° C. and 5% CO2 for 24 hours and then spinned at 1200 rpm for 10 min, which is followed by collection of the supernatant and storing it at −80° C. Cytokine secretion is assayed with Luminex and Upstate multi-plex kits, using a Luminex analysis instrument. The IFN-a MEC value for a compound is the lowest concentration at which the compound stimulates IFN-a production at least 3-fold over the background as determined using the assay method above. Compounds providing values (f.IM) in the range of >0.03 f.LM or =0.03 f.LM are considered TLR7 agonist compounds.

The term "HIV antibody" refers to both non-neutralizing HIV antibodies and neutralizing HIV antibodies, including broadly neutralizing HIV antibodies. The terms "broadly neutralizing HIV-1 antibody" and "broadly neutralizing HIV-1 antibody" (bNAb) refer to neutralizing antibodies which neutralize multiple HIV-1 viral strains.

The acronyms "IL" and "IL-" refer to "interleukin", such as the interleukins

The term "nucleoside sparing", "nucleotide sparing", and "nuc-sparing" refers to an antiretroviral combination, regimen, formulation, or therapy that does not utilize nucleoside or nucleotide pharmaceutical agents, such as nucleoside or nucleotide reverse transcriptase inhibitors (NRTIs)

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes without limitation pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The terms "mL" and "ml" refer to milliliter.

The terms "antiviral agent", "antiretroviral agent", "antiretroviral compound" refer to a compounds or agent used to treat an HIV infection in a human.

The terms "antiviral agent" and "antivirals" as used herein is intended to mean an agent that is effective to inhibit the formation and/or replication of a virus in a human, including but not limited to agents that interfere with either host or viral mechanisms necessary for the formation and/or replication of a virus in a human. The terms "antiviral agent" and "antivirals" include, for example, an HIV integrase catalytic site inhibitor selected from the group consisting: raltegravir (ISENTRESS®; Merck); elvitegravir (Gilead); soltegravir (GSK; ViiV); GSK 1265744 (GSK744) (GSK; ViiV) and dolutegravir; an HIV nucleoside reverse transcriptase inhibitor selected from the group consisting of: abacavir (ZIAGEN®; GSK); didanosine (VIDEX®; BMS); tenofovir disoproxil fumarate (VIREAD®; Gilead); tenofovir alafenamide (TAF); emtricitabine (EMTRIVA®; Gilead); lamivudine (EPIVIR®; GSK/Shire); stavudine (ZERIT®; BMS); zidovudine (RETROVIR®; GSK); abacavir, elvucitabine (Achillion); CMX-157 (Chimerix), and festinavir (Oncolys); an HIV non-nucleoside reverse transcriptase inhibitor selected from the group consisting of: nevirapine (VIRAMUNE®; BI); efavirenz (SUSTIVA®; BMS); etravirine (INTELENCE®; J&J); rilpivirine (TMC278, R278474; J&J); fosdevirine (GSK/ViiV); MK-1439 (Merck), and lersivirine (Pfizer ViiV); an HIV protease inhibitor selected from the group consisting of: atazanavir (REYATAZ®; BMS); darunavir (PREZISTA®; J&J); indinavir (CRIXIVAN®; Merck); lopinavir (KELETRA®; Abbott); nelfinavir (VIRACEPT®; Pfizer); saquinavir (INVIRASE®; Hoffmann-LaRoche); tipranavir (APTIVUS®; BI); ritonavir (NORVIR®; Abbott); and fosamprenavir (LEXIVA®; GSK-Nertex); an HIV entry inhibitor selected from: maraviroc (SELZENTRY®; Pfizer); enfuvirtide (FUZEON®; Trimeris); and BMS-663068 (BMS); and an HIV maturation inhibitor selected from: bevirimat (Myriad Genetics). A boosting agent, such as cobicistat or ritonavir, is included within the terms "antiviral agent" and "antivirals" when used in combination with one or more of the antiviral agents described herein.

The terms "effective amount", "pharmaceutically effective amount", and "therapeutically effective amount" refer to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts. A pharmaceutically effective amount includes amounts of an agent which are effective when combined with other agents.

The terms "composition", "pharmaceutical composition", "formulation", and "pharmaceutical formulation" refer to a composition comprising a pharmaceutically effective amount of a pharmaceutically active agent and a pharmaceutically acceptable carrier or excipient.

The terms "kit" and "pharmaceutical kit" refer to a commercial kit or package comprising, in one or more suitable containers, one or more pharmaceutical compositions and instructions for their use. Such kits may also be referred to by the terms "package" or "pharmaceutical package".

"Alkyl" is a saturated or unsaturated hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ haloalkyl). In one embodiment the haloalkyl group has from 1 to 3 carbon atoms (i.e. $C_1$-$C_3$ haloalkyl) Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethylene (—$CH(CH_3)$—), 1,2-ethylene (—$CH_2CH_2$—), 1,1-propylene (—$CH(CH_2CH_3)$—), 1,2-propylene (—$CH_2CH(CH_3)$—), 1,3-propylene (—$CH_2CH_2CH_2$—), 1,4-butylene (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Aminoalkyl" refers to an acyclic alkyl radical in which one of the hydrogen atoms bonded to a carbon atom, typically a terminal or sp3 carbon atom, is replaced with an amino radical.

"Amidoalkyl" refers to an acyclic alkyl radical in which one of the hydrogen atoms bonded to a carbon atom, typically a terminal or sp3 carbon atom, is replaced with a —$NR^aCOR^b$ group where $R^a$ is hydrogen or alkyl and $R^b$ is alkyl, substituted alkyl, aryl, or substituted aryl as defined herein, e.g., —$(CH_2)_2$—NHC(O)$CH_3$, —$(CH_2)_3$—NH—C(O)—$CH_3$, and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical.

Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp3 carbon atom, but also an sp2 carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp3 carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

"Halogen" refers to F, Cl, Br, or I.

As used herein, the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as $-CF_3$. As used herein, the term "fluoroalkyl" refers to a branched or straight alkyl group substituted with one or more fluorine atoms. Examples include $C_1$-$C_3$ fluoroalkyl groups such as fluoromethyl, 2-fluoroethyl, 3-fluoropropyl, 2-fluoropropyl, difluoromethyl, 2,2-difluoroethyl, 2,2-difluoropropyl, trifluoromethyl, 2,2,2,-trifluoroethyl, and 2,2,2-trifluoropropyl.

As used herein, the term "haloalkoxy" refers to a group $-OR^a$, where $R^a$ is a haloalkyl group as herein defined. As non-limiting examples, haloalkoxy groups include $-O(CH_2)F$, $-O(CH)F_2$, and $-OCF_3$.

The term "substituted" in reference to alkyl, aryl, arylalkyl, carbocyclyl, heterocyclyl, and other groups used herein, for example, "substituted alkyl", "substituted aryl", "substituted arylalkyl", "substituted heterocyclyl", and "substituted carbocyclyl" means a group, alkyl, alkylene, aryl, arylalkyl, heterocyclyl, carbocyclyl respectively, in which one or more hydrogen atoms are each independently replaced with a non-hydrogen substituent. Typical substituents include, but are not limited to, $-X$, $-R$, $-O-$, $=O$, $-OR$, $-SR$, $-S-$, $-NR_2$, $-N(+)R_3$, $=NR$, $-CX_3$, $-CRX_2$, $-CR_2X$, $-CN$, $-OCN$, $-SCN$, $-N=C=O$, $-NCS$, $-NO$, $-NO_2$, $=N_2$, $-N_3$, $-NRC(=O)R$, $-NRC(=O)OR$, $-NRC(=O)NRR$, $-C(=O)NRR$, $-C(=O)OR$, $-OC(=O)NRR$, $-OC(=O)OR$, $-C(=O)R$, $-S(=O)_2OR$, $-S(=O)_2R$, $-OS(=O)_2OR$, $-S(=O)_2NR$, $-S(=O)R$, $-NRS(=O)_2R$, $-NRS(=O)_2NRR$, $-NRS(=O)_2OR$, $-OP(=O)(OR)_2$, $-P(=O)(OR)_2$, $-P(O)(OR)(O)R$, $-C(=O)R$, $-C(=S)$ R, $-C(=O)OR$, $-C(=S)OR$, $-C(=O)SR$, $-C(=S)SR$, $-C(=O)NRR$, $-C(=S)NRR$, $-C(=NR)NRR$, $-NRC(=NR)NRR$, where each X is independently a halogen: F, Cl, Br, or I; and each R is independently H, alkyl, cycloalkyl, aryl, arylalkyl, a heterocycle, or a protecting group or prodrug moiety. Divalent groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., $-OCH_3$, etc.), an amine (e.g., $-NHCH_3$, $-N(CH_3)_2$, and the like), or a thioalkyl group (e.g., $-SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., $-CH_2CH_2-O-CH_3$, etc.), an alkyl amine (e.g., $-CH_2NHCH_3$, $-CH_2N(CH_3)_2$, and the like), or a thioalkyl ether (e.g., $-CH_2-S-CH_3$). If a terminal carbon atom of the alkyl group is replaced with a heteroatom (e.g., O, N, or S), the resulting heteroalkyl groups are, respectively, a hydroxyalkyl group (e.g., $-CH_2CH_2-OH$), an aminoalkyl group (e.g., $-CH_2NH_2$), or an alkyl thiol group (e.g., $-CH_2CH_2-SH$). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. 0, N, P or S). The terms "heterocycle" or "heterocyclyl" includes saturated rings, partially unsaturated rings, and aromatic rings (i.e., heteroaromatic rings). Heterocycles includes aromatic and non-aromatic mono-, bi-, and poly-cyclic rings, whether fused, bridged, or spiro. As used herein, the term "heterocycle" encompasses, but is not limited to "heteroaryl."

Substituted heterocyclyls include, for example, heterocyclic rings substituted with any of the substituents disclosed herein including carbonyl groups. A non-limiting example of a carbonyl substituted heterocyclyl is:

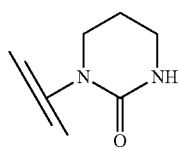

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, azetidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

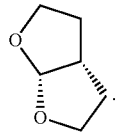

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, and the like, 6-membered sulfur, oxygen, and/or nitrogen containing heterocycles such as piperidinylmethyl, piperazinylmethyl, morpholinylmethyl, pyridinylmethyl, pyridinylmethyl, pyrimidylmethyl, pyrazinylmethyl, and the like.

"Heterocyclylalkenyl" refers to an acyclic alkenyl radical in which one of the hydrogen atoms bonded to a carbon atom, typically a terminal or sp3 carbon atom, but also a sp2 carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 1 to 6 carbon atoms and the heterocyclyl moiety comprises 1 to 14 carbon atoms.

"Heterocyclylalkynyl" refers to an acyclic alkynyl radical in which one of the hydrogen atoms bonded to a carbon atom, typically a terminal or sp3 carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 2 to 20 carbon atoms, e.g., the alkynyl portion of the heterocyclyl alkynyl group comprises 1 to 6 carbon atoms and the heterocyclyl moiety comprises 1 to 14 carbon atoms.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, and the like. Heteroaryl also includes monovalent aromatic heterocyclyl comprising an aryl moiety and a heteroaryl group. Non limiting examples of these heteroaryls are:

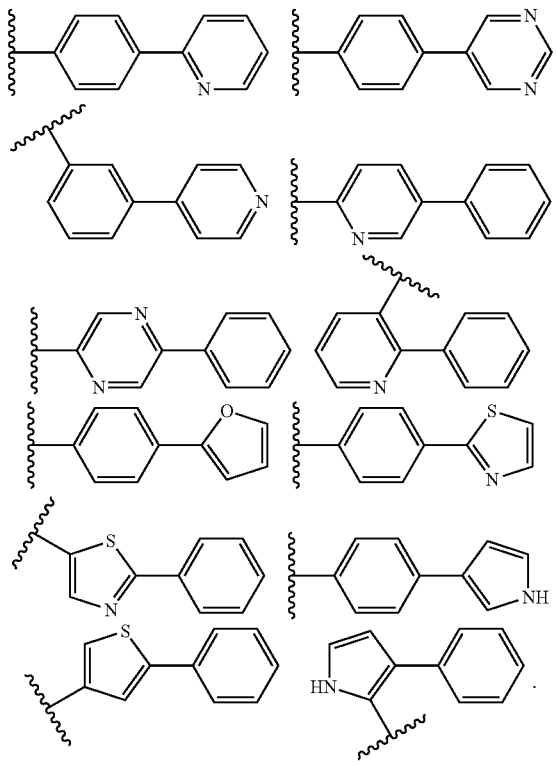

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Carbocycles includes aromatic and non-aromatic mono-, bi-, and poly-cyclic rings, whether fused, bridged, or spiro. Non-limiting examples of monocyclic carbocycles include the cycloalkyls group such as cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl or aryl groups such as phenyl, and the like. Thus, "carbocycle," as used herein, encompasses but is not limited to "aryl", "phenyl" and "biphenyl."

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene. Thus, "carbocyclylene," as used herein, encompasses but is not limited to "arylene."

"Carbocyclylalkyl" refers to an acyclic alkyl radical in which one of the hydrogen atoms bonded to a carbon atom, typically a terminal or sp3 carbon atom, is replaced with a carbocyclyl radical as defined above. Typical carbocyclylalkyl groups include, but are not limited to the arylalkyl groups such as benzyl, 2-phenylethan-1-yl, naphthylmethyl, 2-naphthylethan-1-yl, naphthobenzyl, 2-naphthophenylethan-1-yl or the cycloalkylalkyl groups such as cyclopropylmethyl, cyclobutylethyl, cyclohexylmethyl and the like. The arylalkyl group can comprise 6 to 20 carbon atoms, e.g., the alkyl moiety is 1 to 6 carbon atoms and the aryl moiety is 6 to 14 carbon atoms. The cycloalkylalkyl group can comprise 4 to 20 carbon atoms, e.g., the alkyl moiety is 1 to 6 carbon atoms and the cycloalkyl group is 3 to 14 carbon atoms.

"Arylheteroalkyl" refers to a heteroalkyl as defined herein, in which a hydrogen atom, which may be attached either to a carbon atom or a heteroatom, has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, alkylene-aryl, -alkylene-NH-aryl, -alkylene-NH-alkylene-aryl, -alkylene-S-aryl, -alkylene-S-alkylene-aryl, and the like. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-thiazolyl, —$CH_2$-isoxazolyl, —$CH_2$-pyrazolyl, —$CH_2$-isothiazolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, and the like.

The term "optionally substituted" in reference to a particular moiety of the compound of the Formulae of the invention, for example an optionally substituted aryl group, refers to a moiety having 0, 1, or more substituents.

As will be appreciated by those skilled in the art, the compounds of the present invention are capable of existing in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention also includes tautomeric forms, namely, tautomeric "enols" as herein described. In addition, the scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. Esters can also include esters—as described above—of "tautomeric enols", e.g. as shown below:

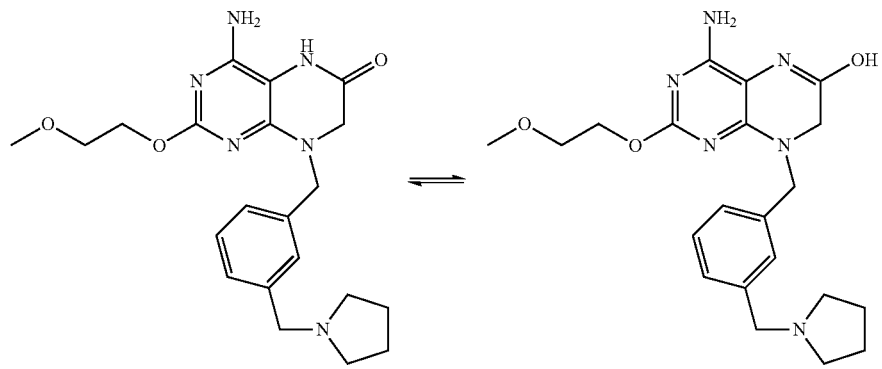 [SMILES: COCCOc1nc(N)c2c(n1)N(Cc1cccc(CN3CCCC3)c1)CC(=O)N2 ; COCCOc1nc(N)c2c(n1)N(Cc1cccc(CN3CCCC3)c1)CC(O)=N2]

The term "ester thereof" includes but is not limited to pharmaceutically acceptable esters thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of the formulas herein should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. The scope of the present invention also includes tautomeric forms, namely, tautomeric "enols" as herein described. In addition, the scope of the present invention includes prodrug forms of the compound herein described.

A compound of the formulas herein and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of the formulas herein and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises use of all amorphous forms of the compounds described herein and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner. The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartarate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Any formula or structure given herein, including the compounds of Formula II and the specific examples of compounds herein, and pharmaceutically acceptable salts thereof, is also intended to represent unlabeled forms as well as isotopically labeled forms of the compounds, or salts thereof. Isotopically labeled compounds or salts thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium) $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds or salts thereof of the present disclosure, for example those into which radioactive isotopes such as $^3$H, $^{13}$C and $^{14}$C are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans).

The disclosure also includes the compound of formula I and pharmaceutically acceptable salts thereof, in which from 1 to n hydrogens attached to a carbon atom is/are replaced by deuterium, in which n is the number of hydrogens in the molecule. Such compounds may exhibit increased resistance to metabolism and are thus useful for increasing the half-life of the compounds herein, or pharmaceutically acceptable salts thereof when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compounds disclosed herein and pharmaceutically acceptable salts thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various generic and subgeneric groups of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 10 mg/kg body weight per day, typically from about 0.001 to about 1 mg/kg body weight per day, more typically from about 0.01 to about 1 mg/kg body weight per day, even more typically from about 0.05 to about 0.5 mg/kg body weight per day. For example, the daily candidate dose for an adult human of approximately 70 kg body weight will range from about 0.05 mg to about 100 mg, or between about 0.1 mg and about 25 mg, or between about 0.4 mg and about 6 mg, and may take the form of single or multiple doses.

In yet another embodiment, the present application discloses pharmaceutical compositions comprising a compound of Formula I or II or a pharmaceutically acceptable salt thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention are used in combination with an additional active therapeutic ingredient or agent.

In one embodiment, combinations of one or more of the TLR7 modulating compounds described herein and additional active agents may be selected to treat patients with an HIV viral infection.

Combinations of the compounds are typically selected based on the condition to be treated, cross-reactivities of ingredients and pharmaco-properties of the combination. For example, when treating an infection (e.g., HIV), the compositions of the invention are combined with other active agents (such as those described herein).

Suitable active agents or ingredients which can be combined with the TLR7 modulating compounds described herein, or a salt thereof, can include one or more compounds selected from the group consisting of TLR7 agonists selected from the group consisting of ANA-975, SM-360320, and mixtures thereof.

In addition, the compounds of the invention may be employed in combination with other therapeutic agents for the treatment or prophylaxis of AIDS and/or one or more other diseases present in a human subject suffering from AIDS (e.g., bacterial and/or fungal infections, other viral infections such as hepatitis B or hepatitis C, or cancers such as Kaposi's sarcoma). The additional therapeutic agent(s) may be coformulated with one or more salts of the invention (e.g., coformulated in a tablet).

Examples of such additional therapeutic agents include agents that are effective for the treatment or prophylaxis of viral, parasitic or bacterial infections, or associated conditions, or for treatment of tumors or related conditions, include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-beta-arabinosyl)-5-iodocytidine (FIAC), tetrahydro-imidazo(4,5, 1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate; cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI); acyclic nucleosides such as acyclovir, penciclovir, famciclovir, ganciclovir, HPMPC, PMEA, PMEG, PMPA, PMPDAP, FPMPA, HPMPA, HPMPDAP, (2R,5R)-9→tetrahydro-5-(phosphonomethoxy)-2-furanyladenine, (2R,5R)-1→tetrahydro-5-(phosphonomethoxy)-2-furanylthymine; other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate); antibacterial agents including bactericidal fluoroquinolones (ciprofloxacin, pefloxacin and the like); aminoglycoside bactericidal antibiotics (streptomycin, gentamicin, amicacin and the like); beta-lactamase inhibitors (cephalosporins, penicillins and the like); other antibacterials including tetracycline, isoniazid, rifampin, cefoperazone, clarithromycin and azithromycin, antiparasitic or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin; renal excretion inhibitors such as probenicid; nucleoside transport inhibitors such as dipyridamole, dilazep and nitrobenzylthioinosine, immunomodulators such as FK506, cyclosporin A, thymosin α-1; cytokines including TNF and TGF-β; interferons including IFN-α, IFN-β, and IFN-γ; interleukins including various interleukins, macrophage/granulocyte colony stimulating factors including GM-CSF, GCSF, M-CSF, cytokine antagonists including anti-TNF antibodies, anti-interleukin antibodies, soluble interleukin receptors, protein kinase C inhibitors and the like.

Examples of suitable active therapeutic agents or ingredients which can be combined with the compounds of the invention, and which have activity against HIV, include:

1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, mozenavir (DMP-450), JE-2147 (AG1776), AG1859, DG35, L-756423, R00334649, KNI-272, DPC-681, DPC-684, and GW640385X, DG17, PPL-100;

2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, MK-1439;

3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (−FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine;

4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, CMX-157, and TAF;

5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, GSK1265744 (GSK744), and dolutegravir;

6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences), and WO 2012/145729, each of which is incorporated by references in its entirety herein;

7) a gp41 inhibitor, e.g., enfuvirtide, sifuvirtide, FB006M, TRI-1144, SPC3, DES6, Locus gp41, CovX, and REP 9;

8) a CXCR4 inhibitor, e.g., AMD-070;

9) an entry inhibitor, e.g., SP01A, TNX-355, 9) a gp120 inhibitor, e.g., BMS-488043 and BlockAide/CR;

10) a G6PD and NADH-oxidase inhibitor, e.g., immunitin;

11) a CCR5 inhibitor, e.g., aplaviroc, vicriviroc, INCB9471, PRO-140, INCB15050, PF-232798, CCR5mAb004, and maraviroc;

12) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon;

13) ribavirin analogs, e.g., rebetol, copegus, levovirin, VX-497, and viramidine (taribavirin);

14) NS5a inhibitors, e.g., BMS-790052, GS-5885, GSK62336805, ACH-2928 AZD2836, AZD7295, BMS-790052, BMS-824393, GS-5885, PPM 301, PPI-461, A-831 and A-689;

15) NS5b polymerase inhibitors, e.g., IDX-375, NM-283, valopicitabine, R1626, PSI-6130 (R1656), HIV-796, BILB 1941, MK-0608, NM-107, R7128, VCH-759, PF-868554, GSK625433, setrobuvir (ANA598), sofosbuvir, and XTL-2125;

16) NS3 protease inhibitors, e.g., SCH-503034 (SCH-7), VX-950 (Telaprevir), ITMN-191, and BILN-2065;

17) alpha-glucosidase 1 inhibitors, e.g., MX-3253 (celgosivir) and UT-231B;

18) hepatoprotectants, e.g., IDN-6556, ME 3738, MitoQ, and LB-84451;

19) non-nucleoside inhibitors of HIV, e.g., benzimidazole derivatives, benzo-1,2,4-thiadiazine derivatives, and phenylalanine derivatives;

20) other drugs for treating HIV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811;

21) pharmacokinetic enhancers, e.g., BAS-100 and SPI452;

22) RNAse H inhibitors, e.g., ODN-93 and ODN-112;

23) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Additional agents for use in the methods herein include monoclonal antibodies that target, and small molecule inhibitors of, Arginase-1, adenosine deaminase, adenosine receptors, IL-4, IL-6 (such as siltuximab/Sylvant™), IL-10, IL-12, IL-18, IL-21, C-Kit, stem cell factor (SCF), granulocyte-macrophage colony-stimulating factor (GM-CSF), transforming growth factor beta (TGF-β), vascular endothelial growth factor (VEGF), histone methyltransferases (HMT), glycogen synthase kinase 3 (GSK3), and CD32b.

Also useful are farnesyltransferase inhibitors, such as Lonafarnib (SCH66336, SARASAR™), Chaetomellic acid A, FPT Inhibitors I, II, and III, FTase Inhibitors I (CAS 149759-96-6) and II (CAS156707-43-6), FTI-276 trifluoroacetate salt, FTI-277 trifluoroacetate salt, FTI-2153, GGTI-297, Gingerol, Gliotoxin, L-744,832 Dihydrochloride, Manumycin A, Tipifarnib (R115777, Zarnestra), α-hydroxy Farnesyl Phosphonic Acid, BZA-5B, Manumycin A, hydroxyfarnesylphosphonic acid, butanoic acid, 2-[[(2S)-2-[(2S,3S)-2-[[(2R)-2-amino-3-mercaptopropyl]amino]-3-methylpentyl]oxy-1-oxo-3-phenylpropyl]amino]-4-(methylsulfonyl)-,1-methylethyl ester, (2S)-(9cl), BMS-214662, BMS-316810, dichlorobenzoprim (2,4-diamino-5-(4-(3,4-dichlorobenzylamino)-3-nitrophenyl)-6-ethylpyrimidine), B-581, B-956 (N-(8(R)-amino-2(S)-benzyl-5(S)-isopropyl-9-sulfanyl-3(Z),6(E)-nonadienoyl)-L-methionine), OSI-754, perillyl alcohol (1-cyclohexene-1-methanol, 4-(1-methylethenyl)-, RPR-114334, Sch-48755, Sch-226374, (7,8-dichloro-5H-dibenzo(b,e)(1,4)diazepin-11-yl)-pyridin-3-ylmethylamine, J-104126, L-639749, L-731734 (pentanamide, 2-((2-((2-amino-3-mercaptopropyl)amino)-3-methylpentyl)amino)-3-methyl-N-(tetrahydro-2-oxo-3-furanyl)-, (3S-(3R*(2R*(2R*(S*),3S*),3R*)))—), L-744832 (butanoic acid, 2-((2-((2-((2-amino-3-mercaptopropyl)amino)-3-methylpentyl)oxy)-1-oxo-3-phenylpropyl)amino)-4-(methylsulfonyl)-, 1-methylethyl ester, (2S-(1(R*(R*)),2R*(S*),3R*))—), L-745631 (1-piperazinepropanethiol, β-amino-2-(2-methoxyethyl)-4-(1-naphthalenylcarbonyl)-, N-acetyl-N-naphthylmethyl-2(S)-((1-(4-cyanobenzyl)-1H-imidazol-5-yl)acetyl)amino-3(S)-methylpentamine, (2alpha)-2-hydroxy-24,25-dihydroxylanost-8-en-3-one, UCF-1-C(2,4-decadienamide, N-(5-hydroxy-5-(74(2-hydroxy-5-oxo-1-cyclopenten-1-yl)amino-oxo-1,3,5-heptatrienyl)-2-oxo-7-oxabicyclo(4.1.0)hept-3-en-3-yl)-2,4,6-trimethyl-, (1S-(1alpha,3 (2E,4E,6S*),5 alpha, 5(1E,3E,5E), 6 alpha))-), UCF-116-B, ARGLABIN (3H-oxireno[8,8a]azuleno[4,5-b]furan-8(4aH)-one, and 5,6,6a,7,9a,9b-hexahydro-1,4a-dimethyl-7-methylene-, (3aR,4aS,6aS,9aS,9bR)—).

Also useful in the methods and combinations herein are inhibitors of 26S proteasome, such as Lactacystin, Bortezomib (PS-341), ritonavir, MG-132 (Z-Leu-Leu-Leu-CHO), MG-115 (Z-LL-Nva-CHO), Proteasome Inhibitor I (Z-Ile-Glu(OtBu)-Ala-Leu-CHO), and Proteasome Inhibitor II (Z-LLF-CHO).

Useful inhibitors of E3 ubiquitin ligase include pro-TAME, RITA (5,5'-(2,5-Furandiyl)bis-2-thiophenemethanol), HLI 373 (5-[[3-Dimethylamino)propyl]amino]-3,10-dimethylpyrimido[4,5-b]quinoline-2,4(3H,10H)-dione dihydrochloride), Nutlin-3 ((±)-4-[4,5-Bis(4-chlorophenyl)-2-(2-isopropoxy-4-methoxy-phenyl)-4,5-dihydro-imidazole-1-carbonyl]-piperazin-2-one), SMER 3 (9H-Indeno[1,2-e][1,2,5]oxadiazolo[3,4-b]pyrazin-9-one), NSC 66811 (2-Methyl-7-[Phenyl(phenylamino)methyl]-8-quinolinol), TAME HCl (N²-[(4-Methylphenyl)sulfonyl]-L-arginine methyl ester hydrochloride), Heclin (N-(4-Acetylphenyl)-3-(5-ethyl-2-furanyl)-2-propenamide), PRT 4165 (2-(3-Pyridinylmethylene)-1H-Indene-1,3(2H)-dione), NAB 2 (N-[(2-Chlorophenyl)methyl]-1-(2,5-dimethylphenyl)-1H-benzimidazole-5-carboxamide), SP 141 (6-Methoxy-1-(1-naphthalenyl)-9H-pyrido[3,4-b]indole), SZL P1-41 (3-(2-Benzothiazolyl)-6-ethyl-7-hydroxy-8-(1-piperidinylmethyl)-4H-1-benzopyran-4-one), PTC 209 (N-(2,6-Dibromo-4-methoxyphenyl)-4-(2-methylimidazo[1,2-a]pyrimidin-3-yl)-2-thiazolamine), SKP C1 (2-[4-Bromo-2-[[4-oxo-3-(3-pyridinylmethyl)-2-thioxo-5-thiazolidinylidene]methyl]phenoxy]acetic acid), A01 ([4-[[4-Chloro-3-(trifluoromethyl)phenyl]sulfonyl]-1-piperazinyl][4-(5-methyl-1H-pyrazol-1-yl)phenyl]methanone), Apcin, Useful agonists of protein kinase C (PKC) include midostaurin (PKC412, CGP41251, 4'-N-benzoyl staurosporine), ruboxistaurin (LY 333531 HCl, (9S)-9-[(Dimethylamino)methyl]-6,7,10,11-tetrahydro-9H,18H-5,21:12,17-dimethenodibenzo[e,k]pyrrolo[3,4-h][1,4,13]oxadiazacyclohexadecine-18,20(19H)-dione hydrochloride), sotrastaurin (AEB071), enzastaurin (LY317615 HCl), sotrastaurin (AEB071), CGP60474, chelerythrine chloride (HY-12048), Fasudil HCl (HY-10341, Go 6983 (HY-13689), and Zoledronic acid (CGP 42446). include phorbol esters, such as PMA, prostratin, and 12-deoxyphorbol 13-phenylacetate (DPP), and non-phorbol ester compounds including bryostatin compounds, including Bryostatin-1, diacylglycerol (DAG) analogs such as LMC03 and LMC07, including DAG lactones, such as HK654, HK434, HK602, and HK204, ingenol derivatives, including ITA, ingenol-3-hexanoate (IngB), and I-3-A, as well as ingol diterpenes, such as 8-methoxyingol 7,12-diacetate 3-phenylacetate, 8-methoxyingol 7,12-diacetate 3-phenylacetate (SJ23B), (5aS,7S,8aR,E)-1,1,4,7,10-pentamethyl-2-(((E)-2-methylbut-2-enoyl)oxy)-9-oxo-1,1a,2,3,6,7,8,9,10,10a-decahydro-5a,8a-epoxycyclopenta[a]cyclopropa [e][10]annulene-6,10a-diyl diacetate, and gnidimacrin.

Again by way of example, the following list discloses exemplary HIV antivirals, with their corresponding U.S. Patent numbers, incorporated by reference with regard to the preparation of such antivirals, which can be combined in the present methods with the TLR7 modulating compounds described herein.

Exemplary HIV Antivirals and Patent Numbers
Examples of HIV antiviral agents useful in the combinations and methods herein include Ziagen (Abacavir sulfate, U.S. Pat. No. 5,034,394); Epzicom (Abacavir sulfate/lamivudine, U.S. Pat. No. 5,034,394); Hepsera (Adefovir dipivoxil, U.S. Pat. No. 4,724,233); Agenerase (Amprenavir, U.S. Pat. No. 5,646,180); Reyataz (Atazanavir sulfate, U.S. Pat. No. 5,849,911); Rescriptor (Delavirdine mesilate, U.S. Pat. No. 5,563,142); Hivid (Dideoxycytidine; Zalcitabine, U.S. Pat. No. 5,028,595); Videx (Dideoxyinosine; Didanosine, U.S. Pat. No. 4,861,759); Sustiva (Efavirenz, U.S. Pat. No. 5,519,021); Emtriva (Emtricitabine, U.S. Pat. No. 6,642,245) Lexiva (Fosamprenavir calcium, U.S. Pat. No. 6,436,989); Virudin; Triapten; Foscavir (Foscarnet sodium, U.S. Pat. No. 6,476,009); Crixivan (Indinavir sulfate, U.S. Pat. No. 5,413,999); Epivir (Lamivudine, U.S. Pat. No. 5,047,407); Combivir (Lamivudine/Zidovudine, U.S. Pat. No. 4,724,232); Aluviran (Lopinavir); Kaletra (Lopinavir/ritonavir, U.S. Pat. No. 5,541,206); Viracept (Nelfinavir mesilate, U.S. Pat. No. 5,484,926); Viramune (Nevirapine, U.S. Pat. No. 5,366,972); Norvir (Ritonavir, U.S. Pat. No. 5,541,206); Invirase; Fortovase (Saquinavir mesilate, U.S. Pat. No. 5,196,438); Zerit (Stavudine, U.S. Pat. No. 4,978,655);
Truvada® (Tenofovir disoproxil fumarate/emtricitabine, U.S. Pat. No. 5,210,085); Viread® (tenofovir disoproxil fumarate)
Complera® (emtricitabine/rilpivirine/tenofovir disoproxil fumarate); Atripla® (efavirenz/emtricitabine/tenofovir disoproxil fumarate); Stribild® (elvitegravir 150 mg/cobicistat 150 mg/emtricitabine 200 mg/tenofovir disoproxil fumarate 300 mg); Aptivus (Tipranavir)
Retrovir (Zidovudine; Azidothymidine, U.S. Pat. No. 4,724,232); and Eviplera® (emtricitabine/rilpivirine/tenofovir disoproxil fumarate).

In yet another embodiment, the present application discloses pharmaceutical compositions comprising a TLR7 modulating compound described herein, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Methods of Treatment

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor. A TLR7 modulating compound may also be referred to as a TLR7 modulating agent, a TLR7 modulator, a compound which modulates TLR7 activity, or the like.

As will be appreciated by those skilled in the art, when treating a viral infection such as HIV, such treatment may be characterized in a variety of ways and measured by a variety of endpoints. The scope of the present invention is intended to encompass all such characterizations.

In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present invention include, among others, detecting a decrease in viral load or antigen in a subject's serum, detection of IFN-gamma-secreting antigen specific T cells, and detection of elevated levels of one or more liver enzymes, such as alanine transferase (ALT) and aspartate transferase (AST). In one embodiment, the detection of IFN-gamma-secreting antigen specific T cells is accomplished using an ELISPOT assay or FACS analysis. Another embodiment includes reducing the viral load associated with HIV infection, including a reduction as measured by PCR testing.

A TLR7 modulating compound as described herein can be administered by any useful route and means, such as by oral or parenteral (e.g., intravenous) administration. Therapeutically effective amounts of a TLR7 modulating compound as described herein are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

The frequency of dosage of a TLR7 modulating compound as described herein will be determined by the needs of the individual patient and can be, for example, once per day or twice, or more times, per day. Administration of a TLR7 modulating compound as described herein continues for as long as necessary to treat the HIV infection. For example, a TLR7 modulating compound as described herein can be administered to a human being infected with HIV for a period of from 20 days to 180 days or, for example, for a period of from 20 days to 90 days or, for example, for a period of from 30 days to 60 days.

Administration can be intermittent, with a period of one or more days during which a patient receives a daily dose of a TLR7 modulating compound as described herein, followed by a period of several or more days during which a patient does not receive a daily dose of a TLR7 modulating compound as described herein. For example, a patient can receive a dose of a TLR7 modulating compound as described herein every other day, or three times per week, once per week (every 7 days), once every other week (every 14 days), once per month, or once every other month. Again by way of example, a patient can receive a dose of a TLR7 modulating compound as described herein each day for a period of from 1 to 14 days, followed by a period of 7 to 30 days during which the patient does not receive a dose of a TLR7 modulating compound as described herein, followed by a subsequent period (e.g., from 1 to 14 days) during which the patient again receives a daily dose of a TLR7 modulating compound as described herein. For other examples, in separate embodiments, a patient can receive an initial single dose of a TLR7 modulating compound as described herein, followed by sequential doses every other day, or three times per week, once per week (every 7 days), once every other week (every 14 days), once per month, or once every other month. Alternating periods of administration of a TLR7 modulating compound as described herein, followed by non-administration of a TLR7 modulating compound as described herein, can be repeated as clinically required to treat the patient.

Each of the TLR7 modulating compounds of Formula II represented below by Examples 1 through 118, and pharmaceutically acceptable salts thereof, may be prepared by methods disclosed in WO 2010/077613 A1 (Desai et al.), which is incorporated by reference herein in its entirety, and by other methods known in the art.

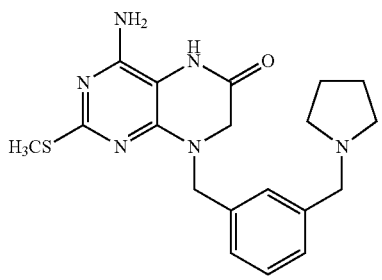

Example 1

8-amino-6-(methylthio)-4-(3-(pyrrolidin-1-ylmethyl)benzyl)-3,4-dihydropyrido[2,3-b]pyrazin-2(1H)-one -continued Example 2

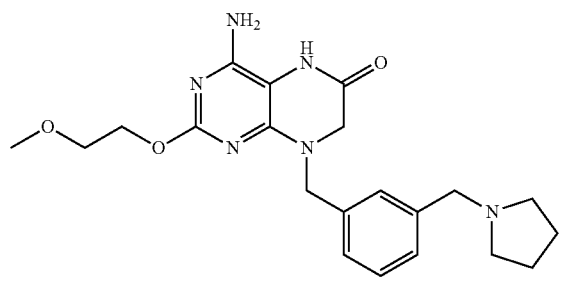

4-amino-2-(2-methoxyethoxy)-8-(3-(pyrrolidin-1-ylmethyl)benzyl)-7,8-dihydropteridin-6(5H)-one Example 3

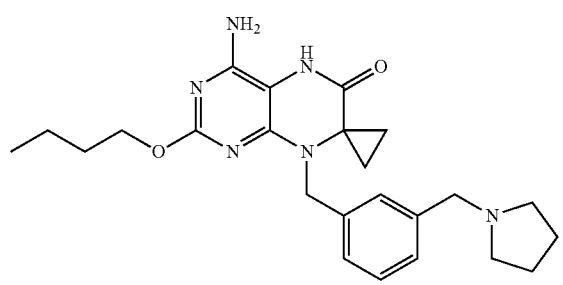

4-Amino-2-n-buyoxy-7-(1''', 2''''-ethylidene)-8-[3'-(pyrrolidin-1''-ylmethyl)-benzyl]-5,6,7,8-tetrahydropteridine-6-one Example 4

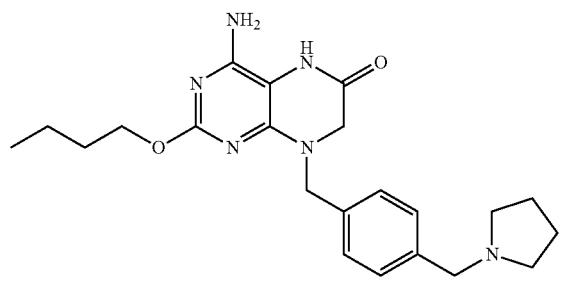

4-amino-2-n-butoxy-8-[4'-(pyrrolidin-1''-ylmethyl)-benzyl]-5,6,7,8-tetrahydropteridin-6-one Example 5

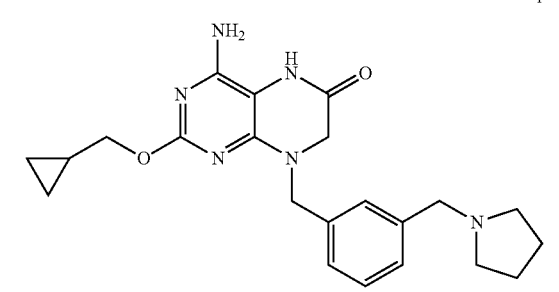

4-amino-2-{(cyclopropyl)methoxy}-8-[3'-(pyrrolidin-1''-ylmethyl)-benzyl]-5,6,7,8-tetrahydropteridin-6-one Example 6

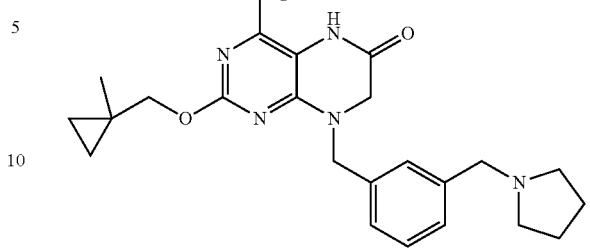

4-amino-2-{(1''''-methylcycloprop-1''''-yl)methoxy}-8-[3'-(pyrrolidin-1''-ylmethyl)-benzyl]-5,6,7,8-tetrahydropteridin-6-one Example 7

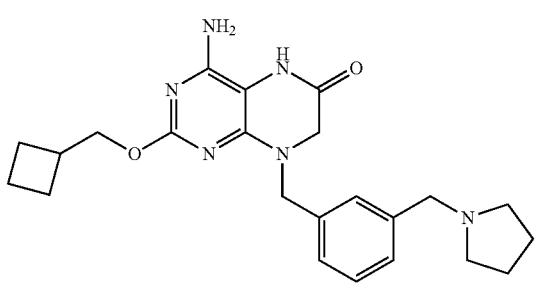

4-amino-2-{(cyclobutyl)methoxy}-8-[3'-(pyrrolidin-1''-ylmethyl)-benzyl]-5,6,7,8-tetrahydropteridin-6-one Example 8

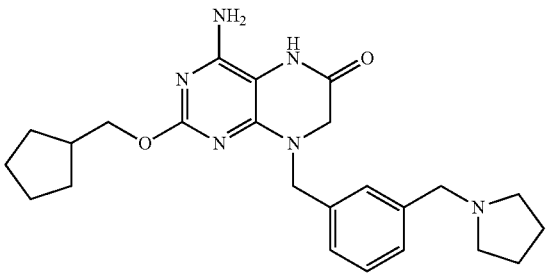

4-amino-2-{(cyclopentyl)methoxy}-8-[3'-(pyrrolidin-1''-ylmethyl)-benzyl]-5,6,7,8-tetrahydropteridin-6-one Example 9

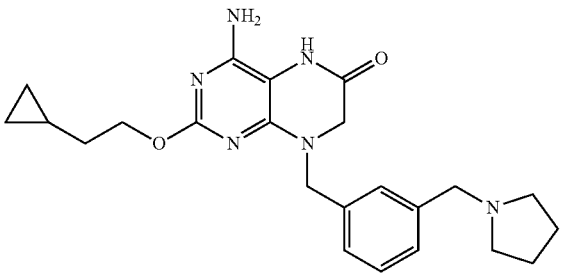

4-amino-2-{2''''-(cyclopropyl)ethoxy}-8-[3'-(pyrrolidin-1''-ylmethyl)-benzyl]-5,6,7,8-tetrahydropteridin-6-one Example 10

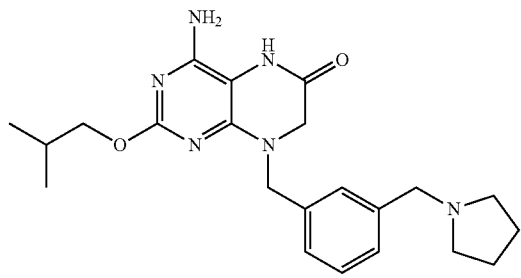

4-amino-2-isobutoxy-8-(3-
(pyrrolidin-1-ylmethyl)-benzyl)-7,8-
dihydropteridin-6(5H)-one Example 11

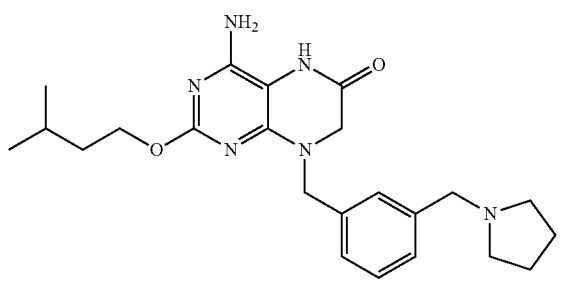

4-amino-2-isopentyloxy)-8-
(3-(pyrrolidin-1-ylmethyl)-benzyl)-7,8-
dihydropteridin-6(5H)-one Example 12

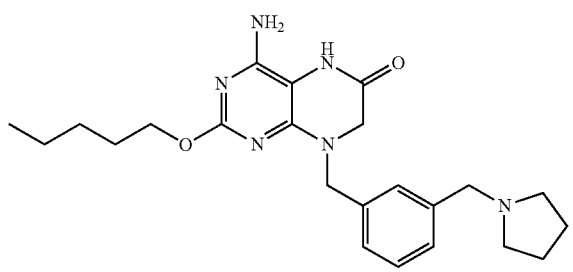

4-amino-2-(pentyloxy)-8-(3-
(pyrrolidin-1-ylmethyl)-benzyl)-7,8-
dihydropteridin-6(5H)-one Example 13

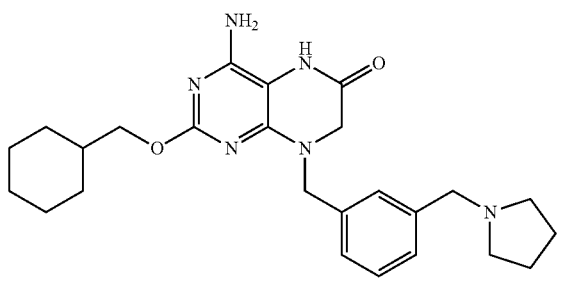

4-amino-2-
(cyclohexylmethoxy)-8-(3-(pyrrolidin-1-
ylmethyl)benzyl)-7,8-dihydropteridin-
6(5H)-one Example 14

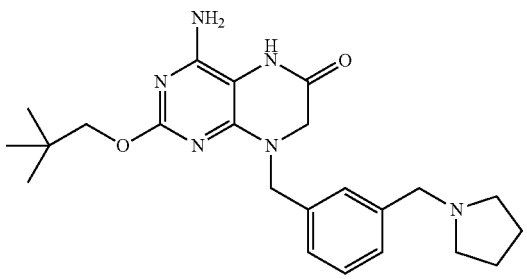

4-amino-2-(neopentyloxy)-8-
(3-(pyrrolidin-1-ylmethyl)benzyl)-7,8-
dihydropteridin-6(5H)-one Example 15

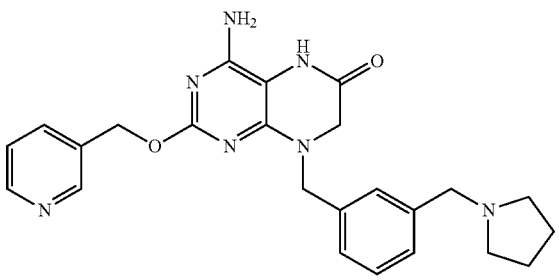

4-amino-2-(benzyloxy)-8-(3-
(pyrrolidin-1-ylmethyl)benzyl)-7,8-
dihydropteridin-6(5H)-one Example 16

4-amino-2-(pyridin-3-
ylmethoxy)-8-(3-(pyrrolidin-1-
ylmethyl)benzyl)-7,8-dihydropteridin-
6(5H)-one Example 17

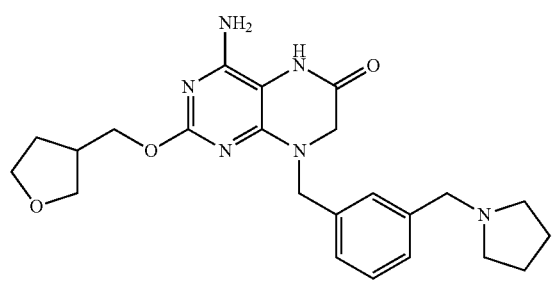

4-amino-8-(3-pyrrolidin-1-
ylmethyl)benzyl)-2-((tetrahydrofuran-3-
yl)methoxy)-7,8-dihydropteridin-6(5H)-one Example 18

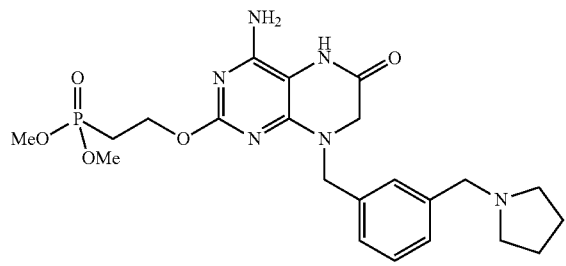

dimethyl (2-((4-amino-6-oxo-
8-(3-(pyrrolidin-1-ylmethyl)benzyl)-
5,6,7,8-tetrahydropteridin-2-
yl)oxy)ethyl)phosphonate Example 19

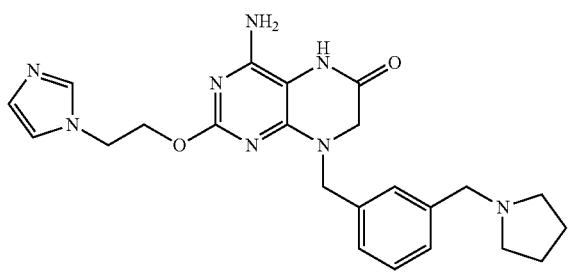

2-(2-(1H-imidazol-1-
yl)ethoxy)-4-amino-8-(3-(pyrrolidin-1-
ylmethyl)benzyl)-7,8-dihydropteridin-
6(5H)-one Example 20

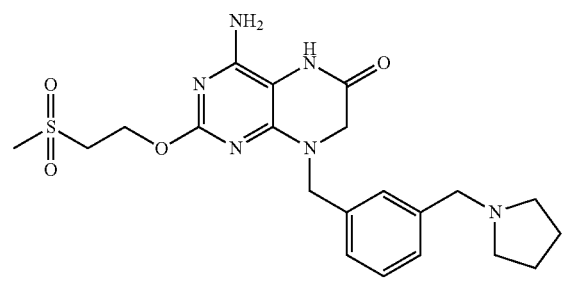

4-amino-2-(2-
(methylsulfonyl)ethoxy)-8-(3-(pyrrolidin-1-
ylmethyl)benzyl)-7,8-dihydropteridin-
6(5H)-one Example 21

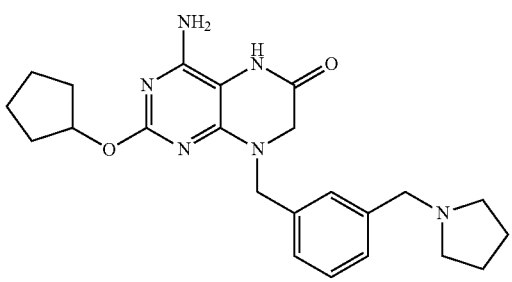

4-amino-2-(cyclopentyloxy)-
8-(3-(pyrrolidin-1-ylmethyl)benzyl)-7,8-
dihydropteridin-6(5H)-one Example 22

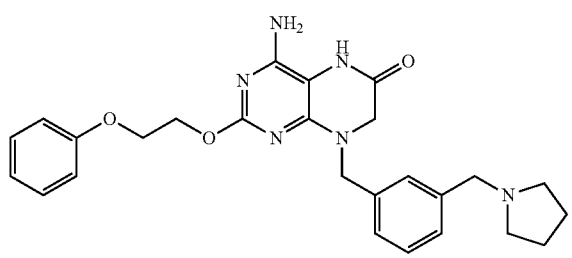

4-amino-2-(2-(2-
oxopyrrolidin-1-yl)ethoxy)-8-(3-(pyrrolidin-
1-ylmethyl)benzyl)-7,8-dihydropteridin-
6(5H)-one Example 23

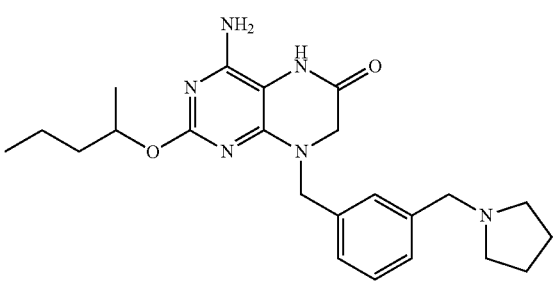

4-amino-2-(2-
phenoxyethoxy)-8-(3-(pyrrolidin-1-
ylmethyl)benzyl)-7,8-dihydropteridin-
6(5H)-one Example 24

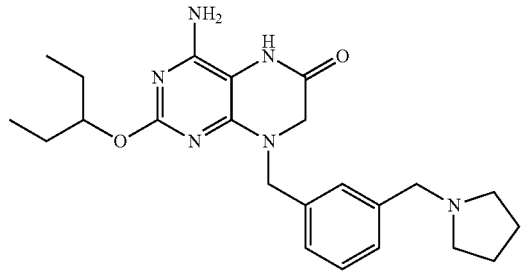

4-amino-2-(pentan-2-
yloxy)-8-(3-(pyrrolidin-1-ylmethyl)benzyl)-
7,8-dihydropteridin-6(5H)-one Example 25

4-amino-2-(pentan-3-
yloxy)-8-(3-(pyrrolidin-1-ylmethyl)benzyl)-
7,8-dihydropteridin-6(5H)-one -continued Example 26

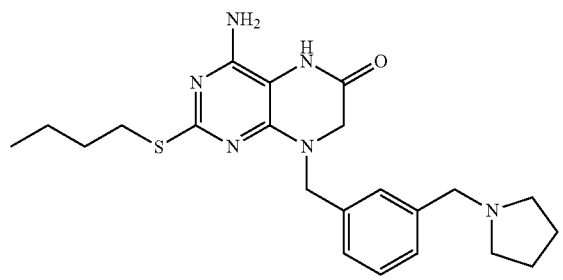

4-amino-2-(butylthio)-8-(3-
(pyrrolidin-1-ylmethyl)benzyl)-7,8-
dihydropteridin-6(5H)-one Example 27

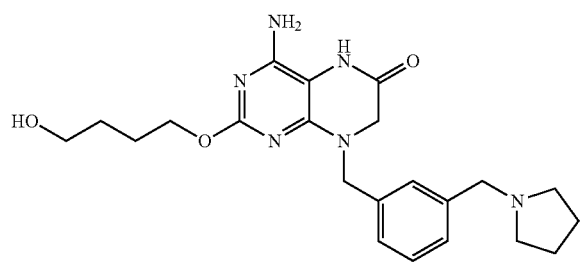

4-amino-2-(4-
hydroxybutoxy)-8-(3-(pyrrolidin-1-
ylmethyl)benzyl)-7,8-dihydropteridin-
6(5H)-one Example 28

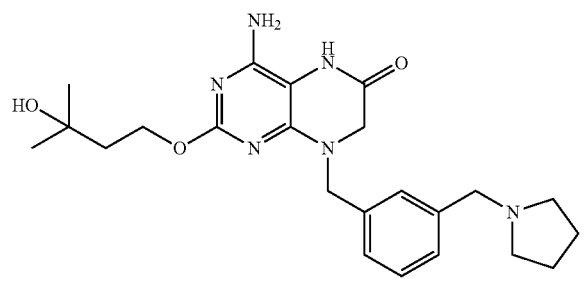

4-amino-2-(3-hydroxy-3-
methylbutoxy)-8-(3-pyrrolidin-1-
ylmethyl)benzyl)-7,8-dihydropteridin-
6(5H)-one Example 29

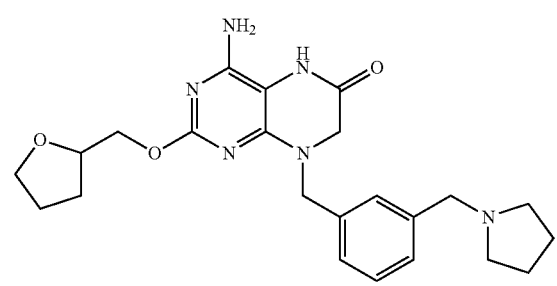

4-amino-8-(-3-(pyrrolidin-1-
ylmethyl)benzyl)-2-((tetrahydrofuran-2-
yl)methoxy)-7,8-dihydropteridin-6(5H)-one -continued Example 30

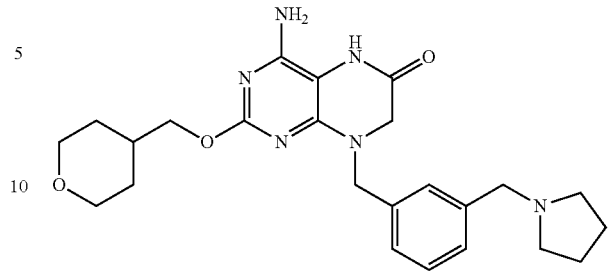

4-amino-8-(3-(pyrrolidin-1-
ylmethyl)benzyl)-2-((tetrahydro-2H-pyran-
4-yl)methoxy)-7,8-dihydropteridin-6(5H)-
one Example 31

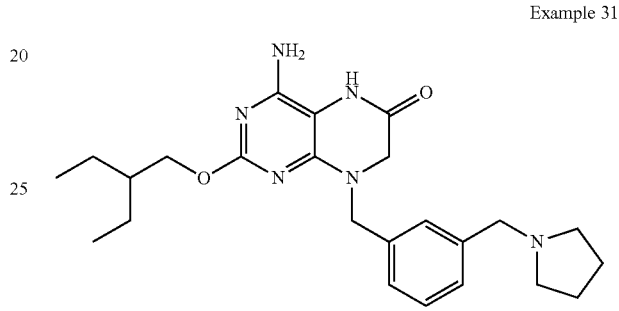

4-amino-2-(2-ethylbutoxy)-8-
(3-(pyrrolidin-1-ylmethyl)benzyl)-7,8-
dihydropteridin-6(5H)-one Example 32

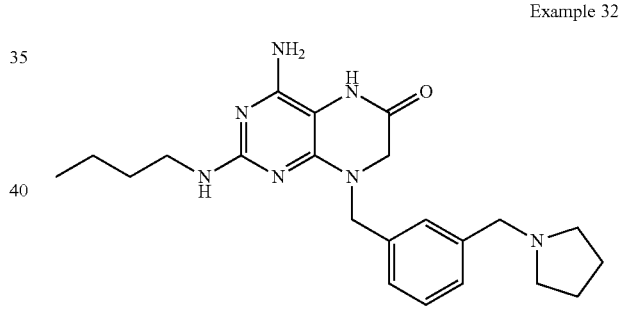

4-amino-2-(butylamino)-8-(3-
(pyrrolidin-1-ylmethyl)benzyl)-7,8-
dihydropteridin-6(5H)-one Example 33

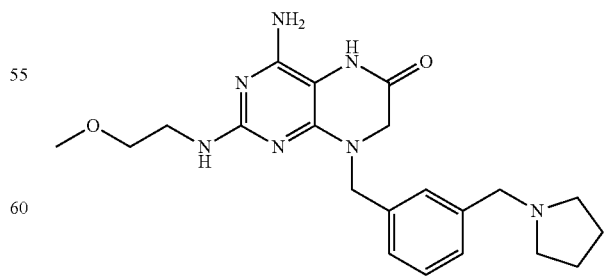

4-amino-2-((2-
methoxyethyl)amino)-8-(3-(pyrrolidin-1-
ylmethyl)benzyl)-7,8-dihydropteridin-
6(5H)-one Example 34

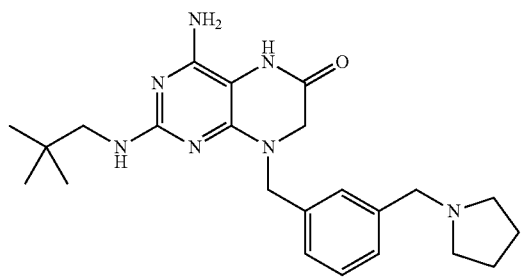

4-amino-2-
(neopentylamino)-8-(3-(pyrrolidin-1-
ylmethyl)benzyl)-7,8-dihydropteridin-
6(5H)-one Example 35

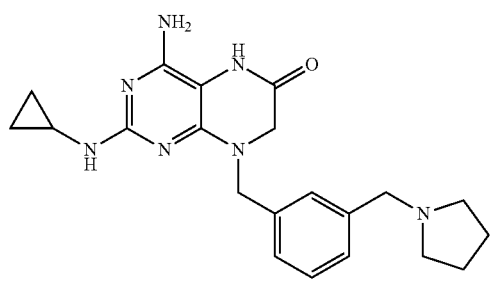

4-amino-2-(cyclopropylamino(8-(3-(pyrrolidin-1-
ylmethyl)benzyl)-7,8-dihydropteridin-
6(5H)-one Example 36

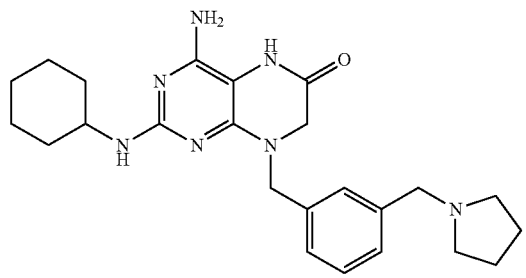

4-amino-2-
(cyclohexylamino)-8-(3-(pyrrolidin-1-
ylmethyl)benzyl)-7,8-dihydropteridin-
6(5H)-one Example 37

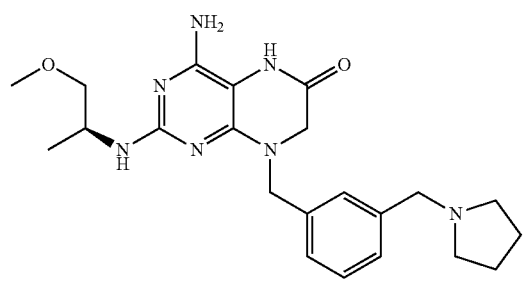

(S)-4-amino-2-((1-
methoxypropan-2-yl)amino)-8-(3-
(pyrrolidin-1-ylmethyl)benzyl)-7,8-
dihydropteridin-6(5H)-one Example 38

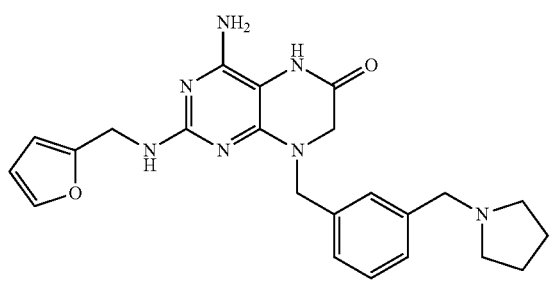

4-amino-2-((furan-2-
ylmethyl)amino)-8-(3-pyrrolidin-1-
ylmethyl)benzyl)-7,8-dihydropteridin-
6(5H)-one Example 39

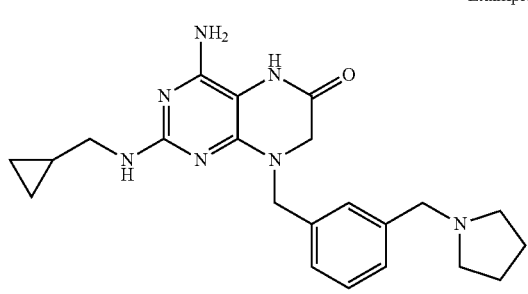

4-amino-2-
((cyclopropylmethyl)amino)-8-(3-
(pyrrolidin-1-ylmethyl)benzyl)-7,8-
dihydropteridin-6(5H)-one Example 40

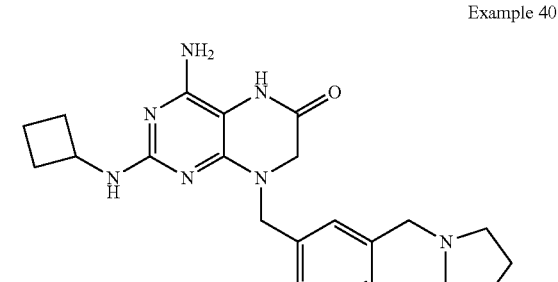

4-amino-2-
(cyclobutylamino)-8-(3-pyrrolidin-1-
ylmethyl)benzyl)-7,8-dihydropteridin-
6(5H)-one Example 41

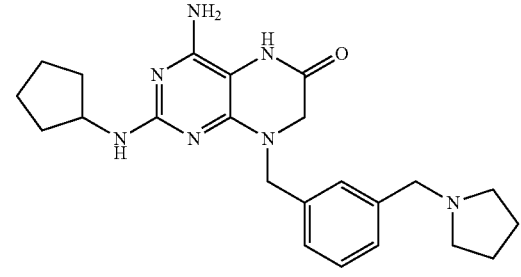

4-amino-2-
(cyclopentylamino)-8-(3-(pyrrolidin-1-
ylmethyl)benzyl)-7,8-dihydropteridin-
6(5H)-one Example 42

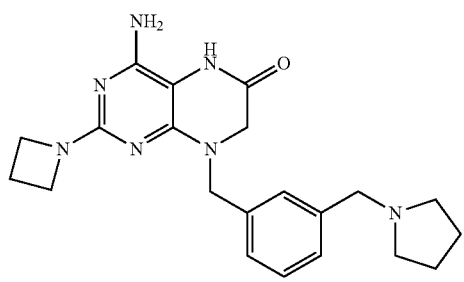

4-amino-2-(azetidin-1-yl)-8-
(3-(pyrrolidin-1-ylmethyl)benzyl)-7,8-
dihydropteridin-6(5H)-one Example 43

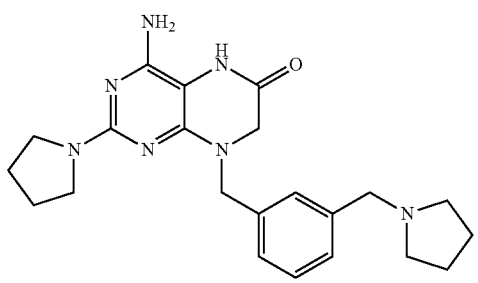

4-amino-2-(pyrrolidin-1-yl)-8-
(3-(pyrrolidin-1-ylmethyl)benzyl)-7,8-
dihydropteridin-6(5H)-one Example 44

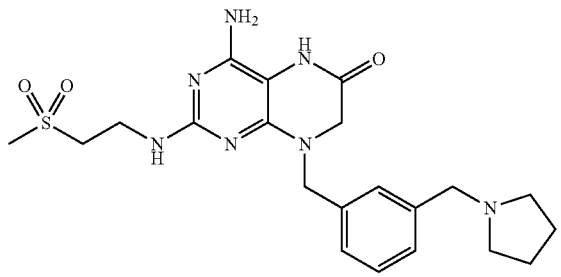

4-amino-2-((2-
(methylsulfonyl)ethyl)amino)-8-(3-
(pyrrolidin-1-ylmethyl)benzyl)-7,8-
dihydropteridin-6(5H)-one Example 45

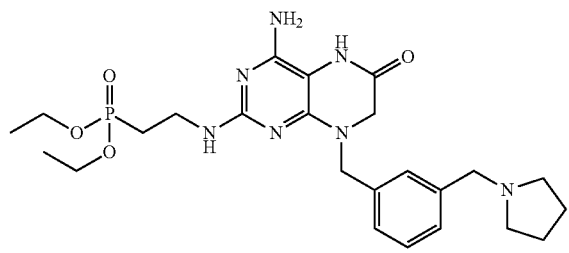

diethyl (2-((4-amino-6-oxo-8-
(3-(pyrrolidin-1-ylmethyl)benzyl)-5,6,7,8-
tetrahydropteridin-2-
yl)amino)ethyl)phosphonate Example 46

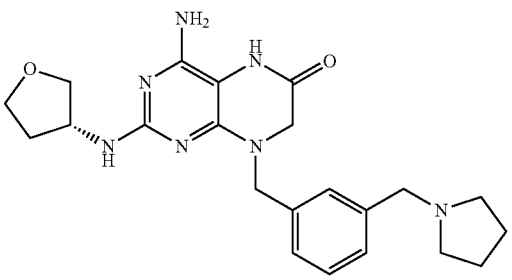

(R)-4-amino-8-(3-(pyrrolidin-
1-ylmethyl)benzyl)-2-((tetrahydrofuran-3-
yl)amino)-7,8-dihydropteridin-6(5H)-one Example 47

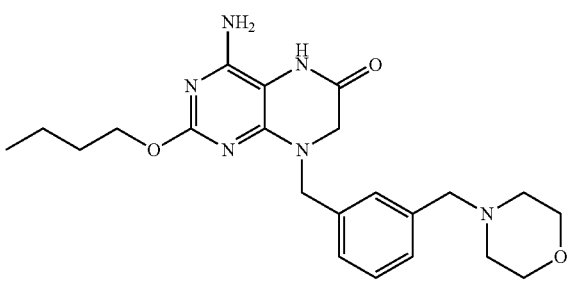

4-amino-2-butoxy-8-(3-
(morpholinomethyl)benzyl)-7,8-
dihydropteridin-6(5H)-one

Example 48

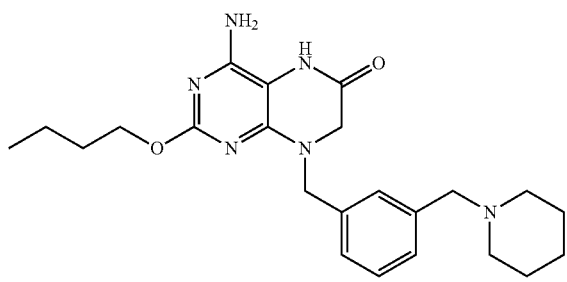

4-amino-2-butoxy-8-(3-
(piperidin-1-ylmethyl)benzyl)-7,8-
dihydropteridin-6(5H)-one Example 49

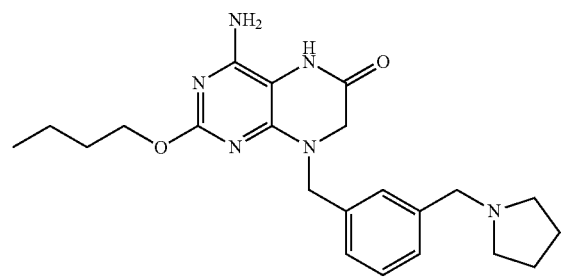

4-amino-2-n-butoxy-8-[3′-
(pyrrolidin-1″-ylmethyl)-benzyl]-5,6,7,8-
tetrahydropteridin-6-one, also known as
4-Amino-2-butoxy-8-[3-(1-
pyrrolidinylmethyl)benzyl]-7,8-dihydro-
6(5H)-pteridinone and GS-9620

Example 50

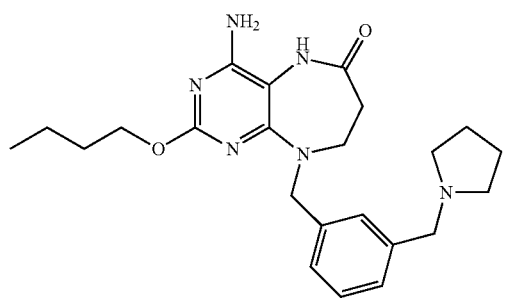

4-amino-2-butoxy-9-(3-(pyrrolidin-1-ylmethl)benzyl)-8,9-dihydro-5H-pyrimido[4,5-b][1,4]diazepin-6(7H)-one Example 51

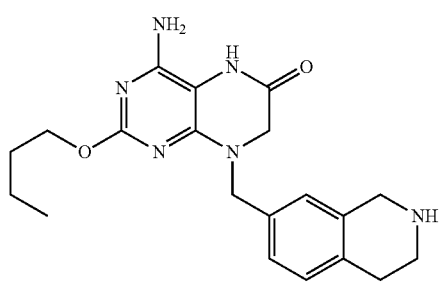

4-amino-2-butoxy-8-((1,2,3,4-tetrahydroisoquinolin-7-yl)methyl)-7,8-dihydropteridin-6(5H)-one Example 52

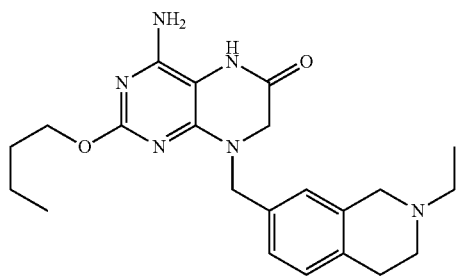

4-amino-2-butoxy-8-((2-ethyl-1,2,3,4-tetrahydroisoquinolin-7-yl)methyl)7,8-dihydropteridin-6(5H)-one Example 53

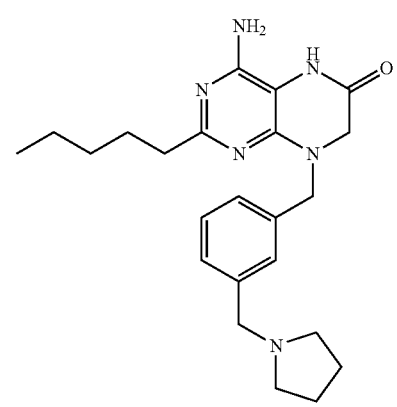

4-amino-2-pentyl-8-(3-(pyrrolidin-1-ylmethyl)benzyl)-7,8-dihydropteridin-6(5H)-one Example 54

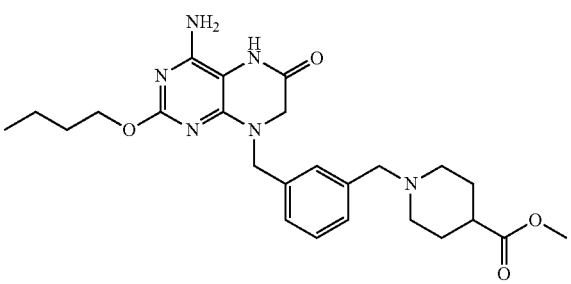

methyl 1-(3-((4-amino-2-butoxy-6-oxo-6,7-dihydropteridin-8(5H)-yl)methyl)benzyl)piperidine-4-carboxylate Example 55

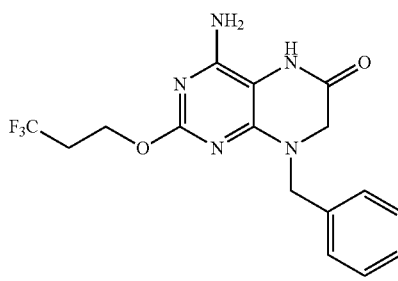

4-amino-8-(3-(pyrrolidin-1-ylmethyl)benzyl)-2-(3,3,3-trifluoropropoxy)-7,8-dihydropteridin-6(5H)-one Example 56

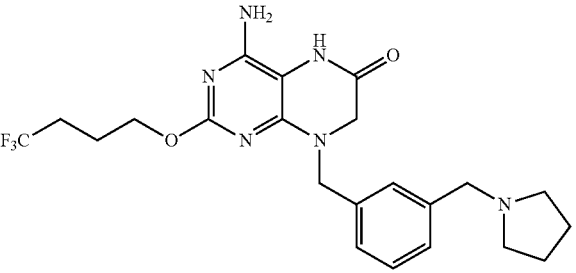

4-amino-8-(3-(pyrrolidin-1-ylmethyl)benzyl)-2-(4,4,4-trifluorobutoxy)-7,8-dihydropteridin-6(5H)-one Example 57

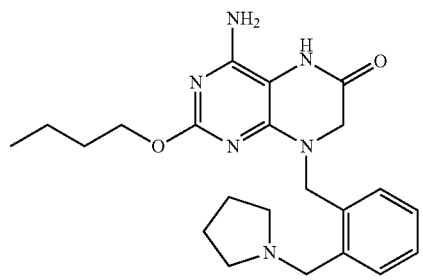

4-amino-2-butoxy-8-(2-(pyrrolidin-1-ylmethyl)benzyl)-7,8-dihydropteridin-6(5H)-one -continued Example 58

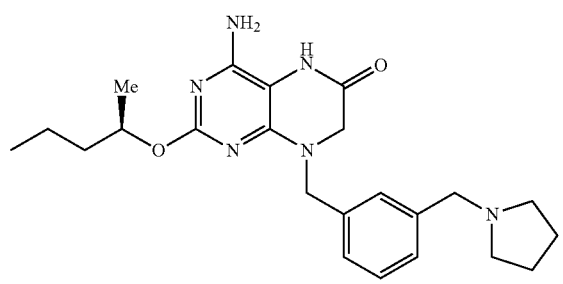

(R)-4-amino-2-(pentan-2-yloxy)-8-(3-(pyrrolidin-1-ylmethyl)benzyl)-7,8-dihydropteridin-6(5H)-one Example 59

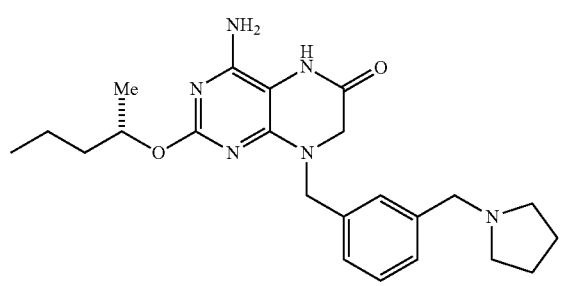

(S)-4-amino-2-(pentan-2-yloxy)-8-(3-(pyrrolidin-1-ylmethyl)benzyl)-7,8-dihydropteridin-6(5H)-one Example 60

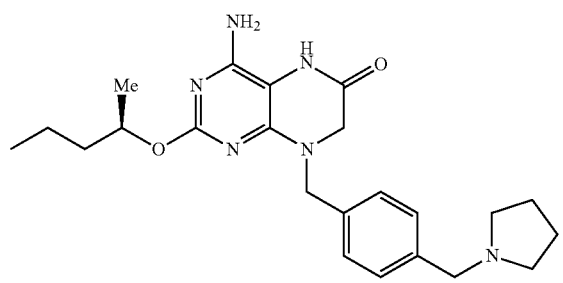

(R)-4-amino-2-(pentan-2-yloxy)-8-(4-(pyrrolidin-1-ylmethyl)benzyl)-7,8-dihydropteridin-6(5H)-one Example 61

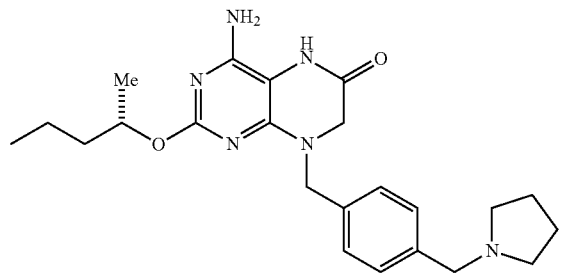

(S)-4-amino-2-(pentan-2-yloxy)-8-(4-(pyrrolidin-1-ylmethyl)benzyl)-7,8-dihydropteridin-6(5H)-one -continued Example 62

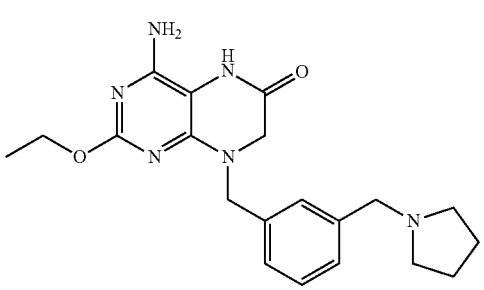

4-amino-2-ethoxy-8-(3-(pyrrolidin-1-ylmethyl)benzyl)-7,8-dihydropteridin-6(5H)-one Example 63

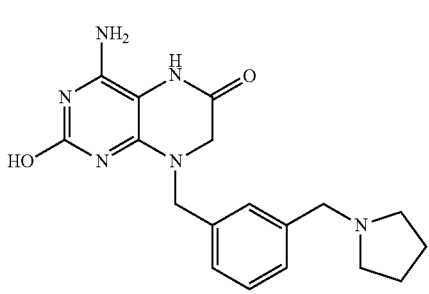

4-amino-2-hydroxy-8-(3-(pyrrolidin-1-ylmethyl)benzyl)-7,8-dihydropteridin-6(5H)-one Example 64

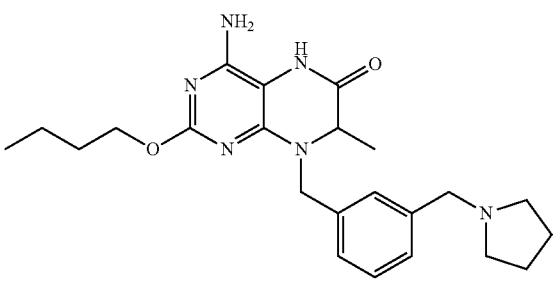

4-amino-2-butoxy-7-methyl-8-(3-(pyrrolidin-1-ylmethyl)benzyl)-7,8-dihydropteridin-6(5H)-one Example 65

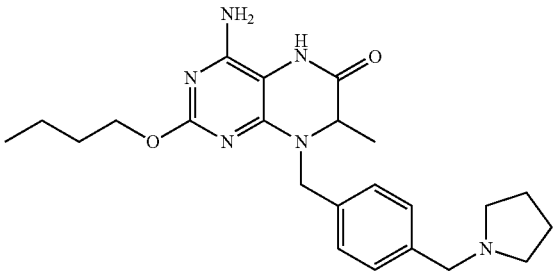

4-amino-2-butoxy-7-methyl-8-(4-(pyrrolidin-1-ylmethyl)benzyl)-7,8-dihydropteridin-6(5H)-one Example 66

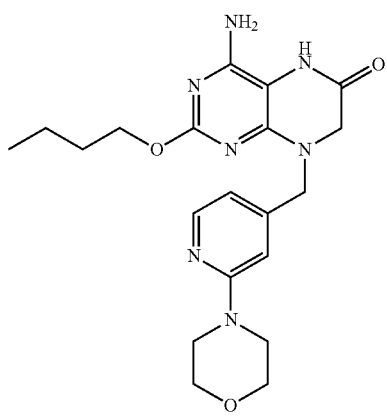

4-amino-2-butoxy-8-((2-morpholinopyridin-4-yl)methyl)-7,8-dihydropteridin-6(5H)-one Example 67

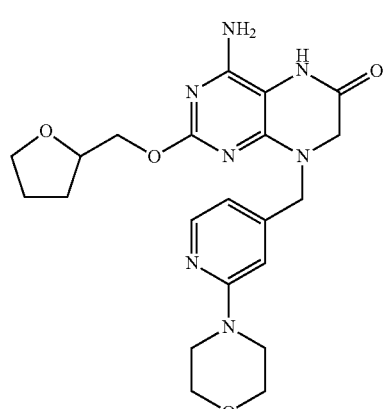

4-amino-8-((2-morpholinopyridin-4-yl)methyl)-2-((tetrahydrofuran-2-yl)methoxy)-7,8-dihydropteridin-6(5H)-one Example 68

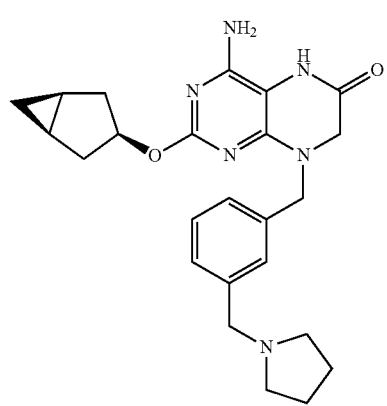

4-amino-2-((1R,3r,5S-bicyclo[3.1.0]hexan-3-yloxy)-8-(3-(pyrrolidin-1-ylmethyl)benzyl)-7,8-dihydropteridin-6(5H)-one Example 69

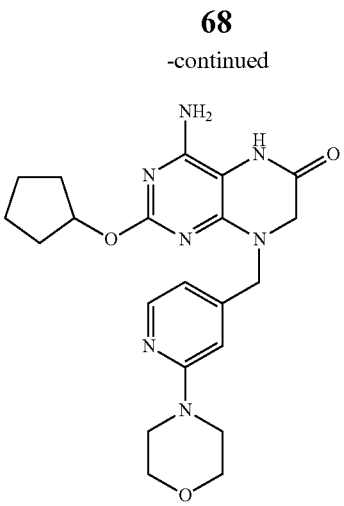

4-amino-2-(cyclopentyloxy)-8-((2-morpholinopyridin-4-yl)methyl)-7,8-dihydropteridin-6(5H)-one Example 70

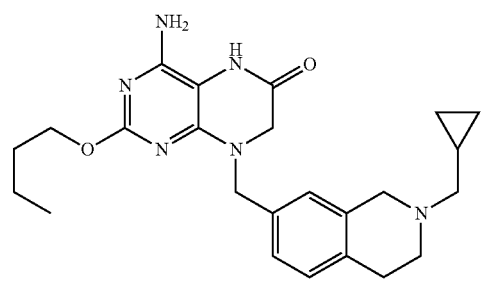

4-amino-2-butoxy-8-((2-(cyclopropylmethyl)-1,2,3,4-tetrahydroisoquinolin-7-yl)methyl)-7,8-dihydropteridin-6(5H)-one Example 71

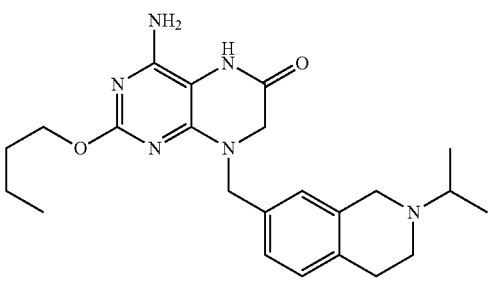

4-amino-2-butoxy-8-((2-isopropyl-1,2,3,4-tetrahydroisoquinolin-7-yl)methyl)-7,8-dihydropteridin-6(5H)-one Example 72

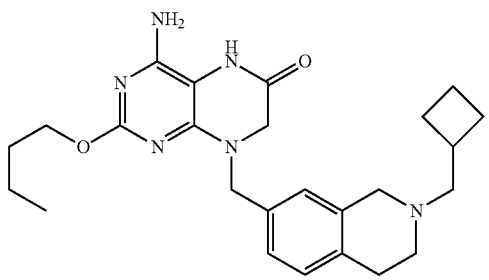

4-amino-2-butoxy-8-((2-
(cyclobutylmethyl)-1,2,3,4-
tetrahydroisoquinolin-7-yl)methyl)-7,8-
dihydropteridin-6(5H)-one Example 73

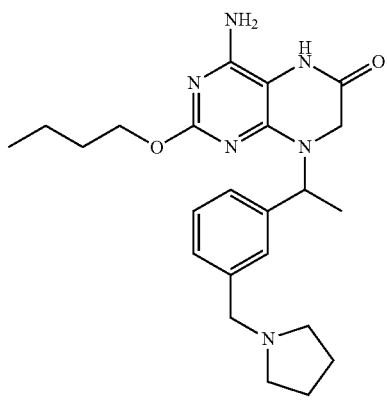

4-amino-2-butoxy-8-(1-(3-
(pyrrolidin-1-ylmethyl)phenyl)ethyl)-7,8-
dihydropteridin-6(5H)-one Example 74

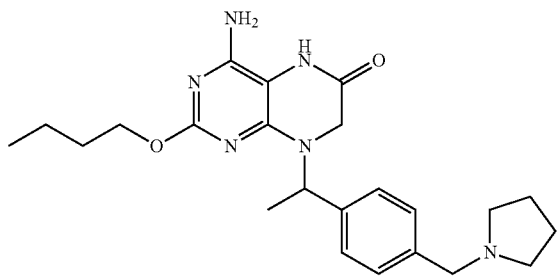

4-amino-2-butoxy-8-(1-(4-
(pyrrolidin-1-ylmethyl)phenyl)ethyl)-7,8-
dihydropteridin-6(5H)-one Example 75

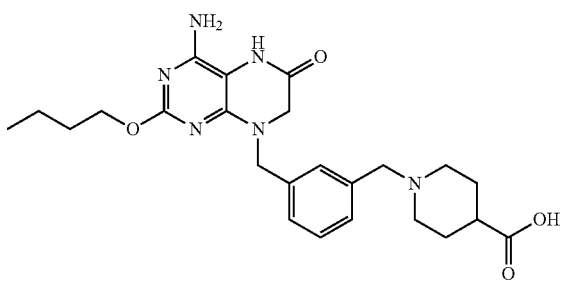

1-(3-((4-amino-2-butoxy-6-
oxo-6,7-dihydropteridin-8(5H)-
yl)methyl)benzyl)piperdine-4-carboxylic
acid Example 76

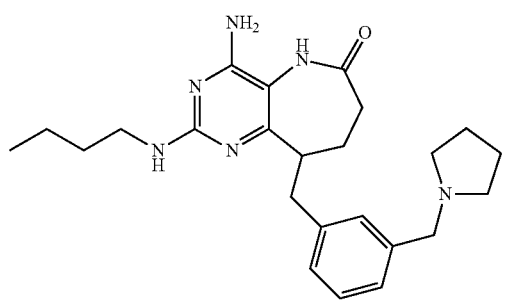

4-amino-2-(butylamino)-9-(3-
(pyrrolidin-1-ylmethyl)benzyl)-8,9-dihydro-
5H-pyrimido[4,5-b][1,4]diazepin-6(7H)-
one Example 77

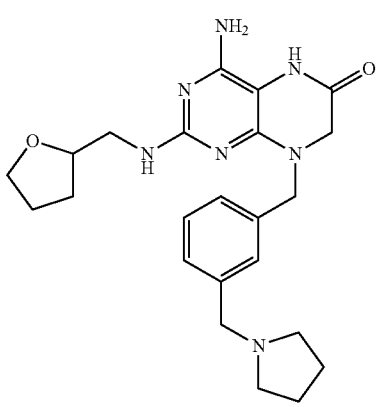

4-amino-8-(3-(pyrrolidin-1-
ylmethyl)benzyl)-2-(((tetrahydrofuran-2-
yl)methyl)amino)-7,8-dihydropteridin-
6(5H)-one Example 78

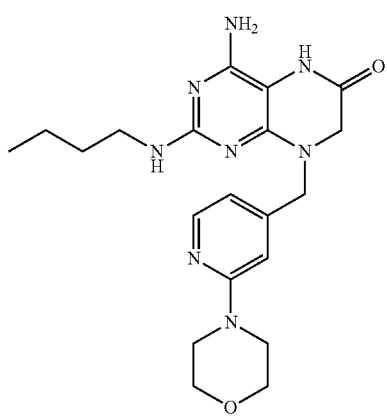

4-amino-2-(butylamino)-8-
((2-morpholinopyridin-4-yl)methyl)-7,8-
dihydropteridin-6(5H)-one Example 79

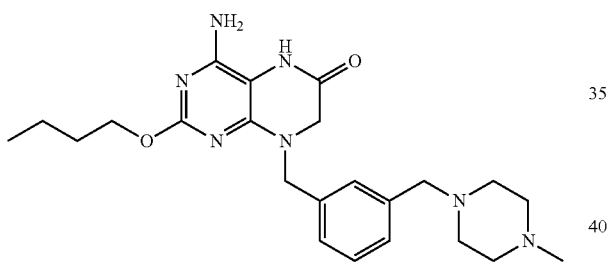

4-amino-2-butoxy-8-(3-((4-
methylpiperazin-1-yl)methyl)benzyl)-7,8-
dihydropteridin-6(5H)-one Example 80

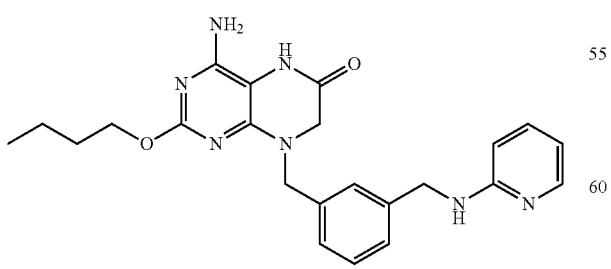

4-amino-2-butoxy-8-(3-
((pyridin-2-ylamino)methyl)benzyl)-7,8-
dihydropteridin-6(5H)-one Example 81

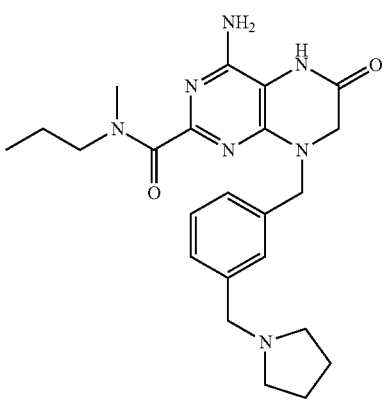

4-amino-2-butoxy-8-(3-((4-
methylpiperazin-1-yl)methyl)benzyl)-7,8-
dihydropteridin-6(5H)-one Example 82

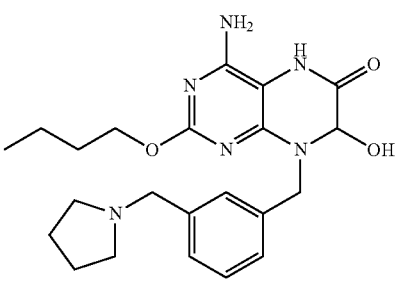

4-amino-2-butoxy-7-
hydroxy-8-(3-(pyrrolidin-1-
ylmethyl)benzyl)-7,8-dihydropteridin-
6(5H)-one Example 83

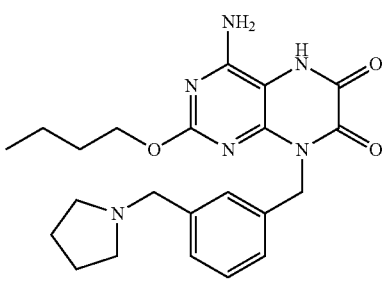

4-amino-2-butoxy-8-(3-
(pyrrolidin-1-ylmethyl)benzyl)pteridine-
6,7(5H,8H)-dione Example 84

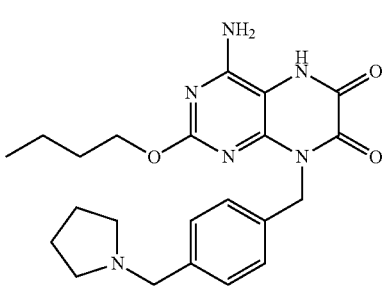

4-amino-2-butoxy-8-(4-
(pyrrolidin-1-ylmethyl)benzyl)pteridine-
6,7(5H,8H)-dione Example 85

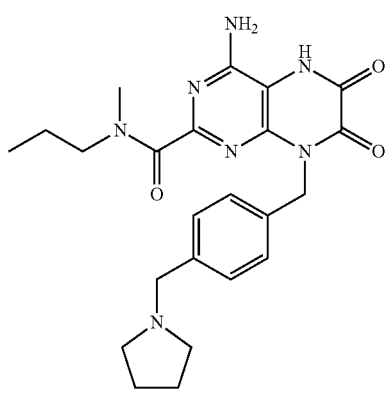

4-amino-N-methyl-6-
oxo-N-propyl-8-(-(pyrrolidin-1-
ylmethyl)benzyl)-5,6,7,8-
tetrahydropteridine-2-carboxamide Example 87

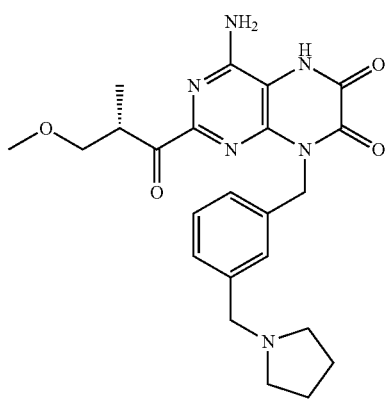

(S)-4-amino-2-((1-
methoxypropan-2-yl)-oxy)-8-(3-(pyrrolidin-
1-ylmethyl)benzyl)-7,8-dihydropteridin-
6(5H)-one Example 88

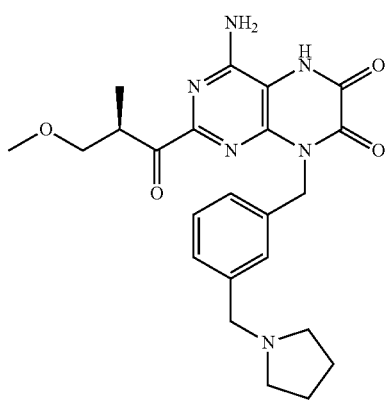

(R)-4-amino-2-((1-
methoxypropan-2-yl)oxy)-8-(3-pyrrolidin-
1-ylmethyl)benzyl)-7,8-dihydropteridin-
6(5H)-one Example 89

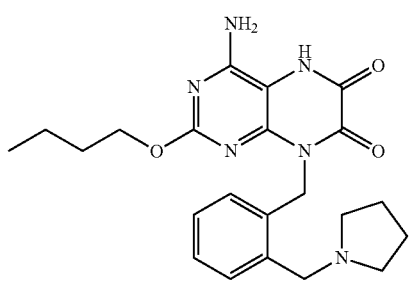

4-amino-2-butoxy-8-(2-
(pyrrolidin-1-ylmethyl)benzyl)pteridine-
6,7(5H,8H)-dione Example 90

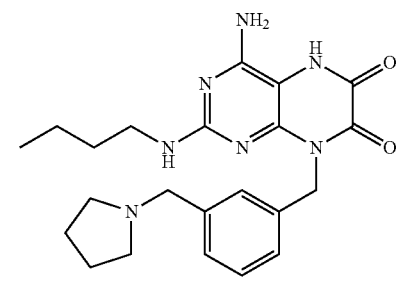

4-amino-2-(butylamino)-8-(3-
(pyrrolidin-1-ylmethyl)benzyl)pteridine-
6,7(5H,8H)-dione Example 91

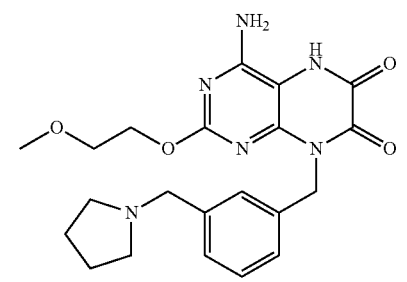

4-amino-2-(butylamino)-8-(3-
(pyrrolidin-1-ylmethyl)benzyl)pteridine-
6,7(5H,8H)-dione Example 92

4-amino-N-methyl-6,7-dioxo-
N-propyl-8-(3-(pyrrolidin-1-
ylmethyl)benzyl)-5,6,7,8-
tetrahydropteridine-2-carboxamide -continued Example 93

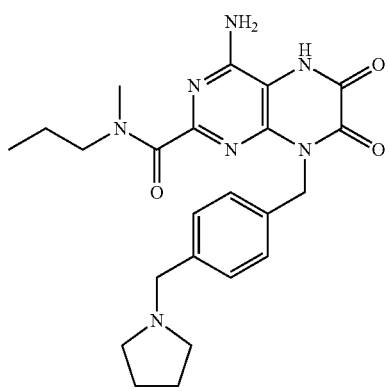

4-amino-N-methyl-6,7-dioxo-
N-propyl-8-(4-(pyrrolidin-1-
ylmethyl)benzyl)-5,6,7,8-
tetrahydropteridine-2-carboxamide Example 94

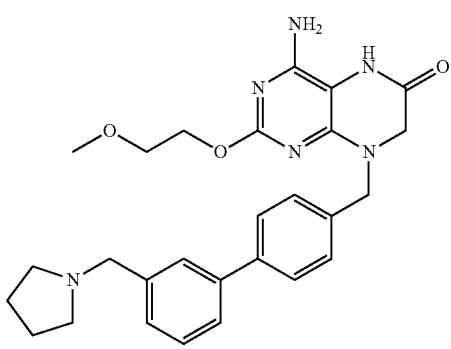

4-amino-2-(2-
methoxyethoxy)-8-((3'-pyrrolidin-1-
ylmethyl)-[1,1'-biphenyl]-4-yl)methyl)-7,8-
dihydropteridin-6(5H)-one Example 95

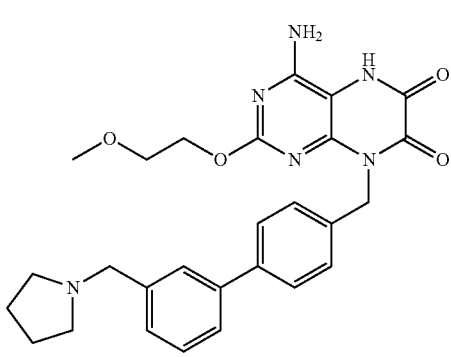

4-amino-2-(2-
methoxyethoxy)-8-((3'-(pyrrolidin-1-
ylmethyl)-[1,1'-biphenyl]-4-
yl)methyl)pteridine-6,7(5H,8H)-dione -continued Example 96

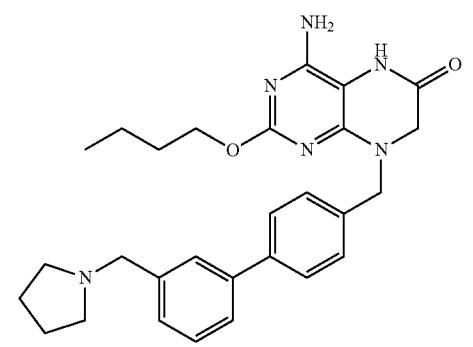

4-amino-2-butoxy-8-
((3'-(pyrrolidin-1-ylmethyl)-[1,1'-biphenyl]-
4-yl)methyl)-7,8-dihydropteridin-6(5H)-
one Example 97

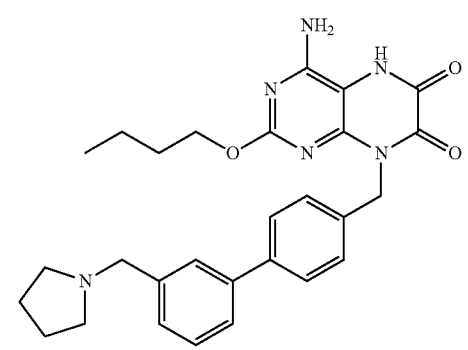

4-amino-2-butoxy-8-((3'-
(pyrrolidin-1-ylmethyl)-[1,1'-biphenyl]-4-
yl)methyl)pteridine-6,7(5H,8H)-dione Example 98

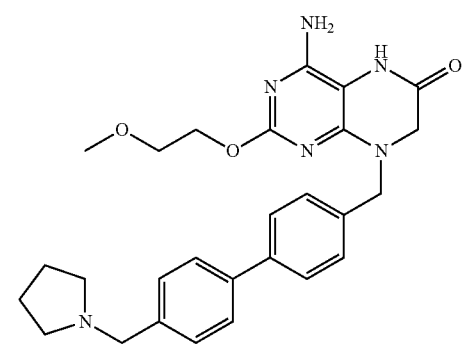

4-amino-2-(2-
methoxyethoxy)-8-((4'-pyrrolidin-1-
ylmethyl)-[1,1'-biphenyl]-4-yl)methyl)-7,8-
dihydropteridin-6(5H)-one Example 99

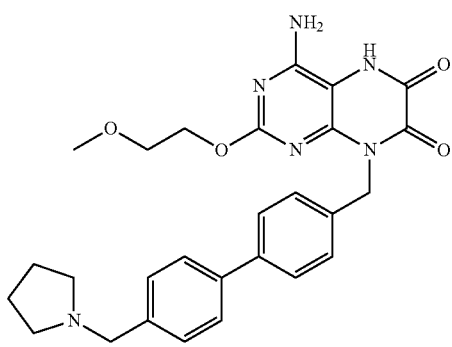

4-amino-2-(2-methoxyethoxy)-8-((4'-pyrrolidin-1-ylmethyl)-[1,1'-biphenyl]-4-yl)methyl)pteridine-6,7(5H,8H)-dione Example 100

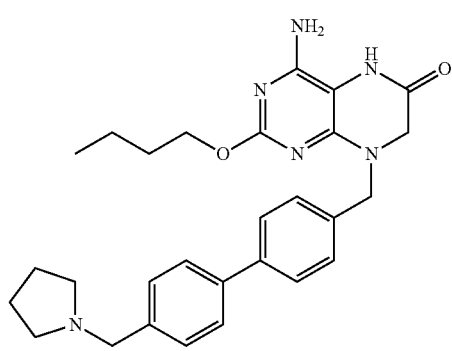

4-amino-2-butoxy-8-((4'-(pyrrolidin-1-ylmethyl)-[1,1'-biphenyl]-4-yl)methyl)-7,8-dihydropteridin-6(5H)-one Example 101

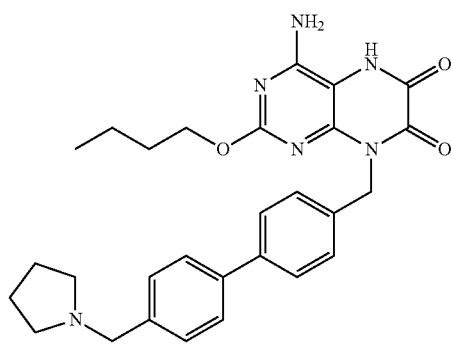

4-amino-2-butoxy-8-((4'-(pyrrolidin-1-ylmethyl)-[1,1'-biphenyl]-4-yl)methyl)pteridine-6,7(5H,8H)-dione Example 102

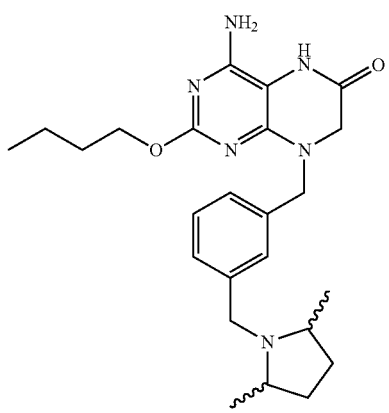

4-amino-2-butoxy-8-(3-((2,5-dimethylpyrrolidin-1-yl)methyl)benzyl)-7,8-dihydropteridin-6(5H)-one Example 103

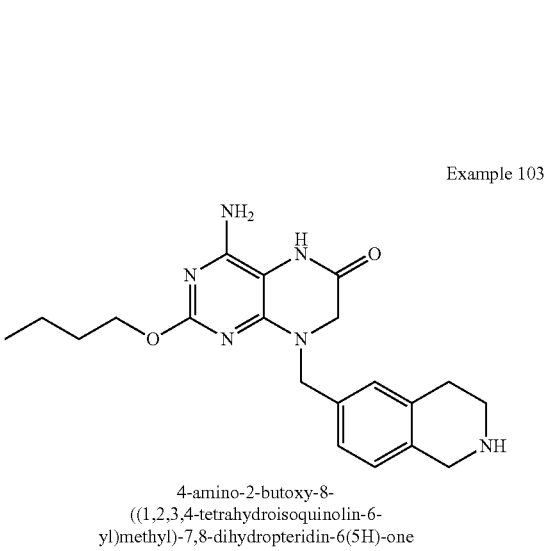

4-amino-2-butoxy-8-((1,2,3,4-tetrahydroisoquinolin-6-yl)methyl)-7,8-dihydropteridin-6(5H)-one Example 104

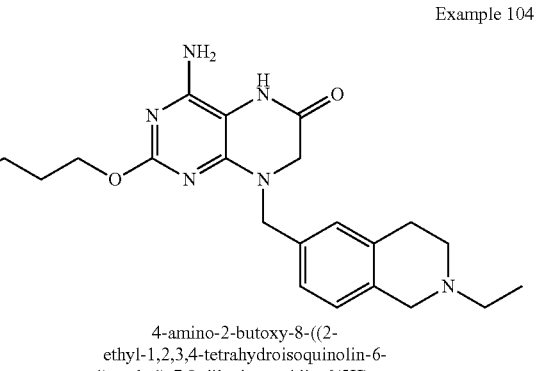

4-amino-2-butoxy-8-((2-ethyl-1,2,3,4-tetrahydroisoquinolin-6-yl)methyl)-7,8-dihydropteridin-6(5H)-one Example 105

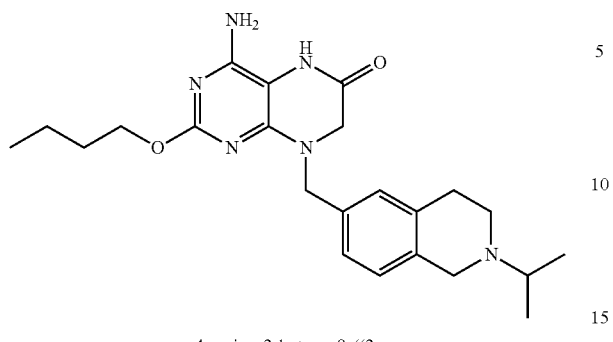

4-amino-2-butoxy-8-((2-
isopropyl-1,2,3,4-tetrahydroisoquinolin-6-
yl)methyl)-7,8-dihydropteridin-6(5H)-one Example 106

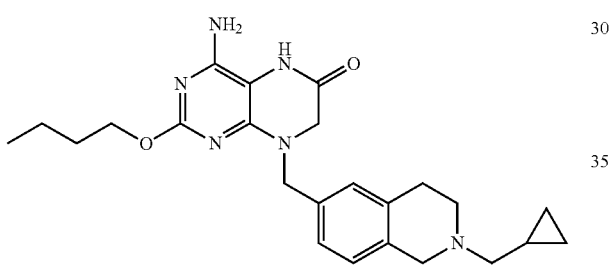

4-amino-2-butoxy-
8-((2-(cyclopropylmethyl)-1,2,3,4-
tetrahydroisoquinolin-6-yl)methyl)-7,8-
dihydropteridin-6(5H)-one Example 107

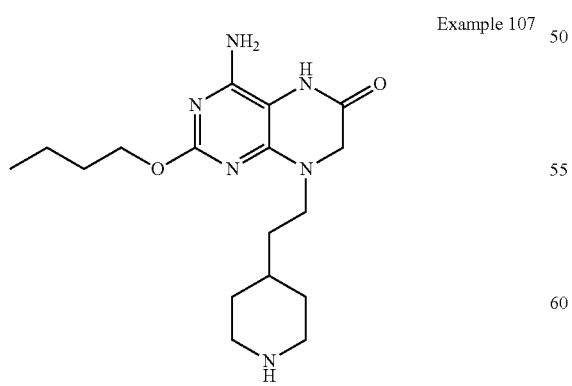

4-amino-2-butoxy-
8-(2-(piperidin-4-yl)ethyl)-7,8-
dihydropteridin-6(5H)-one

Example 108

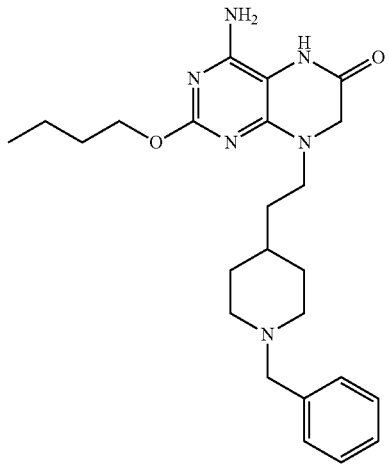

4-amino-8-(2-(1-
benzylpiperidin-4-yl)ethyl)-2-butoxy-7,8-
dihydropteridin-6(5H)-one Example 109

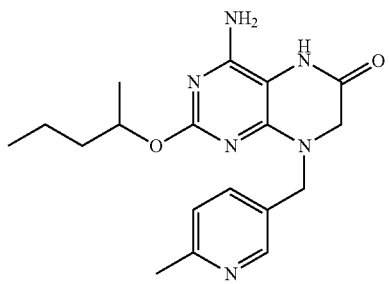

4-amino-8-((6-
methylpyridin-3-yl)methyl)-2-(pentan-2-
yloxy)-7,8-dihydropteridin-6(5H)-one Example 110

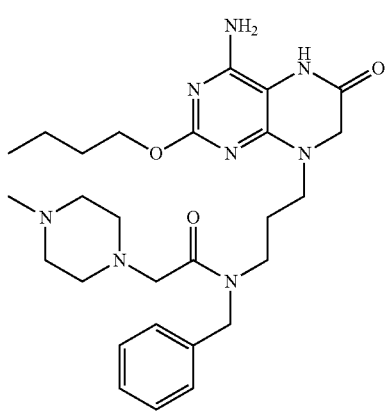

N-(3-(4-amino-2-
butoxy-6-oxo-6,7-dihydropteridin-8(5H)-
yl)propyl)-N-benzyl-2-(4-methylpiperazin-
1-yl)acetamide Example 111

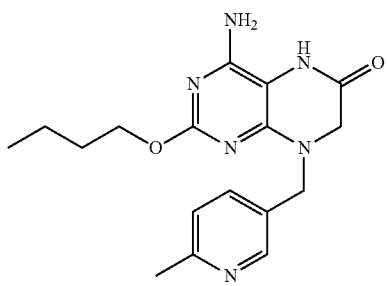

4-amino-2-butoxy-8-((6-
methylpyridin-3-yl)methyl)-7,8-
dihydropteridin-6(5H)-one Example 112

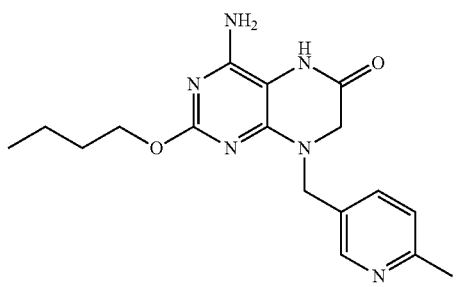

4-amino-2-butoxy-8-((6-
methylpyridin-3-yl)methyl)pteridine-
6,7(5H,8H)-dione

Example 113

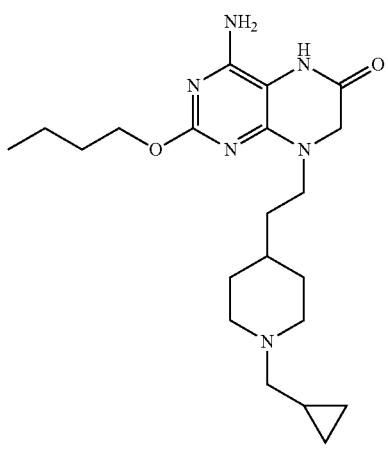

4-amino-2-butoxy-8-(2-(1-
(cyclopropylmethyl)piperidin-4-yl)ethyl)-
7,8-dihydropteridin-6(5H)-one Example 115

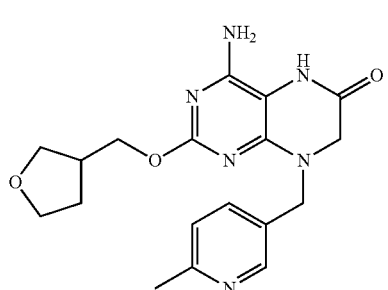

4-amino-8-((6-
methylpyridin-3-yl)methyl)-2-
((tetrahydrofuren-3-yl)methoxy)-7,8-
dihydropteridin-6(5H)-one Example 116

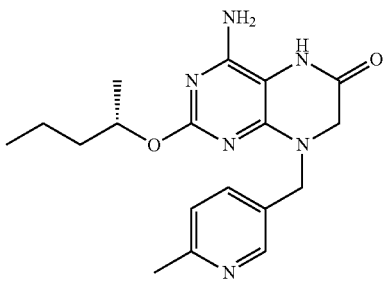

(S)-4-amino-8-((6-
methylpyridin-3-yl)methyl)-2-(pentan-2-
yloxy)-7,8-dihydropteridin-6(5H)-one Example 117

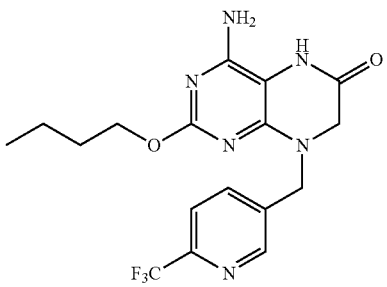

4-amino-2-butoxy-8-((6-
(trifluoromethyl)pyridin-3-yl)methyl)-7,8-
dihydropteridin-6(5H)-one Example 118

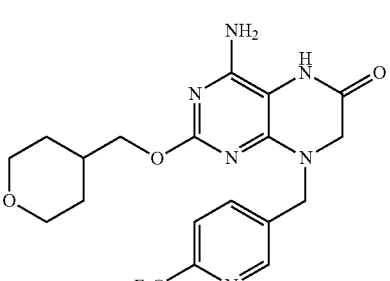

4-amino-2-((tetrahydro-2H-
pyran-4-yl)methoxy)-8-((6-
(trifluoromethyl)pyridin-3-yl)methyl)-
7,8-dihydropteridin-6(5H)-one Prophetic Examples As with the examples herein described, the following compounds may be used in the uses, methods of treatment, regimens, pharmaceutical formulations and kits described herein and may be prepared using synthetic methods analogous to those taught in WO 2010/077613 A1 (Desai et al.):

83
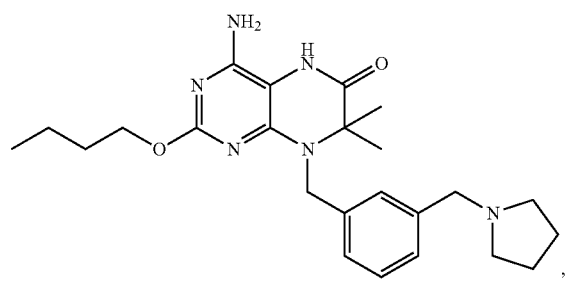
84
-continued
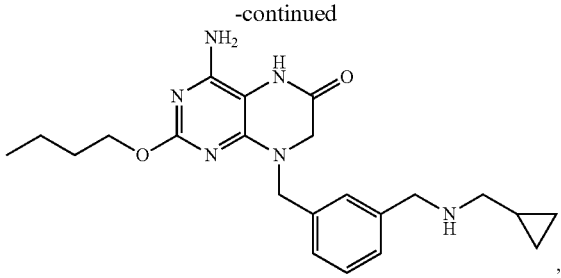
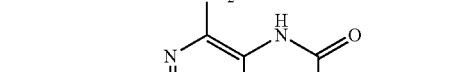
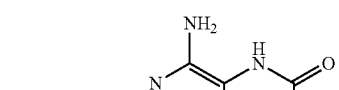
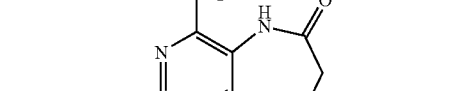

85
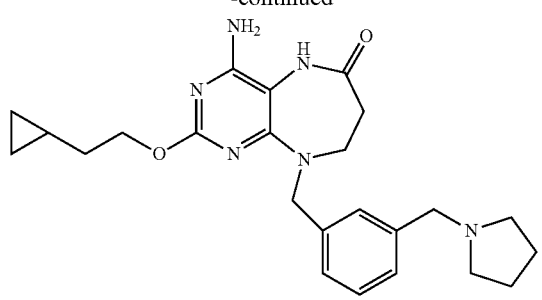
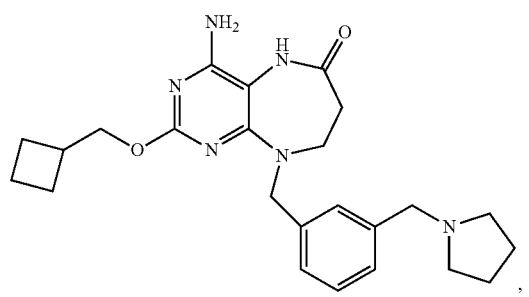
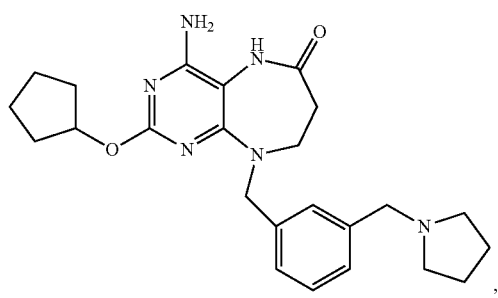
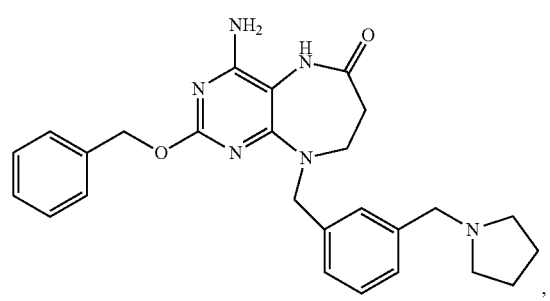
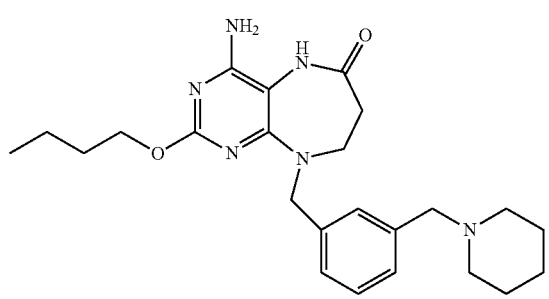
86
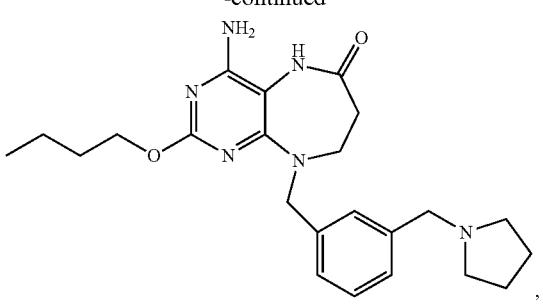
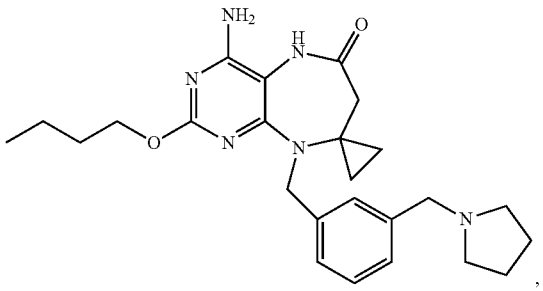
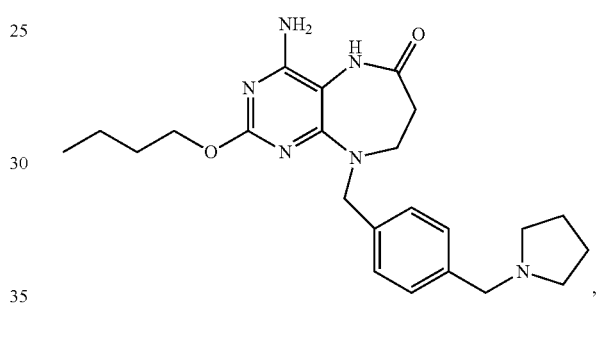
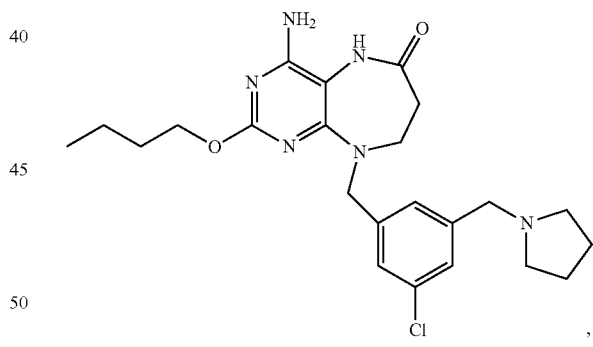
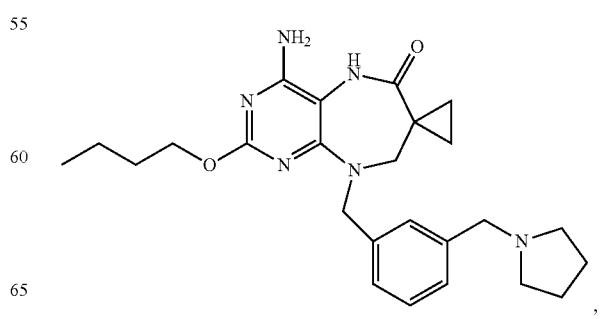

-continued

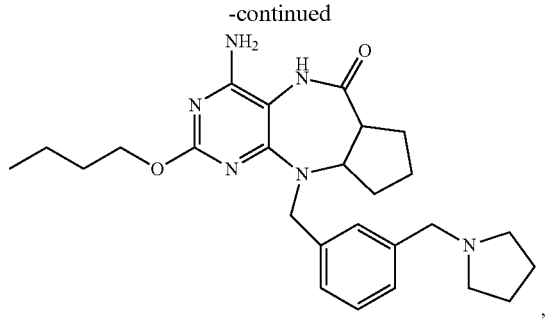

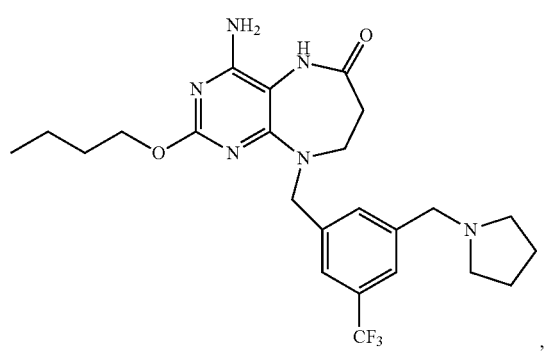

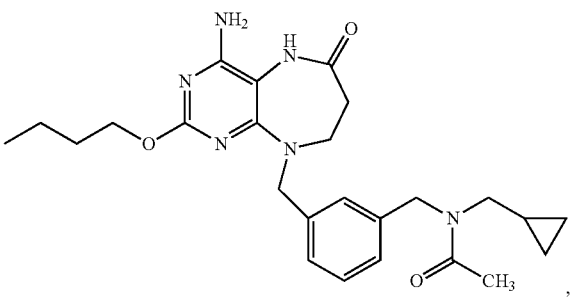

and

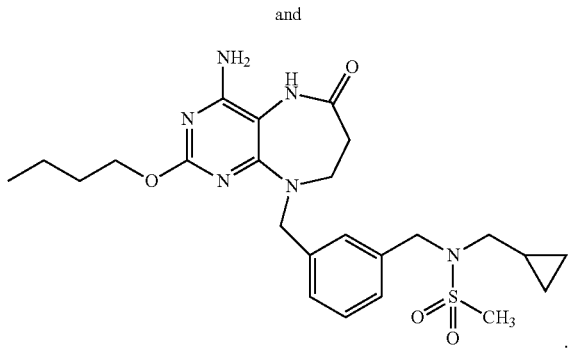

Example 119

6-amino-2-butoxy-9-(3-(pyrrolidin-1-ylmethyl)benzyl)-9H-purin-8-ol

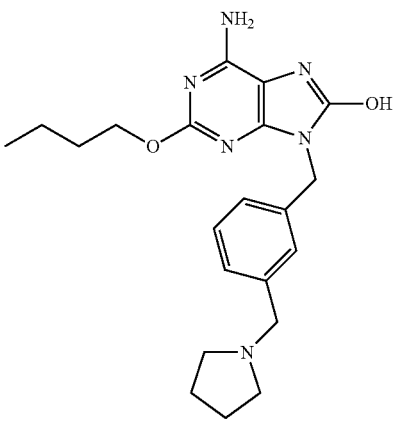 [SMILES: CCCCOc1nc(N)c2nc(O)n(Cc3cccc(CN4CCCC4)c3)c2n1]

The compound of Example 119 can be prepared using the methods of U.S. Pat. No. 7,968,544 (Graupe et al.), in which it appears as Compound W.

Example 120

4-amino-6-(2-methoxyethoxy)-1-((4'-(pyrrolidin-1-ylmethyl)-[1,1-biphenyl]-4-yl)methyl)-1H-imidazo[4,5-c]pyridin-2(3H)-one

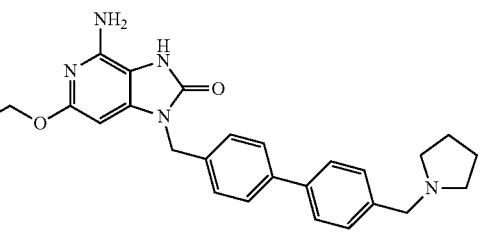

The compound of Example 120 can be prepared using the methods of WO 2011/049825 and U.S. Pat. No. 8,507,507 (Halcomb et al.), in which it appears as Compound AX.

Example 121

4-amino-7-chloro-6-(2-methoxyethoxy)-1-((4'-(pyrrolidin-1-ylmethyl)-[1,1-biphenyl]-4-yl)methyl)-1H-imidazo[4,5-c]pyridin-2(3H)-one

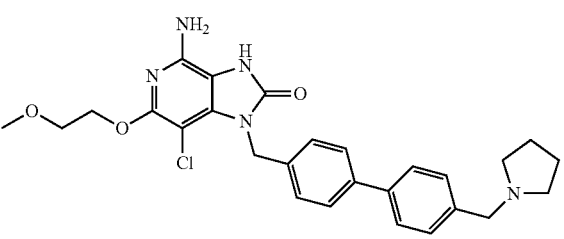 [SMILES: COCCOc1nc(N)c2[nH]c(=O)n(Cc3ccc(-c4ccc(CN5CCCC5)cc4)cc3)c2c1Cl]

The compound of Example 121 can be prepared using the methods of WO 2011/049825 and U.S. Pat. No. 8,507,507 (Halcomb et al.), in which it appears as Compound AY.

Example 122

6-amino-9-benzyl-2-(2-methoxyethoxy)-9H-purin-8-ol

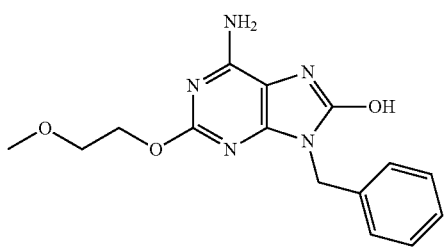 [SMILES: COCCOc1nc(N)c2nc(O)n(Cc3ccccc3)c2n1]

The compound of Example 122, also known as 1V136, CL 087, and SM 360320, may be prepared as described in U.S. Pat. No. 6,329,381, where it appears as Example 88.

Example 123

N-(4-(4-amino-2-ethyl-1H-imidazo[4,5-c]quinolin-1-yl)butyl)methane sulfonamide

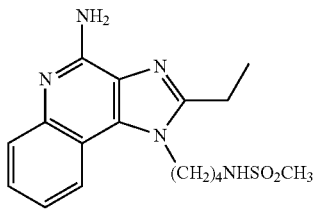

The compound of Example 123, also known as R-852, R-852A, and PF-4878691, may be prepared by the methods disclosed in U.S. Pat. No. 6,677,349, where it appears as Example 236.

Example 124

5-amino-3-((2R,3R,5S)-3-hydroxy-5-(hydroxymethyl)tetrahydrofuran-2-yl)thiazolo[4,5-d]pyrimidine-2,7(3H,4H)-dione

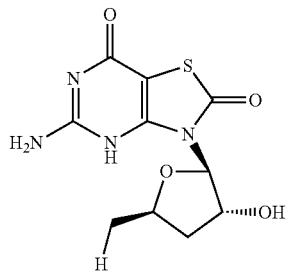 [SMILES: C[C@@H]1C[C@@H](O)[C@H](n2c(=O)sc3c(=O)nc(N)[nH]c32)O1]

The compound of Example 124 may be prepared as described in U.S. Pat. No. 8,097,718, where it appears as Example 122.

Pharmaceutical Compositions

In one embodiment, the present application discloses pharmaceutical compositions comprising a TLR7 modulating compound as described herein, including a compound selected from the group of the compounds of Formula II, Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), and each of the individual compounds of the examples from Example 1 through Example 124, or a pharmaceutically acceptable salt, solvate, and/or ester thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase strand transfer inhibitors, non-catalytic site integrase inhibitors, HIV gp120/41 inhibitors, CCR5 inhibitors, HIV capsid inhibitors, HIV Vif inhibitors, nucleotide inhibitors of HCV, nucleoside inhibitors of HCV, non-nucleoside inhibitors of HCV, and combinations thereof, and a pharmaceutically acceptable carrier or excipient. Examples include nucleoside-sparing and nucleotide-sparing combinations.

In another embodiment, the present application provides pharmaceutical compositions comprising pharmaceutically effective amounts of a TLR7 modulating compound as described herein, or a pharmaceutically acceptable salt, solvate, and/or ester thereof, in combination with at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, AG 1859, capravirine, emivirine, delaviridine, efavirenz, nevirapine, (+) calanolide A, etravirine, doravirine (MK-1439), GW5634, DPC-083, DPC-961, DPC-963, MIV-150, TMC-120, TMC-278 (rilpivirine), BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, Racivir (±-FTC), D-d4FC, phosphazide, fozivudine tidoxil, apricitibine AVX754, amdoxovir, KP-1461, and fosalvudine tidoxil (formerly HDP 99.0003)), tenofovir, tenofovir disoproxil fumarate, tenofovir alafenamide, CMX-157, adefovir dipivoxil, GS-9131, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), dolutegravir, elvitegravir, GSK1265744, BMS-538158, GSK364735C, BMS-707035, MK-2048, BA 011, enfuvirtide, sifuvirtide, FB006M, TRI-1144, AMD-070, SP01A, BMS-488043, BMS-626529, BMS-663068, BlockAide/CR, immunitin, benzimidazole derivatives, benzo-1,2,4-thiadiazine derivatives, phenylalanine derivatives, aplaviroc, vicriviroc, and maraviroc, cenicriviroc (TBR-652), cyclosporine, FK-506, rapamycin, taxol, taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017 and a pharmaceutically acceptable carrier or excipient.

In still another embodiment, the present invention provides pharmaceutical compositions comprising pharmaceutically effective amounts of a TLR7 modulating compound as described herein, or a pharmaceutically acceptable salt, solvate, and/or ester thereof, in combination with two, three, four, five, or more additional therapeutic agents. For example, a TLR7 modulating compound as described herein, or a pharmaceutically acceptable salt, solvate, and/or ester thereof, is combined with two, three, four, five, or more additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, HIV entry inhibitors and HIV integrase inhibitors. The two, three, four, five, or more additional therapeutic agents can be different therapeutic agents selected from the same class of therapeutic agents, or they can be selected from different classes of therapeutic agents. In a particular embodiment, the TLR7 modulating compound as described herein, or a pharmaceutically acceptable salt, solvate, and/or ester thereof, is combined with two, three, four, five, or more additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. In a still more particular embodiment, the pharmaceutical composition of the present invention comprises a compound selected from the group of compounds of Example 4, Example 49 (GS-9620), Example 119, Example 120, and Example 121, or a pharmaceutically acceptable salt, solvate, and/or ester thereof, in combination with two, three, four, five, or more additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. For example, such combinations can comprise a compound selected from the group of compounds of Example 4, Example 49 (GS-9620), Example 119, Example 120, and Example 121, or a pharmaceutically acceptable salt, solvate, and/or ester thereof in combination with two, three, four, five, or more additional therapeutic agents selected from the group consisting of tenofovir disoproxil fumarate (TDF), tenofovir alafenamide (TAF), tenofovir alafenamide hemifumarate, abacavir, abacavir sulfate, GS-9131, emtricitabine, lamuvidine, elvitegravir, efavirenz, atazanavir, darunavir, raltegravir, dolutegravir, GSK774, cobicistat, ritonavir, and rilpivirine (or pharmaceutically acceptable salts, solvates, and/or esters thereof).

Combinations and compositions herein include those comprising pharmaceutically effect amounts of TDF and emtricitabine, plus a third HIV therapeutic agent, as well TAF and emtricitabine, plus a third HIV therapeutic agent. Examples of HIV therapeutic agents that may be used with these combinations include HIV protease inhibitors (PIs), non-nucleoside reverse transcriptase inhibitors (NNRTIs), nucleoside reverse transcriptase inhibitors (NRTIs), Integrase Strand Transfer inhibitors (INSTIs), non-catalytic site integrase inhibitors (NCINIs), Capsid inhibitors, etc., listed herein.

Specific embodiments of ternary combinations which a) may be combined with a pharmaceutically acceptable carrier or excipient to prepare a pharmaceutical composition, or b) may be used in combination in each of the methods described herein, comprise, for example, pharmaceutically effective amounts of each of the compounds listed in the combinations below, or a pharmaceutically acceptable salt thereof: Examples of antiviral agents that may be combined in the pharmaceutical compositions and regimens used in the uses and methods described herein include TDF, TAF, emtricitabine (FTC), lamivudine (3TC), abacavir (ABC), zidovudine (AZT), efavirenz (EFV), rilpivirine (RPV), etravirine (ETV), atazanavir (ATV), atazanavir+ritonavir (ATV/r), atazanavir+cobicistat (ATV/COBI), darunavir (DRV), darunavir+ritonavir (DRV/r), darunavir+cobicistat (DRV/COBI), lopinavir (LPV), lopinavir+ritonavir (LPV/r), lopinavir+cobicistat (LPV/COBI), dolutegravir (DTG), raltegravir (RAL), elvitegravir (EVG), elvitegravir+ritonavir (EVG/r), elvitegravir+cobicistat (EVG/COBI), and maraviroc. As such, provided are separate combinations, each comprising a pharmaceutically effective amount of a TLR7 modulator, including those of each of the formulas and specific examples herein, or a pharmaceutically acceptable salt thereof, in combination with a pharmaceutically effective amount of each agent in the separate antiviral combinations of TDF/TAF, TDF/FTC, TDF/3TC, TDF/ABC, TDF/AZT, TDF/EFV, TDF/RPV, TDF/ETV, TDF/ATV, TDFATV/r, TDF/ATV/COBI, TDF/DRV, TDF/DRV/r. TDF/DRV/COBI, TDF/LPV, TDF/LPV/r, TDF/LPV/COBI, TDF/DTG, TDF/RAL, TDF/EVG, TDF/EVG/r, TDF/EVG/COBI, TDF/maraviroc, TAF/FTC, TAF/3TC, TAF/ABC, TAF/AZT, TAF/EFV, TAF/RPV, TAF/ETV, TAF/ATV, TAF/ATV/r, TAF/ATV/COBI, TAF/DRV, TAF/DRV/r, TAF/DRV/COBI, TAF/LPV, TAF/LPV/r, TAF/LPV/COBI, TAF/DTG, TAF/RAL, TAF/EVG, TAF/EVG/r, TAF/EVG/COBI, TAF/maraviroc, FTC/3TC, FTC/ABC, FTC/AZT, FTC/EFV, FTC/RPV, FTC/ETV, FTC/ATV, FTC/ATV/r, FTC/ATV/COBI, FTC/DRV, FTC/DRV/r, FTC/DRV/COBI, FTC/LPV, FTC/LPV/r, FTC/LPV/COBI, FTC/DTG, FTC/RAL, FTC/EVG, FTC/EVG/r, FTC/EVG/COBI, FTC/maraviroc, 3TC/ABC, 3TC/AZT, 3TC/EFV, 3TC/RPV, 3TC/ETV, 3TC/ATV, 3TC/ATV/r, 3TC/ATV/COBI, 3TC/DRV, 3TC/DRV/r, 3TC/DRV/COBI, 3TC/LPV, 3TC/LPV/r, 3TC/LPV/COBI, 3TC/DTG, 3TC/RAL, 3TC/EVG, 3TC/EVG/r, 3TC/EVG/COBI, 3TC/maraviroc, ABC/AZT, ABC/EFV, ABC/RPV, ABC/ETV, ABC/ATV, ABC/ATV/r, ABC/ATV/COBI, ABC/DRV, ABC/DRV/r, ABC/DRV/COBI, ABC/LPV, ABC/LPV/r, ABC/LPV/COBI, ABC/DTG, ABC/RAL, ABC/EVG, ABC/EVG/r, ABC/EVG/COBI, ABC/maraviroc, AZT/EFV, AZT/RPV, AZT/ETV, AZT/ATV, AZT/ATV/r, AZT/ATV/COBI, AZT/DRV, AZT/DRV/r, AZT/DRV/COBI, AZT/LPV, AZT/LPV/r, AZT/LPV/COBI, AZT/DTG, AZT/RAL, AZT/EVG, AZT/EVG/r, AZT/EVG/COBI, AZT/maraviroc, EFV/RPV, EFV/ETV, EFV/ATV, EFV/ATV/r, EFV/ATV/COBI, EFV/DRV, EFV/DRV/r, EFV/DRV/COBI, EFV/LPV, EFV/LPV/r, EFV/LPV/COBI, EFV/DTG, EFV/RAL, EFV/EVG, EFV/EVG/r, EFV/EVG/COBI, EFV/maraviroc, RPV/ETV, RPV/ATV, RPV/ATV/r, RPV/ATV/COBI, RPV/DRV, RPV/DRV/r, RPV/DRV/COBI, RPV/LPV, RPV/LPV/r, RPV/LPV/COBI, RPV/DTG, RPV/RAL, RPV/EVG, RPV/EVG/r, RPV/EVG/COBI, RPV/maraviroc, ETV/ATV, ETV/ATV/r, ETV/ATV/COBI, ETV/DRV, ETV/DRV/r, ETV/DRV/COBI, ETV/LPV, ETV/LPV/r, ETV/LPV/COBI, ETV/DTG, ETV/RAL, ETV/EVG, ETV/EVG/r, ETV/EVG/

COBI, ETV/maraviroc, ATV/r, ATV/COBI, ATV/DRV, ATV/DRV/r, ATV/DRV/COBI, ATV/LPV, ATV/LPV/r, ATV/LPV/COBI, ATV/DTG, ATV/RAL, ATV/EVG, ATV/EVG/r, ATV/EVG/COBI, ATV/maraviroc, ATV/r/COBI, ATV/rDRV, ATV/rDRV/COBI, ATV/r/LPV, ATV/r/LPV, ATV/r/LPV/COBI, ATV/r/DTG, ATV/r/RAL, ATV/r/EVG, ATV/r/EVG, ATV/r/EVG/COBI, ATV/r/maraviroc, ATV/COBI/DRV, ATV/COB/I DRV/r, ATV/COBI/DRV, ATV/COBI/LPV, ATV/COBI/LPV/r, ATV/COBILPV/COBI, ATV/COBI/DTG, ATV/COBI/RAL, ATV/COBI/EVG, ATV/COBI/EVG/r, ATV/COBI/EVG, ATV/COBI/maraviroc, DRV/r, DRV/COBI, DRV/LPV, DRV/LPV/r, DRV/LPV/COBI, DRV/DTG,
DRV/RAL, DRV/EVG, DRV/EVG/r, DRV/EVG/COBI, DRV/maraviroc, DRV/r, DRV/COBI, DRV/r/LPV, DRV/r/LPV/COBI, DRV/r/DTG, DRV/r/RAL, DRV/r/EVG, DRV/r/EVG/COBI, DRV/maraviroc, DRV/COBI/LPV, DRV/COB/ILPV/r, DRV/COBI/LPV/COBI, DRV/COBI/DTG, DRV/COBI/RAL, DRV/COBI/EVG, DRV/COBI/EVG/r, DRV/COBI/EVG/COBI, DRV/COBI/maraviroc, LPV/r, LPV/COBI, LPV/DTG, LPV/RAL, LPV/EVG, LPV/EVG/r, LPV/EVG/COBI, LPV/maraviroc, LPV/r/LPV/COBI, LPV/r/DTG, LPV/r/RAL, LPV/r/EVG, LPV/r/EVG/COBI, LPV/r/maraviroc, LPV/COBI/DTG, LPV/COBI/RAL, LPV/COBI/EVG, LPV/COBI/EVG/r, LPV/COBI/EVG, LPV/COBI/maraviroc, DTG/RAL, DTG/EVG, DTG/EVG/r, DTG/EVG/COBI, DTG/maraviroc, RAL/EVG, RAL/EVG/r, RAL/EVG/COBI, RAL/maraviroc, EVG/r, EVG/COBI, and EVG/maraviroc. Also provided are separate pharmaceutical compositions, the separate compositions each comprising a pharmaceutically acceptable carrier or excipient, a pharmaceutically effective amount of a TLR7 modulator, including in separate embodiments those of each of the formulas and specific examples herein, or a pharmaceutically acceptable salt thereof, and pharmaceutically effective amounts of each agent in the separate antiviral combinations listed in the preceding sentence. It is understood that the combination of an individual antiviral combination and an individual TLR7 modulator, along with a pharmaceutically acceptable carrier or excipient, comprises a separate pharmaceutical composition.

Specific embodiments of combinations which a) may be combined with a pharmaceutically acceptable carrier or excipient to prepare a pharmaceutical composition, or b) may be used in combination in each of the methods described herein, comprise the separate following examples, wherein "TLR7" refers to a TLR7 modulating compound, including each of those described herein. A specific example within each combination comprises the combination in which "TLR7" represents a compound of Formula II. One specific example within each combination comprises the combination in which "TLR7" represents a compound of Example 4. Another specific example within each combination comprises the combination in which "TLR7" represents a compound of Example 49. A further specific example within each combination comprises the combination in which "TLR7" represents a compound of Example 119. Yet another specific example within each combination comprises the combination in which "TLR7" represents a compound of Example 120. In each case, reference to a compound is understood to include the compound or a pharmaceutically acceptable salt thereof.

Combinations include TLR7/TDF/emtricitabine; TLR7/TAF/emtricitabine; TLR7/TDF/elvitegravir; TLR7/TAF/elvitegravir; TLR7/TDF/elvitegravir; TLR7/TAF/elvitegravir; TLR7/TDF/efavirenz; TLR7/TAF/efavirenz; TLR7/TDF/atazanavir; TLR7/TAF/atazanavir; TLR7/TDF/darunavir; TLR7/TAF/darunavir; TLR7/TDF/raltegravir; TLR7/TAF/raltegravir; TLR7/TDF/rilpivirine; TLR7/TAF/rilpivirine; TLR7/emtricitabine/elvitegravir; TLR7/emtricitabine/efavirenz; TLR7/emtricitabine/atazanavir; TLR7/emtricitabine/darunavir; TLR7/emtricitabine/raltegravir; TLR7/emtricitabine/rilpivirine; TLR7/elvitegravir/efavirenz; TLR7/elvitegravir/atazanavir; TLR7/elvitegravir/darunavir; TLR7/elvitegravir/raltegravir; TLR7/elvitegravir/rilpivirine; TLR7/efavirenz/atazanavir; TLR7/efavirenz/darunavir; TLR7/efavirenz/raltegravir; TLR7/efavirenz/rilpivirine; TLR7/atazanavir/darunavir; TLR7/atazanavir/raltegravir; TLR7/atazanavir/rilpivirine; TLR7/darunavir/raltegravir; TLR7/darunavir/rilpivirine; TLR7/raltegravir/rilpivirine; TLR7/darunavir/ritonavir; TLR7/GSK1265744/rilpivirine; and TLR7/abacavir/lamivudine.

Specific embodiments of quaternary combinations which a) may be combined with a pharmaceutically acceptable carrier or excipient to prepare a pharmaceutical composition, or b) may be used in combination in each of the methods described herein, comprise, for example: TLR7/TDF/emtricitabine/dolutegravir; TLR7/TAF/emtricitabine/dolutegravir; TLR7/TDF/emtricitabine/elvitegravir; TLR7/TAF/emtricitabine/elvitegravir; TLR7/TDF/emtricitabine/efavirenz; TLR7/TAF/emtricitabine/efavirenz; TLR7/TDF/emtricitabine/atazanavir; TLR7/TAF/emtricitabine/atazanavir; TLR7/TDF/emtricitabine/darunavir; TLR7/TAF/emtricitabine/darunavir; TLR7/TDF/emtricitabine/raltegravir; TLR7/TAF/emtricitabine/raltegravir; TLR7/TDF/emtricitabine/rilpivirine; TLR7/TAF/emtricitabine/rilpivirine; TLR7/TDF/elvitegravir/efavirenz; TLR7/TAF/elvitegravir/efavirenz; TLR7/TDF/elvitegravir/atazanavir; TLR7/TAF/elvitegravir/atazanavir; TLR7/TDF/elvitegravir/darunavir; TLR7/TAF/elvitegravir/darunavir; TLR7/TDF/elvitegravir/raltegravir; TLR7/TAF/elvitegravir/raltegravir; TLR7/TDF/elvitegravir/rilpivirine; TLR7/TAF/elvitegravir/rilpivirine; TLR7/TDF/efavirenz/atazanavir; TLR7/TAF/efavirenz/atazanavir; TLR7/TDF/efavirenz/darunavir; TLR7/TAF/efavirenz/darunavir; TLR7/TDF/efavirenz/raltegravir; TLR7/TAF/efavirenz/raltegravir; TLR7/TDF/efavirenz/rilpivirine; TLR7/TAF/efavirenz/rilpivirine; TLR7/TDF/atazanavir/darunavir; TLR7/TAF/atazanavir/darunavir; TLR7/TDF/atazanavir/raltegravir; TLR7/TAF/atazanavir/raltegravir; TLR7/TDF/atazanavir/rilpivirine; TLR7/TAF/atazanavir/rilpivirine; TLR7/TDF/darunavir/raltegravir; TLR7/TAF/darunavir/raltegravir; TLR7/TDF/darunavir/rilpivirine; TLR7/TAF/darunavir/rilpivirine; TLR7/emtricitabine/elvitegravir/efavirenz; TLR7/emtricitabine/elvitegravir/atazanavir; TLR7/emtricitabine/elvitegravir/darunavir; TLR7/emtricitabine/elvitegravir/raltegravir; TLR7/emtricitabine/elvitegravir/rilpivirine; TLR7/emtricitabine/efavirenz/atazanavir; TLR7/emtricitabine/efavirenz/darunavir; TLR7/emtricitabine/efavirenz/raltegravir; TLR7/emtricitabine/efavirenz/rilpivirine; TLR7/emtricitabine/atazanavir/darunavir; TLR7/emtricitabine/atazanavir/raltegravir; TLR7/emtricitabine/atazanavir/rilpivirine; TLR7/emtricitabine/darunavir/raltegravir; TLR7I/emtricitabine/darunavir/rilpivirine; TLR7/emtricitabine/raltegravir/rilpivirine; TLR7/elvitegravir/efavirenz/atazanavir; TLR7/elvitegravir/efavirenz/darunavir; TLR7/elvitegravir/efavirenz/raltegravir; TLR7/elvitegravir/efavirenz/rilpivirine; TLR7/elvitegravir/atazanavir/darunavir; TLR7/elvitegravir/atazanavir/raltegravir; TLR7/elvitegravir/raltegravir/rilpivirine; TLR7/efavirenz/atazanavir/darunavir; TLR7/efavirenz/atazanavir/raltegravir; TLR7/efavirenz/atazanavir/rilpivirine; TLR7/efavirenz/darunavir/raltegravir; TLR7/efavirenz/darunavir/rilpivirine; TLR7/efavirenz/raltegravir/rilpivirine; TLR7/atazanavir/ darunavir/raltegravir; TLR7/atazanavir/darunavir/rilpivirine; TLR7/darunavir/raltegravir/rilpivirine; TLR7/dolutegravir/abacavir/lamivudine; TLR7/raltegravir/darunavir; TLR7/raltegravir/ritonavir/darunavir; TLR7/raltegravir/cobicistat/darunavir; TLR7/raltegravir/atazanavir; TLR7/raltegravir/atazanavir/maraviroc; TLR7/raltegravir/maraviroc/etravirine; TLR7/raltegravir/maraviroc/rilpivirine; TLR7/maraviroc/darunavir/ritonavir; TLR7/maraviroc/darunavir/cobicistat; TLR7/raltegravir/darunavir/ritonavir/maraviroc; TLR7/raltegravir/darunavir/cobicistat/maraviroc; TLR7/raltegravir/darunavir/ritonavir/etravirine; TLR7/raltegravir/darunavir/cobicistat/etravirine; TLR7/atazanavir/ritonavir/efavirenz; TLR7/atazanavir/cobicistat/efavirenz; TLR7/raltegravir/etravirine; TLR7/ritonavir/lopinavir/raltegravir; TLR7/cobicistat/lopinavir/raltegravir; TLR7/ritonavir/darunavir/etravirine; TLR7/cobicistat/darunavir/etravirine; TLR7/ritonavir/lopinavir; and TLR7/ritonavir/lopinavir/maraviroc.

Additional specific embodiments of comprise the combination of a) a pharmaceutically effective amount of a TLR7 modulating compound, including those of each of the formulas and specific examples herein, b) a pharmaceutically acceptable carrier or excipient, and c) a combination of five or more antiviral agents. These combinations may be used to prepare a pharmaceutical composition and/or may be used in combination in each of the methods described herein. Such combinations comprise, for example, a pharmaceutically effective amount of a TLR7 modulating compound, including those of each of the formulas and specific examples herein, including individual embodiments in each combination in which the TLR7 modulating compound is, respectively, a compound of Formula II, a compound of Example 4, a compound of Example 49, a compound of Example 119, a compound of Example 120, and the antiviral agents in each individual group of: TDF/emtricitabine/atazanavir/ritonavir/maraviroc/raltegravir; TAF/emtricitabine/atazanavir/ritonavir/maraviroc/raltegravir; TDF/emtricitabine/atazanavir/cobicistat/maraviroc/raltegravir; TAF/emtricitabine/atazanavir/cobicistat/maraviroc/raltegravir; TDF/emtricitabine/atazanavir/ritonavir/maraviroc/dolutegravir; TAF/emtricitabine/atazanavir/ritonavir/maraviroc/dolutegravir; TDF/emtricitabine/atazanavir/cobicistat/maraviroc/dolutegravir; TAF/emtricitabine/atazanavir/cobicistat/maraviroc/dolutegravir; TDF/emtricitabine/darunavir/ritonavir/maraviroc/raltegravir; TAF/emtricitabine/darunavir/ritonavir/maraviroc/raltegravir; TDF/emtricitabine/darunavir/cobicistat/maraviroc/raltegravir; TAF/emtricitabine/darunavir/cobicistat/maraviroc/raltegravir; TDF/emtricitabine/darunavir/ritonavir/maraviroc/dolutegravir; TAF/emtricitabine/darunavir/ritonavir/maraviroc/dolutegravir; TDF/emtricitabine/darunavir/cobicistat/maraviroc/dolutegravir; TAF/emtricitabine/darunavir/cobicistat/maraviroc/dolutegravir; TDF/emtricitabine/efavirenz/ritonavir/lopinavir/maraviroc; TAF/emtricitabine/efavirenz/ritonavir/lopinavir/maraviroc; TDF/emtricitabine/efavirenz/cobicistat/lopinavir/maraviroc; TAF/emtricitabine/efavirenz/cobicistat/lopinavir/maraviroc; TDF/emtricitabine/cobicistat/lopinavir/maraviroc/raltegravir; TAF/emtricitabine/cobicistat/lopinavir/maraviroc/raltegravir; TDF/emtricitabine/ritonavir/lopinavir/maraviroc/raltegravir; TAF/emtricitabine/ritonavir/lopinavir/maraviroc/raltegravir; TDF/emtricitabine/cobicistat/lopinavir/maraviroc/dolutegravir; TAF/emtricitabine/cobicistat/lopinavir/maraviroc/dolutegravir; TDF/emtricitabine/ritonavir/lopinavir/maraviroc/dolutegravir; TAF/emtricitabine/ritonavir/lopinavir/maraviroc/dolutegravir; TDF/emtricitabine/cobicistat/fosamprenavir/maraviroc/raltegravir; TAF/emtricitabine/cobicistat/fosamprenavir/maraviroc/raltegravir; TDF/emtricitabine/ritonavir/fosamprenavir/maraviroc/raltegravir; TAF/emtricitabine/ritonavir/fosamprenavir/maraviroc/raltegravir; TDF/emtricitabine/cobicistat/fosamprenavir/maraviroc/dolutegravir; TAF/emtricitabine/cobicistat/fosamprenavir/maraviroc/dolutegravir; TDF/emtricitabine/ritonavir/fosamprenavir/maraviroc/dolutegravir; and TAF/emtricitabine/ritonavir/fosamprenavir/maraviroc/dolutegravir.

In each of the combinations above, the specific agents in each combination may be administered in any pharmaceutically effective amount known in the art. In specific embodiments the agents are utilized in the combinations that include them in the following individual doses: tenofovir disoproxil fumarate (TDF) from about 250 mg to from about 350 mg/dose; TAF from about 5 mg to about 50 mg, emtricitabine from about 150 mg to about 250 mg/dose; elvitegravir, when administered in combination with a boosting agent such as cobicistat or ritonavir, from about 100 mg to about 200 mg/dose, and unboosted elvitegravir from about 800 mg to about 1200 mg; efavirenz from about 500 mg to about 700 mg/dose; atazanavir from about 250 mg to about 350 mg/dose; darunavir from about 700 mg to about 900 mg/dose; raltegravir from about 350 mg to about 450 mg/dose; rilpivirine from about 20 mg to about 30 mg/dose (or from about 22.5 mg to about 32.5 mg/dose as rilpivirine HCL); ritonavir from about 50 mg to about 150 mg/dose; dolutegravir from about 30 mg to about 70 mg/dose, abacavir from about 500 mg to about 700 mg/dose, lamivudine from about 250 mg to about 350 mg/dose, GSK1265744 from about 10 mg to about 50 mg/dose, cobicistat from about 100 mg to 200 mg/dose, atazanavir from about 250 mg to about 350 mg/dose, maraviroc from about 100 mg to about 200 mg/dose, etravirine from about 100 mg to about 300 mg/dose, lopinavir from about 300 mg to about 500 mg/dose, and zidovudine from about 500 mg to about 750 mg/day.

In other specific embodiments the agents are utilized in the combinations that include them in the following individual doses: tenofovir disoproxil fumarate (TDF) from about 275 mg to about 325 mg/dose; TAF from about 5 mg to about 30 mg, emtricitabine from about 175 mg to about 225 mg/dose; elvitegravir from about 125 mg to about 175 mg/dose, when boosted by a boosting agent such as cobicistat or ritonavir; efavirenz from about 550 mg to about 650 mg/dose; atazanavir from about 275 mg to about 325 mg/dose; darunavir from about 750 mg to about 850 mg/dose; raltegravir from about 375 mg to about 425 mg/dose; rilpivirine from about 22 mg to about 28 mg/dose (or from about 24.5 mg to about 30.5 mg/dose as rilpivirine HCL); ritonavir from about 75 mg to about 125 mg/dose; dolutegravir from about 40 mg to about 60 mg/dose, abacavir from about 550 mg to about 650 mg/dose, lamivudine from about 275 mg to about 325 mg/dose, GSK1265744 from about 20 mg to about 40 mg/dose, cobicistat from about 125 mg to 175 mg/dose, atazanavir from about 275 mg to about 325 mg/dose, maraviroc from about 125 mg to about 175 mg/dose, etravirine from about 150 mg to about 250 mg/dose, lopinavir from about 350 mg to about 450 mg/dose, and zidovudine from about 550 mg to about 650 mg/day.

In further specific embodiments the agents are utilized in the combinations that include them in the following individual doses: tenofovir disoproxil fumarate (TDF) at about 300 mg/dose; TAF at about 25 mg/dose or at about 10 mg per dose in the presence of a boosting agent, such as cobicistat or ritonavir, emtricitabine at about 200 mg/dose;

elvitegravir at about 150 mg/dose, when boosted by cobicistat or ritonavir; efavirenz at about 600 mg/dose; atazanavir at about 300 mg/dose; darunavir at about 800 mg/dose; raltegravir at about 400 mg/dose; rilpivirine at about 25 mg/dose (or at about 27.5 mg/dose as rilpivirine HCL); ritonavir at about 100 mg/dose; dolutegravir at about 50 mg/dose, abacavir at about 600 mg/dose, lamivudine at about 300 mg/dose, GSK1265744 at about 30 mg/dose, cobicistat at about 150 mg/dose, atazanavir at about 300 mg/dose, maraviroc at about 150 mg/dose, etravirine at about 200 mg/dose, lopinavir at about 400 mg/dose, and zidovudine at about 600 mg/day.

The TLR7 modulating compounds in the combinations above, including those of Formula II, and Examples 4, 49, 119, 120, and 121, or a pharmaceutically acceptable salt thereof, may be administered at from about 0.1 mg to about 15 mg/dose. Other embodiments within each of the combinations include the TLR7 modulating compounds being utilized in dosage ranges of from 0.1 mg to 5 mg/dose, from 2 mg to 6 mg/dose, from 5 mg to 10 mg/dose, and from 10 mg to 15 mg/dose.

It is understood that each of the dose ranges for the TLR7 modulating compounds can be combined in pharmaceutical compositions and pharmaceutical combinations and regiments with each of the doses for the other combination agents discussed above. For instance, the combination listed above as Example 49/TDF/emtricitabine/dolutegravir includes the specific combinations comprising 0.1 mg to 15 mg per dose of Example 49/from about 250 mg-350 mg per dose TDF/from about 150 mg to about 250 mg per dose emtricitabine/from about 30 mg to about 70 mg per dose dolutegravir; 0.1 mg to 15 mg per dose of Example 49/from about 275 mg-325 mg per dose TDF/from about 175 mg to about 225 mg per dose emtricitabine/from about 40 mg to about 60 mg per dose dolutegravir; 0.1 mg to 15 mg per dose of Example 49/300 mg per dose TDF/200 mg per dose emtricitabine/50 mg per dose dolutegravir; from 2 mg to 6 mg per dose of Example 49/from about 250 mg-350 mg per dose TDF/from about 150 mg to about 250 mg per dose emtricitabine/from about 30 mg to about 70 mg per dose dolutegravir; 2 mg to 6 mg per dose of Example 49/from about 275 mg-325 mg per dose TDF/about 175 mg to about 225 mg per dose emtricitabine/from about 40 mg to about 60 mg per dose dolutegravir; 2 mg to 6 mg per dose of Example 49/300 mg per dose TDF/200 mg per dose emtricitabine/50 mg per dose dolutegravir; 5 mg to 10 mg per dose of Example 49/from about 250 mg-350 mg per dose TDF/from about 150 mg to about 250 mg per dose emtricitabine/from about 30 mg to about 70 mg per dose dolutegravir; 5 mg to 10 mg per dose of Example 49/from about 275 mg-325 mg per dose TDF/from about 175 mg to about 225 mg per dose emtricitabine/from about 40 mg to about 60 mg per dose dolutegravir; 5 mg to 10 mg per dose of Example 49/300 mg per dose TDF/200 mg per dose emtricitabine/50 mg per dose dolutegravir; 10 mg to 15 mg per dose of Example 49/from about 250 mg-350 mg per dose TDF/from about 150 mg to about 250 mg per dose emtricitabine/from about 30 mg to about 70 mg per dose dolutegravir; 10 mg to 15 mg per dose of Example 49/from about 275 mg-325 mg per dose TDF/from about 175 mg to about 225 mg per dose emtricitabine/from about 40 mg to about 60 mg per dose dolutegravir; and 10 mg to 15 mg per dose of Example 49/300 mg per dose TDF/200 mg per dose emtricitabine/50 mg per dose dolutegravir. It is understood that each of the corresponding dose range combinations are included for each of the combinations of agents listed herein. It is understood that corresponding combinations are intended wherein, for each specific combination in this paragraph corresponding combinations exist wherein Example 49 is replaced with another compound of Formula II or the other formulas described herein or each of Examples 1 through 121, including Examples 4, 49, 119, 120, and 121. It is also understood that the same breadth of intended combinations applies to each of the formulations listed above combining a TLR7 modulating compound with HIV agents and that embodiments exist wherein each of the combinations is used in the methods herein.

In yet another embodiment, the present application provides a combination pharmaceutical agent comprising:
a) a first pharmaceutical composition comprising a TLR7 modulating compound as described herein, or a pharmaceutically acceptable salt, solvate, or ester thereof; and
b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, HIV capsid inhibitors, interferons, immunomodulatory cytokines (IL-7, IL-15), ribavirin analogs, NS3 protease inhibitors, alpha-glucosidase 1 inhibitors, hepatoprotectants, nucleotide inhibitors of HCV, nucleoside inhibitors of HCV, non-nucleoside inhibitors of HCV, and other drugs for treating HCV, and combinations thereof. Forms of IL-15 useful in the methods herein include human native and recombinant IL-15, including the heterodimer hetIL-15, recombinant human IL-15 (rhIL15).

Within each of the embodiments herein that include "a pharmaceutically effective amount of a compound of Formula II, or a pharmaceutically acceptable salt thereof", including uses, methods of treatment, pharmaceutical compositions, regimens, and kits, it is understood that separate further embodiments are contemplated wherein all other components or elements are as defined for the original embodiment and the "compound of Formula II, or a pharmaceutically acceptable salt thereof" is, in separate embodiments, a compound selected from each of the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), and each of the individual compounds of the examples from Example 1 through Example 124, or a pharmaceutically acceptable salt thereof.

Inducing HIV Gene Expression in a Human Infected with HIV

Provided is a method of inducing HIV gene expression in a human infected with HIV, wherein active HIV gene expression in the human has been suppressed by administration of antiretroviral therapy, the method comprising administering to the human a pharmaceutically a pharmaceutically effective amount of a TLR7 modulating compound, or a pharmaceutically acceptable salt thereof.

Provided is a method of inducing HIV gene expression in a human infected with HIV, wherein active HIV gene expression in the human has been suppressed by administration of combination antiretroviral therapy, the method comprising administering to the human a pharmaceutically effective amount of a compound of Formula II, or a pharmaceutically acceptable salt thereof.

Provided is a method of inducing HIV gene expression in a human infected with HIV, the method comprising administration of combination antiretroviral therapy until active HIV replication is suppressed, followed by administering to the human a pharmaceutically effective amount of a compound of Formula II, or a pharmaceutically acceptable salt thereof.

Provided is a method of inducing HIV gene expression in an HIV-infected human undergoing combination antiretroviral therapy, the method comprising administering to the human a pharmaceutically effective amount of a compound of Formula II, or a pharmaceutically acceptable salt thereof.

Provided is a method of inducing HIV gene expression in HIV infected cells in a human, the method comprising administering to the human a pharmaceutically effective amount of a compound of Formula II, or a pharmaceutically acceptable salt thereof.

Also provided is a method of inducing HIV gene expression in HIV infected cells in a human, the method comprising administering to the human a pharmaceutically effective amount of a compound of Formula II, or a pharmaceutically acceptable salt thereof.

Also provided are separate methods of inducing HIV gene expression in HIV infected cells in a human, each of the separate methods comprising administering to the human a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are group of separate methods of inducing HIV gene expression gene expression in HIV infected cells in a human infected with HIV, each of the separate methods comprising administering to the human infected with HIV a pharmaceutically effective amount of a compound selected from one of the compounds from Example 1 through Example 124, or a pharmaceutically acceptable salt thereof. The first of the group of separate methods of inducing HIV gene expression in HIV infected cells in a human infected with HIV comprises administering to the human infected with HIV a pharmaceutically effective amount of the compound of Example 1, or a pharmaceutically acceptable salt thereof, the second method comprises administering to the human infected with HIV a pharmaceutically effective amount of the compound of Example 2, or a pharmaceutically acceptable salt thereof, etc.

As an example, provided is a method of inducing HIV gene expression in HIV infected cells in a human, the method comprising administering to the human a pharmaceutically effective amount of the compound of Example 4, having the formula:

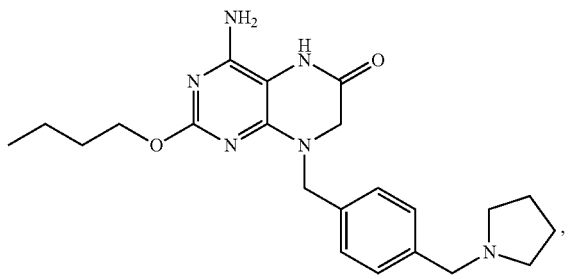 [SMILES: CCCCOc1nc(N)c2c(n1)N(Cc1ccc(CN3CCCC3)cc1)CC(=O)N2]

or a pharmaceutically acceptable salt thereof.

Also provided is a method of inducing HIV gene expression in HIV infected cells in a human infected with HIV, the method comprising administering to the human infected with HIV a pharmaceutically effective amount of the compound of Example 49, having the formula:

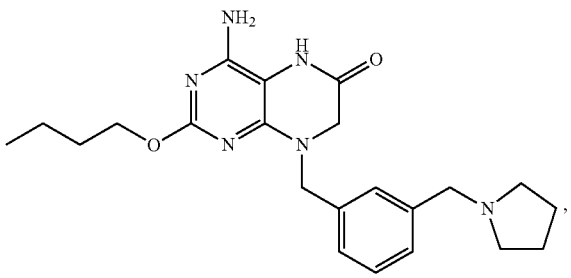 [SMILES: CCCCOc1nc(N)c2c(n1)N(Cc1cccc(CN3CCCC3)c1)CC(=O)N2]

or a pharmaceutically acceptable salt thereof.

Also provided is a method of inducing HIV gene expression in HIV infected cells in a human, the method comprising administering to the human a pharmaceutically effective amount of the compound of Example 119, having the formula:

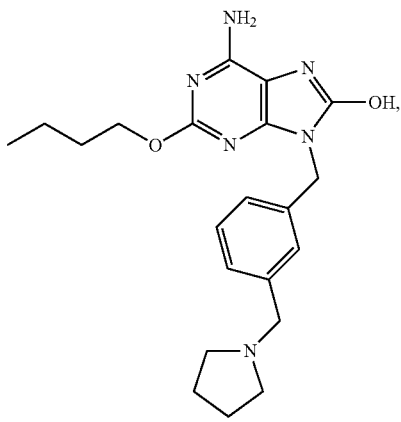 [SMILES: CCCCOc1nc(N)c2nc(O)n(Cc3cccc(CN4CCCC4)c3)c2n1]

or a pharmaceutically acceptable salt thereof.

Also provided is a method of inducing HIV gene expression in HIV infected cells in a human, the method comprising administering to the human a pharmaceutically effective amount of the compound of Example 120, having the formula:

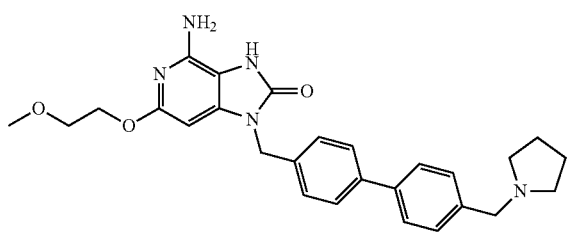 [SMILES: COCCOc1cc2c([nH]c(=O)n2Cc2ccc(-c3ccc(CN4CCCC4)cc3)cc2)c(N)n1]

or a pharmaceutically acceptable salt thereof.

Also provided is a method of inducing HIV gene expression in HIV infected cells in a human, the method comprising administering to the human a pharmaceutically effective amount of the compound of Example 121, or a pharmaceutically acceptable salt thereof.

Latent Reservoir

Provided is a method of inducing HIV gene expression in a latent HIV reservoir in a human infected with HIV, the method comprising administering to the human infected with HIV a pharmaceutically effective amount of a TLR7 modulating compound, or a pharmaceutically acceptable salt thereof.

Also provided is a method of inducing HIV gene expression in a latent HIV reservoir in a human infected with HIV, the method comprising administering to the human infected with HIV a pharmaceutically effective amount of a compound of Formula II, or a pharmaceutically acceptable salt thereof.

Also provided are twenty separate methods of inducing HIV gene expression in HIV infected cells in a latent HIV reservoir in a human infected with HIV, each of the separate methods comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof. It is understood that one of such methods comprises administering to the human infected with HIV a pharmaceutically effective amount of Formula III, or a pharmaceutically acceptable salt thereof, another method comprises administering to the human infected with HIV a pharmaceutically effective amount of Formula III(a), etc.

Also provided are group of separate methods of inducing HIV gene expression in HIV infected cells in a latent HIV reservoir in a human infected with HIV, each of the 120 separate methods comprising administering to the human infected with HIV a pharmaceutically effective amount of a compound selected from one of Examples 1 through 124, or a pharmaceutically acceptable salt thereof. One of each of the compounds from Example 1 to Example 124 are utilized in each of the group of separate methods, with the compound of Example 1, or a pharmaceutically acceptable salt thereof, being used in the first method, the compound of Example 2, or a pharmaceutically acceptable salt thereof, being used in the second method, etc.

For example, provided is a method of inducing HIV gene expression in HIV infected cells in a latent HIV reservoir in a human infected with HIV, the method comprising administering to the human infected with HIV a pharmaceutically effective amount of the compound of Example 4, or a pharmaceutically acceptable salt thereof.

Also provided is a method of inducing HIV gene expression in HIV infected cells in a latent HIV reservoir in a human infected with HIV, the method comprising administering to the human infected with HIV a pharmaceutically effective amount of the compound of Example 49, or a pharmaceutically acceptable salt thereof.

Also provided is a method of inducing HIV gene expression in HIV infected cells in a latent HIV reservoir in a human infected with HIV, the method comprising administering to the human infected with HIV a pharmaceutically effective amount of the compound of Example 119, or a pharmaceutically acceptable salt thereof.

Also provided is a method of inducing HIV gene expression in HIV infected cells in a latent HIV reservoir in a human infected with HIV, the method comprising administering to the human infected with HIV a pharmaceutically effective amount of a compound of Example 120, or a pharmaceutically acceptable salt thereof.

Also provided is a method of inducing HIV gene expression in HIV infected cells in a latent HIV reservoir in a human infected with HIV, the method comprising administering to the human infected with HIV a pharmaceutically effective amount of a compound of Example 121, or a pharmaceutically acceptable salt thereof.

For each of the methods of inducing HIV gene expression in HIV infected cells in a latent HIV reservoir in a human infected with HIV discussed above, there is a further embodiment in which the pharmaceutically effective amount of the referenced compound of Formula II or Example 4, Example 49, Example 119, Example 120, or Example 121 is from 0.1 mg to 15.0 mg of the compound, or a pharmaceutically acceptable salt thereof. There is a further embodiment for each of the methods in which the pharmaceutically effective amount of the referenced compound of Formula II or Example 4, Example 49, Example 119, Example 120, or Example 121 is from 4.0 mg to 6.0 mg of the compound, or a pharmaceutically acceptable salt thereof. There is another embodiment for each of the methods in which the pharmaceutically effective amount of the referenced compound of Formula II or Example 4, Example 49, Example 119, Example 120, or Example 121 is from 5.0 mg to 15.0 mg of the compound, or a pharmaceutically acceptable salt thereof.

Further embodiments for each of the methods, combinations, and pharmaceutical compositions described herein further comprise the addition of one or more latency-reversing agents (LRAs), also known as latency-reversing drugs (LRDs), such as: histone deacetylase inhibitors, including hydroxamic acids (or hydroxamates) such as trichostatin A; cyclic tetrapeptides (such as trapoxin B) and the depsipeptides; benzamides; electrophilic ketones; aliphatic acid compounds such as phenylbutyrate and valproic acid, hydroxamic acids such as vorinostat (suberoylanilide hydroxamic acid—SAHA), belinostat, LAQ824, panobinostat, benzamides (e.g., entinostat (MS-275), CI994, mocetinostat, 4SC-202, abexinostat, ACTR, ACY-1215, AR-42, CG200745, CHR-2845, CHR-3996, CUDC-101, entinostat, GATA, givinostat, kevetrin, mocetinostat, panobinostat, resminostat, romidepsin, runx, SB939, sulforaphane, trichostatin A (TSA), trichostatin B, trichostatin C, trapoxin A, trapoxin B, chlamydocin, sodium salts of butyrate (sodium butyrate), butyric acid, sodium salts of phenylbutyrate, phenylbutyric acid, scriptaid, FR901228, depudecin, oxamflatin, pyroxamide, apicidin B, apicidin C, Helminthsporium carbonum toxin, 2-amino-8-oxo-9, 10-epoxy-decanoyl, 3-(4-aroyl-IH-pyrrol-2-yl)-N-hydroxy-2-propenamide, suberoylanilide hydroxamic acid, FK228 or m-carboxycinnamic acid bis-hydroxamide, ITF2357, MCT-1, MCT-3, NHC-51, and any of the histone deacetylase inhibitor compounds disclosed in Archin M N et al., AIDS 2009; 1799-806, which are incorporated herein by reference;

Akt pathway modulators such as disulfiram (Doyon et al, AIDS 2013 Jan. 14; 27(2):F7-F11);

methylation inhibitors, such as DNMTi, 5-aza-2'deoxycitidine (5-aza-dc), decitabine, DL-ethionine, D-methionine, 5-azacytidine, 5-aza-2'deoxycytidine, 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fiuoro-2'deoxycytosine, procainamide, Zebularine, and (–)-egallocatechin-3-gallate;

protein kinase C (PKC) modulators, such as indolactam, Ingenol and its derivative such as ingenol B, prostratin, bryostatin, rottlerin, isoquinoline sulfonamide H-7 and analogs thereof, 4-aminomethyl-I-[2,3-(di-n-decyloxy)n-propyl]-4-phenylpiperidine, phenothiazine agents, tamoxifen, quercetin, verapamil, adriamycin, polymyxin B, gangliosides, sangivamycin, retinal, staurosporine, aminoacridines, sphingosine and related sphingolipids;

modulators of cytokines, such as TNF-ct, TNF-β, IL-1, IL-6, IL-2, IL-4, IL-6, IL-7, IL-10, IL-15, IL-15SA, Acrp30, AgRP, amphiregulin, angiopoietin-1, AXL, BDNF, bFGF, BLC, BMP-4, BMP-6, b-NGF, BTC, CCL28, Ck beta 8-1, CNTF, CTACK CTAC, Skinkine, Dtk, EGF, EGF-R, ENA-78, eotaxin, eotaxin-2, MPIF-2, eotaxin-3, MIP-4-alpha, Fas Fas/TNFRSF6/Apo-I/CD95, FGF-4, FGF-6, FGF-7, FGF-9, Flt-3 Ligand fms-like tyrosine kinase-3, FKN or FK, GCP-2, GCSF, GDNF Glial, GITR, GITR, GM-CSF, GRO, GRO-a, HCC-4, hematopoietic growth factor, hepatocyte growth factor, I-309, ICAM-1, ICAM-3, IFN-γ, IGFBP-1, IGFBP-2, IGFBP-3, IGFBP-4, IGFBP-6, IGF-I, IGF-I SR, IL-Ia, IL-Iβ, IL-1, IL-1R4, ST2, IL-3, IL-4, IL-5, IL-6, IL-8, IL-10, IL-11, IL-12p40, IL-12p70, IL-13, IL-16, IL-17, IL-21, 1-TAC, alpha chemoattractant, lymphotactin, MCP-1, MCP-2, MCP-3, MCP-4, M-CSF, MDC, MIF, MIG, MIP-I, MIP-Iβ, MIP-Iδ, MIP-3a, MIP-3β, MSP-a, NAP-2, NT-3, NT-4, osteoprotegerin, oncostatin M, PARC, PDGF, P1GF, RANTES, SCF, SDF-1, soluble glycoprotein 130, soluble TNF receptor I, soluble TNF receptor II, TARC, TECK, TGF-beta 1, TGF-beta 3, TIMP-1, TIMP-2, TNF-a, TNF-β, thrombopoietin, TRAIL R3, TRAIL R4, uPAR, VEGF and VEGF-D;

modulators of AV6, HIV-1-reacting protein factor (HRF), Quinolin-8-ol, dactinomycin, aclarubicin, cytarabine, PKC412, englarin A, oxaliplatin, 1-cinnamoyl-3,11-dihydroxymeliacarpin (CDM), nordihydroguaiaretic acid (NDGA), and curcumin (Cur);

BRD4 inhibitors, such as JQ1 ([(R,S)-4-(4-Chlorophenyl)-2,3,9-trimethyl-6H-1-thia-5,7,8,9a-tetraaza-cyclopenta[e]azulen-6-yl]acetic acid tert-butyl ester), GSK525762 (IBET or (S)-2-(6-(4-chlorophenyl)-8-methoxy-1-methyl-4H-benzo[f][1,2,4]triazolo[4,3-a][1,4]diazepin-4-yl)-N-ethylacetamide), OTX015 (HY15743-(6S)-4-(4-chlorophenyl)-N-(4-hydroxyphenyl)-2,3,9-trimethyl-6H-thieno[3,2-f][1,2, 4]triazolo[4,3-a][1,4]diazepine-6-acetamide), CPI-0610, and Ten-010; and recombinant HIV Tat protein.

Method of Inducing Transient HIV Viremia

Also provided is a method for inducing transient HIV-1 viremia in a virologically suppressed human infected with HIV-1, the method comprising administering to the human a pharmaceutically effective amount of a TLR7 modulating compound, or a pharmaceutically acceptable salt thereof.

Also provided is a method for inducing transient HIV-1 viremia in a virologically suppressed human infected with HIV-1, wherein the virologically suppressed human infected with HIV is receiving a combination antiretroviral therapy, the method comprising administering to the human a pharmaceutically effective amount of a TLR7 modulating compound, or a pharmaceutically acceptable salt thereof.

Also provided is a method for inducing transient HIV-1 viremia in a virologically suppressed human infected with HIV-1, wherein the virologically suppressed human infected with HIV is receiving a combination antiretroviral therapy and has a plasma HIV-1 RNA concentration of less than 50 copies of HIV-1 RNA per mL, the method comprising administering to the human a pharmaceutically effective amount of a TLR7 modulating compound, or a pharmaceutically acceptable salt thereof, to increase the plasma HIV-1 RNA concentration in the human to a concentration of greater than 50 copies of HIV-1 RNA per mL. A further embodiment comprises this method in which the plasma HIV-1 RNA concentration in the human is raised to a concentration of from 50 copies of HIV-1 RNA per mL to at least 500 copies of HIV-1 RNA per mL. A further embodiment comprises this method in which the plasma HIV-1 RNA concentration in the human is raised to a concentration of from 50 copies of HIV-1 RNA per mL to at least 1,000 copies of HIV-1 RNA per mL. A further embodiment comprises this method in which the plasma HIV-1 RNA concentration in the human is raised to a concentration of from 50 copies of HIV-1 RNA per mL to at least 2,000 copies of HIV-1 RNA per mL.

Also provided is a method for inducing transient HIV-1 viremia in a virologically suppressed human infected with HIV-1, wherein the virologically suppressed human infected with HIV is receiving a combination antiretroviral therapy and has maintained a plasma HIV-1 RNA concentration of less than 50 copies of HIV-1 RNA per mL for a period of at least three months, the method comprising administering to the human a pharmaceutically effective amount of a TLR7 modulating compound, or a pharmaceutically acceptable salt thereof, to increase the plasma HIV-1 RNA concentration in the human to a concentration of greater than 50 copies of HIV-1 RNA per mL. A further embodiment comprises this method in which the plasma HIV-1 RNA concentration in the human is raised to a concentration of from 50 copies of HIV-1 RNA per mL or below to at least 500 copies of HIV-1 RNA per mL. A further embodiment comprises this method in which the plasma HIV-1 RNA concentration in the human is raised to a concentration of from 50 copies of HIV-1 RNA per mL or below to at least 1,000 copies of HIV-1 RNA per mL. A further embodiment comprises this method in which the plasma HIV-1 RNA concentration in the human is raised to a concentration of from 50 copies of HIV-1 RNA per mL or below to at least 2,000 copies of HIV-1 RNA per mL.

Also provided is a method for inducing transient HIV-1 viremia in a virologically suppressed human infected with HIV-1, wherein the virologically suppressed human infected with HIV is receiving a combination antiretroviral therapy and has maintained a plasma HIV-1 RNA concentration of less than 50 copies of HIV-1 RNA per mL for a period of at least six months, the method comprising administering to the human a pharmaceutically effective amount of a TLR7 modulating compound, or a pharmaceutically acceptable salt thereof, to increase the plasma HIV-1 RNA concentration in the human to a concentration of greater than 50 copies of HIV-1 RNA per mL. A further embodiment comprises this method in which the plasma HIV-1 RNA concentration in the human is raised to a concentration of from 50 copies of HIV-1 RNA per mL to at least 1,000 copies of HIV-1 RNA per mL. A further embodiment comprises this method in which the plasma HIV-1 RNA concentration in the human is raised to a concentration of from 50 copies of HIV-1 RNA per mL to at least 2,000 copies of HIV-1 RNA per mL. Additional separate embodiments exist for these methods in which the viral concentration of 50 copies of HIV-1 RNA per mL or less has been maintained in the human infected with HIV-1 for at least a) one month, b) two months, c) three months, d) four months, e) five months, f) six months, g) seven months, h) eight months, i) nine months, j) ten months, k) eleven months, and l) twelve months. Additional separate embodiments exist for these methods in which the viral concentration of 50 copies of HIV-1 RNA per mL or less has been maintained in the human infected with HIV-1 for a period of a) from about one month to about three months, b) from about two months to about three months, c) from about three months to about six months, d) from about six months to about 9 months, e) from about six months to about one year, f) from about nine months to about one year, g) from about ten months to about one year, h) from about one year to about one year and three months, i) from about one year to about one year and six months, j) from about one year to about one year and nine months, and k) from about one year to about two years.

Within methods for inducing transient HIV-1 viremia in a virologically suppressed human infected with HIV-1 above there are separate additional embodiments wherein the TLR7 modulating compound comprises a pharmaceutically effective amount of a TLR7 modulating compound selected from one of Formula II, Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III (c)(1), Formula III(c)(2), Formula III(d)(1), Formula III(d) (2), Formula III(e)(1), Formula III(e)(2), Formula III(f)(1), Formula III(f)(2), or of one of the individual compounds selected from Examples 1 through 124; or a pharmaceutically acceptable salt thereof.

As one example, provided is a method for inducing transient HIV-1 viremia in a virologically suppressed human infected with HIV-1, wherein the virologically suppressed human infected with HIV is receiving a combination antiretroviral therapy, the method comprising administering to the human a pharmaceutically effective amount of the compound of Example 4, or a pharmaceutically acceptable salt thereof.

As another example, provided is a method for inducing transient HIV-1 viremia in a virologically suppressed human infected with HIV-1, wherein the virologically suppressed human infected with HIV is receiving a combination antiretroviral therapy, the method comprising administering to the human a pharmaceutically effective amount of the compound of Example 49, or a pharmaceutically acceptable salt thereof.

Separate further embodiments within each of the methods for inducing transient HIV-1 viremia in a virologically suppressed human infected with HIV-1 comprise the method wherein the combination antiretroviral therapy is selected from each of the combinations of antiretroviral agents listed herein, wherein the use of each separate combination of antiretroviral agents comprises a separate embodiment.

As one example, provided is a method for inducing transient HIV-1 viremia in a virologically suppressed human infected with HIV-1, wherein the virologically suppressed human infected with HIV is receiving a combination antiretroviral therapy, wherein the combination antiretroviral therapy comprises a pharmaceutically effective amount of TDF, a pharmaceutically effective amount of emtricitabine, and a pharmaceutically effective amount of dolutegravir, the method comprising administering to the human a pharmaceutically effective amount of the compound of Example 4, or a pharmaceutically acceptable salt thereof.

As one example, provided is a method for inducing transient HIV-1 viremia in a virologically suppressed human infected with HIV-1, wherein the virologically suppressed human infected with HIV is receiving a combination antiretroviral therapy, wherein the combination antiretroviral therapy comprises a pharmaceutically effective amount of TDF, a pharmaceutically effective amount of emtricitabine, and a pharmaceutically effective amount of dolutegravir, the method comprising administering to the human a pharmaceutically effective amount of the compound of Example 49, or a pharmaceutically acceptable salt thereof.

Additional separate methods comprise those above in which the combination antiretroviral therapy comprises individually the separate combinations listed in each of Tables A, B, C, D, E, F, G, H, I, and J is administered to the human infected with HIV-1 in combination with from 0.1 mg to 25 mg of a Compound of Example 4. Additional separate methods comprise those above in which the combination antiretroviral therapy comprises individually the separate combinations listed in each of Tables A, B, C, D, E, F, G, H, I, and J is administered to the human infected with HIV-1 in combination with from 0.1 mg to 25 mg of a Compound of Example 49. Other separate embodiments comprise a method for inducing transient HIV-1 viremia in a virologically suppressed human infected with HIV-1, wherein the virologically suppressed human infected with HIV is receiving the pharmaceutically effective amounts of each the combination antiretroviral therapies and TLR7 modulators combined in Tables 1A, 1B, 2A, 2B, 2A, 2B, 3A, 3B, 4A, 4B, 5A, 5B, 6A, 6B, 7A, 7B, 8A, 8B, 9A, 9B, 10A, 10B, 11A, 11B, 12A, 12B, 13A, 13B, 14A, 14B, 15A, 15B, 16A, 16B, 17A, 17B, 18A, 18B, 19A, 19B, 20A, 20B, 21A, 21B, 22A, 22B, 23A, 23B, 24A, 24B, 25A, 25B, 26A, 26B, 26C, 26D, 27A, 27B, 27C, 27D, 28A, 28B, 28C, 28D, 29A, 29B, 29C, 29D, 30A, 30B, 30C, 30D, 31A, 31B, 32A, 32B, 33A, 33B, 34A, 34B, 35A, 35B, 36A, 36B, 37A, 37B, 38A, 38B, 39A, 39B, 40A, 40B, 41, 42, 43, 44, 45, 46, 47, 48, 49, 50, 51, 52, 53, 54, 55, 56, 57, 58, 59, 60, 61, 62, 63, 64, 65 (collectively referred to as "Tables 1A through 65" or "Tables 1A-65") wherein administration of each of the separate combinations in the tables comprises a separate method.

Also provided is a method for inducing transient HIV-1 viremia in a virologically suppressed human infected with HIV-1, wherein the virologically suppressed human infected with HIV is receiving a combination antiretroviral therapy, wherein the combination antiretroviral therapy comprises a pharmaceutically effective amount of TDF or TAF, a pharmaceutically effective amount of elvitegravir, a pharmaceutically effective amount of cobicistat, and a pharmaceutically effective amount of emtricitabine, the method comprising administering to the human a pharmaceutically effective amount of the compound of Example 4, or a pharmaceutically acceptable salt thereof.

Also provided is a method for inducing transient HIV-1 viremia in a virologically suppressed human infected with HIV-1, wherein the virologically suppressed human infected with HIV is receiving a combination antiretroviral therapy, wherein the combination antiretroviral therapy comprises a pharmaceutically effective amount of TDF or TAF, a pharmaceutically effective amount of elvitegravir, a pharmaceutically effective amount of cobicistat, and a pharmaceutically effective amount of emtricitabine, the method comprising administering to the human a pharmaceutically effective amount of the compound of Example 49, or a pharmaceutically acceptable salt thereof.

Additional separate methods comprise those above in which the combination antiretroviral therapy comprises individually the separate combinations listed in Combination Antiretroviral Tables A, B, C, D, E, F, G, H, I, and J is administered to the human infected with HIV-1 in combination with from 0.1 mg to 25 mg of a Compound of Example 4. Additional separate methods comprise those above in which the combination antiretroviral therapy comprises individually the separate combinations listed in Combination Antiretroviral Tables A, B, C, D, E, F, G, H, I, and J is administered to the human infected with HIV-1 in combination with from 0.1 mg to 25 mg of a Compound of Example 49.

Other separate embodiments comprise a method inducing transient HIV-1 viremia in a virologically suppressed human infected with HIV-1, wherein the virologically suppressed human infected with HIV is receiving the pharmaceutically effective amounts of each the combination antiretroviral therapies and TLR7 modulators combined in Tables 1A through 65 wherein administration of each of the separate combinations in the tables comprises a separate method.

Enhancing Gene Expression in a Human/Latent Reservoir

Provided is a method of enhancing HIV gene expression in HIV infected cells in a human infected with HIV, the method comprising administering to the human infected with HIV a pharmaceutically effective amount of a TLR7 modulating compound, or a pharmaceutically acceptable salt thereof.

Also provided is a method of enhancing HIV gene expression in HIV infected cells in a human infected with HIV, the method comprising administering to the human infected with HIV a pharmaceutically effective amount of a compound of Formula II, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of a compound of Formula II, or a pharmaceutically acceptable salt thereof.

Also provided is a method of enhancing HIV gene expression in HIV infected T-cells in a human infected with HIV, the method comprising administering to the human infected with HIV a pharmaceutically effective amount of a compound of Formula II, or a pharmaceutically acceptable salt thereof.

Also provided are separate methods of a) enhancing HIV gene expression in HIV infected cells in a human infected with HIV; b) enhancing HIV gene expression in HIV infected cells in a latent HIV reservoir in a human infected with HIV; and c) enhancing HIV gene expression in HIV infected T-cells in a human infected with HIV, each of the methods individually comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof. It is understood that one of such methods comprises administering to the human infected with HIV a pharmaceutically effective amount of Formula III, or a pharmaceutically acceptable salt thereof, another method comprises administering to the human infected with HIV a pharmaceutically effective amount of Formula III(a), etc.

Also provided are separate methods of enhancing HIV gene expression in HIV infected cells in a human infected with HIV, each of the separate methods comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are group of separate methods of enhancing HIV gene expression in HIV infected cells in a human infected with HIV, each of the separate methods comprising administering to the human infected with HIV a pharmaceutically effective amount of a compound selected from one of the compounds from Example 1 through Example 124, or a pharmaceutically acceptable salt thereof. One of each of the compounds from Example 1 to Example 124 are utilized in each of the group of separate methods of enhancing HIV gene expression in HIV infected cells in a human infected with HIV, with the compound of Example 1, or a pharmaceutically acceptable salt thereof, being used in the first method, the compound of Example 2, or a pharmaceutically acceptable salt thereof, being used in the second method, etc.

Also provided is a method of enhancing HIV gene expression in HIV infected cells in a human infected with HIV, the method comprising administering to the human infected with HIV a pharmaceutically effective amount of the compound of Example 4, or a pharmaceutically acceptable salt thereof.

Also provided is a method of enhancing HIV gene expression in HIV infected cells in a human infected with HIV, the method comprising administering to the human infected with HIV a pharmaceutically effective amount of the compound of Example 49, or a pharmaceutically acceptable salt thereof.

Also provided is a method of enhancing HIV gene expression in HIV infected cells in a human infected with HIV, the method comprising administering to the human infected with HIV a pharmaceutically effective amount of the compound of Example 119, or a pharmaceutically acceptable salt thereof.

Also provided is a method of enhancing HIV gene expression in HIV infected cells in a human infected with HIV, the method comprising administering to the human infected with HIV a pharmaceutically effective amount of a compound of Example 120, or a pharmaceutically acceptable salt thereof.

Also provided is a method of enhancing HIV gene expression in HIV infected cells in a human infected with HIV, the method comprising administering to the human infected with HIV a pharmaceutically effective amount of a compound of Example 121, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of a TLR7 modulating compound, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of a compound of Formula II, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof. It is understood that one of such methods comprises administering to the human infected with HIV a pharmaceutically effective amount of Formula III, or a pharmaceutically acceptable salt thereof, another method comprises administering to the human infected with HIV a pharmaceutically effective amount of Formula III(a), etc.

Also provided are separate methods of enhancing HIV gene expression in HIV infected cells in a latent HIV reservoir in a human infected with HIV, each of the separate methods comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are group of separate methods of enhancing HIV gene expression in HIV infected cells in a latent HIV reservoir in a human infected with HIV, each of the separate methods comprising administering to the human infected with HIV a pharmaceutically effective amount of a compound selected from one of the compounds from Example 1 through Example, or a pharmaceutically acceptable salt thereof. One of each of the compounds from Example 1 to Example 124 are utilized in each of the group of separate methods of enhancing HIV in HIV infected cells in a latent HIV reservoir in a human infected with HIV, with the compound of Example 1, or a pharmaceutically acceptable salt thereof, being used in the first method, the compound of Example 2, or a pharmaceutically acceptable salt thereof, being used in the second method, etc.

For example one of the methods provided is a method of enhancing HIV gene expression in HIV infected cells in a latent HIV reservoir in a human infected with HIV, the method comprising administering to the human infected with HIV a pharmaceutically effective amount of the compound of Example 4, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of the compound of Example 49, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of the compound of Example 119, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of the compound of Example 120, or a pharmaceutically acceptable salt thereof.

Also provided is a method of enhancing HIV gene expression in HIV infected cells in a latent HIV reservoir in a human infected with HIV, the method comprising administering to the human infected with HIV a pharmaceutically effective amount of the compound of Example 121, or a pharmaceutically acceptable salt thereof.

A pharmaceutically effective amount of a TLR7 modulating compound described herein, or a pharmaceutically acceptable salt thereof, includes individual doses of from about 0.1 mg to about 25 mg, which may be delivered daily in one dose or in divided doses, such as twice a day, three times a day, or four times a day. Daily dose ranges include from 0.1 mg to 3 mg, from 2 mg to 6 mg, from 4 mg to 6 mg, from 6 mg to 8 mg, from 8 mg to 10 mg, from 10 mg to 12 mg, from 12 mg to 14 mg, from 14 mg to 16 mg, from 16 mg to 18 mg, from 18 mg to 20 mg, from 20 mg to 22 mg, from 22 mg to 25 mg, from 1 mg to 5 mg, from 2.5 mg to 7.5 mg, from 5 mg to 10 mg, from 7.5 mg to 12.5 mg, from 10 mg to 15 mg, from 12.5 mg to 17.5 mg, from 15 mg to 20 mg, from 17.5 mg to 22.5 mg, and from 20 mg to 25 mg. Each of the methods of treatment, pharmaceutical combinations, and pharmaceutical compositions or formulations herein comprises 21 further embodiments in which the pharmaceutically effective amount of the TLR7 modulating compound, including those of each of the formulas and specific examples herein, comprises in each separate embodiment one of the individual doses ranges listed in the prior sentence. Individual daily doses of TLR7 modulating compound described herein, or a pharmaceutically acceptable salt thereof, includes individual doses of 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16.0 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, and 25 mg. Each of the methods of treatment, pharmaceutical combinations, and pharmaceutical compositions or formulations herein comprises 49 further embodiments in which the pharmaceutically effective amount of the TLR7 modulating compound, including those of each of formulas and specific examples herein, comprises in each separate embodiment one of the individual doses listed in the prior sentence.

Method of Treatment of HIV Infections

Provided is a method of treating an HIV infection in a human, the method comprising administering to the human a pharmaceutically effective amount of a TLR7 modulating compound, or a pharmaceutically acceptable salt thereof.

Also provided is a method of treating an HIV infection in a human, the method comprising administering to a human in need thereof a pharmaceutically effective amount of a TLR7 modulating compound, or a pharmaceutically acceptable salt thereof, sufficient to lower the level of HIV detected in the human's blood or plasma from a first level to a second level, the second level comprising a lower concentration of HIV in the human's blood or plasma than the concentration of HIV in the human's blood or plasma in the first level.

Within each of the methods of treating an HIV infection in a human herein comprising administering to a human in need thereof a pharmaceutically effective amount of a TLR7 modulating compound, or a pharmaceutically acceptable salt thereof, there is a further embodiment comprising the method wherein the second level of concentration of HIV in the human's blood or plasma comprises a viral load (VL) in plasma of less than 50 copies of HIV RNA/ml. Additional separate embodiments within each of the methods comprises the method described wherein the level of HIV in the human's blood or plasma in the second level comprises a viral load (VL) in plasma of a) less than 40 copies of HIV RNA/ml; b) less than 30 copies of HIV RNA/ml; c) less than 20 copies of HIV RNA/ml; d) less than 10 copies of HIV RNA/ml; e) less than 5 copies of HIV RNA/ml; f) less than 3 copies of HIV RNA/ml; less than 1 copy of HIV RNA/ml; and less than 0.5 copies of HIV RNA/ml.

Within each of the methods of treating an HIV infection above there are separate additional embodiments wherein the TLR7 modulating compound comprises a pharmaceutically effective amount of a TLR7 modulating compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), or of one of the individual compounds selected from Examples 1 through 124; or a pharmaceutically acceptable salt thereof.

HIV Treatment Combining Antiretroviral Agents and a TLR7 Modulator

Provided is a method of treatment of an HIV-1 infection in a virologically suppressed human infected with HIV-1, wherein the virologically suppressed human infected with HIV is receiving a combination antiretroviral therapy, the method comprising administering to the human a pharmaceutically effective amount of a TLR7 modulating compound, or a pharmaceutically acceptable salt thereof.

Within the method of treatment of an HIV-1 infection in a virologically suppressed human infected with HIV-1 above there are separate additional embodiments wherein the TLR7 modulating compound comprises a pharmaceutically effective amount of a TLR7 modulating compound selected from one of Formula II, Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), or of one of the individual compounds selected from Examples 1 through 124; or a pharmaceutically acceptable salt thereof.

As one example, provided is a method of treatment of an HIV-1 infection in a virologically suppressed human infected with HIV-1, wherein the virologically suppressed human infected with HIV is receiving a combination antiretroviral therapy, the method comprising administering to the human a pharmaceutically effective amount of the compound of Example 4, or a pharmaceutically acceptable salt thereof.

As another example, provided is a method of treatment of an HIV-1 infection in a virologically suppressed human infected with HIV-1, wherein the virologically suppressed human infected with HIV is receiving a combination antiretroviral therapy, the method comprising administering to the human a pharmaceutically effective amount of the compound of Example 49, or a pharmaceutically acceptable salt thereof.

Separate further embodiments within each of the methods above for treatment of an HIV-1 infection in a virologically suppressed human infected with HIV-1 comprise the method wherein the combination antiretroviral therapy is selected from each of the combinations of antiretroviral agents listed herein, wherein the use of each separate combination of antiretroviral agents comprises a separate embodiment.

As one example, provided is a method of treatment of an HIV-1 infection in a virologically suppressed human infected with HIV-1, wherein the virologically suppressed human infected with HIV is receiving a combination antiretroviral therapy, wherein the combination antiretroviral therapy comprises a pharmaceutically effective amount of TDF, a pharmaceutically effective amount of emtricitabine, and a pharmaceutically effective amount of dolutegravir, the method comprising administering to the human a pharmaceutically effective amount of the compound of Example 4, or a pharmaceutically acceptable salt thereof.

As one example, provided is a method of treatment of an HIV-1 infection in a virologically suppressed human infected with HIV-1, wherein the virologically suppressed human infected with HIV is receiving a combination antiretroviral therapy, wherein the combination antiretroviral therapy comprises a pharmaceutically effective amount of TDF, a pharmaceutically effective amount of emtricitabine, and a pharmaceutically effective amount of dolutegravir, the method comprising administering to the human a pharmaceutically effective amount of the compound of Example 49, or a pharmaceutically acceptable salt thereof.

Additional separate methods comprise those above in which the combination antiretroviral therapy comprises individually the separate combinations listed in in each of Tables A, B, C, D, E, F, G, H, I, and J is administered to the human infected with HIV-1 in combination with from 0.1 mg to 25 mg of a Compound of Example 4. Additional separate methods comprise those above in which the combination antiretroviral therapy comprises individually the separate combinations listed in in each of Tables A, B, C, D, E, F, G, H, I, and J is administered to the human infected with HIV-1 in combination with from 0.1 mg to 25 mg of a Compound of Example 49. Other separate embodiments comprise a method of treatment of an HIV-1 infection in a virologically suppressed human infected with HIV-1, wherein the virologically suppressed human infected with HIV is receiving the pharmaceutically effective amounts of each the combination antiretroviral therapies and TLR7 modulators combined in Tables 1A through 65, wherein administration of each of the separate combinations in the tables comprises a separate method.

Also provided is a method of treatment of an HIV-1 infection in a virologically suppressed human infected with HIV-1, wherein the virologically suppressed human infected with HIV is receiving a combination antiretroviral therapy, wherein the combination antiretroviral therapy comprises a pharmaceutically effective amount of TDF or TAF, a pharmaceutically effective amount of elvitegravir, a pharmaceutically effective amount of cobicistat, and a pharmaceutically effective amount of emtricitabine, the method comprising administering to the human a pharmaceutically effective amount of the compound of Example 4, or a pharmaceutically acceptable salt thereof.

Also provided is a method of treatment of an HIV-1 infection in a virologically suppressed human infected with HIV-1, wherein the virologically suppressed human infected with HIV is receiving a combination antiretroviral therapy, wherein the combination antiretroviral therapy comprises a pharmaceutically effective amount of TDF or TAF, a pharmaceutically effective amount of elvitegravir, a pharmaceutically effective amount of cobicistat, and a pharmaceutically effective amount of emtricitabine, the method comprising administering to the human a pharmaceutically effective amount of the compound of Example 49, or a pharmaceutically acceptable salt thereof.

Additional separate methods comprise those above in which the combination antiretroviral therapy comprises individually the separate combinations listed in Combination Antiretroviral Tables A, B, C, D, E, F, G, H, I, and J is administered to the human infected with HIV-1 in combination with from 0.1 mg to 25 mg of a Compound of Example 4. Additional separate methods comprise those above in which the combination antiretroviral therapy comprises individually the separate combinations listed in Combination Antiretroviral Tables A, B, C, D, E, F, G, H, I, and J is administered to the human infected with HIV-1 in combination with from 0.1 mg to 25 mg of a Compound of Example 49. Other separate embodiments comprise a method of treatment of an HIV-1 infection in a virologically suppressed human infected with HIV-1, wherein the virologically suppressed human infected with HIV is receiving the pharmaceutically effective amounts of each the combination antiretroviral therapies and TLR7 modulators combined in Tables 1A through 65 wherein administration of each of the separate combinations in the tables comprises a separate method.

Provided is a method of treating an HIV infection in a human, the method comprising:
a) administering to a human in need thereof a pharmaceutically effective amount of an antiretroviral agent sufficient to lower the level of HIV detected in the human's blood or plasma from a first level to a second level, the second level comprising a lower concentration of HIV in the human's blood or plasma than the concentration of HIV in the human's blood or plasma in the first level; and
b) administering to the human a pharmaceutically effective amount of a TLR7 modulating compound, or a pharmaceutically acceptable salt thereof.

Provided is a method of treating an HIV infection in a human, the method comprising:
a) administering to a human in need thereof a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and
b) administering to the human a pharmaceutically effective amount of a TLR7 modulating compound, or a pharmaceutically acceptable salt thereof.

Provided is a method of treating an HIV infection in a human, the method comprising:
a) administering to a human in need thereof a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and
b) administering to the human a pharmaceutically effective amount of a compound of Formula II, or a pharmaceutically acceptable salt thereof.

Provided is a method of treating an HIV infection in a human, the method comprising:
c) administering to a human in need thereof a pharmaceutically effective amount of a combination antiretroviral therapy regimen sufficient to lower the level of HIV detected in the human's blood or plasma to a specified level; and
d) administering to the human a pharmaceutically effective amount of a compound of Formula II, or a pharmaceutically acceptable salt thereof.

Provided is a method of treating an HIV infection in a human, the method comprising:
a) a first step of administering to a human in need thereof a pharmaceutically effective amount of a combination antiretroviral therapy regimen sufficient to lower the level of HIV in the human's blood or plasma to below a detectable level; and
b) a second step following the first step, the second step comprising administering to the human a pharmaceutically effective amount of a combination antiretroviral therapy regimen and a pharmaceutically effective amount of a compound of Formula II, or a pharmaceutically acceptable salt thereof.

Provided is a method of treating an HIV infection in a human, the method comprising:
a) a first step of administering to a human in need thereof a pharmaceutically effective amount of a combination antiretroviral therapy regimen sufficient to lower the level of HIV in the human's plasma to below 50 copies of HIV RNA/rd; and
b) a second step following the first step, the second step comprising administering to the human a pharmaceutically effective amount of a combination antiretroviral therapy regimen and a pharmaceutically effective amount of a compound of Formula II, or a pharmaceutically acceptable salt thereof.

Provided is a method of treating an HIV infection in a human, the method comprising:
c) a first step of administering to a human in need thereof a pharmaceutically effective amount of a combination antiretroviral therapy regimen sufficient to lower the level of HIV in the human's blood or plasma to below a detectable level; and
d) a second step following the first step, the second step comprising administering to the human a pharmaceutically effective amount of a combination antiretroviral therapy regimen and a pharmaceutically effective amount of a TLR7 modulating compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), or of one of the individual compounds selected from Examples 1 through 124; or a pharmaceutically acceptable salt thereof.

Within each of the methods herein of treating an HIV infection in a human, the method comprising a first step of administering to a human in need thereof a pharmaceutically effective amount of an antiretroviral agent or a combination antiretroviral therapy (cART) regimen sufficient to lower the level of HIV in the human's blood or plasma to below a detectable level, followed by a second step following the first step, the second step comprising administering to the human a pharmaceutically effective amount of a combination antiretroviral therapy regimen and a pharmaceutically effective amount of a TLR7 modulating compound, there is a further embodiment in which the antiretroviral agent or cART regimen and the TLR7 modulating compound are both administered daily to the human. Within each of these methods herein of treating an HIV infection in a human there are further embodiments in which the antiretroviral agent or cART regimen is administered daily to the human and the TLR7 modulating compound is administered less than daily. Separate additional embodiments within each of these methods of treating an HIV infection in a human comprise administering antiretroviral agent or the cART regimen to the human daily and administering the TLR7 modulating compound to the human once or twice every other day or once or twice every third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, twenty fifth, twenty sixth, twenty seventh, twenty eight, twenty ninth, thirtieth, forty fifth, or sixtieth day.

Also provided are separate methods within the method above, each utilizing in the second step a separate compound of one or more of the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III (f)(1), and Formula III(f)(2), or a pharmaceutically acceptable salt thereof. One of such methods is as described above wherein, in the second step, the human is administered a pharmaceutically effective amount of Formula III, or a pharmaceutically acceptable salt thereof, another method comprises administering to the human infected with HIV a pharmaceutically effective amount of Formula III(a), etc.

Also provided are group of separate methods within the method above, each utilizing in the second step a separate compound selected from the group of the compounds of Examples 1 through 124, or a pharmaceutically acceptable salt thereof. One of such methods is as described above wherein, in the second step, the human is administered a pharmaceutically effective amount of the compound of Example 1, or a pharmaceutically acceptable salt thereof, another method comprises administering to the human infected with HIV a pharmaceutically effective amount of the compound of Example 2, or a pharmaceutically acceptable salt thereof, etc.

As an example, provided is a method of treating an HIV infection in a human, the method comprising:
 a) a first step of administering to a human in need thereof a pharmaceutically effective amount of an antiretroviral agent or a combination antiretroviral therapy regimen sufficient to lower the level of HIV in the human's blood or plasma to below a detectable level; and
 b) a second step following the first step, the second step comprising administering to the human a pharmaceutically effective amount of an antiretroviral agent or a combination antiretroviral therapy regimen and a pharmaceutically effective amount of the compound of Example 4, or a pharmaceutically acceptable salt thereof.

Provided is a method of treating an HIV infection in a human, the method comprising:
 a) a first step of administering to a human in need thereof a pharmaceutically effective amount of a combination antiretroviral therapy regimen sufficient to lower the level of HIV in the human's blood or plasma to below a detectable level; and
 b) a second step following the first step, the second step comprising administering to the human a pharmaceutically effective amount of an antiretroviral agent or a combination antiretroviral therapy regimen and a pharmaceutically effective amount of the compound of Example 49, or a pharmaceutically acceptable salt thereof.

Provided is a method of treating an HIV infection in a human, the method comprising:
 a) a first step of administering to a human in need thereof a pharmaceutically effective amount of a combination antiretroviral therapy regimen sufficient to lower the level of HIV in the human's blood or plasma to below a detectable level; and
 b) a second step following the first step, the second step comprising administering to the human a pharmaceutically effective amount of an antiretroviral agent or a combination antiretroviral therapy regimen and a pharmaceutically effective amount of the compound of Example 119, or a pharmaceutically acceptable salt thereof.

Provided is a method of treating an HIV infection in a human, the method comprising:
 a) a first step of administering to a human in need thereof a pharmaceutically effective amount of a combination antiretroviral therapy regimen sufficient to lower the level of HIV in the human's blood or plasma to below a detectable level; and
 b) a second step following the first step, the second step comprising administering to the human a pharmaceutically effective amount of an antiretroviral agent or a combination antiretroviral therapy regimen and a pharmaceutically effective amount of a compound of Example 120, or a pharmaceutically acceptable salt thereof.

Provided is a method of treating an HIV infection in a human, the method comprising:
 a) a first step of administering to a human in need thereof a pharmaceutically effective amount of a combination antiretroviral therapy regimen sufficient to lower the level of HIV in the human's blood or plasma to below a detectable level; and
 b) a second step following the first step, the second step comprising administering to the human a pharmaceutically effective amount of an antiretroviral agent or a combination antiretroviral therapy regimen and a pharmaceutically effective amount of a compound of Example 121, or a pharmaceutically acceptable salt thereof.

Within each of the methods of treating an HIV infection in a human herein wherein the first step comprises administering to a human in need thereof a pharmaceutically effective amount of an antiretroviral agent or a combination antiretroviral therapy regimen sufficient to lower the level of HIV in the human's blood or plasma to below a detectable level, there is a further embodiment comprising the method wherein the level of HIV in the human's blood or plasma below a detectable level comprises a viral load (VL) in plasma of less than 50 copies of HIV RNA/ml. Additional separate embodiments within each of the methods comprises the method described wherein the level of HIV in the human's blood or plasma below a detectable level comprises a viral load (VL) in plasma of a) less than 40 copies of HIV RNA/ml; b) less than 30 copies of HIV RNA/ml; c) less than 20 copies of HIV RNA/ml; d) less than 10 copies of HIV RNA/ml; e) less than 5 copies of HIV RNA/ml; f) less than 3 copies of HIV RNA/ml; less than 1 copy of HIV RNA/ml; and less than 0.5 copies of HIV RNA/ml.

Non-limiting assays useful in determining the concentration of HIV RNA in blood or plasma include the COBAS® AMPLICOR HIV-1 MONITOR Test, v1.5 (quantification of HIV-1 RNA from 50 to 750,000 copies/mL), COBAS® AmpliPrep/COBAS® TaqMan® HIV-1 Test, v2.0 (quantitates HIV-1 RNA from 20-10,000,000 copies/mL), the Abbott RealTime HIV-1 assay (quantitation of HIV-1 in human plasma from 40 to Ser. No. 10/000,000 copies/mL), or ultra-sensitive single copy quantitative PCR assays (SCA, iSCA, or gSCA). Other useful assays include the VERSANT® HIV-1 RNA 1.0 Assay (kPCR), the NucliSENS EasyQ® HIV-1 v2.0 assay, and the APTIMA® HIV-1 RNA Qualitative Assay.

Combination antiretroviral therapies and compositions which are included for use in each of the methods herein include the marketed products:
  a) STRIBILD® tablets (elvitegravir 150 mg, cobicistat 150 mg, emtricitabine 200 mg, tenofovir disoproxil fumarate 300 mg) (Gilead Sciences, Inc.);
  b) TRUVADA® tablets (emtricitabine 200 mg, tenofovir disoproxil fumarate 300 mg) (Gilead Sciences, Inc.);
  c) ATRIPLA® tablets (efavirenz 600 mg, emtricitabine 200 mg, tenofovir disoproxil fumarate 300 mg) (Gilead Sciences, Inc.);
  d) COMPLERA® tablets (200 mg emtricitabine, 25 mg rilpivirine, 300 mg of tenofovir disoproxil fumarate) (Gilead Sciences, Inc.);
  e) EPZICOM® tablets (Eq. 600 mg base abacavir sulfate, 300 mg lamivudine);
  f) COMBIVIR® tablets (150 mg lamivudine, 300 mg zidovudine (GlaxoSmithKline); and
  g) TRIVIR® tablets (Eq. 300 mg base abacavir sulfate, 150 mg lamivudine, 300 mg zidovudine).

Also included for use in each of the methods herein is an antiretroviral combination of:
a) a pharmaceutically effective amount of elvitegravir;
b) a pharmaceutically effective amount of cobicistat;
c) a pharmaceutically effective amount of emtricitabine; and
d) a pharmaceutically effective amount of tenofovir alafenamide, or a pharmaceutically acceptable salt thereof.

Also included for use in each of the methods herein is an antiretroviral combination of:
  a) a pharmaceutically effective amount of atazanavir, or a pharmaceutically acceptable salt thereof, such as atazanavir sulfate; and
  b) a pharmaceutically effective amount of cobicistat.

Also included for use in each of the methods herein is an antiretroviral combination of a) a pharmaceutically effective amount of TDF, b) a pharmaceutically effective amount of emtricitabine, and c) a pharmaceutically effective amount of a compound selected from the group of efavirenz, rilpivirine, elvitegravir, efavirenz, atazanavir, darunavir, dolutegravir, raltegravir, and tipranavir.

Also included for use in each of the methods herein is an antiretroviral combination of a) a pharmaceutically effective amount of TAF, b) a pharmaceutically effective amount of emtricitabine, and c) a pharmaceutically effective amount of a compound selected from the group of efavirenz, rilpivirine, elvitegravir, efavirenz, atazanavir, darunavir, raltegravir, dolutegravir, and tipranavir.

Also provided is a method of eliminating an HIV infection in a human, the method comprising:
  a) administering to a human in need thereof a pharmaceutically effective amount of a TLR7 modulating compound, or a pharmaceutically acceptable salt thereof Provided is a method of eliminating an HIV infection in a human, the method comprising:
  a) administering to a human in need thereof a pharmaceutically effective amount of a compound of Formula II, or a pharmaceutically acceptable salt thereof; and
  b) administering to the human a pharmaceutically effective amount of one or more antiretroviral agents.

Also provided is a method of eliminating an HIV infection in a human, the method comprising:
  a) administering to a human in need thereof a pharmaceutically effective amount of a combination antiretroviral therapy; and
  b) administering to a human in need thereof a pharmaceutically effective amount of a TLR7 modulating compound, or a pharmaceutically acceptable salt thereof.

Also provided is a method of eliminating an HIV infection in a human, the method comprising:
  c) administering to a human in need thereof a pharmaceutically effective amount of a combination antiretroviral therapy; and
  d) administering to a human in need thereof a pharmaceutically effective amount of a compound of Formula II, or a pharmaceutically acceptable salt thereof.

Also provided is a method of eliminating an HIV infection in a human, the method comprising:
  a) administering to a human in need thereof a pharmaceutically effective amount of a combination antiretroviral therapy;
  b) administering to a human in need thereof a pharmaceutically effective amount of the compound of Example 4, or a pharmaceutically acceptable salt thereof Also provided is a method of eliminating an HIV infection in a human, the method comprising:
  a) administering to a human in need thereof a pharmaceutically effective amount of a combination antiretroviral therapy;
  b) administering to a human in need thereof a pharmaceutically effective amount of the compound of Example 49, or a pharmaceutically acceptable salt thereof Also provided is a method of eliminating an HIV infection in a human, the method comprising:
  a) administering to a human in need thereof a pharmaceutically effective amount of a combination antiretroviral therapy;
  b) administering to a human in need thereof a pharmaceutically effective amount of the compound of Example 119, or a pharmaceutically acceptable salt thereof Also provided is a method of eliminating an HIV infection in a human, the method comprising:
a) administering to a human in need thereof a pharmaceutically effective amount of a combination antiretroviral therapy;
b) administering to a human in need thereof a pharmaceutically effective amount of the compound of Example 120, or a pharmaceutically acceptable salt thereof.

Also provided is a method of eliminating an HIV infection in a human, the method comprising:
c) administering to a human in need thereof a pharmaceutically effective amount of a combination antiretroviral therapy;
d) administering to a human in need thereof a pharmaceutically effective amount of the compound of Example 121, or a pharmaceutically acceptable salt thereof.

Within each of the methods of eliminating an HIV infection in a human described herein there are further separate embodiments in which the TLR7 modulating compound is selected from the group comprising Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), Formula III(f)(2), and each of the individual compounds selected from Examples 1 through 124; or a pharmaceutically acceptable salt thereof.

Within each of the methods herein of eliminating an HIV infection in a human, the method comprising administering to a human in need thereof a pharmaceutically effective amount of an antiretroviral agent or a combination antiretroviral therapy (cART) regimen and administering to the human a pharmaceutically effective amount of a combination antiretroviral therapy regimen and a pharmaceutically effective amount of a TLR7 modulating compound, there is a further embodiment in which the antiretroviral agent or cART regimen and the TLR7 modulating compound are both administered daily to the human. Within each of these methods herein of treating an HIV infection in a human there are further embodiments in which the antiretroviral agent or cART regimen is administered daily to the human and the TLR7 modulating compound is administered less than daily. Separate additional embodiments within each of these methods of treating an HIV infection in a human comprise administering the antiretroviral agent or the cART regimen to the human daily and administering the TLR7 modulating compound to the human once or twice every other day or once or twice every third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, twenty fifth, twenty sixth, twenty seventh, twenty eight, twenty ninth, thirtieth, forty fifth, or sixtieth day.

cART Combinations and Regimens

Each of the methods of treatment above may utilize combinations of antiretroviral compounds, or a pharmaceutically acceptable salt thereof. Examples of combinations of specific dose ranges of antiretroviral agents that may be used in these methods of treatment are included in the tables below. It is understood that in the practice of the methods of treatment herein, the antiretroviral agents listed for each combination may be administered together in a single pharmaceutical composition or in divided forms, such as a single tablet or oral solution per agent or in different pharmaceutical compositions combining different groups of the agents. The amounts of each agent listed are intended to be a daily dosage of each agent, though the daily dosage may be administered to the human in need thereof in the present methods of treatment as a single dose of each agent per day or it may be divided and administered in multiple doses per day, such as dividing the daily dose into two, three, or four divided doses to be administered in a twice daily, three times daily, or four times daily regimen.

Combinations of the agents listed in each of the Pharmaceutical Composition Tables below may be used in each of the methods herein. It is understood that for each of the individual methods discussed herein there are separate methods in which each of the pharmaceutical combinations listed in the Pharmaceutical Composition Tables below are used in the each of the individual methods. For instance, provided in Combination Antiretroviral Table A are eight separate methods of treating an HIV infection in a human, as described above, comprising administering to a human infected with HIV the combinations of the pharmaceutical agents listed as Combination Examples A-1, A-2, A-3, A-4, A-5. A-6, A-7, and A-8 in combination with a TLR7 modulating compound, as described herein.

Combination Antiretroviral Table A

Antiviral combinations and regimens for use in the methods herein comprising elvitegravir, cobicistat, emtricitibine, and TDF or TAF include:

| Comb. Ex. | elvitegravir | cobicistat | emtricitabine | TDF | TAF |
| --- | --- | --- | --- | --- | --- |
| A-1 | 100 mg to 200 mg | 100 mg to 200 mg | 150 mg to 250 mg | 250 mg to 350 mg | 0 mg |
| A-2 | 125 mg to 175 mg | 125 mg to 175 mg | 175 mg to 225 mg | 275 mg to 325 mg | 0 mg |
| A-3 | 145 mg to 155 mg | 145 mg to 155 mg | 190 mg to 210 mg | 290 mg to 310 mg | 0 mg |
| A-4 | 150 mg | 150 mg | 200 mg | 300 mg | 0 mg |
| A-5 | 100 mg to 200 mg | 100 mg to 200 mg | 150 mg to 250 mg | 0 mg | 5 mg to 30 mg |
| A-6 | 125 mg to 175 mg | 125 mg to 175 mg | 175 mg to 225 mg | 0 mg | 5 mg to 30 mg |
| A-7 | 145 mg to 155 mg | 145 mg to 155 mg | 190 mg to 210 mg | 0 mg | 5 mg to 30 mg |
| A-8 | 150 mg | 150 mg | 200 mg | 0 mg | 25 mg |

Combination Antiretroviral Table B

Antiviral combinations and regimens for use in the methods herein comprising emtricitibine and TDF or TAF include:

| Combination Example | emtricitabine | TDF | TAF |
| --- | --- | --- | --- |
| B-1 | 150 mg to 250 mg | 250 mg to 350 mg | 0 mg |
| B-2 | 175 mg to 225 mg | 275 mg to 325 mg | 0 mg |
| B-3 | 200 mg | 300 mg | 0 mg |
| B-4 | 150 mg to 250 mg | 0 mg | 5 mg to 30 mg |
| B-5 | 175 mg to 225 mg | 0 mg | 5 mg to 30 mg |
| B-6 | 175 mg to 225 mg | 0 mg | 25 mg |
| B-7 | 200 mg | 0 mg | 25 mg |

Combination Antiretroviral Table C

Antiviral combinations and regimens for use in the methods herein comprising emtricitibine, TDF or TAF, and raltegravir include:

| Comb. Example | emtricitabine | TDF | raltegravir | TAF |
|---|---|---|---|---|
| C-1 | 150 mg to 250 mg | 250 mg to 350 mg | 350 mg to 450 mg | 0 mg |
| C-2 | 175 mg to 225 mg | 275 mg to 325 mg | 375 mg to 425 mg | 0 mg |
| C-3 | 200 mg | 300 mg | 400 mg | 0 mg |
| C-4 | 150 mg to 250 mg | 0 mg | 350 mg to 450 mg | 5 mg to 30 mg |
| C-5 | 175 mg to 225 mg | 0 mg | 375 mg to 425 mg | 5 mg to 30 mg |
| C-6 | 175 mg to 225 mg | 0 mg | 375 mg to 425 mg | 25 mg |
| C-7 | 200 mg | 0 mg | 400 mg | 25 mg |

Combination Antiretroviral Table D

Antiviral combinations and regimens for use in the methods herein comprising emtricitibine, TDF or TAF, and dolutegravir include:

| Comb. Ex. | emtricitabine | TDF | dolutegravir | TAF |
|---|---|---|---|---|
| D-1 | 150 mg to 250 mg | 250 mg to 350 mg | 30 mg to 70 mg | 0 mg |
| D-2 | 150 mg to 250 mg | 250 mg to 350 mg | 40 mg to 60 mg | 0 mg |
| D-3 | 175 mg to 225 mg | 275 mg to 325 mg | 40 mg to 60 mg | 0 mg |
| D-4 | 190 mg to 210 mg | 290 mg to 310 mg | 45 mg to 55 mg | 0 mg |
| D-5 | 200 mg | 300 mg | 50 mg | 0 mg |
| D-6 | 150 mg to 250 mg | 0 mg | 30 mg to 70 mg | 5 mg to 30 mg |
| D-7 | 150 mg to 250 mg | 0 mg | 40 mg to 60 mg | 5 mg to 30 mg |
| D-8 | 175 mg to 225 mg | 0 mg | 40 mg to 60 mg | 5 mg to 30 mg |
| D-9 | 190 mg to 210 mg | 0 mg | 45 mg to 55 mg | 5 mg to 30 mg |
| D-10 | 200 mg | 0 mg | 50 mg | 25 mg |

Combination Antiretroviral Table E

Antiviral combinations and regimens for use in the methods herein comprising rilpivirine HCl, emtricitibine, and TDF or TAF include:

| Comb. Ex. | Rilpivirine HCl | emtricitabine | TDF | TAF |
|---|---|---|---|---|
| E-1 | 20 mg to 30 mg | 150 mg to 250 mg | 250 mg to 350 mg | 0 mg |
| E-2 | 22 mg to 28 mg | 175 mg to 225 mg | 275 mg to 325 mg | 0 mg |
| E-3 | 27.5 mg | 200 mg | 300 | 0 mg |
| E-4 | 20 mg to 30 mg | 150 mg to 250 mg | 0 mg | 5 mg to 30 mg |
| E-5 | 22 mg to 28 mg | 175 mg to 225 mg | 0 mg | 5 mg to 30 mg |
| E-6 | 27.5 mg | 200 mg | 0 mg | 25 mg |

Combination Antiretroviral Table F

Antiviral combinations and regimens for use in the methods herein comprising efavirenz, emtricitibine, and TDF or TAF include:

| Comb. Ex. | efavirenz | emtricitabine | TDF | TAF |
|---|---|---|---|---|
| F-1 | 500 mg to 700 mg | 150 mg to 250 mg | 150 mg to 250 mg | 0 mg |
| F-2 | 550 mg to 650 mg | 175 mg to 225 mg | 175 mg to 225 mg | 0 mg |
| F-3 | 575 mg to 625 mg | 175 mg to 225 mg | 175 mg to 225 mg | 0 mg |
| F-4 | 600 mg | 200 mg | 200 mg | 0 mg |
| F-5 | 500 mg to 700 mg | 150 mg to 250 mg | 0 mg | 5 mg to 30 mg |
| F-6 | 550 mg to 650 mg | 175 mg to 225 mg | 0 mg | 5 mg to 30 mg |
| F-7 | 575 mg to 625 mg | 175 mg to 225 mg | 0 mg | 5 mg to 30 mg |
| F-8 | 575 mg to 625 mg | 175 mg to 225 mg | 0 mg | 25 mg |
| F-9 | 600 mg | 200 mg | 0 mg | 25 mg |

Combination Antiretroviral Table G

Antiviral combinations and regimens for use in the methods herein comprising elvitregravir, emtricitibine, and TAF, with and without cobicistat, include:

| Combination Example | elvitegravir | emtricitabine | cobicistat | TAF |
|---|---|---|---|---|
| G-1 | 100 mg to 200 mg | 150 mg to 250 mg | 100 mg to 200 mg | 5 mg to 50 mg |
| G-2 | 600 mg to 1200 mg | 150 mg to 250 mg | 0 mg | 5 mg to 50 mg |
| G-3 | 100 mg to 200 mg | 150 mg to 250 mg | 100 mg to 200 mg | 5 mg to 30 mg |
| G-4 | 600 mg to 1200 mg | 150 mg to 250 mg | 0 mg | 5 mg to 30 mg |
| G-5 | 125 mg to 175 mg | 175 mg to 225 mg | 125 mg to 175 mg | 5 mg to 30 mg |
| G-6 | 700 mg to 1200 mg | 175 mg to 225 mg | 0 mg | 5 mg to 30 mg |
| G-7 | 125 mg to 175 mg | 175 mg to 225 mg | 125 mg to 175 mg | 5 mg to 15 mg |
| G-8 | 700 mg to 1200 mg | 175 mg to 225 mg | 0 mg | 5 mg to 15 mg |
| G-9 | 125 mg to 175 mg | 175 mg to 225 mg | 125 mg to 175 mg | 20 mg to 30 mg |
| G-10 | 700 mg to 1200 mg | 175 mg to 225 mg | 0 mg | 20 mg to 30 mg |
| G-11 | 150 mg | 200 mg | 150 mg | 5 mg to 30 mg |
| G-12 | 800 mg to 1200 mg | 200 mg | 0 mg | 5 mg to 30 mg |
| G-13 | 150 mg | 200 mg | 150 mg | 5 mg to 15 mg |
| G-14 | 800 mg to 1200 mg 150 | 200 mg | 0 mg | 5 mg to 15 mg |
| G-15 | 150 mg | 200 mg | 150 mg | 20 mg to 30 mg |
| G-16 | 800 mg to 1200 mg 150 | 200 mg | 0 mg | 20 mg to 30 mg |
| G-17 | 150 mg | 200 mg | 150 mg | 25 mg |
| G-18 | 800 mg to 1200 mg 150 | 200 mg | 0 mg | 25 mg |
| G-19 | 150 mg | 200 mg | 150 mg | 10 mg |
| G-20 | 800 mg to 1200 mg 150 | 200 mg | 0 mg | 10 mg |

Combination Antiretroviral Table H

Antiviral combinations and regimens for use in the methods herein comprising atazanavir sulfate and cobicistat include:

| Combination Example | atazanavir sulfate | cobicistat |
|---|---|---|
| H-1 | 250 mg to 350 mg | 100 mg to 200 mg |
| H-2 | 275 mg to 325 mg | 125 mg to 175 mg |
| H-3 | 290 mg to 310 mg | 140 mg to 160 mg |
| H-4 | 300 mg | 150 mg |

Combination Antiretroviral Table I

Antiviral combinations and regimens for use in the methods herein comprising abacavir (such as administered as abacavir sulfate), lamivudine, and, optionally, dolutegravir include:

| Comb. Ex. | abacavir | lamivudine | dolutegravir |
|---|---|---|---|
| I-1 | 500 mg to 700 mg | 250 mg to 350 mg | 0 mg |
| I-2 | 275 mg to 325 mg | 125 mg to 175 mg | 0 mg |
| I-3 | 290 mg to 310 mg | 140 mg to 160 mg | 0 mg |
| I-4 | 300 mg | 150 mg | 0 mg |
| I-5 | 500 mg to 700 mg | 250 mg to 350 mg | 25 mg to 75 mg |
| I-6 | 275 mg to 325 mg | 125 mg to 175 mg | 40 mg to 60 mg |
| I-7 | 290 mg to 310 mg | 140 mg to 160 mg | 45 mg to 55 mg |
| I-8 | 300 mg | 150 mg | 50 mg |
| I-9 | 600 mg | 300 mg | 50 mg |

Combination Antiretroviral Table J

Antiviral combinations and regimens for use in the methods herein comprising darunavir (such as administered as a Prezista® tablet or oral solution) and ritonavir or cobicistat include:

| Combination Example | darunavir | ritonavir | cobicistat |
|---|---|---|---|
| J-1 | 50 mg to 1000 mg | 50 mg to 150 mg | 0 mg |
| J-2 | 50 mg to 1000 mg | 0 mg | 50 mg to 200 mg |
| J-3 | 500 mg to 900 mg | 50 mg to 150 mg | 0 mg |
| J-4 | 500 mg to 900 mg | 0 mg | 50 mg to 200 mg |
| J-5 | 500 mg to 700 mg | 75 mg to 125 mg | 0 mg |
| J-6 | 500 mg to 700 mg | 0 mg | 75 mg to 175 mg |
| J-7 | 600 mg | 100 mg | 0 mg |
| J-9 | 800 mg | 100 mg | 0 mg |
| J-10 | 600 mg | 0 mg | 50 mg to 150 mg |
| J-11 | 800 mg | 0 mg | 100 mg to 200 mg |
| J-12 | 600 mg | 0 mg | 100 mg |
| J-13 | 800 mg | 0 mg | 150 mg |

In each of the combinations in the Combination Antiretroviral Tables A through J above within each of the relevant ranges include specific examples in which the elvitegravir and cobicistat components are each, independently, present in 100 mg, 125 mg, 150 mg, 175 mg, and 200 mg doses; the emtricitabine component is present in 150 mg, 175 mg, 200 mg, 225 mg, and 250 mg doses; the raltegravir component is present in 350 mg, 375 mg, 400 mg, 425 mg, and 450 mg doses; the dolutegravir component is present in 25 mg, 30 mg, 40 mg, 50 mg, 60 mg, 70 mg, and 75 mg doses; the rilpivirine HCl component is present in 20 mg, 22.5 mg, 25 mg, 27.5 mg, and 30 mg doses; the efavirenz and abacavir components are each, independently, present in 500 mg, 525 mg, 550 mg, 575 mg, 600 mg, 625 mg, 650 mg, 675 mg, and 700 mg doses; the atazanavir sulfate and lamivudine components are each, independently, present in 250 mg, 275 mg, 300 mg, 325 mg, and 350 mg doses; darunavir is present in 50 mg, 100 mg, 200 mg, 300 mg, 400 mg, 500 mg, 600 mg, 700 mg, 800 mg, 900 mg, and 1,000 mg doses; the ritonavir component is present in 50 mg, 75 mg, 100 mg, 125 mg, and 150 mg doses; TDF is present in 150 mg, 175 mg, 200 mg, 250 mg, 275 mg, 300 mg, 325 mg, and 350 mg doses; and TAF is present in 5 mg, 10 mg, 15 mg, 20 mg, 25 mg, and 30 mg doses.

Lowering Viremia and Chronic Set Point of HIV Viral Load

Provided is a method of reducing HIV viremia in a human infected with HIV, the method comprising administering to the human a pharmaceutically effective amount of a TLR7 modulating compound, or a pharmaceutically effective amount thereof.

Also provided is a method of reducing HIV viremia in a human infected with HIV, wherein the human infected with HIV is receiving treatment with one or more antiviral agents, the method comprising administering to the human infected with HIV a pharmaceutically effective amount of a TLR7 modulating compound, or a pharmaceutically effective amount thereof.

Provided is a method of lowering the chronic set point of HIV viral load in a human infected with HIV, the method comprising administering to the human a pharmaceutically effective amount of a TLR7 modulating compound, or a pharmaceutically effective amount thereof.

Also provided is a method of lowering the chronic set point of HIV viral load in a human infected with HIV, the method comprising administering to the human a pharmaceutically effective amount of a compound of Formula II, or a pharmaceutically effective amount thereof.

Also provided is a method of lowering the chronic set point of HIV viral load in an HIV infected human receiving combination antiretroviral therapy, the method comprising administering to the HIV infected human receiving combination antiretroviral therapy a pharmaceutically effective amount of a compound of Formula II, or a pharmaceutically effective amount thereof.

Further provided is a method of lowering the chronic set point of HIV viral load in an HIV infected human receiving highly active antiretroviral therapy, the method comprising administering to the HIV infected human receiving highly active antiretroviral therapy a pharmaceutically effective amount of a compound of Formula II, or a pharmaceutically effective amount thereof.

Also provided are separate methods of reducing HIV viremia in a human infected with HIV and of lowering the chronic set point of HIV viral load in a human infected with HIV, each of the separate methods comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are group of separate methods of reducing HIV viremia in a human infected with HIV and of lowering the chronic set point of HIV viral load in a human infected with HIV, each of the separate methods comprising administering to the human infected with HIV a pharmaceutically effective amount of one compound selected from the 124 compounds of Examples 1 through 124, or a pharmaceutically acceptable salt thereof. One of each of the compounds from Example 1 to Example 124 are utilized in each of the group of separate methods of lowering the chronic set point of HIV viral load in a human infected with HIV, with the compound of Example 1, or a pharmaceutically acceptable salt thereof, being used in the first method, the compound of Example 2, or a pharmaceutically acceptable salt thereof, being used in the second method, etc.

For example, provided is a method of lowering the chronic set point of HIV viral load in a human infected with HIV, the method comprising administering to the human infected with HIV a pharmaceutically effective amount of the compound of Example 4, or a pharmaceutically acceptable salt thereof.

Also provided is a method of lowering the chronic set point of HIV viral load in a human infected with HIV, the method comprising administering to the human infected with HIV a pharmaceutically effective amount of the compound of Example 49, or a pharmaceutically acceptable salt thereof.

Also provided is a method of lowering the chronic set point of HIV viral load in a human infected with HIV, the method comprising administering to the human infected with HIV a pharmaceutically effective amount of the compound of Example 119, or a pharmaceutically acceptable salt thereof.

Also provided is a method of lowering the chronic set point of HIV viral load in a human infected with HIV, the method comprising administering to the human infected with HIV a pharmaceutically effective amount of the compound of Example 120, or a pharmaceutically acceptable salt thereof.

Also provided is a method of lowering the chronic set point of HIV viral load in a human infected with HIV, the method comprising administering to the human infected with HIV a pharmaceutically effective amount of the compound of Example 121, or a pharmaceutically acceptable salt thereof.

Provided is a method of lowering the chronic set point of HIV viral load in a human infected with HIV, the method comprising:
a) a first step of administering to a human in need thereof a pharmaceutically effective amount of a combination antiretroviral therapy regimen sufficient to lower the level of HIV in the human's blood or plasma to below a detectable level; and
b) a second step following the first step, the second step comprising administering to the human a pharmaceutically effective amount of a combination antiretroviral therapy regimen and a pharmaceutically effective amount of a compound of Formula II or a pharmaceutically acceptable salt thereof.

Also provided is a method of lowering the chronic set point of HIV viral load in a human infected with HIV, the method comprising:
a) a first step of administering to a human in need thereof a pharmaceutically effective amount of a combination antiretroviral therapy regimen sufficient to lower the chronic set point of HIV in the human's blood or plasma to a first level of less than 50 copies of HIV-1 RNA/ml of plasma; and
b) a second step following the first step, the second step comprising administering to the human a pharmaceutically effective amount of a combination antiretroviral therapy regimen and a pharmaceutically effective amount of a compound of Formula II or a pharmaceutically acceptable salt thereof, to lower the chronic set point of HIV in the human's blood or plasma to a second level, the second level being less than the first level.

Provided is a method of lowering the chronic set point of HIV viral load in a human infected with HIV, the method comprising:
a) a first step of administering to a human in need thereof a pharmaceutically effective amount of a combination antiretroviral therapy regimen sufficient to lower the level of HIV in the human's blood or plasma to below a detectable level; and b) a second step following the first step, the second step comprising administering to the human a pharmaceutically effective amount of a combination antiretroviral therapy regimen and a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided is a method of lowering the chronic set point of HIV viral load in a human infected with HIV, the method comprising:

a) a first step of administering to a human in need thereof a pharmaceutically effective amount of a combination antiretroviral therapy regimen sufficient to lower the chronic set point of HIV in the human's blood or plasma to a first level of less than 50 copies of HIV-1 RNA/ml of plasma; and b) a second step following the first step, the second step comprising administering to the human a pharmaceutically effective amount of a combination antiretroviral therapy regimen and a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof, to lower the chronic set point of HIV in the human's blood or plasma to a second level, the second level being less than the first level.

Additional separate embodiments within each of the methods described above wherein in one embodiment each, respectively, the designated method of lowering the chronic set point of HIV viral load in a human infected with HIV comprises the method described wherein the second level of the chronic set point of HIV in the human's blood or plasma is a concentration in the human's plasma of a) less than 40 copies of HIV-1 RNA/ml of plasma; b) less than 30 copies of HIV-1 RNA/ml of plasma; c) less than 20 copies of HIV-1 RNA/ml of plasma; d) less than 10 copies of HIV-1 RNA/ml of plasma; e) less than 5 copies of HIV-1 RNA/ml of plasma; f) less than 3 copies of HIV-1 RNA/ml of plasma; g) less than 1 copy of HIV-1 RNA/ml of plasma; h) less than 0.5 copies of HIV-1 RNA/ml of plasma; i) less than 0.3 copies of HIV-1 RNA/ml of plasma; and j) less than 0.1 copies of HIV-1 RNA/ml of plasma.

Also provided are separate embodiments within each of the methods of lowering the chronic set point of HIV viral load in a human infected with HIV, above, each comprising in the second step administering to the human a separate compound of one of the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2), or a pharmaceutically acceptable salt thereof. One of such methods is as described above wherein, in the second step, the human is administered a pharmaceutically effective amount of Formula III, or a pharmaceutically acceptable salt thereof, another method comprises administering to the human infected with HIV a pharmaceutically effective amount of Formula III(a), etc.

Also provided are group of separate methods within the method of lowering the chronic set point of HIV viral load in a human infected with HIV, above, each utilizing in the second step one compound selected from the group of Examples 1 through 124, or a pharmaceutically acceptable salt thereof. One of such methods is as described above wherein, in the second step, the human is administered a pharmaceutically effective amount of the compound of Example 1, or a pharmaceutically acceptable salt thereof, another method comprises administering to the human infected with HIV a pharmaceutically effective amount of the compound of Example 2, or a pharmaceutically acceptable salt thereof, etc.

For example, provided is a method of lowering the chronic set point of HIV viral load in a human infected with HIV, the method comprising:

c) a first step of administering to a human in need thereof a pharmaceutically effective amount of a combination antiretroviral therapy regimen sufficient to lower the level of HIV in the human's blood or plasma to below a detectable level; and d) a second step following the first step, the second step comprising administering to the human a pharmaceutically effective amount of a combination antiretroviral therapy regimen and a pharmaceutically effective amount of the compound of Example 4, or a pharmaceutically acceptable salt thereof.

Also provided is a method of lowering the chronic set point of HIV viral load in a human infected with HIV, the method comprising:

c) a first step of administering to a human in need thereof a pharmaceutically effective amount of a combination antiretroviral therapy regimen sufficient to lower the level of HIV in the human's blood or plasma to below a detectable level; and d) a second step following the first step, the second step comprising administering to the human a pharmaceutically effective amount of a combination antiretroviral therapy regimen and a pharmaceutically effective amount of the compound of Example 49, or a pharmaceutically acceptable salt thereof.

Provided is a method of lowering the chronic set point of HIV viral load in a human infected with HIV, the method comprising:

a) a first step of administering to a human in need thereof a pharmaceutically effective amount of a combination antiretroviral therapy regimen sufficient to lower the level of HIV in the human's blood or plasma to below a detectable level; and b) a second step following the first step, the second step comprising administering to the human a pharmaceutically effective amount of a combination antiretroviral therapy regimen and a pharmaceutically effective amount of the compound of Example 119, or a pharmaceutically acceptable salt thereof.

Provided is a method of lowering the chronic set point of HIV viral load in a human infected with HIV, the method comprising:

a) a first step of administering to a human in need thereof a pharmaceutically effective amount of a combination antiretroviral therapy regimen sufficient to lower the level of HIV in the human's blood or plasma to below a detectable level; and b) a second step following the first step, the second step comprising administering to the human a pharmaceutically effective amount of a combination antiretroviral therapy regimen and a pharmaceutically effective amount of the compound Example 120, or a pharmaceutically acceptable salt thereof.

Provided is a method of lowering the chronic set point of HIV viral load in a human infected with HIV, the method comprising:

c) a first step of administering to a human in need thereof a pharmaceutically effective amount of a combination antiretroviral therapy regimen sufficient to lower the level of HIV in the human's blood or plasma to below a detectable level; and d) a second step following the first step, the second step comprising administering to the human a pharmaceutically effective amount of a combination antiretroviral therapy regimen and a pharmaceutically effective amount of the compound Example 121, or a pharmaceutically acceptable salt thereof.

In each of the methods listed above for lowering the chronic set point of HIV viral load in a human infected with HIV there is a further embodiment in which the detectable level in the first step is a concentration in the human's blood plasma of less than 50 copies of HIV-1 RNA/mL.

Enhancing Immune Activity and Increasing HIV Gene Expression

Provided is a method of enhancing immune cell activity and increasing HIV gene expression in a human infected with HIV, the method comprising administering to the human infected with HIV a pharmaceutically effective amount of a TLR7 modulating compound, or a pharmaceutically acceptable salt thereof.

Also provided is a method of enhancing immune cell activity and increasing HIV gene expression in a human infected with HIV, the method comprising administering to the human infected with HIV a pharmaceutically effective amount of a compound of Formula II, or a pharmaceutically acceptable salt thereof.

Also provided is a method of enhancing immune cell activity and increasing HIV gene expression in a human infected with HIV, the method comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), or Formula III(f)(2); or a pharmaceutically acceptable salt thereof. It is understood that one of such methods comprises administering to the human infected with HIV a pharmaceutically effective amount of Formula III, or a pharmaceutically acceptable salt thereof, another method comprises administering to the human infected with HIV a pharmaceutically effective amount of Formula III(a), etc.

Also provided are separate methods of enhancing immune cell activity and increasing HIV gene expression in a human infected with HIV, each of the separate methods comprising administering to the human infected with HIV a pharmaceutically effective amount of a compound selected from one of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III (c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are group of separate methods of immune cell activity and increasing HIV gene expression in a human infected with HIV, each of the group of separate methods comprising administering to the human infected with HIV a pharmaceutically effective amount of one compound selected from Examples 1 through 124, or a pharmaceutically acceptable salt thereof. One of each of the compounds from Example 1 to Example 124 are utilized in each of the group of separate methods of enhancing immune cell activity and increasing HIV gene expression in a human infected with HIV, with the compound of Example 1, or a pharmaceutically acceptable salt thereof, being used in the first method, the compound of Example 2, or a pharmaceutically acceptable salt thereof, being used in the second method, etc.

For example, provided is a method of enhancing immune cell activity and increasing HIV gene expression in a human infected with HIV, the method comprising administering to the human infected with HIV a pharmaceutically effective amount of the compound of Example 4, or a pharmaceutically acceptable salt thereof.

Also provided is a method of enhancing immune cell activity and increasing HIV gene expression in a human infected with HIV, the method comprising administering to the human infected with HIV a pharmaceutically effective amount of the compound of Example 49, or a pharmaceutically acceptable salt thereof.

Also provided is a method of enhancing immune cell activity and increasing HIV gene expression in a human infected with HIV, the method comprising administering to the human infected with HIV a pharmaceutically effective amount of the compound of Example 119, or a pharmaceutically acceptable salt thereof.

Also provided is a method of enhancing immune cell activity and increasing HIV gene expression in a human infected with HIV, the method comprising administering to the human infected with HIV a pharmaceutically effective amount of the compound of Example 120, or a pharmaceutically acceptable salt thereof.

Also provided is a method of enhancing immune cell activity and increasing HIV gene expression in a human infected with HIV, the method comprising administering to the human infected with HIV a pharmaceutically effective amount of the compound of Example 121, or a pharmaceutically acceptable salt thereof.

Within each of the methods of enhancing immune cell activity and increasing HIV gene expression in a human infected with HIV there are further separate embodiments wherein the immune cell activity is, respectively, in each of the further embodiments one of the activities selected from the group of a) plasmacytoid dendritic cell (PDC) activity, b) B-cell activity; c) T-cell activity, d) CD4 T-cell activity, e) CD8 T-cell activity, and f) natural killer (NK) cell activity, invariant NK T cell activity, monocyte/macrophage activity.

Enhancing Antiviral Efficacy

Also provided is a method of enhancing the efficacy of an antiviral agent in a human infected with HIV, the method comprising administering to the human infected with HIV a pharmaceutically effective amount of a TLR7 modulating compound and a pharmaceutically effective amount of an antiviral agent.

Also provided is a method of enhancing the efficacy of two or more antiviral agents in a human infected with HIV, the method comprising administering to the human infected with HIV a pharmaceutically effective amount of a TLR7 modulating compound and a pharmaceutically effective amount of each of the two or more antiviral agents.

Separate embodiments within the method of enhancing the efficacy of an antiviral agent in a human infected with HIV comprise the method wherein the TLR7 modulating compound is a compound of Formula II, or a pharmaceutically acceptable salt thereof.

Also provided is a method of enhancing the efficacy of an antiviral agent in a human infected with HIV, the method comprising administering to the human infected with HIV a pharmaceutically effective amount of a TLR7 modulating compound and a pharmaceutically effective amount of an antiviral agent and a pharmaceutically effective amount of cobicistat. Separate embodiments within the method of enhancing the efficacy of an antiviral agent in a human infected with HIV comprise the method wherein the TLR7 modulating compound is a compound of Formula II, or a pharmaceutically acceptable salt thereof.

Also provided is a method of enhancing the efficacy of an antiviral agent in a human infected with HIV, the method comprising administering to the human infected with HIV a pharmaceutically effective amount of a TLR7 modulating compound, a pharmaceutically effective amount of an antiviral agent, and a pharmaceutically effective amount of ritonavir. Separate embodiments within the method of enhancing the efficacy of an antiviral agent in a human infected with HIV comprise the method wherein the TLR7 modulating compound is a compound of Formula II, or a pharmaceutically acceptable salt thereof.

Additional separate embodiments of the methods above of enhancing the efficacy of an antiviral agent in a human infected with HIV, comprise the method wherein the compound of Formula II, or a pharmaceutically acceptable salt thereof, is selected from the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof. Additional separate embodiments of the methods above of enhancing the efficacy of an antiviral agent in a human infected with HIV, comprise the method wherein the compound of Formula II is, respectively, a compound of Examples 1 through 124, or a pharmaceutically acceptable salt thereof.

Enhancing the efficacy of an antiviral agent refers the achievement of greater antiviral activity in a human infected with HIV from administration of the antiviral agent and a TLR7 modulating compound than would be achieved by administration of the same dosage or regimen of the antiviral agent alone. Enhancing the efficacy of an antiviral agent includes achieving a lower viral set point or a lower viral load in the human infected with HIV by administration of the antiviral agent and a TLR7 modulating compound than would be achieved by administration of the same dosage or regimen of the antiviral agent alone, as well as achieving a desired viral set point or viral load in the human through the administration of a lower dose of the antiviral agent. Enhancing the efficacy of an antiviral agent also includes achieving elimination of HIV infection in the human infected with HIV.

TLR7 modulating compounds may be used in the methods herein to enhance the efficacy of combination antiviral agents, including those listed in Tables A through J. Combinations of TLR7 modulating compounds and combination antiviral agents whose activity may be enhanced include those seen in Tables 1A through 65.

HIV Vaccines

Provided is a method of treating an HIV infection in a human, the method comprising:
 a) administering to a human in need thereof a pharmaceutically effective amount of a TLR7 modulating compound, or a pharmaceutically acceptable salt thereof; and
 b) administering to the human a pharmaceutically effective amount of an HIV vaccine.

As used herein, the term "HIV vaccine" refers to a vaccine that either protects a human who does not have an HIV infection from contracting the virus or which may have a therapeutic effect for persons infected with HIV or who later contract HIV. Vaccines that may be used to challenge the recipient's immune system include HIV DNA vaccines, live vector vaccines, viral protein or viral peptide vaccines, and virus-like particle (VLPs) vaccines.

TLR7 modulating compounds described herein may also be administered in the methods herein in combination with an HIV vaccine, such as a peptide vaccines, recombinant subunit protein vaccines (including subunit proteins gp120, gp140, and gp160, live vector vaccines encoding HIV-1 antigens, such as those selected from the group of gag, pol, env, nef, rev, tat, vif, vpr, vpu, and antigenic proteins, variants and fusion proteins thereof), inactivated vaccines, modified envelope vaccines, replicons (including Venezuelan equine encephalitis (VEE), Semliki forest virus (SFV), adenovirus-associated virus (AAV), including self-complementary adeno-associated virus (scAAV), and human papillomavirus (HPV) replicon systems), DNA vaccines, vaccine combinations, and virus-like particle vaccines (pseudovirion vaccines). Recombinant HIV vaccines may be produced using vaccine viral vector platforms known in the art, including those developed from Adenoviridae, Poxviridae, Herpesviridae, or Adeno-associated viruses, as well as cytomegalovirus, carynpox, rubella, poliovirus, Venezuelan equine encephalitis virus, lentivirus, *salmonella*, bacilli Calmete-Guerin (BCG), and Sendai vectors.

Examples of HIV vaccines for use with the methods herein include ALVAC-HIV MN120TMG (vCP205), rgp120, monomeric gp120, trimeric gp120, gp120 monomer+gp120 trimer, MN rgp120/HIV-1 and GNE8 rgp120/HIV-1, ALVAC-HIV (vCP1521), ALVAC+gp120/MF59, ALVAC-HIV MN120TMG (vCP205), ALVAC(2)120(B, MN)GNP (vCP1452), ALVAC(1)120(B,MN)GNP (vCP1433), ALVAC-HIV+AIDSVAX® B/E, ALVAC VIH 1433, AIDSVAX B/B, AIDSVAX B/E, tgAAC09 (a Gag-PR-RT AAV HIV vaccine), Ad35, Ad35-GRIN/ENV, Ad35-GRIN, Ad35-ENV, the SeV-G(NP) vaccine, EN41-FPA2 HIV, EN41-UGR7C, Ad4-EnvC150, GSK 692342, GSK 732461, GSK 732462, MRKAd5 HIV-1 Gag, MRKAd5 HIV-1 gag/pol/nef, JS7 DNA, pGA2/JS7, Sub C gp140, trimeric gp140, trimeric gp140+monomeric gp120, trimeric gp140+trimeric gp120, trimeric gp140+monomeric gp120+ trimeric gp120, TBC-M4, MVA-nef, rMVA-HIV (env/gag [TBC-M358], tat/rev/nef-RT [TBC-M335], rFPV-HIV (env/ gag [TBC-F357], tat/rev/nef-RT [TBC-F349], TBC-3B, ADVAX e/g+ADVAX p/N-t (ADVAX), MVA-C+gp140/MF59, DNA-C, DNA-C2, MVA-C, MVA HIV-B (MVATG17401), MVA-mBN120B, MF59, MTP-PE/MF59, DNA-C2+MVA-C, DNA-C2+MVA-C+gp140/MF59, NYVAC, NYVAC-B/rAd5, rAd5/NYVAC-B NYVAC-HIV-PT1, NYVAC-HIV-PT4, DNA+NYVAC+gp120, NYVAC+gp120, Ad26, Ad26.ENVA.01 (rAd26), MVA, Ad26/MVA, HIV gp41, HIV gp41 monomer, HIV gp41 trimer, gp120, gp140, gp160, PENNVAX®-B HIV Vaccine, PENNVAX-G DNA, Salmonella typhi CVD 908-HIV-1 LAI gp 120 (VVG 203), HIV-1MN, rgp120/HIV-1MN, VRC4302, VRC-HIVDNA016-00-VP, VRC-HIVDNA009-00-VP, VRC-HIVDNA009-00-VP, VRC-HIVADV014-00-VP, gp160 MN/LAI-2, VRC-HIVADV027-00-VP, VRC-HIVADV038-00-VP, VRC-HIVDNA044-00-VP, VRC-HIVDNA016-00-VP, VRC rAd5 vaccine (rAd5 gag-pol/env A/B/C), HIV-v, LIPO-4, LIPO-5, LIPO-6T, Modified Vaccinia Ankara (MVA) Vectored HIV-1 (ADMVA), CTL MEP/RC529-SE/GM-CSF (CTL MEP), AVX101, REMUNE® HIV-1 immunogen, HIV p24/MF59, HIV-1p24(gag), HIV SF2 gp120/MF59, rgp120/HIV-1 SF-2 (gp120), rgp120/HIV-1 SF-2, MVA-CMDR, SCBaL/M9, DNA Nat-B env, NYVAC Nat-B env, DNA CON-S env, NYVAC CON-S env, DNA Mosaic env, NYVAC Mosaic env, rAd5 env A, rAd5 env B, rAd5 env C, rAd5 gag-pol, GENEVAX-HIV (APL 400-003), rMVA-HIV (rMVA-HIV env/gag+rMVA-HIV tat/rev/nef-RT), rFPV-HIV (rFPV-HIV env/gag+rFPV-HIV tat/rev/nef-RT), HIV-1 gag DNA plus IL-12 DNA adjuvant, DNA-HIV-PT123, DNA HIVIS, HIVIS 03 DNA, MVA-CMDR, EnvDNA, PolyEnv1, EnvPro, SAAVI DNA-C2, SAAVI MVA-C, HIV-1 C4-V3 Polyvalent Peptide, EP HIV-1043, EP HIV-1090, HIV-MAG, CN54gp140, CN54gp140/GLA-AF, HIV DNA plasmid/recombinant fowlpox vector, HIV62B, MVA/HIV62, pGA2/JS7 DNA/MVA/HIV62, VSV-Indiana HIV gag, MRKAd5 (Clade B), Clade B gag DNA/PLG, MRKAd5 HIV-1 gag/pol/nef, env DNA/PLG, GEO-D03 DNA, Trivalent MRKAd5 HIV-1 gag/pol/nef, HIVAC-1e, MVA.HIVconsv, pSG2.HIVconsv DNA, Electroporated pSG2.HIVconsv, pHIS-HIV-AE, rAAV1-PG9DP, Ad5.ENVA.48 HIV-1, Ad26.ENVA.01 HIV-1, NefTat, gp120W61D, Profectus HIV MAG pDNA, pGA2/JS2 Plasmid DNA, ChAdV63.HIVconsv, HIV gp120/NefTat/AS02A, rgp120/HIV-1IIIB, rgp120/HIV-1MN Monovalent Octameric V3 Peptide Vaccine, HIV-1 C4-V3 Polyvalent Peptide Vaccine, HIV-1 Gag-Pol DNA (APL 400-047), AFO-18, NYVAC-C, UBI HIV-1 MN PND peptide immunogen, UBI microparticulate monovalent HIV-1 MN branched peptide, HIV p17/p24:Ty-VLP, A244 rgp120/HIV-1, Env 2-3, MTP-PE/MF59, P3C541b Lipopeptide, rAd5 Gag-Pol Env A/B/C, rAd5 Gag-Pol, Ad4-H5-VTN, EP-1233, MVA-mBN32, rVSV, pGA2/JS7 DNA, MVA/HIV62, pGA2/JS7 (JS7)DNA, MVA62B, HIV-1 Tat/delta-V2 Env combined, HIV-1 delta-V2 Env, GTU-multiHIV B, E1M184V peptide, VCR-HIVDNA006-00-VP, HIV LFn-p24, VAC-3S, MYM-V101, DCVax-001, DCVax plus poly-ICLC, Vacc-4x, TUTI-16, gp120/ASO2A, gp120/nef/tat/SIV nef/ASO2A, nef/tat/SIV nef/ASO2A, gp120/nef/tat/SIV nef, nef/tat/SIV nef/AS06, VICHREPOL, Ad35-ENVA, Ad5HVR48.ENVA.01, ADVAX e/g, ADVAX p/n-t, Cervico-vaginal CN54gp140-hsp70 conjugate vaccine (TL01), DNA (Gag, Pot, and Env genes from HIV-1 CN54)+Tiantian vaccinia vector, HIV-1 CN54 gag, HIV-1 CN54 pot, HIV-1 CN54 env, MV1-F4-CT1, MVA.HIVA, MVA HIV-B, rAd35, and rVSV$_{IN}$ HIV-1 Gag vaccines, and combinations thereof.

Examples of HIV vaccines that may also be used in the present methods and useful vectors for preparing them include those disclosed in US 2008/0199493 A1 (Picker et al.), US 2013/0142823 (Picker et al.), US20040223977 (Diamond), WO2014039840 (Levy), WO2014026033 (Yamamoto), WO2013182660 (Sorensen et al.), WO2013110818 (Brander et al.), WO2013110790 (Bomsel et al.), WO2013059442 (Song et al.), WO2012156750 (Davis et al.), WO2012137072 (Andrieu et al.), WO2012116142 (Podack et al.), US20120107910 (Liu et al.), WO2012018856 (Rautsola et al.), US20120021000 (Opendra et al.), US20110305749 (Ryttergaard et al.), WO2011117408 (Bourguignon et al.), US20130195904A1 (August et al.), US20110159025 (Littman et al.), US20110123485 (Desrosiers et al.), US20110311585A1 (Berman), US20110159025A1 (Littman et al.), US20110014221 (Kang et al.), US20120263720A1 (Gronvold et al.), US20100304483 (Abulafia-Lapid), US20100215695 (Yu), US20100135994 (Banchereau et al.), US20120045472A1 (Harrison et al.), US20110195083A1 (Anglister et al.), U.S. Pat. No. 7,612,173B2 (Albrecht et al.), US20080199493A1 (Picker et al.), and U.S. Pat. No. 7,364,744B2 (Hovanessian et al.), US20150132332 (Shao et al.), WO2015073291 (Weiner et al.), WO2015048512 (Haynes et al.), WO2015001128 (Benarous et al.), US20140302080 (Barouch et al.), (WO2014039840 (Levy et al.), WO2014026033 (Yamamoto et al.), WO2015007337 (Hoie et al.), US20150132255 (Birger et al.), US20150050310 (Brander et al.), and US20150004190 (Bomsel et al.), the contents of each of which are incorporated herein by reference.

Also useful in the methods and combinations with the vaccines and methods described herein are agents that provide adjuvant activity to a vaccine, such as agonists of TLR3, TLR4, TLR9, NOD-1/2 (NOD-like receptors), and RIG-I (RIG-I-like receptors).

Also provided is a method of enhancing the efficacy of an HIV vaccine, the method comprising administering to a human in need thereof a pharmaceutically effective amount of an HIV vaccine and a pharmaceutically effective amount of a TLR7 modulating compound. One method of enhancing the efficacy of an HIV vaccine comprises a first step of administering to a human in need thereof a pharmaceutically effective amount of a TLR7 modulating compound and a second step of administering to the human in need thereof a pharmaceutically effective amount of an HIV vaccine. Another method of enhancing the efficacy of an HIV vaccine comprises a first step of administering to a human in need thereof a pharmaceutically effective amount of an HIV vaccine and a second step of administering to the human in need thereof a pharmaceutically effective amount of a TLR7 modulating compound. Specific separate embodiments within each of these methods of enhancing efficacy of an HIV vaccine comprise the method indicated wherein the TLR7 modulating compound is a) a compound of Formula II, b) Example 4, c) Example 49, d) Example 119, e) Example 120, and f) Example 121, respectively, or a pharmaceutically acceptable salt thereof. Non-limiting examples of HIV vaccines for use in these methods include those described herein.

HIV Antibodies

Provided is a method of treating an HIV infection in a human, the method comprising:
a) administering to a human in need thereof a pharmaceutically effective amount of a TLR7 modulating compound, or a pharmaceutically acceptable salt thereof; and
b) administering to the human a pharmaceutically effective amount of an HIV antibody.

Also provided is a method of treating an HIV infection in a human, the method comprising:
a) administering to a human in need thereof a pharmaceutically effective amount of a TLR7 modulating compound, or a pharmaceutically acceptable salt thereof; and
b) administering to the human a pharmaceutically effective amount of two or more HIV antibodies.

Provided is a method of treating an HIV infection in a human, the method comprising:
a) administering to a human in need thereof a pharmaceutically effective amount of a compound of Formula II, or a pharmaceutically acceptable salt thereof; and
b) administering to the human a pharmaceutically effective amount of an HIV antibody.

Also provided is a method of treating an HIV infection in a human, the method comprising:
a) administering to a human in need thereof a pharmaceutically effective amount of a compound of Formula II, or a pharmaceutically acceptable salt thereof; and
b) administering to the human a pharmaceutically effective amount of two or more HIV antibodies.

Also provided are twenty further separate embodiments, each comprising the method of treating an HIV infection in a human through administration of a compound of Formula II and an HIV antibody, as just described, wherein in each of the separate embodiments the compound of Formula II is one compound selected from the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof.

Also provided are 124 further separate method of treating an HIV infection in a human through administration of a compound of Formula II and an HIV antibody, as just described, wherein the compound of Formula II is a compound of Examples 1 through 124, or a pharmaceutically acceptable salt thereof. One of such methods of treating an HIV infection in a human through administration of a compound of Formula II and an HIV antibody is as described above wherein, in the first step, the human is administered a pharmaceutically effective amount of the compound of Example 1, or a pharmaceutically acceptable salt thereof, another method comprises administering to the human infected with HIV a pharmaceutically effective amount of the compound of Example 2, or a pharmaceutically acceptable salt thereof, in the first step, etc.

Also provided is a method of treating an HIV infection in a human, the method comprising administering to a human in need thereof:
a) a pharmaceutically effective amount of the compound of Example 4, or a pharmaceutically acceptable salt thereof; and
b) a pharmaceutically effective amount of an HIV antibody.

Also provided is a method of treating an HIV infection in a human, the method comprising administering to a human in need thereof:
a) a pharmaceutically effective amount of the compound of Example 49, or a pharmaceutically acceptable salt thereof; and
b) a pharmaceutically effective amount of an HIV antibody.

Also provided is a method of treating an HIV infection in a human, the method comprising administering to a human in need thereof:
a) a pharmaceutically effective amount of the compound of Example 119, or a pharmaceutically acceptable salt thereof; and
b) a pharmaceutically effective amount of an HIV antibody.

Also provided is a method of treating an HIV infection in a human, the method comprising administering to a human in need thereof:
a) a pharmaceutically effective amount of the compound of Example 120, or a pharmaceutically acceptable salt thereof; and
b) a pharmaceutically effective amount of an HIV antibody.

Also provided is a method of treating an HIV infection in a human, the method comprising administering to a human in need thereof:
a) a pharmaceutically effective amount of the compound of Example 121, or a pharmaceutically acceptable salt thereof; and
b) a pharmaceutically effective amount of an HIV antibody.

For each of the methods described herein comprising administering to a human in need thereof a pharmaceutically effective amount of a TLR7 modulating compound, including those of Formula II, Examples 1-124, etc., and a pharmaceutically effective amount of an HIV antibody, there are further embodiments directed to the sequence of administering each agent.

In one embodiment within each method the TLR7 modulating compound and the HIV antibody may be administered to the human together, such as each being administered in the same day. Pharmaceutically effective amounts of each agent can be administered on a specified regimen, such as once weekly, once every other week, once every three weeks, once per month, etc. In another embodiment within each method the initial doses of the TLR7 modulating compound and the HIV antibody may be administered to the human together, with subsequent administrations being at staggered time points. For instance, following an initial dose of each agent, the TLR7 compound could be administered to the human every day or in 2-, 3-, 4-, 5-, 6-, 7-, 8-, 9-, 10-, 11, 12-, 13-, 14-, or 15 day intervals, wherein the HIV antibody is administered once per week, twice per month, monthly, etc.

In another embodiment within each method the TLR7 modulating compound may be administered in an initial administration, with the HIV antibody being administered to the human in a subsequent administration, such as 1, 2, 3, 4, 5, 6, 7, 8, 9, 10, 11, 12, 13, 14, or 15 days following administration of the TLR7 modulating compound. In another embodiment within each method the HIV antibody may be administered in an initial administration, with the TLR7 modulating compound being administered to the human in a subsequent administration, such as 1, 2, 3, 4, 5, 6, 7, 8, 9, 10, 11, 12, 13, 14, or 15 days following administration of the TLR7 modulating compound.

Similar regimens of administration are understood for the methods described herein comprising administering to a human in need thereof a pharmaceutically effective amount of a TLR7 modulating compound, including those of Formula II, Examples 1-121, etc., a pharmaceutically effective amount of an HIV antibody, and a combination antiretroviral therapy there are further embodiments directed to the sequence of administering each agent. For instance, in instances in which the human in need thereof is already being administered an antiretroviral combination therapy, such as a cART or HAART regimen, the TLR7 modulating compound and the HIV antibody may be added to the ongoing antiretroviral combination therapy using any of the regimens described for them above. In additional embodiments within each method, the TLR7 modulating compound may be administered as the initial agent, followed by subsequent administrations of the agents of the combination antiretroviral therapy and the HIV antibody. In additional embodiments within each method, the TLR7 modulating compound and the HIV antibody may be administered to the human in need thereof in one of the regimens described for them above and the agents of the combination antiretroviral therapy may be administered at a later point in time.

Provided is a method of treating an HIV infection in a human, the method comprising:
a) administering to a human in need thereof a pharmaceutically effective amount of a combination antiretroviral therapy;
b) administering to a human in need thereof a pharmaceutically effective amount of a TLR7 modulating compound, or a pharmaceutically acceptable salt thereof; and
c) administering to the human a pharmaceutically effective amount of an HIV antibody.

Provided is a method of treating an HIV infection in a human, the method comprising:
a) administering to a human in need thereof a pharmaceutically effective amount of a combination antiretroviral therapy;
b) administering to a human in need thereof a pharmaceutically effective amount of a compound of Formula II or a pharmaceutically acceptable salt thereof; and
c) administering to the human a pharmaceutically effective amount of an HIV antibody.

Also provided are 19 further separate embodiments, each comprising the method of treating an HIV infection in a human through administration of a combination antiretroviral therapy, a compound of Formula II, and an HIV antibody, as just described, wherein in each of the separate embodiments the compound of Formula II is one compound selected from the group of Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof.

Also provided are 124 further separate method of treating an HIV infection in a human through administration of a combination antiretroviral therapy, a compound of Formula II, and an HIV antibody, as just described, wherein the compound of Formula II is a compound of Examples 1 through 124, One of each of the compounds from Example 1 to Example 124 are utilized in each of the group of separate methods of treating an HIV infection in a human through administration of a combination antiretroviral therapy, a compound of Formula II, and an HIV antibody, with the compound of Example 1, or a pharmaceutically acceptable salt thereof, being used as the compound of Formula II in the first method, the compound of Example 2, or a pharmaceutically acceptable salt thereof, being used as the compound of Formula II in the second method, etc.

Also provided is a method of treating an HIV infection in a human, the method comprising:
a) administering to a human in need thereof a pharmaceutically effective amount of an antiretroviral agent;
b) administering to a human in need thereof a pharmaceutically effective amount of a TLR7 modulating compound, or a pharmaceutically acceptable salt thereof; and
c) administering to the human a pharmaceutically effective amount of an HIV antibody.

Also provided is a method of treating an HIV infection in a human, the method comprising:
d) administering to a human in need thereof a pharmaceutically effective amount of a combination antiretroviral therapy;
e) administering to a human in need thereof a pharmaceutically effective amount of a compound of Formula II, or a pharmaceutically acceptable salt thereof; and
f) administering to the human a pharmaceutically effective amount of an HIV antibody.

Also provided is a method of treating an HIV infection in a human, the method comprising:
g) administering to a human in need thereof a pharmaceutically effective amount of a combination antiretroviral therapy;
h) administering to a human in need thereof a pharmaceutically effective amount of the compound of Example 4, or a pharmaceutically acceptable salt thereof; and
i) administering to the human a pharmaceutically effective amount of an HIV antibody.

Also provided is a method of treating an HIV infection in a human, the method comprising:
a) administering to a human in need thereof a pharmaceutically effective amount of a combination antiretroviral therapy;
b) administering to a human in need thereof a pharmaceutically effective amount of the compound of Example 49, or a pharmaceutically acceptable salt thereof; and
c) administering to the human a pharmaceutically effective amount of an HIV antibody.

Also provided is a method of treating an HIV infection in a human, the method comprising:
a) administering to a human in need thereof a pharmaceutically effective amount of a combination antiretroviral therapy;
b) administering to a human in need thereof a pharmaceutically effective amount of the compound of Example 119, or a pharmaceutically acceptable salt thereof; and
c) administering to the human a pharmaceutically effective amount of an HIV antibody.

Also provided is a method of treating an HIV infection in a human, the method comprising:
a) administering to a human in need thereof a pharmaceutically effective amount of a combination antiretroviral therapy;

b) administering to a human in need thereof a pharmaceutically effective amount of the compound of Example 120, or a pharmaceutically acceptable salt thereof; and c) administering to the human a pharmaceutically effective amount of an HIV antibody.

Also provided is a method of treating an HIV infection in a human, the method comprising:

a) administering to a human in need thereof a pharmaceutically effective amount of a combination antiretroviral therapy;

b) administering to a human in need thereof a pharmaceutically effective amount of the compound of Example 121, or a pharmaceutically acceptable salt thereof; and administering to the human a pharmaceutically effective amount of an HIV antibody Provided is a method of treating an HIV infection in a human, the method comprising:

a) administering to a human in need thereof a pharmaceutically effective amount of a combination antiretroviral therapy regimen sufficient to lower the level of HIV detected in the human's blood or plasma to a specified level; and b) administering to a human in need thereof a pharmaceutically effective amount of a compound of Formula II, or a pharmaceutically acceptable salt thereof; and c) administering to the human a pharmaceutically effective amount of an HIV antibody.

Also provided are twenty further separate embodiments, each comprising the method of treating an HIV infection in a human through administration of a combination antiretroviral therapy regimen sufficient to lower the level of HIV detected in the human's blood or plasma to a specified level, a compound of Formula II, and an HIV antibody, as just described, wherein in each of the separate embodiments the compound of Formula II is one compound selected from the group of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof.

Also provided are 124 further separate method of treating an HIV infection in a human through administration of a combination antiretroviral therapy regimen sufficient to lower the level of HIV detected in the human's blood or plasma to a specified level, a compound of Formula II, and an HIV antibody, as just described, wherein the compound of Formula II is a compound of Examples 1 through 124.

Also provided is a method of treating an HIV infection in a human, the method comprising:

a) administering to a human in need thereof a pharmaceutically effective amount of a combination antiretroviral therapy regimen sufficient to lower the level of HIV detected in the human's blood or plasma to a specified level;

b) administering to a human in need thereof a pharmaceutically effective amount of the compound of Example 4, or a pharmaceutically acceptable salt thereof; and c) administering to the human a pharmaceutically effective amount of an HIV antibody.

Also provided is a method of treating an HIV infection in a human, the method comprising:

a) administering to a human in need thereof a pharmaceutically effective amount of a combination antiretroviral therapy;

b) administering to a human in need thereof a pharmaceutically effective amount of the compound of Example 49, or a pharmaceutically acceptable salt thereof; and c) administering to the human a pharmaceutically effective amount of an HIV antibody.

Also provided is a method of treating an HIV infection in a human, the method comprising:

a) administering to a human in need thereof a pharmaceutically effective amount of a combination antiretroviral therapy;

b) administering to a human in need thereof a pharmaceutically effective amount of the compound of Example 119, or a pharmaceutically acceptable salt thereof; and c) administering to the human a pharmaceutically effective amount of an HIV antibody.

Also provided is a method of treating an HIV infection in a human, the method comprising:

a) administering to a human in need thereof a pharmaceutically effective amount of a combination antiretroviral therapy;

b) administering to a human in need thereof a pharmaceutically effective amount of the compound of Example 120, or a pharmaceutically acceptable salt thereof; and c) administering to the human a pharmaceutically effective amount of an HIV antibody.

Also provided is a method of treating an HIV infection in a human, the method comprising:

a) administering to a human in need thereof a pharmaceutically effective amount of a combination antiretroviral therapy;

b) administering to a human in need thereof a pharmaceutically effective amount of the compound of Example 121, or a pharmaceutically acceptable salt thereof; and c) administering to the human a pharmaceutically effective amount of an HIV antibody.

HIV antibodies useful in the methods herein include:

CD4-binding site-directed antibodies, including those that bind to the CD4 binding site on gp120 such as VRC01, VRC02, VRC03, VRC04, VROC07, b12, HJ16, NIH45-46, 3BNC60, BNC62, 3BNC117, 12A12, 12A21, 12A30, VRC-PG04, VRC-CH30, VRC-CH31, VRC-CH32, VRC-CH33, VRC-CH34, VRC-PG04, VRC-PG04b, 8ANC131, 8ANC37, 8ANC134, CH103, CH104, CH105, CH106, 3BNC117, 3BNC60, NIH45, NIH46, 12A12, 12A21, 8ANC131, 8ANC134, 1NC9, 1B2530, 7B2, and A32;

Gp-120 variable region 1 and variable region 2 (V1N2)-directed antibodies, such as PG9, PG16, CH01-04, PGT141, PGT142, PGT143, PGT144, PGT145, and CAP256-VRC26;

Glycan V3-directed antibodies, such as the PGT121 series of antibodies, including PGT121, PGT122, PGT123, PGT 124, PGT 125, PGT126, PGT127, PGT128, PGT130, PGT131, PGT-132, PGT135, PGT136, and PGT137, as well as 2G12;

membrane-proximal external region (MPER)-directed antibodies, such as the 2F5, Z13, 4E10, 10E8, PGT150 series of antibodies, M66.6, CAP206-CH12, and 10E81. PG and PGT antibodies are described in WO 2010/107939 and WO 2012/030904.

Additional antibodies for use with the methods herein include PGT-138, PGT-139, PGT-133, PGT-134, PGT-135, PGT-136, PGT-137, PGT-141, PGT-142, PGT-143, PGT-144, PGT-145, PGT-151, PGT-152, PGT-153, PGT-154, PGT-155, PGT-156, PGT-157, and PGT-158.

Additional antibodies for use with the methods herein include bi-specific antibodies. Such bi-specific antibodies will have at least one variable region recognizing a portion of the HIV virus, e.g., gp120 or gp41. In certain embodiments, the bi-specific antibodies include a second variable region recognizing a memory cell surface, such as CD3 or CD4. Exemplary bi-specific antibodies include but are not limited to those inducing the redirected CD8 T cell-dependent lysis of HIV infected cells such as those recognizing HIV gp120/41 envelope (arm A) and CD3 receptor (arm B) as described in WO2013163427 A1. Furthermore, the bi-specific antibodies may include additional platforms such as BiTEs (Amgen), DARTs (Macrogenics), Duobodies (GenMab) as well as other platforms (Xencor, Sanofi, etc.). Additional examples of bispecific antibodies may include those inducing redirected NK cell-mediated lysis of HIV infected cells such as those recognizing HIV gp120/41 envelope (arm A) and NKG2D receptor (arm B) based on Affimed platform.

Additional antibodies for use with the methods herein include bi-specific antibodies such as those inducing the redirected CD8 T cell-dependent lysis of HIV infected cells such as those recognizing HIV gp120/41 envelope (arm A) and CD3 receptor (arm B) as described in WO2013163427 A1. Furthermore, the bi-specific antibodies may include additional platforms such as BiTEs (Amgen), DARTs (Macrogenics), Duobodies (GenMab) as well as other platforms (Xencor, Sanofi, etc.). Additional examples of bispecific antibodies may include those inducing redirected NK cell-mediated lysis of HIV infected cells such as those recognizing HIV gp120/41 envelope (arm A) and NKG2D receptor (arm B) based on Affimed platform.

Immunomodulatory Antibodies and Small Molecule Agents

Specific antibodies for use include also immunomodulatory monoclonal antibodies:
inhibitory anti-PD-1 mAbs such Nivolimumab (BMS-936558 or MDX1106), MK-34775 inhibitory anti-PD-L1 mAbs BMS-936559. MPDL3280A, MED14736, MSB0010718C, and MDX1105-01; inhibitory anti-CTLA-4 mAbs, such as Ipilimumab, and Tremilimumab; inhibitory anti-Tim3 mAbs, such as those from Tesaro, Inc.; inhibitory anti-LAG-3 mAbs, such as BMS-986016, IMP321; inhibitory anti-KIR mAbs, such as Lirilumab (IPH2102/BMS-986015);
stimulatory anti-CD27 mAbs, such as CDX-1127; stimulatory anti-CD40 mAbs, such CP-870,893, and BMS-986090; stimulatory anti-CD47 mAbs, such as those seen in Tseng et al, Proc Natl Acad Sci USA. Jul. 2, 2013; 110(27): 11103-11108; stimulatory anti-CD134 (OX40) mAbs, such as MEDI-6469 or those seen in WO-2009079335, and WO-2006121810;
Stimulatory anti-CD137 mAbs, such as BMS-663513; PF-05082566; additional antibodies against immunomodulatory receptors such as TIGIT, BTLA and others as listed in Chen and Flies, Nat. Rev. Immunol. 13, 227-42 (2013); and nucleic acid encoding fusion proteins that prevent or inhibit HIV infection, administered by themselves or via a vector, such as a VEE, SFV, AAV, scAAV, or HPV vector, including those described in U.S. 2011/0305670A1 (Farzan), such as the eCD4-Ig, eCD4-Ig.A, eCD4-Ig.B, CD4-Ig, E1-Ig, E2-Ig, E3-Ig, e3-CD4-Ig, e4-CD4-Ig, and CCR5mim-Ig, including AAV-expressed eCD4-Ig and scAAV-expressed eCD4-Ig.

In an embodiment, the specific antibodies for use include immunomodulatory monoclonal antibodies:
inhibitory anti-PD-1 mAbs such Nivolimumab (BMS-936558 or MDX1106), MK-34775
inhibitory anti-PD-L1 mAbs BMS-936559. MPDL3280A, MEDI4736, MSB0010718C, and MDX1105-01;
inhibitory anti-CTLA-4 mAbs, such as Ipilimumab, and Tremilimumab;
inhibitory anti-Tim3 mAbs, such as those from Tesaro, Inc.; inhibitory anti-LAG-3 mAbs, such as BMS-986016, IMP321;
inhibitory anti-KIR mAbs, such as Lirilumab (IPH2102/BMS-986015);
stimulatory anti-CD27 mAbs, such as CDX-1127;
stimulatory anti-CD40 mAbs, such CP-870,893, and BMS-986090;
stimulatory anti-CD47 mAbs, such as those seen in Tseng et al, Proc Natl Acad Sci USA. Jul. 2, 2013; 110(27): 11103-11108;
stimulatory anti-CD134 (OX40) mAbs, such as MEDI-6469 or those seen in WO-2009079335, and WO-2006121810;
Stimulatory anti-CD137 mAbs, such as BMS-663513; PF-05082566;
additional antibodies against immunomodulatory receptors such as TIGIT, BTLA and others as listed in Chen and Flies, Nat. Rev. Immunol. 13, 227-42 (2013).

Small molecule immunomodulatory agents to use in combination with TLR7 agonists include indole oxygenase inhibitors (also known as inhibitors of IDO, IDO1, indoleamine-2,3-dioxygenase, indoleamine dioxygenase-1, or indoleamine-pyrrole 2,3-dioxygenase), such as INCB024360, 1-methyl-D-tryptophan, NLG919 PI3K delta inhibitors such as Idelalisib, GS-9820, and GS-9901, and other TLR8 agonist such as VTX-1463 or VTX-2337.

Provided is a method of eliminating an HIV infection in a human, the method comprising:
b) administering to a human in need thereof a pharmaceutically effective amount of a TLR7 modulating compound, or a pharmaceutically acceptable salt thereof; and
c) administering to the human a pharmaceutically effective amount of an HIV antibody.

Provided is a method of eliminating an HIV infection in a human, the method comprising:
c) administering to a human in need thereof a pharmaceutically effective amount of a compound of Formula II, or a pharmaceutically acceptable salt thereof; and
d) administering to the human a pharmaceutically effective amount of an HIV antibody.

Also provided is a method of eliminating an HIV infection in a human, the method comprising:
e) administering to a human in need thereof a pharmaceutically effective amount of a combination antiretroviral therapy;
f) administering to a human in need thereof a pharmaceutically effective amount of a compound of Formula II, or a pharmaceutically acceptable salt thereof; and
g) administering to the human a pharmaceutically effective amount of an HIV antibody.

Also provided is a method of eliminating an HIV infection in a human, the method comprising:
- c) administering to a human in need thereof a pharmaceutically effective amount of a combination antiretroviral therapy;
- d) administering to a human in need thereof a pharmaceutically effective amount of the compound of Example 4, or a pharmaceutically acceptable salt thereof; and
- e) administering to the human a pharmaceutically effective amount of an HIV antibody.

Also provided is a method of eliminating an HIV infection in a human, the method comprising:
- c) administering to a human in need thereof a pharmaceutically effective amount of a combination antiretroviral therapy;
- d) administering to a human in need thereof a pharmaceutically effective amount of the compound of Example 49, or a pharmaceutically acceptable salt thereof; and
- e) administering to the human a pharmaceutically effective amount of an HIV antibody.

Also provided is a method of eliminating an HIV infection in a human, the method comprising:
- c) administering to a human in need thereof a pharmaceutically effective amount of a combination antiretroviral therapy;
- d) administering to a human in need thereof a pharmaceutically effective amount of the compound of Example 119, or a pharmaceutically acceptable salt thereof; and
- e) administering to the human a pharmaceutically effective amount of an HIV antibody.

Also provided is a method of eliminating an HIV infection in a human, the method comprising:
- e) administering to a human in need thereof a pharmaceutically effective amount of a combination antiretroviral therapy;
- f) administering to a human in need thereof a pharmaceutically effective amount of the compound of Example 120, or a pharmaceutically acceptable salt thereof; and
- g) administering to the human a pharmaceutically effective amount of an HIV antibody.

Also provided is a method of eliminating an HIV infection in a human, the method comprising:
- h) administering to a human in need thereof a pharmaceutically effective amount of a combination antiretroviral therapy;
- i) administering to a human in need thereof a pharmaceutically effective amount of the compound of Example 121, or a pharmaceutically acceptable salt thereof; and
- j) administering to the human a pharmaceutically effective amount of an HIV antibody.

Eliminating an HIV infection in a human is understood to include eliminating from the human all active HIV viruses and HIV-infected cells, including those of a latent reservoir of infected cells.

Also provided are separate embodiments comprising the use of a pharmaceutically effective amount of a TLR7 modulating compound as described herein, or a pharmaceutically acceptable salt thereof, for:
- a) use in treating an HIV infection in a human;
- b) use in treating an HIV infection in a virologically suppressed human;
- c) use in inducing HIV gene expression in a human infected with HIV;
- d) use in inducing HIV gene expression in a human infected with HIV wherein active HIV gene expression in the human has been suppressed by administration of antiretroviral therapy;
- e) use in inducing HIV gene expression in a latent HIV reservoir in a human infected with HIV;
- f) use in enhancing HIV gene expression in HIV infected cells in a human infected with HIV;
- g) use in lowering the chronic set point of HIV viral load in a human infected with HIV;
- h) use in inducing transient HIV-1 viremia in a virologically suppressed human infected with HIV-1;
- i) use in reducing HIV viremia in a human infected with HIV;
- j) use in enhancing immune cell activity and increasing HIV gene expression in a human infected with HIV;
- k) use in enhancing the efficacy of an antiviral agent in a human infected with HIV;
- l) use in inducing transient HIV-1 viremia in a virologically suppressed human infected with HIV-1;
- m) use in enhancing the efficacy of an HIV vaccine; and
- n) use in eliminating an HIV infection in a human.

Also provided are separate embodiments comprising the use of a pharmaceutically effective amount of a TLR7 modulating compound as described herein, or a pharmaceutically acceptable salt thereof, for:
- a) the treatment of an HIV infection in a human;
- b) the treatment of an HIV infection in a virologically suppressed human;
- c) the induction of HIV gene expression in a human infected with HIV;
- d) the induction of HIV gene expression in a human infected with HIV wherein active HIV gene expression in the human has been suppressed by administration of antiretroviral therapy;
- e) the induction of HIV gene expression in a latent HIV reservoir in a human infected with HIV;
- f) the enhancement of HIV gene expression in HIV infected cells in a human infected with HIV;
- g) lowering the chronic set point of HIV viral load in a human infected with HIV;
- h) the induction of transient HIV-1 viremia in a virologically suppressed human infected with HIV-1;
- i) for reducing HIV viremia in a human infected with HIV;
- j) the enhancement of immune cell activity and increase of HIV gene expression in a human infected with HIV;
- k) the enhancement of the efficacy of an antiviral agent in a human infected with HIV;
- l) use in inducing transient HIV-1 viremia in a virologically suppressed human infected with HIV-1;
- m) the enhancement of the efficacy of an HIV vaccine; and
- n) the elimination of an HIV infection in a human.

Pharmaceutical Compositions

Provided herein are pharmaceutical compositions that may be used in the methods discussed above.

Provided is a pharmaceutical composition comprising:
- a) a pharmaceutically effective amount of a combination antiretroviral therapy;
- b) a pharmaceutically effective amount of a TLR7 modulating compound, or a pharmaceutically acceptable salt thereof; and c) a pharmaceutically acceptable carrier or excipient.

Provided herein are pharmaceutical compositions that may be used in the methods discussed above.

Provided is a pharmaceutical composition comprising:
a) a pharmaceutically effective amount of a combination antiretroviral therapy;
b) a pharmaceutically effective amount of a compound of Formula II, or a pharmaceutically acceptable salt thereof; and
c) a pharmaceutically acceptable carrier or excipient.

Also provided are twenty further separate embodiments, each comprising pharmaceutical compositions, as just defined, wherein the compound of Formula II is a compound of Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III (c)(2), Formula III(d)(1), Formula III(d)(2), Formula III(e)(1), Formula III(e)(2), Formula III(f)(1), or Formula III(f)(2); or a pharmaceutically acceptable salt thereof.

Also provided are further separate pharmaceutical compositions, as just defined, wherein the compound of Formula II is a compound of Examples 1 through 124, As one example, provided is a pharmaceutical composition comprising:
a) a pharmaceutically effective amount of a combination antiretroviral therapy;
b) a pharmaceutically effective amount of the compound of Example 4, or a pharmaceutically acceptable salt thereof; and
c) a pharmaceutically acceptable carrier or excipient.

As another example, provided is a pharmaceutical composition comprising:
a) a pharmaceutically effective amount of a combination antiretroviral therapy;
b) a pharmaceutically effective amount of the compound of Example 49, or a pharmaceutically acceptable salt thereof; and
c) a pharmaceutically acceptable carrier or excipient.

As a further example, provided is a pharmaceutical composition comprising:
a) a pharmaceutically effective amount of a combination antiretroviral therapy;
b) a pharmaceutically effective amount of the compound of Example 119, or a pharmaceutically acceptable salt thereof; and
c) a pharmaceutically acceptable carrier or excipient.

As still another example, provided is a pharmaceutical composition comprising:
a) a pharmaceutically effective amount of a combination antiretroviral therapy;
b) a pharmaceutically effective amount of the compound of Example 4, or a pharmaceutically acceptable salt thereof; and
c) a pharmaceutically acceptable carrier or excipient.

Elvitegravir/Cobicistat/Emtricitabine/TDF or TAF/TLR7 Modulator Combinations

Pharmaceutically effective amounts of the TLR7 modulating compounds, including those of Formula II, or a pharmaceutically acceptable salt thereof, as well as the compounds of Examples 119, 120, and 121, or a pharmaceutically acceptable salt thereof, can be combined with a pharmaceutically effective amounts of elvitegravir, cobicistat, emtricitabine, and tenofovir disoproxil fumarate (TDF) or tenofovir alafenamide (TAF) for use in the methods of treatment discussed herein. For instance, as separate dosage forms, a pharmaceutically effective dose of the TLR7 modulating compounds may be combined in a treatment regimen with a STRIBILD® tablet (Gilead Sciences, Inc.) containing 150 mg elvitegravir, 150 mg cobicistat, 200 mg emtricitabine, and 300 mg tenofovir disoproxil fumarate.

Provided is a pharmaceutical composition comprising:
a) a pharmaceutically effective amount of elvitegravir;
b) a pharmaceutically effective amount of cobicistat;
c) a pharmaceutically effective amount of emtricitabine;
d) a pharmaceutically effective amount of tenofovir disoproxil fumarate;
e) a pharmaceutically effective amount of a TLR7 modulating compound, or a pharmaceutically acceptable salt thereof; and
f) a pharmaceutically acceptable carrier or excipient.

Provided is a pharmaceutical composition comprising:
g) a pharmaceutically effective amount of elvitegravir;
h) a pharmaceutically effective amount of cobicistat;
i) a pharmaceutically effective amount of emtricitabine;
j) a pharmaceutically effective amount of tenofovir disoproxil fumarate;
k) a pharmaceutically effective amount of a compound of Formula II, or a pharmaceutically acceptable salt thereof; and
l) a pharmaceutically acceptable carrier or excipient.

Also provided is a pharmaceutical composition comprising:
a) a pharmaceutically effective amount of elvitegravir;
b) a pharmaceutically effective amount of cobicistat;
c) a pharmaceutically effective amount of emtricitabine;
d) a pharmaceutically effective amount of tenofovir alafenamide;
e) a pharmaceutically effective amount of a TLR7 modulating compound, or a pharmaceutically acceptable salt thereof; and
f) a pharmaceutically acceptable carrier or excipient.

Also provided is a pharmaceutical composition comprising:
g) a pharmaceutically effective amount of elvitegravir;
h) a pharmaceutically effective amount of cobicistat;
i) a pharmaceutically effective amount of emtricitabine;
j) a pharmaceutically effective amount of tenofovir alafenamide;
k) a pharmaceutically effective amount of a compound of Formula II, or a pharmaceutically acceptable salt thereof; and
l) a pharmaceutically acceptable carrier or excipient.

Provided herein is a series of tables and lists of combinations of antiviral agents and TLR7 modulating compounds in ranges of doses and/or specific doses. Each indicated combination is an embodiment, with each embodiment providing a pharmaceutical composition comprising the pharmaceutically effective amounts of the combined antiviral agents and TLR7 modulating compounds, or a pharmaceutically acceptable salt thereof, alone or combined with one or more pharmaceutically acceptable carriers or excipients.

Each such individual combination of ranges of doses and/or specific doses also provides a pharmaceutically effective amount of the antiviral agents and TLR7 modulating compounds that may be used in each of the methods described herein. Each such individual combination of ranges of doses and/or specific doses described herein administered to a human in need thereof in each of the individual methods described herein comprises a separate embodiment for the method in question. For instance, the use of combination 1A-a with the first method described for treating an HIV infection, above provides a method of treating an HIV infection in a human comprising:

a) administering to a human in need thereof from 100 mg to 200 mg elvitegravir, 100 mg to 200 mg cobicistat, and from 250 mg to 350 mg TDF to lower the level of HIV detected in the human's blood or plasma from a first level to a second level, the second level comprising a lower concentration of HIV in the human's blood or plasma than the concentration of HIV in the human's blood or plasma in the first level; and b) administering to the human from 0.1 mg to 15.0 mg of a compound of Formula II, or a pharmaceutically acceptable salt thereof.

For each of these separate methods there are further embodiments directed to the sequence of administering each agent.

In one embodiment within each method the TLR7 modulating compound (TLR7 modulating agent) and the antiviral agent or agents may be administered to the human together, such as each being administered in the same day. Pharmaceutically effective amounts of each agent can be administered on a specified regimen, such once daily, twice daily, once weekly, once every two weeks, once every three weeks, once per month, once every two months, etc. In another embodiment within each method the initial doses of the TLR7 modulating compound and the antiviral agent or agents may be administered to the human together, with subsequent administrations being at staggered time points. For instance, following an initial dose of each agent, the TLR7 compound could be administered to the human every day or in 2-, 3-, 4-, 5-, 6-, 7-, 8-, 9-, 10-, 11, 12-, 13-, 14-, or 15-day intervals, wherein the HIV antibody is administered once per week, twice per month, monthly, etc., as can each of the individual antiviral agents.

In another embodiment within each method the TLR7 modulating compound may be administered in an initial administration, with the antiviral agent or agents being administered to the human in a subsequent administration, such as 1, 2, 3, 4, 5, 6, 7, 8, 9, 10, 11, 12, 13, 14, or 15 days following administration of the TLR7 modulating compound. In another embodiment within each method the antiviral agents may be administered in an initial administration, with the TLR7 modulating compound being administered to the human in a subsequent administration, such as 1, 2, 3, 4, 5, 6, 7, 8, 9, 10, 11, 12, 13, 14, or 15 days following administration of the TLR7 modulating compound. In another embodiment within each method administration of the TLR7 modulating compound may be added to an existing antiviral agent regimen.

The TLR7 modulating agent may being administered to the human daily with the antiviral agents or, in conjunction with daily antiviral agent administrations, the subsequent administration of TLR7 modulating agent may follow a staggered regimen, such as every 1, 2, 3, 4, 5, 6, 7, 8, 9, 10, 11, 12, 13, 14, or 15 days. In addition, administration of an antiviral agent or agents to a human infected with HIV may be added in a regimen following administration of the TLR7 modulating agent. For instance, the TLR7 modulating agent (compound) may be administered in a single dose, in a series of once or twice daily doses, or in a series of doses staggered across a period of time, followed by administration to the human of a regimen of an antiviral agent or agents.

Pharmaceutical Composition Tables 1A, 2A, 3A, 4A, 5A, 1B, 2B, 3B, 4B, and 5B

Provided are examples separate pharmaceutical compositions and combinations, below, wherein each composition comprises a pharmaceutically acceptable carrier or excipient and the amounts of elvitegravir, cobicistat, emtricitabine, tenofovir disoproxil fumarate (TDF) or tenofovir alafenamide (TAF), and a TLR7 modulating compound as described herein, including the compounds of Formula II, as well as the compounds of Examples 4, 49, 119, and 120, or a pharmaceutically acceptable salt thereof (collectively "TLR7 Modulating Compound" in the table below), in the amounts listed for each composition below. The pharmaceutical compositions in each of the pharmaceutical composition tables herein comprise the pharmaceutically effective amounts indicated for each agent in the composition and a pharmaceutically acceptable carrier or excipient. The pharmaceutical combinations in each of the pharmaceutical composition tables herein comprises a combination of pharmaceutically effective amounts of each of the agents listed in each composition which may be utilized together in the methods of treatment described herein, with the listed pharmaceutical agents of each composition being administered to a human in need thereof as a single pharmaceutical composition, such as a tablet or oral liquid, or the agents may be administered separately or in any of the possible combinations. For instance, a pharmaceutically effective amount of a compound of Formula II, as well as the compounds of Examples 4, 49, 119, and 120, or a pharmaceutically acceptable salt thereof, may be administered to a human in need thereof in a first tablet in conjunction with the administration of a second tablet containing the remaining agents of the combination, such as a STRIBILD® tablet.

Tables 1A, 2A, 3A, 4A, and 5A

The table below serves as Tables 1A, 2A, 3A, 4A, and 5A and provides combinations of agents that can be used in the uses, methods, regimens, and pharmaceutical compositions herein. Each of the listed combinations of agents differs only in the TLR7 Modulating Compound included in the final column. As Table 1A, the TLR7 Modulating Compound is a compound of Formula II, or a pharmaceutically acceptable salt thereof. As Table 2A, the TLR7 Modulating Compound is a compound of Example 4, or a pharmaceutically acceptable salt thereof. As Table 3A, the TLR7 Modulating Compound is a compound of Example 49, or a pharmaceutically acceptable salt thereof. As Table 4A, the TLR7 Modulating Compound is a compound of Example 119, or a pharmaceutically acceptable salt thereof (collectively "TLR7 MC"). Finally, as Table 5A, the TLR7 Modulating Compound is a compound of Example 120, or a pharmaceutically acceptable salt thereof. For instance, Example 1 A-a comprises a combination of elvitegravir at from 100 mg to 200 mg, cobicistat from 100 mg to 200 mg, emtricitabine from 150 mg to 250 mg, TDF from 250 mg to 350 mg, and, as the TLR7 Modulating Compound, 0.1 mg to 15.0 mg of a compound of Formula II, or a pharmaceutically acceptable salt thereof. Example 2 A-a comprises the same amounts of the initial four agents of Example 1 A-a, except it further comprises 0.1 mg to 15.0 mg of the compound of Example 4, or a pharmaceutically acceptable salt thereof, as the "TLR7 MC". This pattern follows the five composition examples in each row of the table.

| Composition Example | elvitegravir | cobicistat | emtricitabine | TDF | TLR7 MC |
|---|---|---|---|---|---|
| 1A-a, 2A-a, 3A-a, 4A-a, and 5A-a | 100 mg to 200 mg | 100 mg to 200 mg | 150 mg to 250 mg | 250 mg to 350 mg | 0.1 mg to 15.0 mg |
| 1A-b, 2A-b, 3A-b, 4A-b, and 5A-b | 100 mg to 200 mg | 100 mg to 200 mg | 150 mg to 250 mg | 250 mg to 350 mg | 2.0 mg to 6 mg |
| 1A-c, 2A-c, 3A-c, 4A-c, and 5A-c | 100 mg to 200 mg | 100 mg to 200 mg | 150 mg to 250 mg | 250 mg to 350 mg | 5.0 mg to 10.0 mg |
| 1A-d, 2A-d, 3A-d, 4A-d, and 5A-d | 100 mg to 200 mg | 100 mg to 200 mg | 150 mg to 250 mg | 250 mg to 350 mg | 10.0 mg to 15.0 mg |
| 1A-e, 2A-e, 3A-e, 4A-e, and 5A-e | 125 mg to 175 mg | 125 mg to 175 mg | 175 mg to 225 mg | 275 mg to 325 mg | 0.1 mg to 15.0 mg |
| 1A-f, 2A-f, 3A-f, 4A-f, and 5A-f | 125 mg to 175 mg | 125 mg to 175 mg | 175 mg to 225 mg | 275 mg to 325 mg | 2.0 mg to 6.0 mg |
| 1A-g, 2A-g, 3A-g, 4A-g, and 5A-g | 125 mg to 175 mg | 125 mg to 175 mg | 175 mg to 225 mg | 275 mg to 325 mg | 5.0 mg to 10.0 mg |
| 1A-h, 2A-h, 3A-h, 4A-h, and 5A-h | 125 mg to 175 mg | 125 mg to 175 mg | 175 mg to 225 mg | 275 mg to 325 mg | 10.0 mg to 15.0 mg |
| 1A-i, 2A-i, 3A-i, 4A-i, and 5A-i | 145 mg to 155 mg | 145 mg to 155 mg | 190 mg to 210 mg | 290 mg to 310 mg | 0.1 mg to 15.0 mg |
| 1A-j, 2A-j, 3A-j, 4A-j, and 5A-j | 145 mg to 155 mg | 145 mg to 155 mg | 190 mg to 210 mg | 290 mg to 310 mg | 2.0 mg to 6.0 mg |
| 1A-k, 2A-k, 3A-k, 4A-k, and 5A-k | 145 mg to 155 mg | 145 mg to 155 mg | 190 mg to 210 mg | 290 mg to 310 mg | 5.0 mg to 10.0 mg |
| 1A-l, 2A-l, 3A-l, 4A-l, and 5A-l | 145 mg to 155 mg | 145 mg to 155 mg | 190 mg to 210 mg | 290 mg to 310 mg | 10.0 mg to 15.0 mg |
| 1A-m, 2A-m, 3A-m, 4A-m, and 5A-m | 150 mg | 150 mg | 200 mg | 300 mg | 0.1 mg to 15.0 mg |
| 1A-n, 2A-n, 3A-n, 4A-n, and 5A-n | 150 mg | 150 mg | 200 mg | 300 mg | 2.0 mg to 6.0 mg |
| 1A-o, 2A-o, 3A-o, 4A-o, and 5A-o | 150 mg | 150 mg | 200 mg | 300 mg | 5.0 mg to 10.0 mg |
| 1A-p, 2A-p, 3A-p, 4A-p, and 5A-p | 150 mg | 150 mg | 200 mg | 300 mg | 10.0 mg to 15.0 mg |
| 1A-q, 2A-q, 3A-q, 4A-q, and 5A-q | 150 mg | 150 mg | 200 mg | 300 mg | 4 mg |
| 1A-r, 2A-r, 3A-r, 4A-r, and 5A-r | 150 mg | 150 mg | 200 mg | 300 mg | 5 mg |
| 1A-s, 2A-s, 3A-s, 4A-s, and 5A-s | 150 mg | 150 mg | 200 mg | 300 mg | 6 mg |
| 1A-t, 2A-t, 3A-t, 4A-t, and 5A-t | 150 mg | 150 mg | 200 mg | 300 mg | 7 mg |
| 1A-u, 2A-u, 3A-u, 4A-u, and 5A-u | 150 mg | 150 mg | 200 mg | 300 mg | 8 mg |
| 1A-v, 2A-v, 3A-v, 4A-v, and 5A-v | 150 mg | 150 mg | 200 mg | 300 mg | 9 mg |
| 1A-w, 2A-w, 3A-w, 4A-w, and 5A-w | 150 mg | 150 mg | 200 mg | 300 mg | 10 mg |
| 1A-x, 2A-x, 3A-x, 4A-x, and 5A-x | 150 mg | 150 mg | 200 mg | 300 mg | 11 mg |
| 1A-y, 2A-y, 3A-y, 4A-y, and 5A-y | 150 mg | 150 mg | 200 mg | 300 mg | 12 mg |
| 1A-z, 2A-z, 3A-z, 4A-z, and 5A-z | 100 mg to 200 mg | 100 mg to 200 mg | 150 mg to 250 mg | 250 mg to 350 mg | 15.0 mg to 20.0 mg |
| 1A-aa, 2A-aa, 3A-aa, 4A-aa, and 5A-aa | 125 mg to 175 mg | 125 mg to 175 mg | 175 mg to 225 mg | 275 mg to 325 mg | 20.0 mg to 25.0 mg |
| 1A-ab, 2A-ab, 3A-ab, 4A-ab, and 5A-ab | 145 mg to 155 mg | 145 mg to 155 mg | 190 mg to 210 mg | 290 mg to 310 mg | 0.1 mg to 15.0 mg |
| 1A-ac, 2A-ac, 3A-ac, 4A-ac, and 5A-ac | 150 mg | 150 mg | 200 mg | 300 mg | 15.0 mg to 20.0 mg |
| 1A-ad, 2A-ad, 3A-ad, 4A-ad, and 5A-ad | 150 mg | 150 mg | 200 mg | 300 mg | 20.0 mg to 25.0 mg |
| 1A-ae, 2A-ae, 3A-ae, 4A-ae, and 5A-ae | 100 mg to 200 mg | 100 mg to 200 mg | 150 mg to 250 mg | 250 mg to 350 mg | 0.1 mg to 25.0 mg |
| 1A-af, 2A-af, 3A-af, 4A-af, and 5A-af | 100 mg to 200 mg | 100 mg to 200 mg | 150 mg to 250 mg | 250 mg to 350 mg | 15 mg to 20 mg |
| 1A-ag, 2A-ag, 3A-ag, 4A-ag, and 5A-ag | 100 mg to 200 mg | 100 mg to 200 mg | 150 mg to 250 mg | 250 mg to 350 mg | 20 mg to 25 mg |
| 1A-ah, 2A-ah, 3A-ah, 4A-ah, and 5A-ah | 50 mg to 200 mg | 50 mg to 200 mg | 50 mg to 250 mg | 50 mg to 350 mg | 0.1 mg to 25.0 mg |
| 1A-ai, 2A-ai, 3A-ai, 4A-ai, and 5A-ai | 50 mg to 150 mg | 50 mg to 150 mg | 50 mg to 200 mg | 50 mg to 300 mg | 0.1 mg to 20.0 mg |
| 1A-aj, 2A-aj, 3A-aj, 4A-aj, and 5A-aj | 50 mg to 125 mg | 50 mg to 125 mg | 50 mg to 175 mg | 50 mg to 250 mg | 0.1 mg to 15.0 mg |

Tables 1B, 2B, 3B, 4B, and 5 B

Following the pattern of Tables 1A through 5A, above, Tables 1B, 2B, 3B, 4B, and 5 B are combined in the table below in which serves as Tables 1A, 2A, 3A, 4A, and 5A and provides combinations of agents that can be used in the uses, methods, regimens, and pharmaceutical compositions herein. Provided are examples separate pharmaceutical compositions and combinations wherein each composition comprises a pharmaceutically acceptable carrier or excipient and the amounts of elvitegravir, cobicistat, emtricitabine, tenofovir alafenamide (TAF), and a TLR7 modulating compound.

As Table 1B, the TLR7 Modulating Compound is a compound of Formula II, or a pharmaceutically acceptable salt thereof. As Table 2B, the TLR7 Modulating Compound is a compound of Example 4, or a pharmaceutically acceptable salt thereof. As Table 3B, the TLR7 Modulating Compound is a compound of Example 49, or a pharmaceutically acceptable salt thereof. As Table 4B, the TLR7 Modulating Compound is a compound of Example 119, or a pharmaceutically acceptable salt thereof. Finally, as Table 5B, the TLR7 Modulating Compound is a compound of Example 120, or a pharmaceutically acceptable salt thereof. For instance, Example 1B-a comprises a combination of elvitegravir at from 100 mg to 200 mg, cobicistat from 100 mg to 200 mg, emtricitabine from 150 mg to 250 mg, TAF from 5 mg to 20 mg, and, as the TLR7 Modulating Compound, 0.1 mg to 15.0 mg of a compound of Formula II, or a pharmaceutically acceptable salt thereof. Example 2B-a comprises the same amounts of the initial four agents of Example 1B-a, except it further comprises 0.1 mg to 15.0 mg of the compound of Example 4, or a pharmaceutically acceptable salt thereof. This pattern follows the five composition examples in each row of the table below.

| Comp. Ex. | elvitegravir | cobicistat | emtricitabine | TAF | TLR7 Modulating Compound |
|---|---|---|---|---|---|
| 1B-a, 2B-a, 3B-a, 4B-a, and 5B-a | 100 mg to 200 mg | 100 mg to 200 mg | 150 mg to 250 mg | 5 mg to 20 mg | 0.1 mg to 15.0 mg |
| 1B-b, 2B-b, 3B-b, 4B-b, and 5B-b | 100 mg to 200 mg | 100 mg to 200 mg | 150 mg to 250 mg | 5 mg to 20 mg | 2.0 mg to 6 mg |
| 1B-c, 2B-c, 3B-c, 4B-c, and 5B-c | 100 mg to 200 mg | 100 mg to 200 mg | 150 mg to 250 mg | 5 mg to 20 mg | 5.0 mg to 10.0 mg |
| 1B-d, 2B-d, 3B-d, 4B-d, and 5B-d | 100 mg to 200 mg | 100 mg to 200 mg | 150 mg to 250 mg | 5 mg to 20 mg | 10.0 mg to 15.0 mg |
| 1B-e, 2B-e, 3B-e, 4B-e, and 5B-e | 125 mg to 175 mg | 125 mg to 175 mg | 175 mg to 225 mg | 5 mg to 15 mg | 0.1 mg to 15.0 mg |
| 1B-f, 2B-f, 3B-f, 4B-f, and 5B-f | 125 mg to 175 mg | 125 mg to 175 mg | 175 mg to 225 mg | 5 mg to 15 mg | 2.0 mg to 6.0 mg |
| 1B-g, 2B-g, 3B-g, 4B-g, and 5B-g | 125 mg to 175 mg | 125 mg to 175 mg | 175 mg to 225 mg | 5 mg to 15 mg | 5.0 mg to 10.0 mg |
| 1B-h, 2B-h, 3B-h, 4B-h, and 5B-h | 125 mg to 175 mg | 125 mg to 175 mg | 175 mg to 225 mg | 5 mg to 15 mg | 10.0 mg to 15.0 mg |
| 1B-i, 2B-i, 3B-i, 4B-i, and 5B-i | 145 mg to 155 mg | 145 mg to 155 mg | 190 mg to 210 mg | 5 mg to 15 mg | 0.1 mg to 15.0 mg |
| 1B-j, 2B-j, 3B-j, 4B-j, and 5B-j | 145 mg to 155 mg | 145 mg to 155 mg | 190 mg to 210 mg | 5 mg to 15 mg | 2.0 mg to 6.0 mg |
| 1B-k, 2B-k, 3B-k, 4B-k, and 5B-k | 145 mg to 155 mg | 145 mg to 155 mg | 190 mg to 210 mg | 5 mg to 15 mg | 5.0 mg to 10.0 mg |
| 1B-l, 2B-l, 3B-l, 4B-l, and 5B-l | 145 mg to 155 mg | 145 mg to 155 mg | 190 mg to 210 mg | 5 mg to 15 mg | 10.0 mg to 15.0 mg |
| 1B-m, 2B-m, 3B-m, 4B-m, and 5B-m | 150 mg | 150 mg | 200 mg | 7.5 mg to 12.5 mg | 0.1 mg to 15.0 mg |
| 1B-n, 2B-n, 3B-n, 4B-n, and 5B-n | 150 mg | 150 mg | 200 mg | 7.5 mg to 12.5 mg | 2.0 mg to 6.0 mg |
| 1B-o, 2B-o, 3B-o, 4B-o, and 5B-o | 150 mg | 150 mg | 200 mg | 7.5 mg to 12.5 mg | 5.0 mg to 10.0 mg |
| 1B-p, 2B-p, 3B-p, 4B-p, and 5B-p | 150 mg | 150 mg | 200 mg | 7.5 mg to 12.5 mg | 10.0 mg to 15.0 mg |
| 1B-q, 2B-q, 3B-q, 4B-q, and 5B-q | 150 mg | 150 mg | 200 mg | 10 mg | 4 mg |
| 1B-r, 2B-r, 3B-r, 4B-r, and 5B-r | 150 mg | 150 mg | 200 mg | 10 mg | 5 mg |
| 1B-s, 2B-s, 3B-s, 4B-s, and 5B-s | 150 mg | 150 mg | 200 mg | 10 mg | 6 mg |
| 1B-t, 2B-t, 3B-t, 4B-t, and 5B-t | 150 mg | 150 mg | 200 mg | 10 mg | 7 mg |
| 1B-u, 2B-u, 3B-u, 4B-u, and 5B-u | 150 mg | 150 mg | 200 mg | 10 mg | 8 mg |
| 1B-v, 2B-v, 3B-v, 4B-v, and 5B-v | 150 mg | 150 mg | 200 mg | 10 mg | 9 mg |
| 1B-w, 2B-w, 3B-w, 4B-w, and 5B-w | 150 mg | 150 mg | 200 mg | 10 mg | 10 mg |
| 1B-x, 2B-x, 3B-x, 4B-x, and 5B-x | 150 mg | 150 mg | 200 mg | 10 mg | 11 mg |
| 1B-y, 2B-y, 3B-y, 4B-y, and 5B-y | 150 mg | 150 mg | 200 mg | 10 mg | 12 mg |
| 1B-z, 2B-z, 3B-z, 4B-z, and 5B-z | 100 mg to 200 mg | 100 mg to 200 mg | 150 mg to 250 mg | 5 mg to 20 mg | 0.1 mg to 25.0 mg |
| 1B-aa, 2B-aa, 3B-aa, 4B-aa, and 5B-aa | 100 mg to 200 mg | 100 mg to 200 mg | 150 mg to 250 mg | 5 mg to 20 mg | 15 mg to 20 mg |
| 1B-ab, 2B-ab, 3B-ab, 4B-ab, and 5B-ab | 100 mg to 200 mg | 100 mg to 200 mg | 150 mg to 250 mg | 5 mg to 20 mg | 20 mg to 25 mg |

| Comp. Ex. | elvitegravir | cobicistat | emtricitabine | TAF | TLR7 Modulating Compound |
|---|---|---|---|---|---|
| 1B-ac, 2B-ac, 3B-ac, 4B-ac, and 5B-ac | 50 mg to 200 mg | 50 mg to 200 mg | 50 mg to 250 mg | 1 mg to 15 mg | 0.1 mg to 25.0 mg |
| 1B-ad, 2B-ad, 3B-ad, 4B-ad, and 5B-ad | 50 mg to 150 mg | 50 mg to 150 mg | 50 mg to 200 mg | 1 mg to 10 mg | 0.1 mg to 20.0 mg |
| 1B-ae, 2B-ae, 3B-ae, 4B-ae, and 5B-ae | 50 mg to 125 mg | 50 mg to 125 mg | 50 mg to 175 mg | 1 mg to 8 mg | 0.1 mg to 15.0 mg |

Also provided is a pharmaceutical kit comprising:
1) a series of daily doses of a single pharmaceutical composition comprising:
   a. a pharmaceutically effective amount of elvitegravir;
   b. a pharmaceutically effective amount of TDF;
   c. a pharmaceutically effective amount of a compound of Formula II, or a pharmaceutically acceptable salt thereof;
   d. a pharmaceutically effective amount of cobicistat;
   e. a pharmaceutically effective amount of emtricitabine; and
   f. a pharmaceutically acceptable carrier or excipient; and
2) directions for the administration of the daily doses of the pharmaceutical composition.

Also provided is a pharmaceutical kit comprising:
3) a series of daily doses of a single pharmaceutical composition comprising:
   g. a pharmaceutically effective amount of elvitegravir;
   h. a pharmaceutically effective amount of TAF;
   i. a pharmaceutically effective amount of a compound of Formula II, or a pharmaceutically acceptable salt thereof;
   j. a pharmaceutically effective amount of cobicistat;
   k. a pharmaceutically effective amount of emtricitabine; and
   l. a pharmaceutically acceptable carrier or excipient; and
4) directions for the administration of the daily doses of the pharmaceutical composition.

Further provided is a pharmaceutical kit comprising:
1) a series of doses of a first pharmaceutical composition comprising:
   a) a pharmaceutically effective amount of elvitegravir;
   b) a pharmaceutically effective amount of cobicistat
   c) a pharmaceutically effective amount of TDF;
   d) a pharmaceutically effective amount of emtricitabine; and
   e) a pharmaceutically acceptable carrier or excipient; and
2) a series of doses of a second pharmaceutical composition comprising a pharmaceutically effective amount of a compound of Formula II, or a pharmaceutically acceptable salt thereof and a pharmaceutically acceptable carrier or excipient; and
3) directions for the administration of the doses of the first and second pharmaceutical composition; wherein the first and second pharmaceutical compositions are both administered once daily.

Another embodiment comprises the kit immediately above wherein the first and second pharmaceutical compositions are both administered twice daily.

Further provided is a pharmaceutical kit comprising:
1) a series of doses of a first pharmaceutical composition comprising:
   f) a pharmaceutically effective amount of elvitegravir;
   g) a pharmaceutically effective amount of cobicistat
   h) a pharmaceutically effective amount of TAF;
   i) a pharmaceutically effective amount of emtricitabine; and
   j) a pharmaceutically acceptable carrier or excipient; and
2) a series of doses of a second pharmaceutical composition comprising a pharmaceutically effective amount of a compound of Formula II, or a pharmaceutically acceptable salt thereof and a pharmaceutically acceptable carrier or excipient; and
3) directions for the administration of the doses of the first and second pharmaceutical composition; wherein the first and second pharmaceutical compositions are both administered once daily.

Another embodiment within each of the kits above comprises the kit wherein the first and second pharmaceutical compositions are both administered twice daily.

Another embodiment within each of the kits above comprises the kit wherein the first pharmaceutical composition is administered twice daily and the second pharmaceutical composition is administered less than daily. Further embodiments comprise those wherein the first pharmaceutical composition is administered daily and the second pharmaceutical composition is administered, respectively, every other day, or every $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, or $30^{th}$ day.

Within the first embodiment of the pharmaceutical kit above comprising pharmaceutically effective amounts of elvitegravir, cobicistat, emtricitabine, tenofovir disoproxil fumarate, and a compound of Formula II, there is a further embodiment comprising the kit, as described, wherein the first pharmaceutical composition comprises 150 mg of elvitegravir, 150 mg of cobicistat, 200 mg of emtricitabine, and 300 mg of tenofovir disoproxil fumarate, and the second pharmaceutical composition comprises from 0.1 to 25 mg of a compound of Formula II, or a pharmaceutically acceptable salt thereof.

Within the embodiment of the pharmaceutical kit above, there is a further embodiment comprising the kit, as described, wherein the first pharmaceutical composition comprises 150 mg of elvitegravir, 150 mg of cobicistat, 200 mg of emtricitabine, and 300 mg of tenofovir disoproxil fumarate, and the second pharmaceutical composition comprises from 0.1 to 15 mg of a compound of Formula II, or a pharmaceutically acceptable salt thereof.

Within the second embodiment of the pharmaceutical kit above comprising pharmaceutically effective amounts of elvitegravir, cobicistat, emtricitabine, TAF, and a compound of Formula II, there is a further embodiment comprising the kit, as described, wherein the first pharmaceutical composition comprises 150 mg of elvitegravir, 150 mg of cobicistat, 200 mg of emtricitabine, and 10 mg of TAF, and the second pharmaceutical composition comprises from 0.1 to 25 mg of a compound of Formula II, or a pharmaceutically acceptable salt thereof.

Within the embodiment of the pharmaceutical kit above, there is a further embodiment comprising the kit, as described, wherein the first pharmaceutical composition comprises 150 mg of elvitegravir, 150 mg of cobicistat, 200 mg of emtricitabine, and 10 mg of TAF, and the second pharmaceutical composition comprises from 0.1 to 15 mg of a compound of Formula II, or a pharmaceutically acceptable salt thereof.

Within each of the embodiments above wherein the kit comprises a first and second pharmaceutical composition, there are four additional embodiments wherein all other components or elements are as described above and:
- a) in the first additional embodiment, the second pharmaceutical composition comprises from 0.1 to 15 mg of the compound of Example 4, or a pharmaceutically acceptable salt thereof;
- b) in the second additional embodiment, the second pharmaceutical composition comprises from 0.1 to 15 mg of the compound of Example 49, or a pharmaceutically acceptable salt thereof;
- c) in the third additional embodiment, the second pharmaceutical composition comprises from 0.1 to 15 mg of the compound of Example 119, or a pharmaceutically acceptable salt thereof;
- d) in the fourth additional embodiment, the second pharmaceutical composition comprises from 0.1 to 15 mg of the compound of Example 120, or a pharmaceutically acceptable salt thereof.

Combinations of Emtricitabine/TDF/TLR7 and Emtricitabine/TAF/TLR7 Modulators

Pharmaceutically effective amounts of the TLR7 modulating compounds of Formula II, or a pharmaceutically acceptable salt thereof, as well as the compounds of Examples 119, 120, and 121, or a pharmaceutically acceptable salt thereof, can be combined with pharmaceutically effective amounts of emtricitabine and tenofovir disoproxil fumarate (TDF) for use in the methods of treatment discussed herein. For instance, as separate dosage forms, a pharmaceutically effective dose of the TLR7 modulating compounds may be combined in a treatment regimen with a TRUVADA® tablet, which is available from Gilead Sciences, Inc. and contain 200 mg of emtricitabine and 300 mg of TDF.

Also provided is a pharmaceutical composition comprising:
- a) a pharmaceutically effective amount of emtricitabine;
- b) a pharmaceutically effective amount of tenofovir disoproxil fumarate;
- c) a pharmaceutically effective amount of TLR7 modulating compound, or a pharmaceutically acceptable salt thereof; and
- d) a pharmaceutically acceptable carrier or excipient.

Also provided is a pharmaceutical composition comprising:
- a) a pharmaceutically effective amount of emtricitabine;
- b) a pharmaceutically effective amount of TAF;
- c) a pharmaceutically effective amount of TLR7 modulating compound, or a pharmaceutically acceptable salt thereof; and
- d) a pharmaceutically acceptable carrier or excipient.

Pharmaceutical Composition Tables 6A, 7A, 8A, 9A, 10A, 6B, 7B, 8B, 9B, and 10B

Provided are separate pharmaceutical compositions and combinations useful in the uses, methods, and regimens herein, wherein each composition comprises a pharmaceutically acceptable carrier or excipient and the amounts of emtricitabine, TDF or TAF, and a TLR7 Modulating Compound, or a pharmaceutically acceptable salt thereof (collectively "TLR7 MC" in the table below), in the amounts listed for each composition below. The table below serves as Tables 6A, 7A, 8A, 9A, and 10A and provides combinations of agents that can be used in the uses, methods, regimens, and pharmaceutical compositions herein. Each of the listed combinations of agents differs only in the TLR7 Modulating Compound included in the final column. As Table 6A, the TLR7 Modulating Compound is a compound of Formula II, or a pharmaceutically acceptable salt thereof. As Table 7A, the TLR7 Modulating Compound is a compound of Example 4, or a pharmaceutically acceptable salt thereof. As Table 8A, the TLR7 Modulating Compound is a compound of Example 49, or a pharmaceutically acceptable salt thereof. As Table 9A, the TLR7 Modulating Compound is a compound of Example 119, or a pharmaceutically acceptable salt thereof. Finally, as Table 10A, the TLR7 Modulating Compound is a compound of Example 120, or a pharmaceutically acceptable salt thereof. For instance, Example 6 A-a comprises a combination of emtricitabine at from 150 mg to 250 mg, TDF from 250 mg to 350 mg, and, as the TLR7 Modulating Compound, 0.1 mg to 15.0 mg of a compound of Formula II, or a pharmaceutically acceptable salt thereof. Example 7A-a comprises the same amounts of the initial two agents of Example 6A-a (emtricitabine and TDF), except it further comprises 0.1 mg to 15.0 mg of the compound of Example 4, or a pharmaceutically acceptable salt thereof. This pattern follows the five composition examples in each row of the table.

Tables 6A, 7A, 8A, 9A, and 10A

| Comp. Ex. | emtricitabine | TDF | TLR7 MC |
| --- | --- | --- | --- |
| 6A-a, 7A-a, 8A-a, 9A-a, and 10A-a | 150 mg to 250 mg | 250 mg to 350 mg | 0.1 mg to 15 mg |
| 6A-b, 7A-b, 8A-b, 9A-b, and 10A-b | 150 mg to 250 mg | 250 mg to 350 mg | 2.0 mg to 6.0 mg |
| 6A-c, 7A-c, 8A-c, 9A-c, and 10A-C | 150 mg to 250 mg | 250 mg to 350 mg | 5.0 mg to 10.0 mg |
| 6A-d, 7A-d, 8A-d, 9A-d, and 10A-d | 150 mg to 250 mg | 250 mg to 350 mg | 10.0 mg to 15.0 mg |
| 6A-e, 7A-e, 8A-e, 9A-e, and 10A-e | 175 mg to 225 mg | 275 mg to 325 mg | 0.1 mg to 15 mg |
| 6A-f, 7A-f, 8A-f, 9A-f, and 10A-f | 175 mg to 225 mg | 275 mg to 325 mg | 2.0 mg to 6.0 mg |

-continued

| Comp. Ex. | emtricitabine | TDF | TLR7 MC |
|---|---|---|---|
| 6A-g, 7A-g, 8A-g, 9A-g, and 10A-g | 175 mg to 225 mg | 275 mg to 325 mg | 5.0 mg to 10.0 mg |
| 6A-h, 7A-h, 8A-h, 9A-h, and 10A-h | 175 mg to 225 mg | 275 mg to 325 mg | 10.0 mg to 15.0 mg |
| 6A-i, 7A-i, 8A-i, 9A-i, and 10A-i | 175 mg to 225 mg | 275 mg to 325 mg | 4 mg |
| 6A-j, 7A-j, 8A-j, 9A-j, and 10A-j | 175 mg to 225 mg | 275 mg to 325 mg | 5 mg |
| 6A-k, 7A-k, 8A-k, 9A-k, and 10A-k | 175 mg to 225 mg | 275 mg to 325 mg | 6 mg |
| 6A-l, 7A-l, 8A-l, 9A-l, and 10A-l | 175 mg to 225 mg | 275 mg to 325 mg | 7 mg |
| 6A-m, 7A-m, 8A-m, 9A-m, and 10A-m | 175 mg to 225 mg | 275 mg to 325 mg | 8 mg |
| 6A-n, 7A-n, 8A-n, 9A-n, and 10A-n | 175 mg to 225 mg | 275 mg to 325 mg | 9 mg |
| 6A-o, 7A-o, 8A-o, 9A-o, and 10A-o | 175 mg to 225 mg | 275 mg to 325 mg | 10 mg |
| 6A-p, 7A-p, 8A-p, 9A-p, and 10A-p | 175 mg to 225 mg | 275 mg to 325 mg | 11 mg |
| 6A-q, 7A-q, 8A-q, 9A-q, and 10A-q | 175 mg to 225 mg | 275 mg to 325 mg | 12 mg |
| 6A-r, 7A-r, 8A-r, 9A-r, and 10A-r | 200 mg | 300 mg | 0.1 mg to 15 mg |
| 6A-s, 7A-s, 8A-s, 9A-s, and 10A-S | 200 mg | 300 mg | 2.0 mg to 6.0 mg |
| 6A-t, 7A-t, 8A-t, 9A-t, and 10A-t | 200 mg | 300 mg | 5.0 mg to 10.0 mg |
| 6A-u, 7A-u, 8A-u, 9A-u, and 10A-u | 200 mg | 300 mg | 10.0 mg to 15.0 mg |
| 6A-v, 7A-v, 8A-v, 9A-v, and 10A-v | 200 mg | 300 mg | 4 mg |
| 6A-w, 7A-w, 8A-w, 9A-w, and 10A-w | 200 mg | 300 mg | 5 mg |
| 6A-x, 7A-x, 8A-x, 9A-x, and 10A-x | 200 mg | 300 mg | 6 mg |
| 6A-y, 7A-y, 8A-y, 9A-y, and 10A-y | 200 mg | 300 mg | 7 mg |
| 6A-z, 7A-z, 8A-z, 9A-z, and 10A-z | 200 mg | 300 mg | 8 mg |
| 6A-aa, 7A-aa, 8A-aa, 9A-aa, and 10A-aa | 200 mg | 300 mg | 9 mg |
| 6A-ab, 7A-ab, 8A-ab, 9A-ab, and 10A-ab | 200 mg | 300 mg | 10 mg |
| 6A-ac, 7A-ac, 8A-ac, 9A-ac, and 10A-ac | 200 mg | 300 mg | 11 mg |
| 6A-ad, 7A-ad, 8A-ad, 9A-ad, and 10A-ad | 200 mg | 300 mg | 12 mg |
| 6A-ae, 7A-ae, 8A-ae, 9A-ae, and 10A-ae | 150 mg to 250 mg | 250 mg to 350 mg | 0.1 mg to 25.0 mg |
| 6A-af, 7A-af, 8A-af, 9A-af, and 10A-af | 150 mg to 250 mg | 250 mg to 350 mg | 15 mg to 20 mg |
| 6A-ag, 7A-ag, 8A-ag, 9A-ag, and 10A-ag | 150 mg to 250 mg | 250 mg to 350 mg | 20 mg to 25 mg |
| 6A-ah, 7A-ah, 8A-ah, 9A-ah, and 10A-ah | 50 mg to 250 mg | 50 mg to 350 mg | 0.1 mg to 25.0 mg |
| 6A-ai, 7A-ai, 8A-ai, 9A-ai, and 10A-ai | 50 mg to 200 mg | 50 mg to 300 mg | 0.1 mg to 20.0 mg |
| 6A-aj, 7A-aj, 8A-aj, 9A-aj, and 10A-aj | 50 mg to 175 mg | 50 mg to 250 mg | 0.1 mg to 15.0 mg |

Table 6B, 7B, 8B, 9B, and 10B

The table below serves as Tables 6B, 7B, 8B, 9B, and 10B and provides combinations of agents that can be used in the uses, methods, regimens, and pharmaceutical compositions herein. Each of the listed combinations of agents differs only in the TLR7 Modulating Compound included in the final column. In Table 6B, the TLR7 Modulating Compound is a compound of Formula II, or a pharmaceutically acceptable salt thereof. In Table 7B, it is a compound of Example 4, or a pharmaceutically acceptable salt thereof. In Table 8A, it is a compound of Example 49, or a pharmaceutically acceptable salt thereof. In Table 9A, the TLR7 Modulating Compound is a compound of Example 119, or a pharmaceutically acceptable salt thereof. Finally, in Table 10A, it is a compound of Example 120, or a pharmaceutically acceptable salt thereof. For instance, Example 6 B-a comprises a combination of emtricitabine at from 150 mg to 250 mg, TAF from 15 mg to 35 mg, and, as the TLR7 Modulating Compound, 0.1 mg to 15.0 mg of a compound of Formula II, or a pharmaceutically acceptable salt thereof. Example 7B-a comprises the same amounts of the initial two agents of Example 6B-a, except it further comprises 0.1 mg to 15.0 mg of the compound of Example 4, or a pharmaceutically acceptable salt thereof. This pattern follows the five composition examples in each row of the table.

| Comp. Ex. | emtricitabine | TAF | TLR7 MC |
|---|---|---|---|
| 6B-a, 7B-a, 8B-a, 9B-a, and 10B-a | 150 mg to 250 mg | 15 mg to 35 mg | 0.1 mg to 15 mg |
| 6B-b, 7B-b, 8B-b, 9B-b, and 10B-b | 150 mg to 250 mg | 15 mg to 35 mg | 2.0 mg to 6.0 mg |
| 6B-c, 7B-c, 8B-c, 9B-c, and 10B-c | 150 mg to 250 mg | 15 mg to 35 mg | 5.0 mg to 10.0 mg |
| 6B-d, 7B-d, 8B-d, 9B-d, and 10B-d | 150 mg to 250 mg | 15 mg to 35 mg | 10.0 mg to 15.0 mg |
| 6B-e, 7B-e, 8B-e, 9B-e, and 10B-e | 175 mg to 225 mg | 20 mg to 30 mg | 0.1 mg to 15 mg |
| 6B-f, 7B-f, 8B-f, 9B-f, and 10B-f | 175 mg to 225 mg | 20 mg to 30 mg | 2.0 mg to 6.0 mg |
| 6B-g, 7B-g, 8B-g, 9B-g, and 10B-g | 175 mg to 225 mg | 20 mg to 30 mg | 5.0 mg to 10.0 mg |
| 6B-h, 7B-h, 8B-h, 9B-h, and 10B-h | 175 mg to 225 mg | 20 mg to 30 mg | 10.0 mg to 15.0 mg |
| 6B-i, 7B-i, 8B-i, 9B-i, and 10B-i | 175 mg to 225 mg | 20 mg to 30 mg | 4 mg |
| 6B-j, 7B-j, 8B-j, 9B-j, and 10B-j | 175 mg to 225 mg | 20 mg to 30 mg | 5 mg |
| 6B-k, 7B-k, 8B-k, 9B-k, and 10B-k | 175 mg to 225 mg | 20 mg to 30 mg | 6 mg |
| 6B-l, 7B-l, 8B-l, 9B-l, and 10B-l | 175 mg to 225 mg | 20 mg to 30 mg | 7 mg |
| 6B-m, 7B-m, 8B-m, 9B-m, and 10B-m | 175 mg to 225 mg | 20 mg to 30 mg | 8 mg |
| 6B-n, 7B-n, 8B-n, 9B-n, and 10B-n | 175 mg to 225 mg | 20 mg to 30 mg | 9 mg |
| 6B-o, 7B-o, 8B-o, 9B-o, and 10B-o | 175 mg to 225 mg | 20 mg to 30 mg | 10 mg |
| 6B-p, 7B-p, 8B-p, 9B-p, and 10B-p | 175 mg to 225 mg | 20 mg to 30 mg | 11 mg |
| 6B-q, 7B-q, 8B-q, 9B-q, and 10B-q | 175 mg to 225 mg | 20 mg to 30 mg | 12 mg |
| 6B-r, 7B-r, 8B-r, 9B-r, and 10B-r | 200 mg | 25 mg | 0.1 mg to 15 mg |
| 6B-s, 7B-s, 8B-s, 9B-s, and 10B-s | 200 mg | 25 mg | 2.0 mg to 6.0 mg |
| 6B-t, 7B-t, 8B-t, 9B-t, and 10B-t | 200 mg | 25 mg | 5.0 mg to 10.0 mg |
| 6B-u, 7B-u, 8B-u, 9B-u, and 10B-u | 200 mg | 25 mg | 10.0 mg to 15.0 mg |
| 6B-v, 7B-v, 8B-v, 9B-v, and 10B-v | 200 mg | 25 mg | 4 mg |
| 6B-w, 7B-w, 8B-w, 9B-w, and 10B-w | 200 mg | 25 mg | 5 mg |
| 6B-x, 7B-x, 8B-x, 9B-x, and 10B-x | 200 mg | 25 mg | 6 mg |
| 6B-y, 7B-y, 8B-y, 9B-y, and 10B-y | 200 mg | 25 mg | 7 mg |
| 6B-z, 7B-z, 8B-z, 9B-z, and 10B-z | 200 mg | 25 mg | 8 mg |
| 6B-aa, 7B-aa, 8B-aa, 9B-aa, and 10B-aa | 200 mg | 25 mg | 9 mg |
| 6B-ab, 7B-ab, 8B-ab, 9B-ab, and 10B-ab | 200 mg | 25 mg | 10 mg |
| 6B-ac, 7B-ac, 8B-ac, 9B-ac, and 10B-ac | 200 mg | 25 mg | 11 mg |
| 6B-ad, 7B-ad, 8B-ad, 9B-ad, and 10B-ad | 200 mg | 25 mg | 12 mg |
| 6B-ae, 7B-ae, 8B-ae, 9B-ae, and 10B-ae | 150 mg to 250 mg | 15 mg to 35 mg | 0.1 mg to 25.0 mg |
| 6B-af, 7B-af, 8B-af, 9B-af, and 10B-af | 150 mg to 250 mg | 15 mg to 35 mg | 15 mg to 20 mg |
| 6B-ag, 7B-ag, 8B-ag, 9B-ag, and 10B-ag | 150 mg to 250 mg | 15 mg to 35 mg | 20 mg to 25 mg |
| 6B-ah, 7B-ah, 8B-ah, 9B-ah, and 10B-ah | 50 mg to 250 mg | 1 mg to 15 mg | 0.1 mg to 25.0 mg |
| 6B-ai, 7B-ai, 8B-ai, 9B-ai, and 10B-ai | 50 mg to 200 mg | 1 mg to 10 mg | 0.1 mg to 20.0 mg |
| 6B-aj, 7B-aj, 8B-aj, 9B-aj, and 10B-aj | 50 mg to 175 mg | 1 mg to 8 mg | 0.1 mg to 15.0 mg |

Combinations of Emtricitabine/TDF/TLR7 Modulators/Raltegravir

Provided are a pharmaceutical combination and a composition, each comprising:
- a) a pharmaceutically effective amount of emtricitabine;
- b) a pharmaceutically effective amount of tenofovir disoproxil fumarate;
- c) a pharmaceutically effective amount of a TLR7 modulating compound, or a pharmaceutically acceptable salt thereof;
- d) a pharmaceutically effective amount of an integrase strand transfer inhibitor; and
- e) a pharmaceutically acceptable carrier or excipient.

Provided are a pharmaceutical combination and a composition, each comprising:
- a) a pharmaceutically effective amount of emtricitabine;
- b) a pharmaceutically effective amount of tenofovir disoproxil fumarate;
- c) a pharmaceutically effective amount of a compound of Formula II, or a pharmaceutically acceptable salt thereof;
- d) a pharmaceutically effective amount of an integrase strand transfer inhibitor; and
- e) a pharmaceutically acceptable carrier or excipient.

Provided are a pharmaceutical combination and a composition, each comprising:
- a) a pharmaceutically effective amount of emtricitabine;
- b) a pharmaceutically effective amount of tenofovir alafenamide;
- c) a pharmaceutically effective amount of a TLR7 modulating compound, or a pharmaceutically acceptable salt thereof;
- d) a pharmaceutically effective amount of an integrase strand transfer inhibitor; and
- e) a pharmaceutically acceptable carrier or excipient.

Provided are a pharmaceutical combination and a composition, each comprising:
- a) a pharmaceutically effective amount of emtricitabine;
- b) a pharmaceutically effective amount of tenofovir alafenamide;
- c) a pharmaceutically effective amount of a compound of Formula II, or a pharmaceutically acceptable salt thereof;
- d) a pharmaceutically effective amount of an integrase strand transfer inhibitor; and e) a pharmaceutically acceptable carrier or excipient.

Also are a pharmaceutical combination and a composition, each comprising: a pharmaceutically effective amount of emtricitabine;
- a) a pharmaceutically effective amount of tenofovir disoproxil fumarate;
- b) a pharmaceutically effective amount of a TLR7 modulating compound, or a pharmaceutically acceptable salt thereof;
- c) a pharmaceutically effective amount of raltegravir; and
- d) a pharmaceutically acceptable carrier or excipient.

Also are a pharmaceutical combination and a composition, each comprising: a pharmaceutically effective amount of emtricitabine;
- e) a pharmaceutically effective amount of tenofovir disoproxil fumarate;
- f) a pharmaceutically effective amount of a compound of Formula II, or a pharmaceutically acceptable salt thereof;
- g) a pharmaceutically effective amount of raltegravir; and
- h) a pharmaceutically acceptable carrier or excipient.

Also are a pharmaceutical combination and a composition, each comprising: a pharmaceutically effective amount of emtricitabine;
- b) a pharmaceutically effective amount of tenofovir alafenamide;
- c) a pharmaceutically effective amount of a TLR7 modulating compound, or a pharmaceutically acceptable salt thereof;
- d) a pharmaceutically effective amount of raltegravir; and
- e) a pharmaceutically acceptable carrier or excipient.

Also are a pharmaceutical combination and a composition, each comprising:
- a) a pharmaceutically effective amount of emtricitabine;
- b) a pharmaceutically effective amount of tenofovir alafenamide;
- c) a pharmaceutically effective amount of a compound of Formula II, or a pharmaceutically acceptable salt thereof;
- d) a pharmaceutically effective amount of raltegravir; and
- e) a pharmaceutically acceptable carrier or excipient.

Pharmaceutical Composition Tables 11A Through 15B

Following the pattern of the tables above, provided are separate pharmaceutical compositions and combinations comprising a pharmaceutically acceptable carrier or excipient and the amounts of emtricitabine, tenofovir disoproxil fumarate (TDF) or tenofovir alafenamide (TAF), a TLR7 Modulating Compound (TLR7 MC), or a pharmaceutically acceptable salt thereof (collectively "Formula II" in the table below), and raltegravir in the amounts listed for each composition below.

The table below serves as Tables 11A, 12A, 13A, 14A, and 15A and provides combinations of agents that can be used in the uses, methods, regimens, and pharmaceutical compositions herein. Each of the listed combinations of agents includes amounts of emtricitabine, TDF, and raltegravir, and differs only in the TLR7 Modulating Compound included. In the separate tables the TLR7 Modulating Compound, or a pharmaceutically acceptable salt thereof, comprises a) a compound of Formula II in Table 11A, b) the compound of Example 4 in Table 12A, c) the compound of Example 49 in Table 13A, d) the compound of Example 119 in Table 14A, and e) the compound of Example 120 in Table 15A.

Tables 11A, 12A, 13A, 14A, and 15A

| Comp. Ex. | emtricitabine | TDF | TLR7 MC | raltegravir |
| --- | --- | --- | --- | --- |
| 11A-a, 12A-a, 13A-a, 14A-a, and 15A-a | 150 mg to 250 mg | 250 mg to 350 mg | 0.1 mg to 15 mg | 350 mg to 450 mg |
| 11A-b, 12A-b, 13A-b, 14A-b, and 15A-b | 150 mg to 250 mg | 250 mg to 350 mg | 2 mg to 6 mg | 350 mg to 450 mg |
| 11A-c, 12A-c, 13A-c, 14A-c, and 15A-c | 150 mg to 250 mg | 250 mg to 350 mg | 5 mg to 10 mg | 350 mg to 450 mg |
| 11A-d, 12A-d, 13A-d, 14A-d, and 15A-d | 150 mg to 250 mg | 250 mg to 350 mg | 10 mg to 15 mg | 350 mg to 450 mg |

-continued

| Comp. Ex. | emtricitabine | TDF | TLR7 MC | raltegravir |
|---|---|---|---|---|
| 11A-e, 12A-e, 13A-e, 14A-e, and 15A-e | 175 mg to 225 mg | 275 mg to 325 mg | 0.1 mg to 15 mg | 375 mg to 425 mg |
| 11A-f, 12A-f, 13A-f, 14A-f, and 15A-f | 175 mg to 225 mg | 275 mg to 325 mg | 2 mg to 6 mg | 375 mg to 425 mg |
| 11A-g, 12A-g, 13A-g, 14A-g, and 15A-g | 175 mg to 225 mg | 275 mg to 325 mg | 5 mg to 10 mg | 375 mg to 425 mg |
| 11A-h, 12A-h, 13A-h, 14A-h, and 15A-h | 175 mg to 225 mg | 275 mg to 325 mg | 10 mg to 15 mg | 375 mg to 425 mg |
| 11A-i, 12A-i, 13A-i, 14A-i, and 15A-i | 175 mg to 225 mg | 275 mg to 325 mg | 4 mg | 375 mg to 425 mg |
| 11A-j, 12A-j, 13A-j, 14A-j, and 15A-j | 175 mg to 225 mg | 275 mg to 325 mg | 5 mg | 375 mg to 425 mg |
| 11A-k, 12A-k, 13A-k, 14A-k, and 15A-k | 175 mg to 225 mg | 275 mg to 325 mg | 6 mg | 375 mg to 425 mg |
| 11A-l, 12A-l, 13A-l, 14A-l, and 15A-l | 175 mg to 225 mg | 275 mg to 325 mg | 7 mg | 375 mg to 425 mg |
| 11A-m, 12A-m, 13A-m, 14A-m, and 15A-m | 175 mg to 225 mg | 275 mg to 325 mg | 8 mg | 375 mg to 425 mg |
| 11A-n, 12A-n, 13A-n, 14A-n, and 15A-n | 175 mg to 225 mg | 275 mg to 325 mg | 9 mg | 375 mg to 425 mg |
| 11A-o, 12A-o, 13A-o, 14A-o, and 15A-o | 175 mg to 225 mg | 275 mg to 325 mg | 10 mg | 375 mg to 425 mg |
| 11A-p, 12A-p, 13A-p, 14A-p, and 15A-p | 175 mg to 225 mg | 275 mg to 325 mg | 11 mg | 375 mg to 425 mg |
| 11A-q, 12A-q, 13A-q, 14A-q, and 15A-q | 175 mg to 225 mg | 275 mg to 325 mg | 12 mg | 375 mg to 425 mg |
| 11A-r, 12A-r, 13A-r, 14A-r, and 15A-r | 200 mg | 300 mg | 0.1 mg to 15 mg | 400 mg |
| 11A-s, 12A-s, 13A-s, 14A-s, and 15A-s | 200 mg | 300 mg | 2 mg to 6 mg | 400 mg |
| 11A-t, 12A-t, 13A-t, 14A-t, and 15A-t | 200 mg | 300 mg | 5 mg to 10 mg | 400 mg |
| 11A-u, 12A-u, 13A-u, 14A-u, and 15A-u | 200 mg | 300 mg | 10 mg to 15 mg | 400 mg |
| 11A-v, 12A-v, 13A-v, 14A-v, and 15A-v | 200 mg | 300 mg | 4 mg | 400 mg |
| 11A-w, 12A-w, 13A-w, 14A-w, and 15A-w | 200 mg | 300 mg | 4.1 mg | 400 mg |
| 11A-x, 12A-x, 13A-x, 14A-x, and 15A-x | 200 mg | 300 mg | 4.2 mg | 400 mg |
| 11A-y, 12A-y, 13A-y, 14A-y, and 15A-y | 200 mg | 300 mg | 4.3 mg | 400 mg |
| 11A-z, 12A-z, 13A-z, 14A-z, and 15A-z | 200 mg | 300 mg | 4.4 mg | 400 mg |
| 11A-aa, 12A-aa, 13A-aa, 14A-aa, and 15A-aa | 200 mg | 300 mg | 4.5 mg | 400 mg |
| 11A-ab, 12A-ab, 13A-ab, 14A-ab, and 15A-ab | 200 mg | 300 mg | 4.6 mg | 400 mg |
| 11A-ac, 12A-ac, 13A-ac, 14A-ac, and 15A-ac | 200 mg | 300 mg | 4.7 mg | 400 mg |
| 11A-ad, 12A-ad, 13A-ad, 14A-ad, and 15A-ad | 200 mg | 300 mg | 4.8 mg | 400 mg |
| 11A-ae, 12A-ae, 13A-ae, 14A-ae, and 15A-ae | 200 mg | 300 mg | 4.9 mg | 400 mg |
| 11A-af, 12A-af, 13A-af, 14A-af, and 15A-af | 200 mg | 300 mg | 5.0 mg | 400 mg |
| 11A-ag, 12A-ag, 13A-ag, 14A-ag, and 15A-ag | 200 mg | 300 mg | 5.1 mg | 400 mg |
| 11A-ah, 12A-ah, 13A-ah, 14A-ah, and 15A-ah | 200 mg | 300 mg | 5.2 mg | 400 mg |
| 11A-ai, 12A-ai, 13A-ai, 14A-ai, and 15A-ai | 200 mg | 300 mg | 5.3 mg | 400 mg |
| 11A-aj, 12A-aj, 13A-aj, 14A-aj, and 15A-aj | 200 mg | 300 mg | 5.4 mg | 400 mg |
| 11A-ak, 12A-ak, 13A-ak, 14A-ak, and 15A-ak | 200 mg | 300 mg | 5.5 mg | 400 mg |
| 11A-al, 12A-al, 13A-al, 14A-al, and 15A-al | 200 mg | 300 mg | 5.6 mg | 400 mg |
| 11A-am, 12A-am, 13A-am, 14A-am, and 15A-am | 200 mg | 300 mg | 5.7 mg | 400 mg |
| 11A-an, 12A-an, 13A-an, 14A-an, and 15A-an | 200 mg | 300 mg | 5.8 mg | 400 mg |
| 11A-ao, 12A-ao, 13A-ao, 14A-ao, and 15A-ao | 200 mg | 300 mg | 5.9 mg | 400 mg |
| 11A-ap, 12A-ap, 13A-ap, 14A-ap, and 15A-ap | 200 mg | 300 mg | 6.0 mg | 400 mg |

-continued

| Comp. Ex. | emtricitabine | TDF | TLR7 MC | raltegravir |
|---|---|---|---|---|
| 11A-aq, 12A-aq, 13A-aq, 14A-q, and 15A-q | 200 mg | 300 mg | 6.1 mg | 400 mg |
| 11A-ar, 12A-ar, 13A-ar, 14A-ar, and 15A-ar | 200 mg | 300 mg | 6.2 mg | 400 mg |
| 11A-as, 12A-as, 13A-as, 14A-as, and 15A-as | 200 mg | 300 mg | 6.3 mg | 400 mg |
| 11A-at, 12A-at, 13A-at, 14A-at, and 15A-at | 200 mg | 300 mg | 6.4 mg | 400 mg |
| 11A-au, 12A-au, 13A-au, 14A-au, and 15A-au | 200 mg | 300 mg | 6.5 mg | 400 mg |
| 11A-av, 12A-av, 13A-av, 14A-av, and 15A-av | 200 mg | 300 mg | 6.6 mg | 400 mg |
| 11A-aw, 12A-aw, 13A-aw, 14A-aw, and 15A-aw | 200 mg | 300 mg | 6.7 mg | 400 mg |
| 11A-ax, 12A-ax, 13A-ax, 14A-ax, and 15A-ax | 200 mg | 300 mg | 6.8 mg | 400 mg |
| 11A-ay, 12A-ay, 13A-ay, 14A-ay, and 15A-ay | 200 mg | 300 mg | 6.9 mg | 400 mg |
| 11A-az, 12A-az, 13A-az, 14A-az, and 15A-az | 200 mg | 300 mg | 7.0 mg | 400 mg |
| 11A-ba, 12A-ba, 13A-ba, 14A-ba, and 15A-ba | 200 mg | 300 mg | 7.1 mg | 400 mg |
| 11A-bb, 12A-bb, 13A-bb, 14A-bb, and 15A-bb | 200 mg | 300 mg | 7.2 mg | 400 mg |
| 11A-bc, 12A-bc, 13A-bc, 14A-bc, and 15A-bc | 200 mg | 300 mg | 7.3 mg | 400 mg |
| 11A-bd, 12A-bd, 13A-bd, 14A-bd, and 15A-bd | 200 mg | 300 mg | 7.4 mg | 400 mg |
| 11A-be, 12A-be, 13A-be, 14A-be, and 15A-be | 200 mg | 300 mg | 7.5 mg | 400 mg |
| 11A-bf, 12A-bf, 13A-bf, 14A-bf, and 15A-bf | 200 mg | 300 mg | 7.6 mg | 400 mg |
| 11A-bg, 12A-bg, 13A-bg, 14A-bg, and 15A-bg | 200 mg | 300 mg | 7.7 mg | 400 mg |
| 11A-bh, 12A-bh, 13A-bh, 14A-bh, and 15A-bh | 200 mg | 300 mg | 7.8 mg | 400 mg |
| 11A-bi, 12A-bi, 13A-bi, 14A-bi, and 15A-bi | 200 mg | 300 mg | 7.9 mg | 400 mg |
| 11A-bj, 12A-bj, 13A-bj, 14A-bj, and 15A-bj | 200 mg | 300 mg | 8.0 mg | 400 mg |
| 11A-bk, 12A-bk, 13A-bk, 14A-bk, and 15A-bk | 200 mg | 300 mg | 8.1 mg | 400 mg |
| 11A-bl, 12A-bl, 13A-bl, 14A-bl, and 15A-bl | 200 mg | 300 mg | 8.2 mg | 400 mg |
| 11A-bm, 12A-bm, 13A-bm, 14A-bm, and 15A-bm | 200 mg | 300 mg | 8.3 mg | 400 mg |
| 11A-bn, 12A-bn, 13A-bn, 14A-bn, and 15A-bn | 200 mg | 300 mg | 8.4 mg | 400 mg |
| 11A-bo, 12A-bo, 13A-bo, 14A-bo, and 15A-bo | 200 mg | 300 mg | 8.5 mg | 400 mg |
| 11A-bp, 12A-bp, 13A-bp, 14A-bp, and 15A-bp | 200 mg | 300 mg | 8.6 mg | 400 mg |
| 11A-bq, 12A-bq, 13A-bq, 14A-bq, and 15A-bq | 200 mg | 300 mg | 8.7 mg | 400 mg |
| 11A-br, 12A-br, 13A-br, 14A-br, and 15A-br | 200 mg | 300 mg | 8.8 mg | 400 mg |
| 11A-bs, 12A-bs, 13A-bs, 14A-bs, and 15A-bs | 200 mg | 300 mg | 8.9 mg | 400 mg |
| 11A-bt, 12A-bt, 13A-bt, 14A-bt, and 15A-bt | 200 mg | 300 mg | 9.0 mg | 400 mg |
| 11A-bu, 12A-bu, 13A-bu, 14A-bu, and 15A-bu | 200 mg | 300 mg | 9.1 mg | 400 mg |
| 11A-bv, 12A-bv, 13A-bv, 14A-bv, and 15A-bv | 200 mg | 300 mg | 9.2 mg | 400 mg |
| 11A-bw, 12A-bw, 13A-bw, 14A-bw, and 15A-bw | 200 mg | 300 mg | 9.3 mg | 400 mg |
| 11A-bx, 12A-bx, 13A-bx, 14A-bx, and 15A-bx | 200 mg | 300 mg | 9.4 mg | 400 mg |
| 11A-by, 12A-by, 13A-by, 14A-by, and 15A-by | 200 mg | 300 mg | 9.5 mg | 400 mg |
| 11A-bz, 12A-bz, 13A-bz, 14A-bz, and 15A-bz | 200 mg | 300 mg | 9.6 mg | 400 mg |
| 11A-ca, 12A-ca, 13A-ca, 14A-ca, and 15A-ca | 200 mg | 300 mg | 9.7 mg | 400 mg |
| 11A-cb, 12A-cb, 13A-cb, 14A-cb, and 15A-cb | 200 mg | 300 mg | 9.8 mg | 400 mg |

-continued

| Comp. Ex. | emtricitabine | TDF | TLR7 MC | raltegravir |
|---|---|---|---|---|
| 11A-cc, 12A-cc, 13A-cc, 14A-cc, and 15A-cc | 200 mg | 300 mg | 9.9 mg | 400 mg |
| 11A-cd, 12A-cd, 13A-cd, 14A-cd, and 15A-cd | 200 mg | 300 mg | 10.0 mg | 400 mg |
| 11A-ce, 12A-ce, 13A-ce, 14A-ce, and 15A-ce | 200 mg | 300 mg | 10.1 mg | 400 mg |
| 11A-cf, 12A-cf, 13A-cf, 14A-cf, and 15A-cf | 200 mg | 300 mg | 10.2 mg | 400 mg |
| 11A-cg, 12A-cg, 13A-cg, 14A-cg, and 15A-cg | 200 mg | 300 mg | 10.3 mg | 400 mg |
| 11A-ch, 12A-ch, 13A-ch, 14A-ch, and 15A-ch | 200 mg | 300 mg | 10.4 mg | 400 mg |
| 11A-ci, 12A-ci, 13A-ci, 14A-ci, and 15A-ci | 200 mg | 300 mg | 10.5 mg | 400 mg |
| 11A-cj, 12A-cj, 13A-cj, 14A-cj, and 15A-cj | 200 mg | 300 mg | 10.6 mg | 400 mg |
| 11A-ck, 12A-ck, 13A-ck, 14A-ck, and 15A-ck | 200 mg | 300 mg | 10.7 mg | 400 mg |
| 11A-cl, 12A-cl, 13A-cl, 14A-cl, and 15A-cl | 200 mg | 300 mg | 10.8 mg | 400 mg |
| 11A-cm, 12A-cm, 13A-cm, 14A-cm, and 15A-cm | 200 mg | 300 mg | 10.9 mg | 400 mg |
| 11A-cn, 12A-cn, 13A-cn, 14A-cn, and 15A-cn | 200 mg | 300 mg | 11.0 mg | 400 mg |
| 11A-co, 12A-co, 13A-co, 14A-co, and 15A-co | 200 mg | 300 mg | 11.1 mg | 400 mg |
| 11A-cp, 12A-cp, 13A-cp, 14A-cp, and 15A-cp | 200 mg | 300 mg | 11.2 mg | 400 mg |
| 11A-cq, 12A-cq, 13A-cq, 14A-cq, and 15A-cq | 200 mg | 300 mg | 11.3 mg | 400 mg |
| 11A-cr, 12A-cr, 13A-cr, 14A-cr, and 15A-cr | 200 mg | 300 mg | 11.4 mg | 400 mg |
| 11A-cs, 12A-cs, 13A-cs, 14A-cs, and 15A-cs | 200 mg | 300 mg | 11.5 mg | 400 mg |
| 11A-ct, 12A-ct, 13A-ct, 14A-ct, and 15A-ct | 200 mg | 300 mg | 11.6 mg | 400 mg |
| 11A-cu, 12A-cu, 13A-cu, 14A-cu, and 15A-cu | 200 mg | 300 mg | 11.7 mg | 400 mg |
| 11A-cv, 12A-cv, 13A-cv, 14A-cv, and 15A-cv | 200 mg | 300 mg | 11.8 mg | 400 mg |
| 11A-cw, 12A-cw, 13A-cw, 14A-cw, and 15A-cw | 200 mg | 300 mg | 11.9 mg | 400 mg |
| 11A-cx, 12A-cx, 13A-cx, 14A-cx, and 15A-cx | 200 mg | 300 mg | 12.0 mg | 400 mg |
| 11A-cy, 12A-cy, 13A-cy, 14A-cy, and 15A-cy | 150 mg to 250 mg | 250 mg to 350 mg | 0.1 mg to 15 mg | 0.1 mg to 25.0 mg |
| 11A-cz, 12A-cz, 13A-cz, 14A-cz, and 15A-cz | 150 mg to 250 mg | 250 mg to 350 mg | 0.1 mg to 15 mg | 15 mg to 20 mg |
| 11A-da, 12A-da, 13A-da, 14A-da, and 15A-da | 150 mg to 250 mg | 250 mg to 350 mg | 0.1 mg to 15 mg | 20 mg to 25 mg |
| 11A-db, 12A-db, 13A-db, 14A-db, and 15A-db | 50 mg to 250 mg | 50 mg to 350 mg | 0.1 mg to 25.0 mg | 350 mg to 450 mg |
| 11A-dc, 12A-dc, 13A-dc, 14A-dc, and 15A-dc | 50 mg to 200 mg | 50 mg to 300 mg | 0.1 mg to 20.0 mg | 200 mg to 400 mg |
| 11A-dd, 12A-dd, 13A-dd, 14A-dd, and 15A-dd | 50 mg to 175 mg | 50 mg to 250 mg | 0.1 mg to 15.0 mg | 200 mg to 350 mg |

Tables 11B, 12B, 13B, 14B, and 15B

The table below serves as Tables 11B, 12B, 13B, 14B, and 15B and provides combinations of agents that can be used in the uses, methods, regimens, and pharmaceutical compositions herein. Each of the listed combinations of agents includes amounts of emtricitabine, TAF, and raltegravir, and differs only in the TLR7 Modulating Compound (TLR7 MC) included. In the separate tables the TLR7 Modulating Compound, or a pharmaceutically acceptable salt thereof, comprises a) a compound of Formula II in Table 11B, b) the compound of Example 4 in Table 12B, c) the compound of Example 49 in Table 13B, d) the compound of Example 119 in Table 14B, and e) the compound of Example 120 in Table 15B.

| Comp. Ex. | emtricitabine | TAF | TLR7 MC | raltegravir |
|---|---|---|---|---|
| 11B-a, 12B-a, 13B-a, 14B-a, and 15B-a | 150 mg to 250 mg | 15 mg to 35 mg | 0.1 mg to 15 mg | 350 mg to 450 mg |
| 11B-b, 12B-b, 13B-b, 14B-b, and 15B-b | 150 mg to 250 mg | 15 mg to 35 mg | 2 mg to 6 mg | 350 mg to 450 mg |
| 11B-c, 12B-c, 13B-c, 14B-c, and 15B-c | 150 mg to 250 mg | 15 mg to 35 mg | 5 mg to 10 mg | 350 mg to 450 mg |

| Comp. Ex. | emtricitabine | TAF | TLR7 MC | raltegravir |
|---|---|---|---|---|
| 11B-d, 12B-d, 13B-d, 14B-d, and 15B-d | 150 mg to 250 mg | 15 mg to 35 mg | 10 mg to 15 mg | 350 mg to 450 mg |
| 11B-e, 12B-e, 13B-e, 14B-e, and 15B-e | 175 mg to 225 mg | 20 mg to 30 mg | 0.1 mg to 15 mg | 375 mg to 425 mg |
| 11B-f, 12B-f, 13B-f, 14B-f, and 15B-f | 175 mg to 225 mg | 20 mg to 30 mg | 2 mg to 6 mg | 375 mg to 425 mg |
| 11B-g, 12B-g, 13B-g, 14B-g, and 15B-g | 175 mg to 225 mg | 20 mg to 30 mg | 5 mg to 10 mg | 375 mg to 425 mg |
| 11B-h, 12B-h, 13B-h, 14B-h, and 15B-h | 175 mg to 225 mg | 20 mg to 30 mg | 10 mg to 15 mg | 375 mg to 425 mg |
| 11B-i, 12B-i, 13B-i, 14B-i, and 15B-i | 175 mg to 225 mg | 20 mg to 30 mg | 4 mg | 375 mg to 425 mg |
| 11B-j, 12B-j, 13B-j, 14B-j, and 15B-j | 175 mg to 225 mg | 20 mg to 30 mg | 5 mg | 375 mg to 425 mg |
| 11B-k, 12B-k, 13B-k, 14B-k, and 15B-k | 175 mg to 225 mg | 20 mg to 30 mg | 6 mg | 375 mg to 425 mg |
| 11B-l, 12B-l, 13B-l, 14B-l, and 15B-l | 175 mg to 225 mg | 20 mg to 30 mg | 7 mg | 375 mg to 425 mg |
| 11B-m, 12B-m, 13B-m, 14B-m, and 15B-m | 175 mg to 225 mg | 20 mg to 30 mg | 8 mg | 375 mg to 425 mg |
| 11B-n, 12B-n, 13B-n, 14B-n, and 15B-n | 175 mg to 225 mg | 20 mg to 30 mg | 9 mg | 375 mg to 425 mg |
| 11B-o, 12B-o, 13B-o, 14B-o, and 15B-o | 175 mg to 225 mg | 20 mg to 30 mg | 10 mg | 375 mg to 425 mg |
| 11B-p, 12B-p, 13B-p, 14B-p, and 15B-p | 175 mg to 225 mg | 20 mg to 30 mg | 11 mg | 375 mg to 425 mg |
| 11B-q, 12B-q, 13B-q, 14B-q, and 15B-q | 175 mg to 225 mg | 20 mg to 30 mg | 12 mg | 375 mg to 425 mg |
| 11B-r, 12B-r, 13B-r, 14B-r, and 15B-r | 200 mg | 25 mg | 0.1 mg to 15 mg | 400 mg |
| 11B-s, 12B-s, 13B-s, 14B-s, and 15B-s | 200 mg | 25 mg | 2 mg to 6 mg | 400 mg |
| 11B-t, 12B-t, 13B-t, 14B-t, and 15B-t | 200 mg | 25 mg | 5 mg to 10 mg | 400 mg |
| 11B-u, 12B-u, 13B-u, 14B-u, and 15B-u | 200 mg | 25 mg | 10 mg to 15 mg | 400 mg |
| 11B-v, 12B-v, 13B-v, 14B-v, and 15B-v | 200 mg | 25 mg | 4 mg | 400 mg |
| 11B-w, 12B-w, 13B-w, 14B-w, and 15B-w | 200 mg | 25 mg | 4.1 mg | 400 mg |
| 11B-x, 12B-x, 13B-x, 14B-x, and 15B-x | 200 mg | 25 mg | 4.2 mg | 400 mg |
| 11B-y, 12B-y, 13B-y, 14B-y, and 15B-y | 200 mg | 25 mg | 4.3 mg | 400 mg |
| 11B-z, 12B-z, 13B-z, 14B-z, and 15B-z | 200 mg | 25 mg | 4.4 mg | 400 mg |
| 11B-aa, 12B-aa, 13B-aa, 14B-aa, and 15B-aa | 200 mg | 25 mg | 4.5 mg | 400 mg |
| 11B-ab, 12B-ab, 13B-ab, 14B-ab, and 15B-ab | 200 mg | 25 mg | 4.6 mg | 400 mg |
| 11B-ac, 12B-ac, 13B-ac, 14B-ac, and 15B-ac | 200 mg | 25 mg | 4.7 mg | 400 mg |
| 11B-ad, 12B-ad, 13B-ad, 14B-ad, and 15B-ad | 200 mg | 25 mg | 4.8 mg | 400 mg |
| 11B-ae, 12B-ae, 13B-ae, 14B-ae, and 15B-ae | 200 mg | 25 mg | 4.9 mg | 400 mg |
| 11B-af, 12B-af, 13B-af, 14B-af, and 15B-af | 200 mg | 25 mg | 5.0 mg | 400 mg |
| 11B-ag, 12B-ag, 13B-ag, 14B-ag, and 15B-ag | 200 mg | 25 mg | 5.1 mg | 400 mg |
| 11B-ah, 12B-ah, 13B-ah, 14B-ah, and 15B-ah | 200 mg | 25 mg | 5.2 mg | 400 mg |
| 11B-ai, 12B-ai, 13B-ai, 14B-ai, and 15B-ai | 200 mg | 25 mg | 5.3 mg | 400 mg |
| 11B-aj, 12B-aj, 13B-aj, 14B-aj, and 15B-aj | 200 mg | 25 mg | 5.4 mg | 400 mg |
| 11B-ak, 12B-ak, 13B-ak, 14B-ak, and 15B-ak | 200 mg | 25 mg | 5.5 mg | 400 mg |
| 11B-al, 12B-al, 13B-al, 14B-al, and 15B-al | 200 mg | 25 mg | 5.6 mg | 400 mg |
| 11B-am, 12B-am, 13B-am, 14B-am, and 15B-am | 200 mg | 25 mg | 5.7 mg | 400 mg |
| 11B-an, 12B-an, 13B-an, 14B-an, and 15B-an | 200 mg | 25 mg | 5.8 mg | 400 mg |
| 11B-ao, 12B-ao, 13B-ao, 14B-ao, and 15B-ao | 200 mg | 25 mg | 5.9 mg | 400 mg |

| Comp. Ex. | emtricitabine | TAF | TLR7 MC | raltegravir |
|---|---|---|---|---|
| 11B-ap, 12B-ap, 13B-ap, 14B-ap, and 15B-ap | 200 mg | 25 mg | 6.0 mg | 400 mg |
| 11B-aq, 12B-aq, 13B-aq, 14B-q, and 15B-q | 200 mg | 25 mg | 6.1 mg | 400 mg |
| 11B-ar, 12B-ar, 13B-ar, 14B-ar, and 15B-ar | 200 mg | 25 mg | 6.2 mg | 400 mg |
| 11B-as, 12B-as, 13B-as, 14B-as, and 15B-as | 200 mg | 25 mg | 6.3 mg | 400 mg |
| 11B-at, 12B-at, 13B-at, 14B-at, and 15B-at | 200 mg | 25 mg | 6.4 mg | 400 mg |
| 11B-au, 12B-au, 13B-au, 14B-au, and 15B-au | 200 mg | 25 mg | 6.5 mg | 400 mg |
| 11B-av, 12B-av, 13B-av, 14B-av, and 15B-av | 200 mg | 25 mg | 6.6 mg | 400 mg |
| 11B-aw, 12B-aw, 13B-aw, 14B-aw, and 15B-aw | 200 mg | 25 mg | 6.7 mg | 400 mg |
| 11B-ax, 12B-ax, 13B-ax, 14B-ax, and 15B-ax | 200 mg | 25 mg | 6.8 mg | 400 mg |
| 11B-ay, 12B-ay, 13B-ay, 14B-ay, and 15B-ay | 200 mg | 25 mg | 6.9 mg | 400 mg |
| 11B-az, 12B-az, 13B-az, 14B-az, and 15B-az | 200 mg | 25 mg | 7.0 mg | 400 mg |
| 11B-ba, 12B-ba, 13B-ba, 14B-ba, and 15B-ba | 200 mg | 25 mg | 7.1 mg | 400 mg |
| 11B-bb, 12B-bb, 13B-bb, 14B-bb, and 15B-bb | 200 mg | 25 mg | 7.2 mg | 400 mg |
| 11B-bc, 12B-bc, 13B-bc, 14B-bc, and 15B-bc | 200 mg | 25 mg | 7.3 mg | 400 mg |
| 11B-bd, 12B-bd, 13B-bd, 14B-bd, and 15B-bd | 200 mg | 25 mg | 7.4 mg | 400 mg |
| 11B-be, 12B-be, 13B-be, 14B-be, and 15B-be | 200 mg | 25 mg | 7.5 mg | 400 mg |
| 11B-bf, 12B-bf, 13B-bf, 14B-bf, and 15B-bf | 200 mg | 25 mg | 7.6 mg | 400 mg |
| 11B-bg, 12B-bg, 13B-bg, 14B-bg, and 15B-bg | 200 mg | 25 mg | 7.7 mg | 400 mg |
| 11B-bh, 12B-bh, 13B-bh, 14B-bh, and 15B-bh | 200 mg | 25 mg | 7.8 mg | 400 mg |
| 11B-bi, 12B-bi, 13B-bi, 14B-bi, and 15B-bi | 200 mg | 25 mg | 7.9 mg | 400 mg |
| 11B-bj, 12B-bj, 13B-bj, 14B-bj, and 15B-bj | 200 mg | 25 mg | 8.0 mg | 400 mg |
| 11B-bk, 12B-bk, 13B-bk, 14B-bk, and 15B-bk | 200 mg | 25 mg | 8.1 mg | 400 mg |
| 11B-bl, 12B-bl, 13B-bl, 14B-bl, and 15B-bl | 200 mg | 25 mg | 8.2 mg | 400 mg |
| 11B-bm, 12B-bm, 13B-bm, 14B-bm, and 15B-bm | 200 mg | 25 mg | 8.3 mg | 400 mg |
| 11B-bn, 12B-bn, 13B-bn, 14B-bn, and 15B-bn | 200 mg | 25 mg | 8.4 mg | 400 mg |
| 11B-bo, 12B-bo, 13B-bo, 14B-bo, and 15B-bo | 200 mg | 25 mg | 8.5 mg | 400 mg |
| 11B-bp, 12B-bp, 13B-bp, 14B-bp, and 15B-bp | 200 mg | 25 mg | 8.6 mg | 400 mg |
| 11B-bq, 12B-bq, 13B-bq, 14B-bq, and 15B-bq | 200 mg | 25 mg | 8.7 mg | 400 mg |
| 11B-br, 12B-br, 13B-br, 14B-br, and 15B-br | 200 mg | 25 mg | 8.8 mg | 400 mg |
| 11B-bs, 12B-bs, 13B-bs, 14B-bs, and 15B-bs | 200 mg | 25 mg | 8.9 mg | 400 mg |
| 11B-bt, 12B-bt, 13B-bt, 14B-bt, and 15B-bt | 200 mg | 25 mg | 9.0 mg | 400 mg |
| 11B-bu, 12B-bu, 13B-bu, 14B-bu, and 15B-bu | 200 mg | 25 mg | 9.1 mg | 400 mg |
| 11B-bv, 12B-bv, 13B-bv, 14B-bv, and 15B-bv | 200 mg | 25 mg | 9.2 mg | 400 mg |
| 11B-bw, 12B-bw, 13B-bw, 14B-bw, and 15B-bw | 200 mg | 25 mg | 9.3 mg | 400 mg |
| 11B-bx, 12B-bx, 13B-bx, 14B-bx, and 15B-bx | 200 mg | 25 mg | 9.4 mg | 400 mg |
| 11B-by, 12B-by, 13B-by, 14B-by, and 15B-by | 200 mg | 25 mg | 9.5 mg | 400 mg |
| 11B-bz, 12B-bz, 13B-bz, 14B-bz, and 15B-bz | 200 mg | 25 mg | 9.6 mg | 400 mg |
| 11B-ca, 12B-ca, 13B-ca, 14B-ca, and 15B-ca | 200 mg | 25 mg | 9.7 mg | 400 mg |

-continued

| Comp. Ex. | emtricitabine | TAF | TLR7 MC | raltegravir |
|---|---|---|---|---|
| 11B-cb, 12B-cb, 13B-cb, 14B-cb, and 15B-cb | 200 mg | 25 mg | 9.8 mg | 400 mg |
| 11B-cc, 12B-cc, 13B-cc, 14B-cc, and 15B-cc | 200 mg | 25 mg | 9.9 mg | 400 mg |
| 11B-cd, 12B-cd, 13B-cd, 14B-cd, and 15B-cd | 200 mg | 25 mg | 10.0 mg | 400 mg |
| 11B-ce, 12B-ce, 13B-ce, 14B-ce, and 15B-ce | 200 mg | 25 mg | 10.1 mg | 400 mg |
| 11B-cf, 12B-cf, 13B-cf, 14B-cf, and 15B-cf | 200 mg | 25 mg | 10.2 mg | 400 mg |
| 11B-cg, 12B-cg, 13B-cg, 14B-cg, and 15B-cg | 200 mg | 25 mg | 10.3 mg | 400 mg |
| 11B-ch, 12B-ch, 13B-ch, 14B-ch, and 15B-ch | 200 mg | 25 mg | 10.4 mg | 400 mg |
| 11B-ci, 12B-ci, 13B-ci, 14B-ci, and 15B-ci | 200 mg | 25 mg | 10.5 mg | 400 mg |
| 11B-cj, 12B-cj, 13B-cj, 14B-cj, and 15B-cj | 200 mg | 25 mg | 10.6 mg | 400 mg |
| 11B-ck, 12B-ck, 13B-ck, 14B-ck, and 15B-ck | 200 mg | 25 mg | 10.7 mg | 400 mg |
| 11B-cl, 12B-cl, 13B-cl, 14B-cl, and 15B-cl | 200 mg | 25 mg | 10.8 mg | 400 mg |
| 11B-cm, 12B-cm, 13B-cm, 14B-cm, and 15B-cm | 200 mg | 25 mg | 10.9 mg | 400 mg |
| 11B-cn, 12B-cn, 13B-cn, 14B-cn, and 15B-cn | 200 mg | 25 mg | 11.0 mg | 400 mg |
| 11B-co, 12B-co, 13B-co, 14B-co, and 15B-co | 200 mg | 25 mg | 11.1 mg | 400 mg |
| 11B-cp, 12B-cp, 13B-cp, 14B-cp, and 15B-cp | 200 mg | 25 mg | 11.2 mg | 400 mg |
| 11B-cq, 12B-cq, 13B-cq, 14B-cq, and 15B-cq | 200 mg | 25 mg | 11.3 mg | 400 mg |
| 11B-cr, 12B-cr, 13B-cr, 14B-cr, and 15B-cr | 200 mg | 25 mg | 11.4 mg | 400 mg |
| 11B-cs, 12B-cs, 13B-cs, 14B-cs, and 15B-cs | 200 mg | 25 mg | 11.5 mg | 400 mg |
| 11B-ct, 12B-ct, 13B-ct, 14B-ct, and 15B-ct | 200 mg | 25 mg | 11.6 mg | 400 mg |
| 11B-cu, 12B-cu, 13B-cu, 14B-cu, and 15B-cu | 200 mg | 25 mg | 11.7 mg | 400 mg |
| 11B-cv, 12B-cv, 13B-cv, 14B-cv, and 15B-cv | 200 mg | 25 mg | 11.8 mg | 400 mg |
| 11B-cw, 12B-cw, 13B-cw, 14B-cw, and 15B-cw | 200 mg | 25 mg | 11.9 mg | 400 mg |
| 11B-cx, 12B-cx, 13B-cx, 14B-cx, and 15B-cx | 200 mg | 25 mg | 12.0 mg | 400 mg |
| 11B-cy, 12B-cy, 13B-cy, 14B-cy, and 15B-cy | 150 mg to 250 mg | 15 mg to 35 mg | 0.1 mg to 15 mg | 0.1 mg to 25.0 mg |
| 11B-cz, 12B-cz, 13B-cz, 14B-cz, and 15B-cz | 150 mg to 250 mg | 15 mg to 35 mg | 0.1 mg to 15 mg | 15 mg to 20 mg |
| 11B-da, 12B-da, 13B-da, 14B-da, and 15B-da | 150 mg to 250 mg | 15 mg to 35 mg | 0.1 mg to 15 mg | 20 mg to 25 mg |
| 11B-db, 12B-db, 13B-db, 14B-db, and 15B-db | 50 mg to 250 mg | 1 mg to 15 mg | 0.1 mg to 25.0 mg | 350 mg to 450 mg |
| 11B-dc, 12B-dc, 13B-dc, 14B-dc, and 15B-dc | 50 mg to 200 mg | 1 mg to 10 mg | 0.1 mg to 20.0 mg | 200 mg to 400 mg |
| 11B-dd, 12B-dd, 13B-dd, 14B-dd, and 15B-dd | 50 mg to 175 mg | 1 mg to 8 mg | 0.1 mg to 15.0 mg | 200 mg to 350 mg |

Also provided is a pharmaceutical kit, the kit comprising:
1) a series of daily doses of a single pharmaceutical composition comprising:
  a. a pharmaceutically effective amount of emtricitabine;
  b. a pharmaceutically effective amount of tenofovir disoproxil fumarate;
  c. a pharmaceutically effective amount of a compound of Formula II, or a pharmaceutically acceptable salt thereof;
  d. a pharmaceutically effective amount of raltegravir; and
  e. a pharmaceutically acceptable carrier or excipient; and 2) directions for the administration of the daily doses of the pharmaceutical composition.

Also provided are separate pharmaceutical kits, as just described, wherein the pharmaceutical composition comprises, in each of the separate pharmaceutical kits, one of the pharmaceutical compositions described above having raltegravir as a component or element.

Further provided is a pharmaceutical kit, the kit comprising:
1) a series of doses of a first pharmaceutical composition comprising:
  a) a pharmaceutically effective amount of emtricitabine;
  b) a pharmaceutically effective amount of tenofovir disoproxil fumarate;

c) a pharmaceutically effective amount of a compound of Formula II, or a pharmaceutically acceptable salt thereof;
d) a pharmaceutically acceptable carrier or excipient; and
2) a series of doses of a second pharmaceutical composition comprising a pharmaceutically effective amount of raltegravir and a pharmaceutically acceptable carrier or excipient; and
3) directions for the administration of the doses of the first and second pharmaceutical composition; wherein the first and second pharmaceutical compositions are both administered once daily.

Further provided is a pharmaceutical kit, the kit comprising:
1. a series of daily doses of a first pharmaceutical composition comprising:
   b) a pharmaceutically effective amount of emtricitabine;
   c) a pharmaceutically effective amount of tenofovir disoproxil fumarate;
   d) a pharmaceutically effective amount of a compound of Formula II, or a pharmaceutically acceptable salt thereof;
   e) a pharmaceutically acceptable carrier or excipient; and
2) a series of daily doses of a second pharmaceutical composition comprising a pharmaceutically effective amount of raltegravir and a pharmaceutically acceptable carrier or excipient; and
3) directions for the administration of the daily doses of the first and second pharmaceutical composition; wherein the first and second pharmaceutical compositions are both administered twice daily.

Further provided is a pharmaceutical kit, the kit comprising:
1) a series of doses of a first pharmaceutical composition comprising:
   a) a pharmaceutically effective amount of emtricitabine;
   b) a pharmaceutically effective amount of tenofovir disoproxil fumarate;
   c) a pharmaceutically effective amount of a compound of Formula II, or a pharmaceutically acceptable salt thereof;
   d) a pharmaceutically acceptable carrier or excipient; and
2) a series of doses of a second pharmaceutical composition comprising a pharmaceutically effective amount of raltegravir and a pharmaceutically acceptable carrier or excipient; and
3) directions for the administration of the doses of the first and second pharmaceutical composition; wherein the first pharmaceutical composition is administered once daily and second pharmaceutical composition is administered twice daily.

Further provided is a pharmaceutical kit, the kit comprising:
1) a series of doses of a first pharmaceutical composition comprising:
   a) a pharmaceutically effective amount of emtricitabine;
   b) a pharmaceutically effective amount of tenofovir disoproxil fumarate;
   c) a pharmaceutically acceptable carrier or excipient; and
2) a series of doses of a second pharmaceutical composition comprising a pharmaceutically effective amount of raltegravir and a pharmaceutically acceptable carrier or excipient; and
3) a series of doses of a third pharmaceutical composition comprising a pharmaceutically effective amount of a compound of Formula II, or a pharmaceutically acceptable salt thereof; and
directions for the administration of the doses of the first and second pharmaceutical composition; wherein each of the first pharmaceutical composition, the second pharmaceutical composition, and the third pharmaceutical composition is administered once daily.

Within the embodiment of the pharmaceutical kit immediately above, there is a further embodiment comprising the kit, as described, wherein the second pharmaceutical composition comprises from 10 mg to 500 mg of raltegravir. Within the embodiment of the pharmaceutical kit immediately above, there is a further embodiment comprising the kit, as described, wherein the second pharmaceutical composition comprises from 300 mg to 500 mg of raltegravir. Within the embodiment of the pharmaceutical kit immediately above, there is a another embodiment comprising the kit, as described, wherein the second pharmaceutical composition comprises from 350 mg to 450 mg of raltegravir. Within the embodiment of the pharmaceutical kit immediately above, there is a another embodiment comprising the kit, as described, wherein the second pharmaceutical composition comprises 400 mg of raltegravir.

Further provided is a pharmaceutical kit, the kit comprising:
1) a series of doses of a first pharmaceutical composition comprising:
   a) a pharmaceutically effective amount of emtricitabine;
   b) a pharmaceutically effective amount of tenofovir disoproxil fumarate;
   c) a pharmaceutically acceptable carrier or excipient; and
2) a series of doses of a second pharmaceutical composition comprising a pharmaceutically effective amount of raltegravir and a pharmaceutically acceptable carrier or excipient; and
3) a series of doses of a third pharmaceutical composition comprising a pharmaceutically effective amount of a compound of Formula II, or a pharmaceutically acceptable salt thereof; and
4) directions for the administration of the doses of the first and second pharmaceutical composition; wherein the first pharmaceutical composition and third pharmaceutical composition are each administered once daily and the second pharmaceutical composition is administered twice daily.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 10 mg to 500 mg of raltegravir, and the third pharmaceutical composition comprises from 0.1 to 15 mg of a compound of Formula II, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 15 mg to 35 mg of raltegravir, and the third pharmaceutical composition comprises from 0.1 to 15 mg of a compound of Formula II, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 90 mg to 110 mg of raltegravir, and the third pharmaceutical composition comprises from 0.1 to 15 mg of a compound of Formula II, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 375 mg to 425 mg of raltegravir, and the third pharmaceutical composition comprises from 0.1 to 15 mg of a compound of Formula II, or a pharmaceutically acceptable salt thereof.

Within each of the embodiments above wherein the kit comprises a first, second, and third pharmaceutical composition, there are four additional embodiments wherein all other components or elements are as described above and:
1) in the first additional embodiment, the third pharmaceutical composition comprises from 0.1 to 15 mg of the compound of Example 4, or a pharmaceutically acceptable salt thereof;
2) in the second additional embodiment, the third pharmaceutical composition comprises from 0.1 to 15 mg of the compound of Example 49, or a pharmaceutically acceptable salt thereof;
3) in the third additional embodiment, the third pharmaceutical composition comprises from 0.1 to 15 mg of the compound of Example 119, or a pharmaceutically acceptable salt thereof;
4) in the fourth additional embodiment, the third pharmaceutical composition comprises from 0.1 to 15 mg of the compound of Example 120, or a pharmaceutically acceptable salt thereof.

Combinations of Emtricitabine/TDF/TLR7 Modulators/Dolutegravir

Pharmaceutically effective amounts of the TLR7 modulating compounds, including those of Formula II, or a pharmaceutically acceptable salt thereof, as well as the compounds of Examples 119, 120, and 121, or a pharmaceutically acceptable salt thereof, can be combined with pharmaceutically effective amounts of emtricitabine, TDF or TAF, and dolutegravir for use in the methods of treatment discussed herein. For instance, as separate dosage forms, a pharmaceutically effective dose of the TLR7 modulating compounds may be combined in a treatment regimen with a TRUVADA® tablet (200 mg of emtricitabine and 300 mg of tenofovir disoproxil fumarate), which is available from Gilead Sciences, and a TIVICAY® tablet (50 mg dolutegravir), which is available from GlaxoSmithKline.

Also provided is a pharmaceutical composition comprising:
a) a pharmaceutically effective amount of emtricitabine;
b) a pharmaceutically effective amount of tenofovir disoproxil fumarate;
c) a pharmaceutically effective amount of a TLR7 modulating, or a pharmaceutically acceptable salt thereof;
d) a pharmaceutically effective amount of dolutegravir; and
e) a pharmaceutically acceptable carrier or excipient.

Also provided is a pharmaceutical composition comprising:
a) a pharmaceutically effective amount of emtricitabine;
b) a pharmaceutically effective amount of tenofovir alafenamide;
c) a pharmaceutically effective amount of a TLR7 modulating, or a pharmaceutically acceptable salt thereof;
d) a pharmaceutically effective amount of dolutegravir; and
e) a pharmaceutically acceptable carrier or excipient.

Also provided is a pharmaceutical composition comprising:
a) a pharmaceutically effective amount of emtricitabine;
b) a pharmaceutically effective amount of tenofovir disoproxil fumarate;
c) a pharmaceutically effective amount of a compound of Formula II, or a pharmaceutically acceptable salt thereof;
d) a pharmaceutically effective amount of dolutegravir; and
e) a pharmaceutically acceptable carrier or excipient.

Also provided is a pharmaceutical composition comprising:
f) a pharmaceutically effective amount of emtricitabine;
g) a pharmaceutically effective amount of tenofovir alafenamide;
h) a pharmaceutically effective amount of a compound of Formula II, or a pharmaceutically acceptable salt thereof;
i) a pharmaceutically effective amount of dolutegravir; and
j) a pharmaceutically acceptable carrier or excipient.

Pharmaceutical Composition Tables 16a, 17a, 18a, 19a, 20a, 16B, 17B, 18B, 19B, and 20B Provided are separate pharmaceutical compositions and combinations wherein each composition comprises a pharmaceutically acceptable carrier or excipient and the amounts of emtricitabine, TDF or TAF, dolutegravir, and a TLR7 Modulating Compound, or a pharmaceutically acceptable salt thereof, in the amounts listed for each composition below.

Following the pattern of the tables above, the table below serves as Tables 16A, 17A, 18A, 19A, and 20A and provides combinations of agents that can be used in the uses, methods, regimens, and pharmaceutical compositions herein. Each of the listed combinations of agents includes amounts of emtricitabine, TDF, and dolutegravir, and differs only in the TLR7 Modulating Compound included. In the separate tables the TLR7 Modulating Compound, or a pharmaceutically acceptable salt thereof, comprises a) a compound of Formula II in Table 16A, b) the compound of Example 4 in Table 17A, c) the compound of Example 49 in Table 18A, d) the compound of Example 119 in Table 19A, and e) the compound of Example 120 in Table 20A.

Tables 16a, 17a, 18a, 19a, and 20a

| Comp. Ex. | emtricitabine | TDF | TLR7 MC | dolutegravir |
|---|---|---|---|---|
| 16A-a, 17A-a, 18A-a, 19A-a, and 20A-a | 150 mg to 250 mg | 250 mg to 350 mg | 0.1 mg to 15 mg | 30 mg to 70 mg |
| 16A-b, 17A-b, 18A-b, 19A-b, and 20A-b | 150 mg to 250 mg | 250 mg to 350 mg | 2 mg to 6 mg | 30 mg to 70 mg |

| Comp. Ex. | emtricitabine | TDF | TLR7 MC | dolutegravir |
|---|---|---|---|---|
| 16A-c, 17A-c, 18A-c, 19A-c, and 20A-c | 150 mg to 250 mg | 250 mg to 350 mg | 5 mg to 10 mg | 30 mg to 70 mg |
| 16A-d, 17A-d, 18A-d, 19A-d, and 20A-d | 150 mg to 250 mg | 250 mg to 350 mg | 10 mg to 15 mg | 30 mg to 70 mg |
| 16A-e, 17A-e, 18A-e, 19A-e, and 20A-e | 150 mg to 250 mg | 250 mg to 350 mg | 0.1 mg to 15 mg | 40 mg to 60 mg |
| 16A-f, 17A-f, 18A-f, 19A-f, and 20A-f | 150 mg to 250 mg | 250 mg to 350 mg | 2 mg to 6 mg | 40 mg to 60 mg |
| 16A-g, 17A-g, 18A-g, 19A-g, and 20A-g | 150 mg to 250 mg | 250 mg to 350 mg | 5 mg to 10 mg | 40 mg to 60 mg |
| 16A-h, 17A-h, 18A-h, 19A-h, and 20A-h | 150 mg to 250 mg | 250 mg to 350 mg | 10 mg to 15 mg | 40 mg to 60 mg |
| 16A-i, 17A-i, 18A-i, 19A-i, and 20A-i | 175 mg to 225 mg | 275 mg to 325 mg | 0.1 mg to 15 mg | 40 mg to 60 mg |
| 16A-j, 17A-j, 18A-j, 19A-j, and 20A-j | 175 mg to 225 mg | 275 mg to 325 mg | 2 mg to 6 mg | 40 mg to 60 mg |
| 16A-k, 17A-k, 18A-k, 19A-k, and 20A-k | 175 mg to 225 mg | 275 mg to 325 mg | 5 mg to 10 mg | 40 mg to 60 mg |
| 16A-I, 17A-I, 18A-I, 19A-I, and 20A-I | 175 mg to 225 mg | 275 mg to 325 mg | 10 mg to 15 mg | 40 mg to 60 mg |
| 16A-m, 17A-m, 18A-m, 19A-m, and 20A-m | 190 mg to 210 mg | 290 mg to 310 mg | 0.1 mg to 15 mg | 45 mg to 55 mg |
| 16A-n, 17A-n, 18A-n, 19A-n, and 20A-n | 190 mg to 210 mg | 290 mg to 310 mg | 2 mg to 6 mg | 45 mg to 55 mg |
| 16A-o, 17A-o, 18A-o, 19A-o, and 20A-o | 190 mg to 210 mg | 290 mg to 310 mg | 5 mg to 10 mg | 45 mg to 55 mg |
| 16A-p, 17A-p, 18A-p, 19A-p, and 20A-p | 190 mg to 210 mg | 290 mg to 310 mg | 10 mg to 15 mg | 45 mg to 55 mg |
| 16A-q, 17A-q, 18A-q, 19A-q, and 20A-q | 200 mg | 300 mg | 0.1 mg to 15 mg | 50 mg |
| 16A-r, 17A-r, 18A-r, 19A-r, and 20A-r | 200 mg | 300 mg | 2 mg to 6 mg | 50 mg |
| 16A-s, 17A-s, 18A-s, 19A-s, and 20A-s | 200 mg | 300 mg | 5 mg to 10 mg | 50 mg |
| 16A-t, 17A-t, 18A-t, 19A-t, and 20A-t | 200 mg | 300 mg | 10 mg to 15 mg | 50 mg |
| 16A-u, 17A-u, 18A-u, 19A-u, and 20A-u | 200 mg | 300 mg | 0.1 mg | 50 mg |
| 16A-v, 17A-v, 18A-v, 19A-v, and 20A-v | 200 mg | 300 mg | 0.2 mg | 50 mg |
| 16A-w, 17A-w, 18A-w, 19A-w, and 20A-w | 200 mg | 300 mg | 0.3 mg | 50 mg |
| 16A-x, 17A-x, 18A-x, 19A-x, and 20A-x | 200 mg | 300 mg | 0.4 mg | 50 mg |
| 16A-y, 17A-y, 18A-y, 19A-y, and 20A-y | 200 mg | 300 mg | 0.5 mg | 50 mg |
| 16A-z, 17A-z, 18A-z, 19A-z, and 20A-z | 200 mg | 300 mg | 0.6 mg | 50 mg |
| 16A-aa, 17A-aa, 18A-aa, 19A-aa, and 20A-aa | 200 mg | 300 mg | 0.7 mg | 50 mg |
| 16A-ab, 17A-ab, 18A-ab, 19A-ab, and 20A-ab | 200 mg | 300 mg | 0.8 mg | 50 mg |
| 16A-ac, 17A-ac, 18A-ac, 19A-ac, and 20A-ac | 200 mg | 300 mg | 0.9 mg | 50 mg |
| 16A-ad, 17A-ad, 18A-ad, 19A-ad, and 20A-ad | 200 mg | 300 mg | 1.0 mg | 50 mg |
| 16A-ae, 17A-ae, 18A-ae, 19A-ae, and 20A-ae | 200 mg | 300 mg | 1.1 mg | 50 mg |
| 16A-af, 17A-af, 18A-af, 19A-af, and 20A-af | 200 mg | 300 mg | 1.2 mg | 50 mg |
| 16A-ag, 17A-ag, 18A-ag, 19A-ag, and 20A-ag | 200 mg | 300 mg | 1.3 mg | 50 mg |
| 16A-ah, 17A-ah, 18A-ah, 19A-ah, and 20A-ah | 200 mg | 300 mg | 1.4 mg | 50 mg |
| 16A-ai, 17A-ai, 18A-ai, 19A-ai, and 20A-ai | 200 mg | 300 mg | 1.5 mg | 50 mg |
| 16A-aj, 17A-aj, 18A-aj, 19A-aj, and 20A-aj | 200 mg | 300 mg | 1.6 mg | 50 mg |
| 16A-ak, 17A-ak, 18A-ak, 19A-ak, and 20A-ak | 200 mg | 300 mg | 1.7 mg | 50 mg |
| 16A-al, 17A-al, 18A-al, 19A-al, and 20A-al | 200 mg | 300 mg | 1.8 mg | 50 mg |
| 16A-am, 17A-am, 18A-am, 19A-am, and 20A-am | 200 mg | 300 mg | 1.9 mg | 50 mg |
| 16A-an, 17A-an, 18A-an, 19A-an, and 20A-an | 200 mg | 300 mg | 2.0 mg | 50 mg |

-continued

| Comp. Ex. | emtricitabine | TDF | TLR7 MC | dolutegravir |
|---|---|---|---|---|
| 16A-ao, 17A-ao, 18A-ao, 19A-ao, and 20A-ao | 200 mg | 300 mg | 2.1 mg | 50 mg |
| 16A-ap, 17A-ap, 18A-ap, 19A-ap, and 20A-ap | 200 mg | 300 mg | 2.2 mg | 50 mg |
| 16A-aq, 17A-aq, 18A-aq, 19A-aq, and 20A-aq | 200 mg | 300 mg | 2.3 mg | 50 mg |
| 16A-ar, 17A-ar, 18A-ar, 19A-ar, and 20A-ar | 200 mg | 300 mg | 2.4 mg | 50 mg |
| 16A-as, 17A-as, 18A-as, 19A-as, and 20A-as | 200 mg | 300 mg | 2.5 mg | 50 mg |
| 16A-at, 17A-at, 18A-at, 19A-at, and 20A-at | 200 mg | 300 mg | 2.6 mg | 50 mg |
| 16A-au, 17A-au, 18A-au, 19A-au, and 20A-au | 200 mg | 300 mg | 2.7 mg | 50 mg |
| 16A-av, 17A-av, 18A-av, 19A-av, and 20A-av | 200 mg | 300 mg | 2.8 mg | 50 mg |
| 16A-aw, 17A-aw, 18A-aw, 19A-aw, and 20A-aw | 200 mg | 300 mg | 2.9 mg | 50 mg |
| 16A-ax, 17A-ax, 18A-ax, 19A-ax, and 20A-ax | 200 mg | 300 mg | 3.0 mg | 50 mg |
| 16A-ay, 17A-ay, 18A-ay, 19A-ay, and 20A-ay | 200 mg | 300 mg | 3.1 mg | 50 mg |
| 16A-az, 17A-az, 18A-az, 19A-az, and 20A-az | 200 mg | 300 mg | 3.2 mg | 50 mg |
| 16A-ba, 17A-ba, 18A-ba, 19A-ba, and 20A-ba | 200 mg | 300 mg | 3.3 mg | 50 mg |
| 16A-bb, 17A-bb, 18A-bb, 19A-bb, and 20A-bb | 200 mg | 300 mg | 3.4 mg | 50 mg |
| 16A-bc, 17A-bc, 18A-bc, 19A-bc, and 20A-bc | 200 mg | 300 mg | 3.5 mg | 50 mg |
| 16A-bd, 17A-bd, 18A-bd, 19A-bd, and 20A-bd | 200 mg | 300 mg | 3.6 mg | 50 mg |
| 16A-be, 17A-be, 18A-be, 19A-be, and 20A-be | 200 mg | 300 mg | 3.7 mg | 50 mg |
| 16A-bf, 17A-bf, 18A-bf, 19A-bf, and 20A-bf | 200 mg | 300 mg | 3.8 mg | 50 mg |
| 16A-bg, 17A-bg, 18A-bg, 19A-bg, and 20A-bg | 200 mg | 300 mg | 3.9 mg | 50 mg |
| 16A-bh, 17A-bh, 18A-bh, 19A-bh, and 20A-bh | 200 mg | 300 mg | 4.0 mg | 50 mg |
| 16A-bi, 17A-bi, 18A-bi, 19A-bi, and 20A-bi | 200 mg | 300 mg | 4.1 mg | 50 mg |
| 16A-bj, 17A-bj, 18A-bj, 19A-bj, and 20A-bj | 200 mg | 300 mg | 4.2 mg | 50 mg |
| 16A-bk, 17A-bk, 18A-bk, 19A-bk, and 20A-bk | 200 mg | 300 mg | 4.3 mg | 50 mg |
| 16A-bl, 17A-bl, 18A-bl, 19A-bl, and 20A-bl | 200 mg | 300 mg | 4.4 mg | 50 mg |
| 16A-bm, 17A-bm, 18A-bm, 19A-bm, and 20A-bm | 200 mg | 300 mg | 4.5 mg | 50 mg |
| 16A-bn, 17A-bn, 18A-bn, 19A-bn, and 20A-bn | 200 mg | 300 mg | 4.6 mg | 50 mg |
| 16A-bo, 17A-bo, 18A-bo, 19A-bo, and 20A-bo | 200 mg | 300 mg | 4.7 mg | 50 mg |
| 16A-bp, 17A-bp, 18A-bp, 19A-bp, and 20A-bp | 200 mg | 300 mg | 1.8 mg | 50 mg |
| 16A-bq, 17A-bq, 18A-bq, 19A-bq, and 20A-bq | 200 mg | 300 mg | 4.9 mg | 50 mg |
| 16A-br, 17A-br, 18A-br, 19A-br, and 20A-br | 200 mg | 300 mg | 5.0 mg | 50 mg |
| 16A-bs, 17A-bs, 18A-bs, 19A-bs, and 20A-bs | 200 mg | 300 mg | 5.1 mg | 50 mg |
| 16A-bt, 17A-bt, 18A-bt, 19A-bt, and 20A-bt | 200 mg | 300 mg | 52 mg | 50 mg |
| 16A-bu, 17A-bu, 18A-bu, 19A-bu, and 20A-bu | 200 mg | 300 mg | 5.3 mg | 50 mg |
| 16A-bv, 17A-bv, 18A-bv, 19A-bv, and 20A-bv | 200 mg | 300 mg | 5.4 mg | 50 mg |
| 16A-bw, 17A-bw, 18A-bw, 19A-bw, and 20A-bw | 200 mg | 300 mg | 5.5 mg | 50 mg |
| 16A-bx, 17A-bx, 18A-bx, 19A-bx, and 20A-bx | 200 mg | 300 mg | 5.6 mg | 50 mg |
| 16A-by, 17A-by, 18A-by, 19A-by, and 20A-by | 200 mg | 300 mg | 5.7 mg | 50 mg |
| 16A-bz, 17A-bz, 18A-bz, 19A-bz, and 20A-bz | 200 mg | 300 mg | 5.8 mg | 50 mg |

| Comp. Ex. | emtricitabine | TDF | TLR7 MC | dolutegravir |
|---|---|---|---|---|
| 16A-ca, 17A-ca, 18A-ca, 19A-ca, and 20A-ca | 200 mg | 300 mg | 5.9 mg | 50 mg |
| 16A-cb, 17A-cb, 18A-cb, 19A-cb, and 20A-cb | 200 mg | 300 mg | 5.0 mg | 50 mg |
| 16A-cc, 17A-cc, 18A-cc, 19A-cc, and 20A-cc | 200 mg | 300 mg | 6.1 mg | 50 mg |
| 16A-cd, 17A-cd, 18A-cd, 19A-cd, and 20A-cd | 200 mg | 300 mg | 6.2 mg | 50 mg |
| 16A-ce, 17A-ce, 18A-ce, 19A-ce, and 20A-ce | 200 mg | 300 mg | 6.3 mg | 50 mg |
| 16A-cf, 17A-cf, 18A-cf, 19A-cf, and 20A-cf | 200 mg | 300 mg | 6.4 mg | 50 mg |
| 16A-cg, 17A-cg, 18A-cg, 19A-cg, and 20A-cg | 200 mg | 300 mg | 6.5 mg | 50 mg |
| 16A-ch, 17A-ch, 18A-ch, 19A-ch, and 20A-ch | 200 mg | 300 mg | 6.6 mg | 50 mg |
| 16A-ci, 17A-ci, 18A-ci, 19A-ci, and 20A-ci | 200 mg | 300 mg | 6.7 mg | 50 mg |
| 16A-cj, 17A-cj, 18A-cj, 19A-cj, and 20A-cj | 200 mg | 300 mg | 6.8 mg | 50 mg |
| 16A-ck, 17A-ck, 18A-ck, 19A-ck, and 20A-ck | 200 mg | 300 mg | 6.9 mg | 50 mg |
| 16A-cl, 17A-cl, 18A-cl, 19A-cl, and 20A-cl | 200 mg | 300 mg | 7.0 mg | 50 mg |
| 16A-cm, 17A-cm, 18A-cm, 19A-cm, and 20A-cm | 200 mg | 300 mg | 7.1 mg | 50 mg |
| 16A-cn, 17A-cn, 18A-cn, 19A-cn, and 20A-cn | 200 mg | 300 mg | 7.2 mg | 50 mg |
| 16A-co, 17A-co, 18A-co, 19A-co, and 20A-co | 200 mg | 300 mg | 7.3 mg | 50 mg |
| 16A-cp, 17A-cp, 18A-cp, 19A-cp, and 20A-cp | 200 mg | 300 mg | 7.4 mg | 50 mg |
| 16A-cq, 17A-cq, 18A-cq, 19A-cq, and 20A-cq | 200 mg | 300 mg | 7.5 mg | 50 mg |
| 16A-cr, 17A-cr, 18A-cr, 19A-cr, and 20A-cr | 200 mg | 300 mg | 7.6 mg | 50 mg |
| 16A-cs, 17A-cs, 18A-cs, 19A-cs, and 20A-cs | 200 mg | 300 mg | 7.7 mg | 50 mg |
| 16A-ct, 17A-ct, 18A-ct, 19A-ct, and 20A-ct | 200 mg | 300 mg | 7.8 mg | 50 mg |
| 16A-cu, 17A-cu, 18A-cu, 19A-cu, and 20A-cu | 200 mg | 300 mg | 7.9 mg | 50 mg |
| 16A-cv, 17A-cv, 18A-cv, 19A-cv, and 20A-cv | 200 mg | 300 mg | 8.0 mg | 50 mg |
| 16A-cw, 17A-cw, 18A-cw, 19A-cw, and 20A-cw | 200 mg | 300 mg | 8.1 mg | 50 mg |
| 16A-cx, 17A-cx, 18A-cx, 19A-cx, and 20A-cx | 200 mg | 300 mg | 8.2 mg | 50 mg |
| 16A-cy, 17A-cy, 18A-cy, 19A-cy, and 20A-cy | 200 mg | 300 mg | 8.3 mg | 50 mg |
| 16A-cz, 17A-cz, 18A-cz, 19A-cz, and 20A-cz | 200 mg | 300 mg | 8.4 mg | 50 mg |
| 16A-da, 17A-da, 18A-da, 19A-da, and 20A-da | 200 mg | 300 mg | 8.5 mg | 50 mg |
| 16A-db, 17A-db, 18A-db, 19A-db, and 20A-db | 200 mg | 300 mg | 8.6 mg | 50 mg |
| 16A-dc, 17A-dc, 18A-dc, 19A-dc, and 20A-dc | 200 mg | 300 mg | 8.7 mg | 50 mg |
| 16A-dd, 17A-dd, 18A-dd, 19A-dd, and 20A-dd | 200 mg | 300 mg | 8.8 mg | 50 mg |
| 16A-de, 17A-de, 18A-de, 19A-de, and 20A-de | 200 mg | 300 mg | 8.9 mg | 50 mg |
| 16A-df, 17A-df, 18A-df, 19A-df, and 20A-df | 200 mg | 300 mg | 9.0 mg | 50 mg |
| 16A-dg, 17A-dg, 18A-dg, 19A-dg, and 20A-dg | 200 mg | 300 mg | 9.1 mg | 50 mg |
| 16A-dh, 17A-dh, 18A-dh, 19A-dh, and 20A-dh | 200 mg | 300 mg | 9.2 mg | 50 mg |
| 16A-di, 17A-di, 18A-di, 19A-di, and 20A-di | 200 mg | 300 mg | 9.3 mg | 50 mg |
| 16A-dj, 17A-dj, 18A-dj, 19A-dj, and 20A-dj | 200 mg | 300 mg | 9.4 mg | 50 mg |
| 16A-dk, 17A-dk, 18A-dk, 19A-dk, and 20A-dk | 200 mg | 300 mg | 9.5 mg | 50 mg |
| 16A-dl, 17A-dl, 18A-dl, 19A-dl, and 20A-dl | 200 mg | 300 mg | 9.6 mg | 50 mg |

| Comp. Ex. | emtricitabine | TDF | TLR7 MC | dolutegravir |
|---|---|---|---|---|
| 16A-dm, 17A-dm, 18A-dm, 19A-dm, and 20A-dm | 200 mg | 300 mg | 9.7 mg | 50 mg |
| 16A-dn, 17A-dn, 18A-dn, 19A-dn, and 20A-dn | 200 mg | 300 mg | 9.8 mg | 50 mg |
| 16A-do, 17A-do, 18A-do, 19A-do, and 20A-do | 200 mg | 300 mg | 9.9 mg | 50 mg |
| 16A-dp, 17A-dp, 18A-dp, 19A-dp, and 20A-dp | 200 mg | 300 mg | 10.0 mg | 50 mg |
| 16A-dq, 17A-dq, 18A-dq, 19A-dq, and 20A-dq | 200 mg | 300 mg | 10.1 mg | 50 mg |
| 16A-dr, 17A-dr, 18A-dr, 19A-dr, and 20A-dr | 200 mg | 300 mg | 10.2 mg | 50 mg |
| 16A-ds, 17A-ds, 18A-ds, 19A-ds, and 20A-ds | 200 mg | 300 mg | 10.3 mg | 50 mg |
| 16A-dt, 17A-dt, 18A-dt, 19A-dt, and 20A-dt | 200 mg | 300 mg | 10.4 mg | 50 mg |
| 16A-du, 17A-du, 18A-du, 19A-du, and 20A-du | 200 mg | 300 mg | 10.5 mg | 50 mg |
| 16A-dv, 17A-dv, 18A-dv, 19A-dv, and 20A-dv | 200 mg | 300 mg | 10.6 mg | 50 mg |
| 16A-dw, 17A-dw, 18A-dw, 19A-dw, and 20A-dw | 200 mg | 300 mg | 10.7 mg | 50 mg |
| 16A-dx, 17A-dx, 18A-dx, 19A-dx, and 20A-dx | 200 mg | 300 mg | 10.8 mg | 50 mg |
| 16A-dy, 17A-dy, 18A-dy, 19A-dy, and 20A-dy | 200 mg | 300 mg | 10.9 mg | 50 mg |
| 16A-dz, 17A-dz, 18A-dz, 19A-dz, and 20A-dz | 200 mg | 300 mg | 11.0 mg | 50 mg |
| 16A-ea, 17A-ea, 18A-ea, 19A-ea, and 20A-ea | 200 mg | 300 mg | 11.1 mg | 50 mg |
| 16A-eb, 17A-eb, 18A-eb, 19A-eb, and 20A-eb | 200 mg | 300 mg | 11.2 mg | 50 mg |
| 16A-ec, 17A-ec, 18A-ec, 19A-ec, and 20A-ec | 200 mg | 300 mg | 11.3 mg | 50 mg |
| 16A-ed, 17A-ed, 18A-ed, 19A-ed, and 20A-ed | 200 mg | 300 mg | 11.4 mg | 50 mg |
| 16A-ee, 17A-ee, 18A-ee, 19A-ee, and 20A-ee | 200 mg | 300 mg | 11.5 mg | 50 mg |
| 16A-ef, 17A-ef, 18A-ef, 19A-ef, and 20A-ef | 200 mg | 300 mg | 11.6 mg | 50 mg |
| 16A-eg, 17A-eg, 18A-eg, 19A-eg, and 20A-eg | 200 mg | 300 mg | 11.7 mg | 50 mg |
| 16A-eh, 17A-eh, 18A-eh, 19A-eh, and 20A-eh | 200 mg | 300 mg | 11.8 mg | 50 mg |
| 16A-ei, 17A-ei, 18A-ei, 19A-ei, and 20A-ei | 200 mg | 300 mg | 11.9 mg | 50 mg |
| 16A-ej, 17A-ej, 18A-ej, 19A-ej, and 20A-ej | 200 mg | 300 mg | 12.0 mg | 50 mg |
| 16A-ek, 17A-ek, 18A-ek, 19A-ek, and 20A-ek | 150 mg to 250 mg | 250 mg to 350 mg | 15 mg to 20 mg | 30 mg to 70 mg |
| 16A-el, 17A-el, 18A-el, 19A-el, and 20A-el | 150 mg to 250 mg | 250 mg to 350 mg | 20 mg to 25 mg | 30 mg to 70 mg |
| 16A-em, 17A-em, 18A-em, 19A-em, and 20A-em | 150 mg to 250 mg | 250 mg to 350 mg | 0.1 mg to 25 mg | 30 mg to 70 mg |
| 16A-en, 17A-en, 18A-en, 19A-en, and 20A-en | 50 mg to 250 mg | 50 mg to 350 mg | 0.1 mg to 25.0 mg | 25 mg to 70 mg |
| 16A-eo, 17A-eo, 18A-eo, 19A-eo, and 20A-eo | 50 mg to 200 mg | 50 mg to 300 mg | 0.1 mg to 20.0 mg | 25 mg to 50 mg |
| 16A-ep, 17A-ep, 18A-ep, 19A-ep, and 20A-ep | 50 mg to 175 mg | 50 mg to 250 mg | 0.1 mg to 15.0 mg | 25 mg to 40 mg |

Tables 16B, 17B, 18B, 19B, and 20B

Following the pattern of the tables above, the table below serves as Tables 16B, 17B, 18B, 19B, and 20B and provides combinations of agents that can be used in the uses, methods, regimens, and pharmaceutical compositions herein. Each of the listed combinations of agents includes amounts of emtricitabine, TAF, and dolutegravir, and differs only in the TLR7 Modulating Compound included. In the separate tables the TLR7 Modulating Compound, or a pharmaceutically acceptable salt thereof (collectively "TLR7 MC"), comprises a) a compound of Formula II in Table 16B, b) the compound of Example 4 in Table 17B, c) the compound of Example 49 in Table 18B, d) the compound of Example 119 in Table 19B, and e) the compound of Example 120 in Table 20B.

| Comp. Ex. | emtricitabine | TAF | TLR7 MC | dolutegravir |
|---|---|---|---|---|
| 16B-a, 17B-a, 18B-a, 19B-a, and 20B-a | 150 mg to 250 mg | 15 mg to 35 mg | 0.1 mg to 15 mg | 30 mg to 70 mg |
| 16B-b, 17B-b, 18B-b, 19B-b, and 20B-b | 150 mg to 250 mg | 15 mg to 35 mg | 2 mg to 6 mg | 30 mg to 70 mg |
| 16B-c, 17B-c, 18B-c, 19B-c, and 20B-c | 150 mg to 250 mg | 15 mg to 35 mg | 5 mg to 10 mg | 30 mg to 70 mg |
| 16B-d, 17B-d, 18B-d, 19B-d, and 20B-d | 150 mg to 250 mg | 15 mg to 35 mg | 10 mg to 15 mg | 30 mg to 70 mg |
| 16B-e, 17B-e, 18B-e, 19B-e, and 20B-e | 150 mg to 250 mg | 15 mg to 35 mg | 0.1 mg to 15 mg | 40 mg to 60 mg |
| 16B-f, 17B-f, 18B-f, 19B-f, and 20B-f | 150 mg to 250 mg | 15 mg to 35 mg | 2 mg to 6 mg | 40 mg to 60 mg |
| 16B-g, 17B-g, 18B-g, 19B-g, and 20B-g | 150 mg to 250 mg | 15 mg to 35 mg | 5 mg to 10 mg | 40 mg to 60 mg |
| 16B-h, 17B-h, 18B-h, 19B-h, and 20B-h | 150 mg to 250 mg | 15 mg to 35 mg | 10 mg to 15 mg | 40 mg to 60 mg |
| 16B-i, 17B-i, 18B-i, 19B-i, and 20B-i | 175 mg to 225 mg | 20 mg to 30 mg | 0.1 mg to 15 mg | 40 mg to 60 mg |
| 16B-j, 17B-j, 18B-j, 19B-j, and 20B-j | 175 mg to 225 mg | 20 mg to 30 mg | 2 mg to 6 mg | 40 mg to 60 mg |
| 16B-k, 17B-k, 18B-k, 19B-k, and 20B-k | 175 mg to 225 mg | 20 mg to 30 mg | 5 mg to 10 mg | 40 mg to 60 mg |
| 16B-l, 17B-l, 18B-l, 19B-l, and 20B-l | 175 mg to 225 mg | 20 mg to 30 mg | 10 mg to 15 mg | 40 mg to 60 mg |
| 16B-m, 17B-m, 18B-m, 19B-m, and 20B-m | 190 mg to 210 mg | 22.5 mg to 27.5 mg | 0.1 mg to 15 mg | 45 mg to 55 mg |
| 16B-n, 17B-n, 18B-n, 19B-n, and 20B-n | 190 mg to 210 mg | 22.5 mg to 27.5 mg | 2 mg to 6 mg | 45 mg to 55 mg |
| 16B-o, 17B-o, 18B-o, 19B-o, and 20B-o | 190 mg to 210 mg | 22.5 mg to 27.5 mg | 5 mg to 10 mg | 45 mg to 55 mg |
| 16B-p, 17B-p, 18B-p, 19B-p, and 20B-p | 190 mg to 210 mg | 22.5 mg to 27.5 mg | 10 mg to 15 mg | 45 mg to 55 mg |
| 16B-q, 17B-q, 18B-q, 19B-q, and 20B-q | 200 mg | 25 mg | 0.1 mg to 15 mg | 50 mg |
| 16B-r, 17B-r, 18B-r, 19B-r, and 20B-r | 200 mg | 25 mg | 2 mg to 6 mg | 50 mg |
| 16B-s, 17B-s, 18B-s, 19B-s, and 20B-s | 200 mg | 25 mg | 5 mg to 10 mg | 50 mg |
| 16B-t, 17B-t, 18B-t, 19B-t, and 20B-t | 200 mg | 25 mg | 10 mg to 15 mg | 50 mg |
| 16B-u, 17B-u, 18B-u, 19B-u, and 20B-u | 200 mg | 25 mg | 0.1 mg | 50 mg |
| 16B-v, 17B-v, 18B-v, 19B-v, and 20B-v | 200 mg | 25 mg | 0.2 mg | 50 mg |
| 16B-w, 17B-w, 18B-w, 19B-w, and 20B-w | 200 mg | 25 mg | 0.3 mg | 50 mg |
| 16B-x, 17B-x, 18B-x, 19B-x, and 20B-x | 200 mg | 25 mg | 0.4 mg | 50 mg |
| 16B-y, 17B-y, 18B-y, 19B-y, and 20B-y | 200 mg | 25 mg | 0.5 mg | 50 mg |
| 16B-z, 17B-z, 18B-z, 19B-z, and 20B-z | 200 mg | 25 mg | 0.6 mg | 50 mg |
| 16B-aa, 17B-aa, 18B-aa, 19B-aa, and 20B-aa | 200 mg | 25 mg | 0.7 mg | 50 mg |
| 16B-ab, 17B-ab, 18B-ab, 19B-ab, and 20B-ab | 200 mg | 25 mg | 0.8 mg | 50 mg |
| 16B-ac, 17B-ac, 18B-ac, 19B-ac, and 20B-ac | 200 mg | 25 mg | 0.9 mg | 50 mg |
| 16B-ad, 17B-ad, 18B-ad, 19B-ad, and 20B-ad | 200 mg | 25 mg | 1.0 mg | 50 mg |
| 16B-ae, 17B-ae, 18B-ae, 19B-ae, and 20B-ae | 200 mg | 25 mg | 1.1 mg | 50 mg |
| 16B-af, 17B-af, 18B-af, 19B-af, and 20B-af | 200 mg | 25 mg | 1.2 mg | 50 mg |
| 16B-ag, 17B-ag, 18B-ag, 19B-ag, and 20B-ag | 200 mg | 25 mg | 1.3 mg | 50 mg |
| 16B-ah, 17B-ah, 18B-ah, 19B-ah, and 20B-ah | 200 mg | 25 mg | 1.4 mg | 50 mg |
| 16B-ai, 17B-ai, 18B-ai, 19B-ai, and 20B-ai | 200 mg | 25 mg | 1.5 mg | 50 mg |
| 16B-aj, 17B-aj, 18B-aj, 19B-aj, and 20B-aj | 200 mg | 25 mg | 1.6 mg | 50 mg |
| 16B-ak, 17B-ak, 18B-ak, 19B-ak, and 20B-ak | 200 mg | 25 mg | 1.7 mg | 50 mg |
| 16B-al, 17B-al, 18B-al, 19B-al, and 20B-al | 200 mg | 25 mg | 1.8 mg | 50 mg |
| 16B-am, 17B-am, 18B-am, 19B-am, and 20B-am | 200 mg | 25 mg | 1.9 mg | 50 mg |

-continued

| Comp. Ex. | emtricitabine | TAF | TLR7 MC | dolutegravir |
|---|---|---|---|---|
| 16B-an, 17B-an, 18B-an, 19B-an, and 20B-an | 200 mg | 25 mg | 2.0 mg | 50 mg |
| 16B-ao, 17B-ao, 18B-ao, 19B-ao, and 20B-ao | 200 mg | 25 mg | 2.1 mg | 50 mg |
| 16B-ap, 17B-ap, 18B-ap, 19B-ap, and 20B-ap | 200 mg | 25 mg | 2.2 mg | 50 mg |
| 16B-aq, 17B-aq, 18B-aq, 19B-aq, and 20B-aq | 200 mg | 25 mg | 2.3 mg | 50 mg |
| 16B-ar, 17B-ar, 18B-ar, 19B-ar, and 20B-ar | 200 mg | 25 mg | 2.4 mg | 50 mg |
| 16B-as, 17B-as, 18B-as, 19B-as, and 20B-as | 200 mg | 25 mg | 2.5 mg | 50 mg |
| 16B-at, 17B-at, 18B-at, 19B-at, and 20B-at | 200 mg | 25 mg | 2.6 mg | 50 mg |
| 16B-au, 17B-au, 18B-au, 19B-au, and 20B-au | 200 mg | 25 mg | 2.7 mg | 50 mg |
| 16B-av, 17B-av, 18B-av, 19B-av, and 20B-av | 200 mg | 25 mg | 2.8 mg | 50 mg |
| 16B-aw, 17B-aw, 18B-aw, 19B-aw, and 20B-aw | 200 mg | 25 mg | 2.9 mg | 50 mg |
| 16B-ax, 17B-ax, 18B-ax, 19B-ax, and 20B-ax | 200 mg | 25 mg | 3.0 mg | 50 mg |
| 16B-ay, 17B-ay, 18B-ay, 19B-ay, and 20B-ay | 200 mg | 25 mg | 3.1 mg | 50 mg |
| 16B-az, 17B-az, 18B-az, 19B-az, and 20B-az | 200 mg | 25 mg | 3.2 mg | 50 mg |
| 16B-ba, 17B-ba, 18B-ba, 19B-ba, and 20B-ba | 200 mg | 25 mg | 3.3 mg | 50 mg |
| 16B-bb, 17B-bb, 18B-bb, 19B-bb, and 20B-bb | 200 mg | 25 mg | 3.4 mg | 50 mg |
| 16B-bc, 17B-bc, 18B-bc, 19B-bc, and 20B-bc | 200 mg | 25 mg | 3.5 mg | 50 mg |
| 16B-bd, 17B-bd, 18B-bd, 19B-bd, and 20B-bd | 200 mg | 25 mg | 3.6 mg | 50 mg |
| 16B-be, 17B-be, 18B-be, 19B-be, and 20B-be | 200 mg | 25 mg | 3.7 mg | 50 mg |
| 16B-bf, 17B-bf, 18B-bf, 19B-bf, and 20B-bf | 200 mg | 25 mg | 3.8 mg | 50 mg |
| 16B-bg, 17B-bg, 18B-bg, 19B-bg, and 20B-bg | 200 mg | 25 mg | 3.9 mg | 50 mg |
| 16B-bh, 17B-bh, 18B-bh, 19B-bh, and 20B-bh | 200 mg | 25 mg | 4.0 mg | 50 mg |
| 16B-bi, 17B-bi, 18B-bi, 19B-bi, and 20B-bi | 200 mg | 25 mg | 4.1 mg | 50 mg |
| 16B-bj, 17B-bj, 18B-bj, 19B-bj, and 20B-bj | 200 mg | 25 mg | 4.2 mg | 50 mg |
| 16B-bk, 17B-bk, 18B-bk, 19B-bk, and 20B-bk | 200 mg | 25 mg | 4.3 mg | 50 mg |
| 16B-bl, 17B-bl, 18B-bl, 19B-bl, and 20B-bl | 200 mg | 25 mg | 4.4 mg | 50 mg |
| 16B-bm, 17B-bm, 18B-bm, 19B-bm, and 20B-bm | 200 mg | 25 mg | 4.5 mg | 50 mg |
| 16B-bn, 17B-bn, 18B-bn, 19B-bn, and 20B-bn | 200 mg | 25 mg | 4.6 mg | 50 mg |
| 16B-bo, 17B-bo, 18B-bo, 19B-bo, and 20B-bo | 200 mg | 25 mg | 4.7 mg | 50 mg |
| 16B-bp, 17B-bp, 18B-bp, 19B-bp, and 20B-bp | 200 mg | 25 mg | 1.8 mg | 50 mg |
| 16B-bq, 17B-bq, 18B-bq, 19B-bq, and 20B-bq | 200 mg | 25 mg | 4.9 mg | 50 mg |
| 16B-br, 17B-br, 18B-br, 19B-br, and 20B-br | 200 mg | 25 mg | 5.0 mg | 50 mg |
| 16B-bs, 17B-bs, 18B-bs, 19B-bs, and 20B-bs | 200 mg | 25 mg | 5.1 mg | 50 mg |
| 16B-bt, 17B-bt, 18B-bt, 19B-bt, and 20B-bt | 200 mg | 25 mg | 52 mg | 50 mg |
| 16B-bu, 17B-bu, 18B-bu, 19B-bu, and 20B-bu | 200 mg | 25 mg | 5.3 mg | 50 mg |
| 16B-bv, 17B-bv, 18B-bv, 19B-bv, and 20B-bv | 200 mg | 25 mg | 5.4 mg | 50 mg |
| 16B-bw, 17B-bw, 18B-bw, 19B-bw, and 20B-bw | 200 mg | 25 mg | 5.5 mg | 50 mg |
| 16B-bx, 17B-bx, 18B-bx, 19B-bx, and 20B-bx | 200 mg | 25 mg | 5.6 mg | 50 mg |
| 16B-by, 17B-by, 18B-by, 19B-by, and 20B-by | 200 mg | 25 mg | 5.7 mg | 50 mg |

-continued

| Comp. Ex. | emtricitabine | TAF | TLR7 MC | dolutegravir |
|---|---|---|---|---|
| 16B-bz, 17B-bz, 18B-bz, 19B-bz, and 20B-bz | 200 mg | 25 mg | 5.8 mg | 50 mg |
| 16B-ca, 17B-ca, 18B-ca, 19B-ca, and 20B-ca | 200 mg | 25 mg | 5.9 mg | 50 mg |
| 16B-cb, 17B-cb, 18B-cb, 19B-cb, and 20B-cb | 200 mg | 25 mg | 5.0 mg | 50 mg |
| 16B-cc, 17B-cc, 18B-cc, 19B-cc, and 20B-cc | 200 mg | 25 mg | 6.1 mg | 50 mg |
| 16B-cd, 17B-cd, 18B-cd, 19B-cd, and 20B-cd | 200 mg | 25 mg | 6.2 mg | 50 mg |
| 16B-ce, 17B-ce, 18B-ce, 19B-ce, and 20B-ce | 200 mg | 25 mg | 6.3 mg | 50 mg |
| 16B-cf, 17B-cf, 18B-cf, 19B-cf, and 20B-cf | 200 mg | 25 mg | 6.4 mg | 50 mg |
| 16B-cg, 17B-cg, 18B-cg, 19B-cg, and 20B-cg | 200 mg | 25 mg | 6.5 mg | 50 mg |
| 16B-ch, 17B-ch, 18B-ch, 19B-ch, and 20B-ch | 200 mg | 25 mg | 6.6 mg | 50 mg |
| 16B-ci, 17B-ci, 18B-ci, 19B-ci, and 20B-ci | 200 mg | 25 mg | 6.7 mg | 50 mg |
| 16B-cj, 17B-cj, 18B-cj, 19B-cj, and 20B-cj | 200 mg | 25 mg | 6.8 mg | 50 mg |
| 16B-ck, 17B-ck, 18B-ck, 19B-ck, and 20B-ck | 200 mg | 25 mg | 6.9 mg | 50 mg |
| 16B-cl, 17B-cl, 18B-cl, 19B-cl, and 20B-cl | 200 mg | 25 mg | 7.0 mg | 50 mg |
| 16B-cm, 17B-cm, 18B-cm, 19B-cm, and 20B-cm | 200 mg | 25 mg | 7.1 mg | 50 mg |
| 16B-cn, 17B-cn, 18B-cn, 19B-cn, and 20B-cn | 200 mg | 25 mg | 7.2 mg | 50 mg |
| 16B-co, 17B-co, 18B-co, 19B-co, and 20B-co | 200 mg | 25 mg | 7.3 mg | 50 mg |
| 16B-cp, 17B-cp, 18B-cp, 19B-cp, and 20B-cp | 200 mg | 25 mg | 7.4 mg | 50 mg |
| 16B-cq, 17B-cq, 18B-cq, 19B-cq, and 20B-cq | 200 mg | 25 mg | 7.5 mg | 50 mg |
| 16B-cr, 17B-cr, 18B-cr, 19B-cr, and 20B-cr | 200 mg | 25 mg | 7.6 mg | 50 mg |
| 16B-cs, 17B-cs, 18B-cs, 19B-cs, and 20B-cs | 200 mg | 25 mg | 7.7 mg | 50 mg |
| 16B-ct, 17B-ct, 18B-ct, 19B-ct, and 20B-ct | 200 mg | 25 mg | 7.8 mg | 50 mg |
| 16B-cu, 17B-cu, 18B-cu, 19B-cu, and 20B-cu | 200 mg | 25 mg | 7.9 mg | 50 mg |
| 16B-cv, 17B-cv, 18B-cv, 19B-cv, and 20B-cv | 200 mg | 25 mg | 8.0 mg | 50 mg |
| 16B-cw, 17B-cw, 18B-cw, 19B-cw, and 20B-cw | 200 mg | 25 mg | 8.1 mg | 50 mg |
| 16B-cx, 17B-cx, 18B-cx, 19B-cx, and 20B-cx | 200 mg | 25 mg | 8.2 mg | 50 mg |
| 16B-cy, 17B-cy, 18B-cy, 19B-cy, and 20B-cy | 200 mg | 25 mg | 8.3 mg | 50 mg |
| 16B-cz, 17B-cz, 18B-cz, 19B-cz, and 20B-cz | 200 mg | 25 mg | 8.4 mg | 50 mg |
| 16B-da, 17B-da, 18B-da, 19B-da, and 20B-da | 200 mg | 25 mg | 8.5 mg | 50 mg |
| 16B-db, 17B-db, 18B-db, 19B-db, and 20B-db | 200 mg | 25 mg | 8.6 mg | 50 mg |
| 16B-dc, 17B-dc, 18B-dc, 19B-dc, and 20B-dc | 200 mg | 25 mg | 8.7 mg | 50 mg |
| 16B-dd, 17B-dd, 18B-dd, 19B-dd, and 20B-dd | 200 mg | 25 mg | 8.8 mg | 50 mg |
| 16B-de, 17B-de, 18B-de, 19B-de, and 20B-de | 200 mg | 25 mg | 8.9 mg | 50 mg |
| 16B-df, 17B-df, 18B-df, 19B-df, and 20B-df | 200 mg | 25 mg | 9.0 mg | 50 mg |
| 16B-dg, 17B-dg, 18B-dg, 19B-dg, and 20B-dg | 200 mg | 25 mg | 9.1 mg | 50 mg |
| 16B-dh, 17B-dh, 18B-dh, 19B-dh, and 20B-dh | 200 mg | 25 mg | 9.2 mg | 50 mg |
| 16B-di, 17B-di, 18B-di, 19B-di, and 20B-di | 200 mg | 25 mg | 9.3 mg | 50 mg |
| 16B-dj, 17B-dj, 18B-dj, 19B-dj, and 20B-dj | 200 mg | 25 mg | 9.4 mg | 50 mg |
| 16B-dk, 17B-dk, 18B-dk, 19B-dk, and 20B-dk | 200 mg | 25 mg | 9.5 mg | 50 mg |

-continued

| Comp. Ex. | emtricitabine | TAF | TLR7 MC | dolutegravir |
|---|---|---|---|---|
| 16B-dl, 17B-dl, 18B-dl, 19B-dl, and 20B-dl | 200 mg | 25 mg | 9.6 mg | 50 mg |
| 16B-dm, 17B-dm, 18B-dm, 19B-dm, and 20B-dm | 200 mg | 25 mg | 9.7 mg | 50 mg |
| 16B-dn, 17B-dn, 18B-dn, 19B-dn, and 20B-dn | 200 mg | 25 mg | 9.8 mg | 50 mg |
| 16B-do, 17B-do, 18B-do, 19B-do, and 20B-do | 200 mg | 25 mg | 9.9 mg | 50 mg |
| 16B-dp, 17B-dp, 18B-dp, 19B-dp, and 20B-dp | 200 mg | 25 mg | 10.0 mg | 50 mg |
| 16B-dq, 17B-dq, 18B-dq, 19B-dq, and 20B-dq | 200 mg | 25 mg | 10.1 mg | 50 mg |
| 16B-dr, 17B-dr, 18B-dr, 19B-dr, and 20B-dr | 200 mg | 25 mg | 10.2 mg | 50 mg |
| 16B-ds, 17B-ds, 18B-ds, 19B-ds, and 20B-ds | 200 mg | 25 mg | 10.3 mg | 50 mg |
| 16B-dt, 17B-dt, 18B-dt, 19B-dt, and 20B-dt | 200 mg | 25 mg | 10.4 mg | 50 mg |
| 16B-du, 17B-du, 18B-du, 19B-du, and 20B-du | 200 mg | 25 mg | 10.5 mg | 50 mg |
| 16B-dv, 17B-dv, 18B-dv, 19B-dv, and 20B-dv | 200 mg | 25 mg | 10.6 mg | 50 mg |
| 16B-dw, 17B-dw, 18B-dw, 19B-dw, and 20B-dw | 200 mg | 25 mg | 10.7 mg | 50 mg |
| 16B-dx, 17B-dx, 18B-dx, 19B-dx, and 20B-dx | 200 mg | 25 mg | 10.8 mg | 50 mg |
| 16B-dy, 17B-dy, 18B-dy, 19B-dy, and 20B-dy | 200 mg | 25 mg | 10.9 mg | 50 mg |
| 16B-dz, 17B-dz, 18B-dz, 19B-dz, and 20B-dz | 200 mg | 25 mg | 11.0 mg | 50 mg |
| 16B-ea, 17B-ea, 18B-ea, 19B-ea, and 20B-ea | 200 mg | 25 mg | 11.1 mg | 50 mg |
| 16B-eb, 17B-eb, 18B-eb, 19B-eb, and 20B-eb | 200 mg | 25 mg | 11.2 mg | 50 mg |
| 16B-ec, 17B-ec, 18B-ec, 19B-ec, and 20B-ec | 200 mg | 25 mg | 11.3 mg | 50 mg |
| 16B-ed, 17B-ed, 18B-ed, 19B-ed, and 20B-ed | 200 mg | 25 mg | 11.4 mg | 50 mg |
| 16B-ee, 17B-ee, 18B-ee, 19B-ee, and 20B-ee | 200 mg | 25 mg | 11.5 mg | 50 mg |
| 16B-ef, 17B-ef, 18B-ef, 19B-ef, and 20B-ef | 200 mg | 25 mg | 11.6 mg | 50 mg |
| 16B-eg, 17B-eg, 18B-eg, 19B-eg, and 20B-eg | 200 mg | 25 mg | 11.7 mg | 50 mg |
| 16B-eh, 17B-eh, 18B-eh, 19B-eh, and 20B-eh | 200 mg | 25 mg | 11.8 mg | 50 mg |
| 16B-ei, 17B-ei, 18B-ei, 19B-ei, and 20B-ei | 200 mg | 25 mg | 11.9 mg | 50 mg |
| 16B-ej, 17B-ej, 18B-ej, 19B-ej, and 20B-ej | 200 mg | 25 mg | 12.0 mg | 50 mg |
| 16B-ek, 17B-ek, 18B-ek, 19B-ek, and 20B-ek | 150 mg to 250 mg | 15 mg to 35 mg | 0.1 mg to 25 mg | 30 mg to 70 mg |
| 16B-el, 17B-el, 18B-el, 19B-el, and 20B-el | 150 mg to 250 mg | 15 mg to 35 mg | 15 mg to 20 mg | 30 mg to 70 mg |
| 16B-em, 17B-em, 18B-em, 19B-em, and 20B-em | 150 mg to 250 mg | 15 mg to 35 mg | 20 mg to 25 mg | 30 mg to 70 mg |
| 16B-en, 17B-en, 18B-en, 19B-en, and 20B-en | 50 mg to 250 mg | 1 mg to 15 mg | 0.1 mg to 25.0 mg | 25 mg to 70 mg |
| 16B-eo, 17B-eo, 18B-eo, 19B-eo, and 20B-eo | 50 mg to 200 mg | 1 mg to 10 mg | 0.1 mg to 20.0 mg | 25 mg to 50 mg |
| 16B-ep, 17B-ep, 18B-ep, 19B-ep, and 20B-ep | 50 mg to 175 mg | 1 mg to 8 mg | 0.1 mg to 15.0 mg | 25 mg to 40 mg |

Also provided is a pharmaceutical kit, the kit comprising:
1) a series of daily doses of a single pharmaceutical composition comprising:
 a) a pharmaceutically effective amount of emtricitabine;
 b) a pharmaceutically effective amount of tenofovir disoproxil fumarate;
 c) a pharmaceutically effective amount of a TLR7 modulating compound, or a pharmaceutically acceptable salt thereof;
 d) a pharmaceutically effective amount of dolutegravir; and
 e) a pharmaceutically acceptable carrier or excipient; and
2) directions for the administration of the daily doses of the pharmaceutical composition.

Also provided is a pharmaceutical kit, the kit comprising:
3) a series of daily doses of a single pharmaceutical composition comprising:
 f) a pharmaceutically effective amount of emtricitabine;

g) a pharmaceutically effective amount of tenofovir disoproxil fumarate;
h) a pharmaceutically effective amount of a TLR7 modulating compound, or a pharmaceutically acceptable salt thereof;
i) a pharmaceutically effective amount of dolutegravir; and
j) a pharmaceutically acceptable carrier or excipient; and
4) directions for the administration of the daily doses of the pharmaceutical composition.

Also provided are separate pharmaceutical kits, as just described, wherein the pharmaceutical composition comprises, in each of the separate pharmaceutical kits, one of the pharmaceutical compositions described above having dolutegravir as a component or element.

Further provided is a pharmaceutical kit, the kit comprising:
1) a series of doses of a first pharmaceutical composition comprising:
   a) a pharmaceutically effective amount of emtricitabine;
   b) a pharmaceutically effective amount of tenofovir disoproxil fumarate;
   c) a pharmaceutically effective amount of a TLR7 modulating compound, or a pharmaceutically acceptable salt thereof;
2) a pharmaceutically acceptable carrier or excipient; and
3) a series of doses of a second pharmaceutical composition comprising a pharmaceutically effective amount of dolutegravir and a pharmaceutically acceptable carrier or excipient; and
4) directions for the administration of the doses of the first and second pharmaceutical composition; wherein the first and second pharmaceutical compositions are both administered once daily.

Further provided is a pharmaceutical kit, the kit comprising:
a series of daily doses of a first pharmaceutical composition comprising:
   a) a pharmaceutically effective amount of emtricitabine;
   b) a pharmaceutically effective amount of tenofovir disoproxil fumarate;
   c) a pharmaceutically effective amount of a TLR7 modulating compound, or a pharmaceutically acceptable salt thereof;
   d) a pharmaceutically acceptable carrier or excipient; and
a series of daily doses of a second pharmaceutical composition comprising a pharmaceutically effective amount of dolutegravir and a pharmaceutically acceptable carrier or excipient; and
directions for the administration of the daily doses of the first and second pharmaceutical composition; wherein the first and second pharmaceutical compositions are both administered twice daily.

Further provided is a pharmaceutical kit, the kit comprising:
a series of doses of a first pharmaceutical composition comprising:
   a) a pharmaceutically effective amount of emtricitabine;
   b) a pharmaceutically effective amount of tenofovir disoproxil fumarate;
   c) a pharmaceutically effective amount of a TLR7 modulating compound, or a pharmaceutically acceptable salt thereof;
   d) a pharmaceutically acceptable carrier or excipient; and
a series of doses of a second pharmaceutical composition comprising a pharmaceutically effective amount of dolutegravir and a pharmaceutically acceptable carrier or excipient; and
directions for the administration of the doses of the first and second pharmaceutical composition; wherein the first pharmaceutical composition is administered once daily and second pharmaceutical composition is administered twice daily.

Further provided is a pharmaceutical kit, the kit comprising:
1) a series of doses of a first pharmaceutical composition comprising:
   a) a pharmaceutically effective amount of emtricitabine;
   b) a pharmaceutically effective amount of tenofovir disoproxil fumarate;
   c) a pharmaceutically acceptable carrier or excipient; and
2) a series of doses of a second pharmaceutical composition comprising a pharmaceutically effective amount of dolutegravir and a pharmaceutically acceptable carrier or excipient; and
3) a series of doses of a third pharmaceutical composition comprising a pharmaceutically effective amount of a TLR7 modulating compound, or a pharmaceutically acceptable salt thereof; and
4) directions for the administration of the doses of the first and second pharmaceutical composition; wherein each of the first pharmaceutical composition, the second pharmaceutical composition, and the third pharmaceutical composition is administered once daily.

Within the embodiment of the pharmaceutical kit immediately above, there is a further embodiment comprising the kit, as described, wherein the second pharmaceutical composition comprises from 30 mg to 70 mg of dolutegravir. Within the embodiment of the pharmaceutical kit immediately above, there is a further embodiment comprising the kit, as described, wherein the second pharmaceutical composition comprises from 40 mg to 60 mg of dolutegravir. Within the embodiment of the pharmaceutical kit immediately above, there is a another embodiment comprising the kit, as described, wherein the second pharmaceutical composition comprises from 45 mg to 55 mg of dolutegravir. Within the embodiment of the pharmaceutical kit immediately above, there is a another embodiment comprising the kit, as described, wherein the second pharmaceutical composition comprises 50 mg of dolutegravir.

Further provided is a pharmaceutical kit, the kit comprising:
a series of doses of a first pharmaceutical composition comprising:
   1) a pharmaceutically effective amount of emtricitabine;
   2) a pharmaceutically effective amount of tenofovir disoproxil fumarate;
   3) a pharmaceutically acceptable carrier or excipient; and
a series of doses of a second pharmaceutical composition comprising a pharmaceutically effective amount of dolutegravir and a pharmaceutically acceptable carrier or excipient; and
a series of doses of a third pharmaceutical composition comprising a pharmaceutically effective amount of a TLR7 modulating compound, or a pharmaceutically acceptable salt thereof; and
directions for the administration of the doses of the first and second pharmaceutical composition; wherein the first pharmaceutical composition and third pharmaceutical composition are each administered once daily and the second pharmaceutical composition is administered twice daily.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 30 mg to 70 mg of dolutegravir, and the third pharmaceutical composition comprises from 0.1 to 15 mg of a TLR7 modulating compound, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 40 mg to 60 mg of dolutegravir, and the third pharmaceutical composition comprises from 0.1 to 15 mg of a TLR7 modulating compound, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises from 45 mg to 55 mg of dolutegravir and the third pharmaceutical composition comprises from 0.1 to 15 mg of a TLR7 modulating compound, or a pharmaceutically acceptable salt thereof.

Within the embodiment of the pharmaceutical kit above, there is a further embodiment comprising the kit, as described, wherein the first pharmaceutical composition comprises 200 mg of emtricitabine and 300 mg of tenofovir disoproxil fumarate, the second pharmaceutical composition comprises 50 mg of dolutegravir, and the third pharmaceutical composition comprises from 0.1 to 15 mg of a TLR7 modulating compound, or a pharmaceutically acceptable salt thereof.

It is understood that each description of the kits provided for herein containing a TLR7 modulating compound includes separate individual kits wherein the TLR7 modulating compound is of each Formula and compound example disclosed herein.

For instance, within each of the embodiments above wherein the kit comprises a first, second, and third pharmaceutical composition, there are five additional embodiments wherein all other components or elements are as described above and:

a) in the first additional embodiment, the third pharmaceutical composition comprises from 0.1 to 15 mg of t compound of Example 4, or a pharmaceutically acceptable salt thereof;

b) in the second additional embodiment, the third pharmaceutical composition comprises from 0.1 to 15 mg of the compound of Example 49, or a pharmaceutically acceptable salt thereof;

c) in the third additional embodiment, the third pharmaceutical composition comprises from 0.1 to 15 mg of the compound of Example 119, or a pharmaceutically acceptable salt thereof;

d) in the fourth additional embodiment, the third pharmaceutical composition comprises from 0.1 to 15 mg of the compound of Example 120, or a pharmaceutically acceptable salt thereof; and e) in the fifth additional embodiment, the third pharmaceutical composition comprises from 0.1 to 15 mg of the compound of Example 121, or a pharmaceutically acceptable salt thereof.

Compositions Comprising TDF and a TLR7 Modulator

Pharmaceutically effective amounts of the TLR7 modulating compounds of Formula II, or a pharmaceutically acceptable salt thereof, as well as the compounds of Examples 119, 120, and 121, or a pharmaceutically acceptable salt thereof, can be combined with a pharmaceutically effective amount of tenofovir disoproxil fumarate (TDF) for use in the methods of treatment discussed herein. For instance, as separate dosage forms, a pharmaceutically effective dose of the TLR7 modulating compounds may be combined in a treatment regimen with a Viread® TDF tablet, which are available from Gilead Sciences, Inc. in 150 mg, 200 mg, 250 mg, and 300 mg strengths.

Provided is a pharmaceutical composition comprising:

a) a pharmaceutically effective amount of tenofovir disoproxil fumarate;

b) a pharmaceutically effective amount of a TLR7 modulating compound, or a pharmaceutically acceptable salt thereof; and c) a pharmaceutically acceptable carrier or excipient.

Provided is a pharmaceutical composition comprising:

d) a pharmaceutically effective amount of tenofovir disoproxil fumarate;

e) a pharmaceutically effective amount of a compound of Formula II, or a pharmaceutically acceptable salt thereof; and f) a pharmaceutically acceptable carrier or excipient.

Provided is a pharmaceutical composition comprising:

g) a pharmaceutically effective amount of TAF;

h) a pharmaceutically effective amount of a TLR7 modulating compound, or a pharmaceutically acceptable salt thereof; and i) a pharmaceutically acceptable carrier or excipient.

Provided is a pharmaceutical composition comprising:

j) a pharmaceutically effective amount of TAF;

k) a pharmaceutically effective amount of a compound of Formula II, or a pharmaceutically acceptable salt thereof; and l) a pharmaceutically acceptable carrier or excipient.

Specific pharmaceutical compositions and combinations comprising a pharmaceutically acceptable carrier or excipient and the individual amounts of TDF or TAF, and b) a pharmaceutically effective amount of a TLR7 Modulating Compound or a pharmaceutically acceptable salt thereof (collectively referred to as "TLR7 MC"). Following the pattern of the tables above, the table below serves as Tables 21A, 22A, 23A, 24A, and 25A and provides combinations of agents that can be used in the uses, methods, regimens, and pharmaceutical compositions herein. Each of the listed combinations of agents includes amounts of TDF and differs only in the TLR7 Modulating Compound included. In the separate tables the TLR7 Modulating Compound, or a pharmaceutically acceptable salt thereof, comprises a) a compound of Formula II in Table 21A, b) the compound of Example 4 in Table 22A, c) the compound of Example 49 in Table 23A, d) the compound of Example 119 in Table 24A, and e) the compound of Example 120 in Table 25A.

Tables 21A, 22A, 23A, 24A, and 25A

| Composition Example No. | TDF | TLR7 MC |
|---|---|---|
| 21A-a, 22A-a, 23A-a, 24A-a, and 25A-a | 25 mg to 350 mg | 0.1 mg to 15 mg |
| 21A-b, 22A-b, 23A-b, 24A-b, and 25A-b | 25 mg to 350 mg | 2 mg to 6 mg |
| 21A-c, 22A-c, 23A-c, 24A-c, and 25A-c | 25 mg to 350 mg | 5 mg to 10 mg |
| 21A-d, 22A-d, 23A-d, 24A-d, and 25A-d | 25 mg to 350 mg | 10 mg to 15 mg |
| 21A-e, 22A-e, 23A-e, 24A-e, and 25A-e | 30 mg to 50 mg | 0.1 mg to 15 mg |
| 21A-f, 22A-f, 23A-f, 24A-f, and 25A-f | 30 mg to 50 mg | 2 mg to 6 mg |
| 21A-g, 22A-g, 23A-g, 24A-g, and 25A-g | 30 mg to 50 mg | 5 mg to 10 mg |
| 21A-h, 22A-h, 23A-h, 24A-h, and 25A-h | 30 mg to 50 mg | 10 mg to 15 mg |
| 21A-i, 22A-i, 23A-i, 24A-i, and 25A-i | 75 mg to 125 mg | 0.1 mg to 15 mg |
| 21A-j, 22A-j, 23A-j, 24A-j, and 25A-j | 75 mg to 125 mg | 2 mg to 6 mg |
| 21A-k, 22A-k, 23A-k, 24A-k, and 25A-k | 75 mg to 125 mg | 5 mg to 15 mg |
| 21A-l, 22A-l, 23A-l, 24A-l, and 25A-l | 75 mg to 125 mg | 10 mg to 15 mg |
| 21A-m, 22A-m, 23A-m, 24A-m, and 25A-m | 125 mg to 175 mg | 0.1 mg to 15 mg |
| 21A-n, 22A-n, 23A-n, 24A-n, and 25A-n | 125 mg to 175 mg | 2 mg to 6 mg |
| 21A-o, 22A-o, 23A-o, 24A-o, and 25A-o | 125 mg to 175 mg | 5 mg to 10 mg |
| 21A-p, 22A-p, 23A-p, 24A-p, and 25A-p | 125 mg to 175 mg | 10 mg to 15 mg |
| 21A-q, 22A-q, 23A-q, 24A-q, and 25A-q | 175 mg to 225 mg | 0.1 mg to 15 mg |
| 21A-r, 22A-r, 23A-r, 24A-r, and 25A-r | 175 mg to 225 mg | 2 mg to 6 mg |
| 21A-s, 22A-s, 23A-s, 24A-s, and 25A-s | 175 mg to 225 mg | 5 mg to 10 mg |
| 21A-t, 22A-t, 23A-t, 24A-t, and 25A-t | 175 mg to 225 mg | 10 mg to 15 mg |
| 21A-u, 22A-u, 23A-u, 24A-u, and 25A-u | 275 mg to 325 mg | 0.1 mg to 15 mg |
| 21A-v, 22A-v, 23A-v, 24A-v, and 25A-v | 275 mg to 325 mg | 2 mg to 6 mg |
| 21A-w, 22A-w, 23A-w, 24A-w, and 25A-w | 275 mg to 325 mg | 5 mg to 10 mg |
| 21A-x, 22A-x, 23A-x, 24A-x, and 25A-x | 275 mg to 325 mg | 10 mg to 15 mg |
| 21A-y, 22A-y, 23A-y, 24A-y, and 25A-y | 40 mg | 0.1 mg to 15 mg |
| 21A-z, 22A-z, 23A-z, 24A-z, and 25A-z | 40 mg | 2 mg to 6 mg |
| 21A-aa, 22A-aa, 23A-aa, 24A-aa, and 25A-aa | 40 mg | 5 mg to 10 mg |
| 21A-ab, 22A-ab, 23A-ab, 24A-ab, and 25A-ab | 40 mg | 10 mg to 15 mg |
| 21A-ac, 22A-ac, 23A-ac, 24A-ac, and 25A-ac | 50 mg | 0.1 mg to 15 mg |
| 21A-ad, 22A-ad, 23A-ad, 24A-ad, and 25A-ad | 50 mg | 2 mg to 6 mg |
| 21A-ae, 22A-ae, 23A-ae, 24A-ae, and 25A-ae | 50 mg | 5 mg to 10 mg |
| 21A-af, 22A-af, 23A-af, 24A-af, and 25A-af | 50 mg | 10 mg to 15 mg |
| 21A-ag, 22A-ag, 23A-ag, 24A-ag, and 25A-ag | 75 mg | 0.1 mg to 15 mg |
| 21A-ah, 22A-ah, 23A-ah, 24A-ah, and 25A-ah | 75 mg | 2 mg to 6 mg |
| 21A-ai, 22A-ai, 23A-ai, 24A-ai, and 25A-ai | 75 mg | 5 mg to 10 mg |
| 21A-aj, 22A-aj, 23A-aj, 24A-aj, and 25A-aj | 75 mg | 10 mg to 15 mg |
| 21A-ak, 22A-ak, 23A-ak, 24A-ak, and 25A-ak | 100 mg | 0.1 mg to 15 mg |
| 21A-al, 22A-al, 23A-al, 24A-al, and 25A-al | 100 mg | 2 mg to 6 mg |
| 21A-am, 22A-am, 23A-am, 24A-am, and 25A-am | 100 mg | 5 mg to 10 mg |
| 21A-an, 22A-an, 23A-an, 24A-an, and 25A-an | 100 mg | 10 mg to 15 mg |
| 21A-ao, 22A-ao, 23A-ao, 24A-ao, and 25A-ao | 150 mg | 0.1 mg to 15 mg |
| 21A-ap, 22A-ap, 23A-ap, 24A-ap, and 25A-ap | 150 mg | 2 mg to 6 mg |
| 21A-aq, 22A-aq, 23A-aq, 24A-aq, and 25A-aq | 150 mg | 5 mg to 10 mg |
| 21A-ar, 22A-ar, 23A-ar, 24A-ar, and 25A-ar | 150 mg | 10 mg to 15 mg |
| 21A-as, 22A-as, 23A-as, 24A-as, and 25A-as | 200 mg | 0.1 mg to 15 mg |
| 21A-at, 22A-at, 23A-at, 24A-at, and 25A-at | 200 mg | 2 mg to 6 mg |
| 21A-au, 22A-au, 23A-au, 24A-au, and 25A-au | 200 mg | 5 mg to 10 mg |
| 21A-av, 22A-av, 23A-av, 24A-av, and 25A-av | 200 mg | 10 mg to 15 mg |
| 21A-aw, 22A-aw, 23A-aw, 24A-aw, and 25A-aw | 300 mg | 0.1 mg to 15 mg |
| 21A-ax, 22A-ax, 23A-ax, 24A-ax, and 25A-ax | 300 mg | 2 mg to 6 mg |
| 21A-ay, 22A-ay, 23A-ay, 24A-ay, and 25A-ay | 300 mg | 5 mg to 10 mg |
| 21A-az, 22A-az, 23A-az, 24A-az, and 25A-az | 300 mg | 10 mg to 15 mg |
| 21A-ba, 22A-ba, 23A-ba, 24A-ba, and 25A-ba | 25 mg to 350 mg | 0.1 mg to 25.0 mg |
| 21A-bb, 22A-bb, 23A-bb, 24A-bb, and 25A-bb | 25 mg to 350 mg | 15 mg to 20 mg |
| 21A-bc, 22A-bc, 23A-bc, 24A-bc, and 25A-bc | 25 mg to 350 mg | 20 mg to 25 mg |
| 21A-bd, 22A-bd, 23A-bd, 24A-bd, and 25A-bd | 50 mg to 350 mg | 0.1 mg to 25.0 mg |
| 21A-be, 22A-be, 23A-be, 24A-be, and 25A-be | 50 mg to 300 mg | 0.1 mg to 20.0 mg |
| 21A-bf, 22A-bf, 23A-bf, 24A-bf, and 25A-bf | 50 mg to 250 mg | 0.1 mg to 15.0 mg |

Tables 21B, 22B, 23B, 24B, and 25B

Following the pattern of the tables above, the table below serves as Tables 21B, 22B, 23B, 24B, and 25B and provides combinations of agents that can be used in the uses, methods, regimens, and pharmaceutical compositions herein. Each of the listed combinations of agents includes amounts of TAF and differs only in the TLR7 Modulating Compound included. In the separate tables the TLR7 Modulating Compound, or a pharmaceutically acceptable salt thereof, comprises a) a compound of Formula II in Table 21B, b) the compound of Example 4 in Table 22B, c) the compound of Example 49 in Table 23B, d) the compound of Example 119 in Table 24B, and e) the compound of Example 120 in Table 25B.

| Composition Example No. | TAF | TLR7 MC |
|---|---|---|
| 21B-a, 22B-a, 23B-a, 24B-a, and 25B-a | 5 mg to 35 mg | 0.1 mg to 15 mg |
| 21B-b, 22B-b, 23B-b, 24B-b, and 25B-b | 5 mg to 35 mg | 2 mg to 6 mg |
| 21B-c, 22B-c, 23B-c, 24B-c, and 25B-c | 5 mg to 35 mg | 5 mg to 10 mg |
| 21B-d, 22B-d, 23B-d, 24B-d, and 25B-d | 5 mg to 35 mg | 10 mg to 15 mg |
| 21B-e, 22B-e, 23B-e, 24B-e, and 25B-e | 10 mg to 30 mg | 0.1 mg to 15 mg |

-continued

| Composition Example No. | TAF | TLR7 MC |
|---|---|---|
| 21B-f, 22B-f, 23B-f, 24B-f, and 25B-f | 10 mg to 30 mg | 2 mg to 6 mg |
| 21B-g, 22B-g, 23B-g, 24B-g, and 25B-g | 10 mg to 30 mg | 5 mg to 10 mg |
| 21B-h, 22B-h, 23B-h, 24B-h, and 25B-h | 10 mg to 30 mg | 10 mg to 15 mg |
| 21B-i, 22B-i, 23B-i, 24B-i, and 25B-i | 10 mg to 20 mg | 0.1 mg to 15 mg |
| 21B-j, 22B-j, 23B-j, 24B-j, and 25B-j | 10 mg to 20 mg | 2 mg to 6 mg |
| 21B-k, 22B-k, 23B-k, 24B-k, and 25B-k | 10 mg to 20 mg | 5 mg to 15 mg |
| 21B-l, 22B-l, 23B-l, 24B-l, and 25B-l | 10 mg to 20 mg | 10 mg to 15 mg |
| 21B-m, 22B-m, 23B-m, 24B-m, and 25B-m | 20 mg to 30 mg | 0.1 mg to 15 mg |
| 21B-n, 22B-n, 23B-n, 24B-n, and 25B-n | 20 mg to 30 mg | 2 mg to 6 mg |
| 21B-o, 22B-o, 23B-o, 24B-o, and 25B-o | 20 mg to 30 mg | 5 mg to 10 mg |
| 21B-p, 22B-p, 23B-p, 24B-p, and 25B-p | 20 mg to 30 mg | 10 mg to 15 mg |
| 21B-q, 22B-q, 23B-q, 24B-q, and 25B-q | 5 mg to 15 mg | 0.1 mg to 15 mg |
| 21B-r, 22B-r, 23B-r, 24B-r, and 25B-r | 5 mg to 15 mg | 2 mg to 6 mg |
| 21B-s, 22B-s, 23B-s, 24B-s, and 25B-s | 5 mg to 15 mg | 5 mg to 10 mg |
| 21B-t, 22B-t, 23B-t, 24B-t, and 25B-t | 5 mg to 15 mg | 10 mg to 15 mg |
| 21B-u, 22B-u, 23B-u, 24B-u, and 25B-u | 15 mg to 25 mg | 0.1 mg to 15 mg |
| 21B-v, 22B-v, 23B-v, 24B-v, and 25B-v | 15 mg to 25 mg | 2 mg to 6 mg |
| 21B-w, 22B-w, 23B-w, 24B-w, and 25B-w | 15 mg to 25 mg | 5 mg to 10 mg |
| 21B-x, 22B-x, 23B-x, 24B-x, and 25B-x | 15 mg to 25 mg | 10 mg to 15 mg |
| 21B-y, 22B-y, 23B-y, 24B-y, and 25B-y | 10 mg | 0.1 mg to 15 mg |
| 21B-z, 22B-z, 23B-z, 24B-z, and 25B-z | 10 mg | 2 mg to 6 mg |
| 21B-aa, 22B-aa, 23B-aa, 24B-aa, and 25B-aa | 10 mg | 5 mg to 10 mg |
| 21B-ab, 22B-ab, 23B-ab, 24B-ab, and 25B-ab | 10 mg | 10 mg to 15 mg |
| 21B-ac, 22B-ac, 23B-ac, 24B-ac, and 25B-ac | 15 mg | 0.1 mg to 15 mg |
| 21B-ad, 22B-ad, 23B-ad, 24B-ad, and 25B-ad | 15 mg | 2 mg to 6 mg |
| 21B-ae, 22B-ae, 23B-ae, 24B-ae, and 25B-ae | 15 mg | 5 mg to 10 mg |
| 21B-af, 22B-af, 23B-af, 24B-af, and 25B-af | 15 mg | 10 mg to 15 mg |
| 21B-ag, 22B-ag, 23B-ag, 24B-ag, and 25B-ag | 20 mg | 0.1 mg to 15 mg |
| 21B-ah, 22B-ah, 23B-ah, 24B-ah, and 25B-ah | 20 mg | 2 mg to 6 mg |
| 21B-ai, 22B-ai, 23B-ai, 24B-ai, and 25B-ai | 20 mg | 5 mg to 10 mg |
| 21B-aj, 22B-aj, 23B-aj, 24B-aj, and 25B-aj | 20 mg | 10 mg to 15 mg |
| 21B-ak, 22B-ak, 23B-ak, 24B-ak, and 25B-ak | 25 mg | 0.1 mg to 15 mg |
| 21B-al, 22B-al, 23B-al, 24B-al, and 25B-al | 25 mg | 2 mg to 6 mg |
| 21B-am, 22B-am, 23B-am, 24B-am, and 25B-am | 25 mg | 5 mg to 10 mg |
| 21B-an, 22B-an, 23B-an, 24B-an, and 25B-an | 25 mg | 10 mg to 15 mg |
| 21B-ao, 22B-ao, 23B-ao, 24B-ao, and 25B-ao | 30 mg | 0.1 mg to 15 mg |
| 21B-ap, 22B-ap, 23B-ap, 24B-ap, and 25B-ap | 30 mg | 2 mg to 6 mg |
| 21B-aq, 22B-aq, 23B-aq, 24B-aq, and 25B-aq | 30 mg | 5 mg to 10 mg |
| 21B-ar, 22B-ar, 23B-ar, 24B-ar, and 25B-ar | 30 mg | 10 mg to 15 mg |
| 21B-as, 22B-as, 23B-as, 24B-as, and 25B-as | 35 mg | 0.1 mg to 15 mg |
| 21B-at, 22B-at, 23B-at, 24B-at, and 25B-at | 35 mg | 2 mg to 6 mg |
| 21B-au, 22B-au, 23B-au, 24B-au, and 25B-au | 35 mg | 5 mg to 10 mg |
| 21B-av, 22B-av, 23B-av, 24B-av, and 25B-av | 35 mg | 10 mg to 15 mg |
| 21B-aw, 22B-aw, 23B-aw, 24B-aw, and 25B-aw | 5 mg to 35 mg | 0.1 mg to 25.0 mg |
| 21B-ax, 22B-ax, 23B-ax, 24B-ax, and 25B-ax | 5 mg to 35 mg | 15 mg to 20 mg |
| 21B-ay, 22B-ay, 23B-ay, 24B-ay, and 25B-ay | 5 mg to 35 mg | 20 mg to 25 mg |
| 21B-az, 22B-az, 23B-az, 24B-az, and 25B-az | 1 mg to 25 mg | 0.1 mg to 25.0 mg |
| 21B-ba, 22B-ba, 23B-ba, 24B-ba, and 25B-ba | 1 mg to 20 mg | 0.1 mg to 20.0 mg |
| 21B-bb, 22B-bb, 23B-bb, 24B-bb, and 25B-bb | 1 mg to 15 mg | 0.1 mg to 15.0 mg |

Also provided is a pharmaceutical kit, the kit comprising:
1) a series of daily doses of a single pharmaceutical composition comprising:
   a) a pharmaceutically effective amount of tenofovir disoproxil fumarate;
   b) a pharmaceutically effective amount of a TLR7 modulating compound, or a pharmaceutically acceptable salt thereof; and
   c) a pharmaceutically acceptable carrier or excipient; and
2) directions for the administration of the daily doses of the pharmaceutical composition.

Also provided is a pharmaceutical kit, the kit comprising:
a) a series of daily doses of a single pharmaceutical composition comprising a pharmaceutically effective amount of tenofovir disoproxil fumarate for daily administration;
b) a series of doses of a pharmaceutically effective amount of a TLR7 modulating compound for less than daily administration, or a pharmaceutically acceptable salt thereof; and
c) and directions for the administration of the daily doses of tenofovir disoproxil fumarate and the less than daily administration of the doses of the TLR7 modulating compound.

Also provided is a pharmaceutical kit, the kit comprising:
i. a series of daily doses of a single pharmaceutical composition comprising:
   b. a pharmaceutically effective amount of tenofovir disoproxil fumarate;
   c. a pharmaceutically effective amount of a compound of Formula II, or a pharmaceutically acceptable salt thereof; and
   d. a pharmaceutically acceptable carrier or excipient; and
3) directions for the administration of the daily doses of the pharmaceutical composition.

Provided are a series of individual pharmaceutical kits as just described wherein each individual kit is provided comprises a pharmaceutically acceptable carrier or excipient, one of the pharmaceutically effective amounts of tenofovir disoproxil fumarate and a compound of Formula II, or a pharmaceutically acceptable salt thereof, set forth in each of the individual Composition Example Nos. seen in Pharmaceutical Composition Table 21, Pharmaceutical Composition Table 22, Pharmaceutical Composition Table 23, Pharmaceutical Composition Table 24, and Pharmaceutical Composition Table 25.

Further provided is a pharmaceutical kit, the kit comprising a series of doses of a first pharmaceutical composition comprising a pharmaceutically effective amount of tenofovir disoproxil fumarate and a pharmaceutically acceptable carrier or excipient; a series of doses of a second pharmaceutical composition comprising a pharmaceutically effective amount of a compound of Formula II, or a pharmaceutically acceptable salt thereof; and a pharmaceutically acceptable carrier or excipient; and directions for the administration of the doses of the first and second pharmaceutical composition; wherein the first and second pharmaceutical compositions are both administered once daily. Further provided is a pharmaceutical kit, the kit comprising the series of doses of the first pharmaceutical composition, the second pharmaceutical composition and the directions just described, wherein the first and second pharmaceutical compositions are both administered twice daily. Also provided is a pharmaceutical kit, the kit comprising the series of doses of the first pharmaceutical composition, the second pharmaceutical composition and the directions just described, wherein the first pharmaceutical composition is administered once daily and the second pharmaceutical compositions is administered twice daily.

Combinations of Rilpivirine/Emtricitabine/TDF/TLR7 Modulators

Pharmaceutically effective amounts of the TLR7 modulating compounds of Formula II, or a pharmaceutically acceptable salt thereof, as well as the compounds of Examples 119, 120, and 121, or a pharmaceutically acceptable salt thereof, can be combined with pharmaceutically effective amounts of emtricitabine, rilpivirine, and tenofovir disoproxil fumarate (TDF) for use in the methods of treatment discussed herein. For instance, as separate dosage forms, a pharmaceutically effective dose of the TLR7 modulating compounds may be combined in a treatment regimen with a COMPLERA® tablet, which is available from Gilead Sciences, Inc. and contain 200 mg of emtricitabine, 25 mg rilpivirine, and 300 mg of TDF.

Also provided is a pharmaceutical composition comprising:
  a) a pharmaceutically effective amount of rilpivirine, or a pharmaceutically acceptable salt thereof;
  b) a pharmaceutically effective amount of emtricitabine;
  c) a pharmaceutically effective amount of tenofovir disoproxil fumarate;
  d) a pharmaceutically effective amount of a compound of Formula II, or a pharmaceutically acceptable salt thereof; and
  e) a pharmaceutically acceptable carrier or excipient.

Also provided is a pharmaceutical composition comprising:
  f) a pharmaceutically effective amount of rilpivirine HCl;
  g) a pharmaceutically effective amount of emtricitabine;
  h) a pharmaceutically effective amount of tenofovir disoproxil fumarate;
  i) a pharmaceutically effective amount of a compound of Formula II, or a pharmaceutically acceptable salt thereof; and
  j) a pharmaceutically acceptable carrier or excipient.

Also provided are several separate pharmaceutical compositions, each comprising 1) a pharmaceutically effective amount of rilpivirine; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound selected from one of the group of Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof. Each of the separate pharmaceutical compositions comprises one formula, for instance, one embodiment comprises 1) a pharmaceutically effective amount of rilpivirine or a pharmaceutically acceptable salt thereof; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Formula III, or a pharmaceutically acceptable salt thereof, another comprises 1) a pharmaceutically effective amount of rilpivirine or a pharmaceutically acceptable salt thereof; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Formula III(a), or a pharmaceutically acceptable salt thereof, etc.

Also provided are another group of separate pharmaceutical compositions, each of the separate compositions comprising comprises 1) a pharmaceutically effective amount of rilpivirine or a pharmaceutically acceptable salt thereof; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound selected from the group of Examples 1 through 121. The first of the group of separate compositions comprises 1) a pharmaceutically effective amount of rilpivirine or a pharmaceutically acceptable salt thereof; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of the compound of Example 1, or a pharmaceutically acceptable salt thereof, the next separate composition comprises 1) a pharmaceutically effective amount of rilpivirine or a pharmaceutically acceptable salt thereof; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of the compound of Example 2, or a pharmaceutically acceptable salt thereof, etc.

Tables 26a Through 30B

Also provided are the specific pharmaceutical compositions and combinations comprising a pharmaceutically acceptable carrier or excipient and the individual amounts of a) rilpivirine or a pharmaceutically acceptable salt thereof; b) emtricitabine; c) TDF or TAF, and b) a pharmaceutically effective amount of a TLR7 Modulating Compound or a pharmaceutically acceptable salt thereof (collectively "TLR7 MC").

Following the pattern of the tables above, provided are separate pharmaceutical compositions and combinations comprising a pharmaceutically acceptable carrier or excipient and the amounts of rilpivirine or rilpivirine HCl, emtricitabine, tenofovir disoproxil fumarate (TDF) or tenofovir alafenamide (TAF), a TLR7 Modulating Compound (TLR7 MC), or a pharmaceutically acceptable salt thereof, and raltegravir in the amounts listed for each composition below.

The table below serves as Tables 26A, 27A, 28A, 29A, and 30A and provides combinations of agents that can be used in the uses, methods, regimens, and pharmaceutical compositions herein. In the separate tables the TLR7 Modulating Compound, or a pharmaceutically acceptable salt thereof, comprises a) a compound of Formula II in Table 26A, b) the compound of Example 4 in Table 27A, c) the compound of Example 49 in Table 28A, d) the compound of Example 119 in Table 29A, and e) the compound of Example 120 in Table 30A.

Tables 26A, 27A, 28A, 29A, and 30A

| Comp. Ex. | rilpivirine | emtricitabine | TDF | TLR7 MC |
| --- | --- | --- | --- | --- |
| 26A-a, 27A-a, 28A-a, 29A-a, and 30A-a | 20 mg to 30 mg | 150 mg to 250 mg | 250 mg to 350 mg | 0.1 mg to 15 mg |
| 26A-b, 27A-b, 28A-b, 29A-b, and 30A-b | 20 mg to 30 mg | 150 mg to 250 mg | 250 mg to 350 mg | 2 mg to 6 mg |
| 26A-c, 27A-c, 28A-c, 29A-c, and 30A-c | 20 mg to 30 mg | 150 mg to 250 mg | 250 mg to 350 mg | 5 mg to 10 mg |
| 26A-d, 27A-d, 28A-d, 29A-d, and 30A-d | 20 mg to 30 mg | 150 mg to 250 mg | 250 mg to 350 mg | 10 mg to 15 mg |
| 26A-e, 27A-e, 28A-e, 29A-e, and 30A-e | 22 mg to 28 mg | 175 mg to 225 mg | 275 mg to 325 mg | 0.1 mg to 15 mg |
| 26A-f, 27A-f, 28A-f, 29A-f, and 30A-f | 22 mg to 28 mg | 175 mg to 225 mg | 275 mg to 325 mg | 2 mg to 6 mg |
| 26A-g, 27A-g, 28A-g, 29A-g, and 30A-g | 22 mg to 28 mg | 175 mg to 225 mg | 275 mg to 325 mg | 5 mg to 10 mg |
| 26A-h, 27A-h, 28A-h, 29A-h, and 30A-h | 22 mg to 28 mg | 175 mg to 225 mg | 275 mg to 325 mg | 10 mg to 15 mg |
| 26A-i, 27A-i, 28A-i, 29A-i, and 30A-i | 25 mg | 200 mg | 300 | 4 mg |
| 26A-j, 27A-j, 28A-j, 29A-j, and 30A-j | 25 mg | 200 mg | 300 | 5 mg |
| 26A-k, 27A-k, 28A-k, 29A-k, and 30A-k | 25 mg | 200 mg | 300 | 6 mg |
| 26A-l, 27A-l, 28A-l, 29A-l, and 30A-l | 25 mg | 200 mg | 300 | 7 mg |
| 26A-m, 27A-m, 28A-m, 29A-m, and 30A-m | 25 mg | 200 mg | 300 | 8 mg |
| 26A-n, 27A-n, 28A-n, 29A-n, and 30A-n | 25 mg | 200 mg | 300 | 9 mg |
| 26A-o, 27A-o, 28A-o, 29A-o, and 30A-o | 25 mg | 200 mg | 300 | 10 mg |
| 26A-p, 27A-p, 28A-p, 29A-p, and 30A-p | 25 mg | 200 mg | 300 | 11 mg |
| 26A-q, 27A-q, 28A-q, 29A-q, and 30A-q | 25 mg | 200 mg | 300 | 12 mg |
| 26A-r, 27A-r, 28A-r, 29A-r, and 30A-r | 20 mg to 30 mg | 150 mg to 250 mg | 250 mg to 350 mg | 0.1 mg to 25.0 mg |
| 26A-s, 27A-s, 28A-s, 29A-s, and 30A-s | 20 mg to 30 mg | 150 mg to 250 mg | 250 mg to 350 mg | 15 mg to 20 mg |
| 26A-t, 27A-t, 28A-t, 29A-t, and 30A-t | 20 mg to 30 mg | 150 mg to 250 mg | 250 mg to 350 mg | 20 mg to 25 mg |
| 26A-u, 27A-u, 28A-u, 29A-u, and 30A-u | 10 mg to 25 mg | 50 mg to 250 mg | 50 mg to 350 mg | 0.1 mg to 25.0 mg |
| 26A-v, 27A-v, 28A-v, 29A-v, and 30A-v | 10 mg to 20 mg | 50 mg to 200 mg | 50 mg to 300 mg | 0.1 mg to 20.0 mg |
| 26A-w, 27A-w, 28A-w, 29A-w, and 30A-w | 10 mg to 15 mg | 50 mg to 175 mg | 50 mg to 250 mg | 0.1 mg to 15.0 mg |

The table below serves as Tables 26B, 27B, 28B, 29B, and 30B and provides combinations of agents that can be used in the uses, methods, regimens, and pharmaceutical compositions herein. In the separate tables the TLR7 Modulating Compound, or a pharmaceutically acceptable salt thereof, comprises a) a compound of Formula II in Table 26B, b) the compound of Example 4 in Table 27B, c) the compound of Example 49 in Table 28B, d) the compound of Example 119 in Table 29B, and e) the compound of Example 120 in Table 30B.

Tables 26B, 27B, 28B, 29B, and 30B

| Comp. Ex. | rilpivirine | emtricitabine | TAF | TRL7 MC |
|---|---|---|---|---|
| 26B-a, 27B-a, 28B-a, 29B-a, and 30B-a | 20 mg to 30 mg | 150 mg to 250 mg | 15 mg to 35 mg | 0.1 mg to 15 mg |
| 26B-b, 27B-b, 28B-b, 29B-b, and 30B-b | 20 mg to 30 mg | 150 mg to 250 mg | 15 mg to 35 mg | 2 mg to 6 mg |
| 26B-c, 27B-c, 28B-c, 29B-c, and 30B-c | 20 mg to 30 mg | 150 mg to 250 mg | 15 mg to 35 mg | 5 mg to 10 mg |
| 26B-d, 27B-d, 28B-d, 29B-d, and 30B-d | 20 mg to 30 mg | 150 mg to 250 mg | 15 mg to 35 mg | 10 mg to 15 mg |
| 26B-e, 27B-e, 28B-e, 29B-e, and 30B-e | 22 mg to 28 mg | 175 mg to 225 mg | 20 mg to 30 mg | 0.1 mg to 15 mg |
| 26B-f, 27B-f, 28B-f, 29B-f, and 30B-f | 22 mg to 28 mg | 175 mg to 225 mg | 20 mg to 30 mg | 2 mg to 6 mg |
| 26B-g, 27B-g, 28B-g, 29B-g, and 30B-g | 22 mg to 28 mg | 175 mg to 225 mg | 20 mg to 30 mg | 5 mg to 10 mg |
| 26B-h, 27B-h, 28B-h, 29B-h, and 30B-h | 22 mg to 28 mg | 175 mg to 225 mg | 20 mg to 30 mg | 10 mg to 15 mg |
| 26B-i, 27B-i, 28B-i, 29B-i, and 30B-i | 25 mg | 200 mg | 25 mg | 4 mg |
| 26B-j, 27B-j, 28B-j, 29B-j, and 30B-j | 25 mg | 200 mg | 25 mg | 5 mg |
| 26B-k, 27B-k, 28B-k, 29B-k, and 30B-k | 25 mg | 200 mg | 25 mg | 6 mg |
| 26B-l, 27B-l, 28B-l, 29B-l, and 30B-l | 25 mg | 200 mg | 25 mg | 7 mg |
| 26B-m, 27B-m, 28B-m, 29B-m, and 30B-m | 25 mg | 200 mg | 25 mg | 8 mg |
| 26B-n, 27B-n, 28B-n, 29B-n, and 30B-n | 25 mg | 200 mg | 25 mg | 9 mg |
| 26B-o, 27B-o, 28B-o, 29B-o, and 30B-o | 25 mg | 200 mg | 25 mg | 10 mg |
| 26B-p, 27B-p, 28B-p, 29B-p, and 30B-p | 25 mg | 200 mg | 25 mg | 11 mg |
| 26B-q, 27B-q, 28B-q, 29B-q, and 30B-q | 25 mg | 200 mg | 25 mg | 12 mg |
| 26B-r, 27B-r, 28B-r, 29B-r, and 30B-r | 20 mg to 30 mg | 150 mg to 250 mg | 15 mg to 35 mg | 0.1 mg to 25.0 mg |
| 26B-s, 27B-s, 28B-s, 29B-s, and 30B-s | 20 mg to 30 mg | 150 mg to 250 mg | 15 mg to 35 mg | 15 mg to 20 mg |
| 26B-t, 27B-t, 28B-t, 29B-t, and 30B-t | 20 mg to 30 mg | 150 mg to 250 mg | 15 mg to 35 mg | 20 mg to 25 mg |
| 26B-u, 27B-u, 28B-u, 29B-u, and 30B-u | 10 mg to 25 mg | 50 mg to 250 mg | 1 mg to 25 mg | 0.1 mg to 25.0 mg |
| 26B-v, 27B-v, 28B-v, 29B-v, and 30B-v | 10 mg to 20 mg | 50 mg to 200 mg | 1 mg to 20 mg | 0.1 mg to 20.0 mg |
| 26B-w, 27B-w, 28B-w, 29B-w, and 30B-w | 10 mg to 15 mg | 50 mg to 175 mg | 1 mg to 15 mg | 0.1 mg to 15.0 mg |

Tables 26C, 27C, 28C, 29C, and 30C

Also provided are the specific pharmaceutical compositions and combinations comprising a pharmaceutically acceptable carrier or excipient and the individual amounts of a) rilpivirine HCl; b) emtricitabine; c) TDF, and b) a pharmaceutically effective amount of TLR7 Modulating Compound (TLR7 MC) or a pharmaceutically acceptable salt thereof). The table below serves as Tables 26C, 27C, 28C, 29C, and 30C and provides combinations of agents that can be used in the uses, methods, regimens, and pharmaceutical compositions herein. In the separate tables the TLR7 Modulating Compound, or a pharmaceutically acceptable salt thereof, comprises a) a compound of Formula II in Table 26C, b) the compound of Example 4 in Table 27C, c) the compound of Example 49 in Table 28C, d) the compound of Example 119 in Table 29C, and e) the compound of Example 120 in Table 30C.

| Comp. Ex. | Rilpivirine HCl | emtricitabine | TDF | TLR7 MC |
|---|---|---|---|---|
| 26C-a, 27C-a, 28C-a, 29C-a, and 30C-a | 22.5 mg to 32.5 mg | 150 mg to 250 mg | 250 mg to 350 mg | 0.1 mg to 15 mg |
| 26C-b, 27C-b, 28C-b, 29C-b, and 30C-b | 22.5 mg to 32.5 mg | 150 mg to 250 mg | 250 mg to 350 mg | 2 mg to 6 mg |
| 26C-c, 27C-c, 28C-c, 29C-c, and 30C-c | 22.5 mg to 32.5 mg | 150 mg to 250 mg | 250 mg to 350 mg | 5 mg to 10 mg |
| 26C-d, 27C-d, 28C-d, 29C-d, and 30C-d | 22.5 mg to 32.5 mg | 150 mg to 250 mg | 250 mg to 350 mg | 10 mg to 15 mg |
| 26C-e, 27C-e, 28C-e, 29C-e, and 30C-e | 24.5 mg to 30.5 mg | 175 mg to 225 mg | 275 mg to 325 mg | 0.1 mg to 15 mg |
| 26C-f, 27C-f, 28C-f, 29C-f, and 30C-f | 24.5 mg to 30.5 mg | 175 mg to 225 mg | 275 mg to 325 mg | 2 mg to 6 mg |
| 26C-g, 27C-g, 28C-g, 29C-g, and 30C-g | 24.5 mg to 30.5 mg | 175 mg to 225 mg | 275 mg to 325 mg | 5 mg to 10 mg |
| 26C-h, 27C-h, 28C-h, 29C-h, and 30C-h | 24.5 mg to 30.5 mg | 175 mg to 225 mg | 275 mg to 325 mg | 10 mg to 15 mg |
| 26C-i, 27C-i, 28C-i, 29C-i, and 30C-i | 27.5 mg | 200 mg | 300 | 4 mg |
| 26C-j, 27C-j, 28C-j, 29C-j, and 30C-j | 27.5 mg | 200 mg | 300 | 5 mg |
| 26C-k, 27C-k, 28C-k, 29C-k, and 30C-k | 27.5 mg | 200 mg | 300 | 6 mg |
| 26C-l, 27C-l, 28C-l, 29C-l, and 30C-l | 27.5 mg | 200 mg | 300 | 7 mg |
| 26C-m, 27C-m, 28C-m, 29C-m, and 30C-m | 27.5 mg | 200 mg | 300 | 8 mg |
| 26C-n, 27C-n, 28C-n, 29C-n, and 30C-n | 27.5 mg | 200 mg | 300 | 9 mg |
| 26C-o, 27C-o, 28C-o, 29C-o, and 30C-o | 27.5 mg | 200 mg | 300 | 10 mg |
| 26C-p, 27C-p, 28C-p, 29C-p, and 30C-p | 27.5 mg | 200 mg | 300 | 11 mg |
| 26C-q, 27C-q, 28C-q, 29C-q, and 30C-q | 27.5 mg | 200 mg | 300 | 12 mg |
| 26C-r, 27C-r, 28C-r, 29C-r, and 30C-r | 22.5 mg to 32.5 mg | 150 mg to 250 mg | 250 mg to 350 mg | 0.1 mg to 25.0 mg |
| 26C-s, 27C-s, 28C-s, 29C-s, and 30C-s | 22.5 mg to 32.5 mg | 150 mg to 250 mg | 250 mg to 350 mg | 15 mg to 20 mg |
| 26C-t, 27C-t, 28C-t, 29C-t, and 30C-t | 22.5 mg to 32.5 mg | 150 mg to 250 mg | 250 mg to 350 mg | 20 mg to 25 mg |
| 26C-u, 27C-u, 28C-u, 29C-u, and 30C-u | 10 mg to 27.5 mg | 50 mg to 250 mg | 50 mg to 350 mg | 0.1 mg to 25.0 mg |
| 26C-v, 27C-v, 28C-v, 29C-v, and 30C-v | 10 mg to 22.5 mg | 50 mg to 200 mg | 50 mg to 300 mg | 0.1 mg to 20.0 mg |
| 26C-w, 27C-w, 28C-w, 29C-w, and 30C-w | 10 mg to 17.5 mg | 50 mg to 175 mg | 50 mg to 250 mg | 0.1 mg to 15.0 mg |

Tables 26D, 27D, 28D, 29D, and 30D

Also provided are the specific pharmaceutical compositions and combinations comprising a pharmaceutically acceptable carrier or excipient and the individual amounts of a) rilpivirine HCl; b) emtricitabine; c) TAF, and b) a pharmaceutically effective amount of TLR7 Modulating Compound (TLR7 MC) or a pharmaceutically acceptable salt thereof). The table below serves as Tables 26D, 27D, 28D, 29D, and 30D and provides combinations of agents that can be used in the uses, methods, regimens, and pharmaceutical compositions herein. In the separate tables the TLR7 Modulating Compound, or a pharmaceutically acceptable salt thereof, comprises a) a compound of Formula II in Table 26D, b) the compound of Example 4 in Table 27D, c) the compound of Example 49 in Table 28D, d) the compound of Example 119 in Table 29D, and e) the compound of Example 120 in Table 30D.

| Comp. Ex. | Rilpivirine HCl | emtricitabine | TAF | TLR7 MC |
| --- | --- | --- | --- | --- |
| 26D-a, 27D-a, 28D-a, 29D-a, and 30D-a | 22.5 mg to 32.5 mg | 150 mg to 250 mg | 15 mg to 35 mg | 0.1 mg to 15 mg |
| 26D-b, 27D-b, 28D-b, 29D-b, and 30D-b | 22.5 mg to 32.5 mg | 150 mg to 250 mg | 15 mg to 35 mg | 2 mg to 6 mg |
| 26D-c, 27D-c, 28D-c, 29D-c, and 30D-c | 22.5 mg to 32.5 mg | 150 mg to 250 mg | 15 mg to 35 mg | 5 mg to 10 mg |
| 26D-d, 27D-d, 28D-d, 29D-d, and 30D-d | 22.5 mg to 32.5 mg | 150 mg to 250 mg | 15 mg to 35 mg | 10 mg to 15 mg |
| 26D-e, 27D-e, 28D-e, 29D-e, and 30D-e | 24.5 mg to 30.5 mg | 175 mg to 225 mg | 20 mg to 30 mg | 0.1 mg to 15 mg |
| 26D-f, 27D-f, 28D-f, 29D-f, and 30D-f | 24.5 mg to 30.5 mg | 175 mg to 225 mg | 20 mg to 30 mg | 2 mg to 6 mg |
| 26D-g, 27D-g, 28D-g, 29D-g, and 30D-g | 24.5 mg to 30.5 mg | 175 mg to 225 mg | 20 mg to 30 mg | 5 mg to 10 mg |
| 26D-h, 27D-h, 28D-h, 29D-h, and 30D-h | 24.5 mg to 30.5 mg | 175 mg to 225 mg | 20 mg to 30 mg | 10 mg to 15 mg |
| 26D-i, 27D-i, 28D-i, 29D-i, and 30D-i | 27.5 mg | 200 mg | 25 mg | 4 mg |
| 26D-j, 27D-j, 28D-j, 29D-j, and 30D-j | 27.5 mg | 200 mg | 25 mg | 5 mg |
| 26D-k, 27D-k, 28D-k, 29D-k, and 30D-k | 27.5 mg | 200 mg | 25 mg | 6 mg |
| 26D-l, 27D-l, 28D-l, 29D-l, and 30D-l | 27.5 mg | 200 mg | 25 mg | 7 mg |
| 26D-m, 27D-m, 28D-m, 29D-m, and 30D-m | 27.5 mg | 200 mg | 25 mg | 8 mg |
| 26D-n, 27D-n, 28D-n, 29D-n, and 30D-n | 27.5 mg | 200 mg | 25 mg | 9 mg |
| 26D-o, 27D-o, 28D-o, 29D-o, and 30D-o | 27.5 mg | 200 mg | 25 mg | 10 mg |
| 26D-p, 27D-p, 28D-p, 29D-p, and 30D-p | 27.5 mg | 200 mg | 25 mg | 11 mg |
| 26D-q, 27D-q, 28D-q, 29D-q, and 30D-q | 27.5 mg | 200 mg | 25 mg | 12 mg |
| 26D-r, 27D-r, 28D-r, 29D-r, and 30D-r | 22.5 mg to 32.5 mg | 150 mg to 250 mg | 250 mg to 350 mg | 0.1 mg to 25.0 mg |
| 26D-s, 27D-s, 28D-s, 29D-s, and 30D-s | 22.5 mg to 32.5 mg | 150 mg to 250 mg | 250 mg to 350 mg | 15 mg to 20 mg |
| 26D-t, 27D-t, 28D-t, 29D-t, and 30D-t | 22.5 mg to 32.5 mg | 150 mg to 250 mg | 250 mg to 350 mg | 20 mg to 25 mg |
| 26D-u, 27D-u, 28D-u, 29D-u, and 30D-u | 10 mg to 27.5 mg | 50 mg to 250 mg | 1 mg to 25 mg | 0.1 mg to 25.0 mg |
| 26D-v, 27D-v, 28D-v, 29D-v, and 30D-v | 10 mg to 22.5 mg | 50 mg to 250 mg | 1 mg to 20 mg | 0.1 mg to 20.0 mg |
| 26D-w, 27D-w, 28D-w, 29D-w, and 30D-w | 10 mg to 17.5 mg | 50 mg to 175 mg | 1 mg to 15 mg | 0.1 mg to 15.0 mg |

Combinations of Efavirenz/Emtricitabine/TDF/TLR7Modulators

Pharmaceutically effective amounts of the TLR7 modulating compounds, including those of Formula II, or a pharmaceutically acceptable salt thereof, as well as the compounds of Examples 119, 120, and 121, or a pharmaceutically acceptable salt thereof, can be combined with pharmaceutically effective amounts of efavirenz, emtricitabine, and tenofovir disoproxil fumarate (TDF) for use in the methods of treatment discussed herein. For instance, as separate dosage forms, a pharmaceutically effective dose of a TLR7 modulating compound, or pharmaceutically acceptable salt thereof, may be combined in a treatment regimen with an ATRIPLA® tablet (600 mg efavirenz, 200 mg emtricitabine and 300 mg tenofovir disoproxil fumarate), which is available from Gilead Sciences, Inc.

Also provided is a pharmaceutical composition comprising:
- a) a pharmaceutically effective amount of efavirenz;
- b) a pharmaceutically effective amount of emtricitabine;
- c) a pharmaceutically effective amount of tenofovir disoproxil fumarate;
- d) a pharmaceutically effective amount of a TLR7 modulating compound, or a pharmaceutically acceptable salt thereof; and
- e) a pharmaceutically acceptable carrier or excipient.

Also provided is a pharmaceutical composition comprising:
- f) a pharmaceutically effective amount of efavirenz;
- g) a pharmaceutically effective amount of emtricitabine;
- h) a pharmaceutically effective amount of tenofovir disoproxil fumarate;
- i) a pharmaceutically effective amount of a compound of Formula II, or a pharmaceutically acceptable salt thereof; and
- j) a pharmaceutically acceptable carrier or excipient.

Also provided is a pharmaceutical composition comprising:
- k) a pharmaceutically effective amount of efavirenz;
- l) a pharmaceutically effective amount of emtricitabine;
- m) a pharmaceutically effective amount of TAF;
- n) a pharmaceutically effective amount of a TLR7 modulating compound, or a pharmaceutically acceptable salt thereof; and
- o) a pharmaceutically acceptable carrier or excipient.

Also provided is a pharmaceutical composition comprising:
- p) a pharmaceutically effective amount of efavirenz;
- q) a pharmaceutically effective amount of emtricitabine;
- r) a pharmaceutically effective amount of TAF;
- s) a pharmaceutically effective amount of a compound of Formula II, or a pharmaceutically acceptable salt thereof; and
- t) a pharmaceutically acceptable carrier or excipient.

Also provided are 19 separate pharmaceutical compositions, each comprising 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound selected from one of the group of Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof. Each of the separate pharmaceutical compositions comprises one formula, for instance, one embodiment comprises 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Formula III, or a pharmaceutically acceptable salt thereof, another comprises 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Formula III(a), or a pharmaceutically acceptable salt thereof, etc.

Also provided are another group of separate pharmaceutical, each of the separate compositions comprising comprises 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound selected from the group of Examples 1 through 124. The first of the group of separate compositions comprises 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Example 1, or a pharmaceutically acceptable salt thereof, the next separate composition comprises 1) a pharmaceutically effective amount of efavirenz; 2) a pharmaceutically effective amount of emtricitabine; 3) a pharmaceutically effective amount of tenofovir disoproxil fumarate; 4) a pharmaceutically acceptable carrier or excipient; and 5) a pharmaceutically effective amount of a compound of Example 2, or a pharmaceutically acceptable salt thereof, etc.

Tables 31A through 35A

Also provided are the specific pharmaceutical compositions and combinations comprising a pharmaceutically acceptable carrier or excipient and the individual pharmaceutically effective amounts of a) efavirenz; b) emtricitabine; c) TDF or TAF, and b) a pharmaceutically effective amount of a TLR7 Modulating Compound or a pharmaceutically acceptable salt thereof (TLR7 MC).

Following the pattern of the tables above, the table below serves as Tables 31A, 32A, 33A, 34A, and 35A and provides combinations of agents that can be used in the uses, methods, regimens, and pharmaceutical compositions herein. Each of the listed combinations of agents includes amounts of efavirenz emtricitabine, and TDF, and differs only in the TLR7 Modulating Compound included. In the separate tables the TLR7 Modulating Compound, or a pharmaceutically acceptable salt thereof, comprises a) a compound of Formula II in Table 31A, b) the compound of Example 4 in Table 32A, c) the compound of Example 49 in Table 33A, d) the compound of Example 119 in Table 34A, and e) the compound of Example 120 in Table 35A.

Tables 31A, 32A, 33A, 34A, and 35A

| Comp. Ex. | efavirenz | emtricitabine | TDF | TLR7 MC |
|---|---|---|---|---|
| 31A-a, 32A-a, 33A-a, 34A-a, and 35A-a | 500 mg to 700 mg | 150 mg to 250 mg | 150 mg to 250 mg | 0.1 mg to 15 mg |
| 31A-b, 32A-b, 33A-b, 34A-b, and 35A-b | 500 mg to 700 mg | 150 mg to 250 mg | 150 mg to 250 mg | 2 mg to 6 mg |
| 31A-c, 32A-c, 33A-c, 34A-c, and 35A-c | 500 mg to 700 mg | 150 mg to 250 mg | 150 mg to 250 mg | 5 mg to 10 mg |
| 31A-d, 32A-d, 33A-d, 34A-d, and 35A-d | 500 mg to 700 mg | 150 mg to 250 mg | 150 mg to 250 mg | 10 mg to 15 mg |
| 31A-e, 32A-e, 33A-e, 34A-e, and 35A-e | 550 mg to 650 mg | 175 mg to 225 mg | 175 mg to 225 mg | 0.1 mg to 15 mg |
| 31A-f, 32A-f, 33A-f, 34A-f, and 35A-f | 550 mg to 650 mg | 175 mg to 225 mg | 175 mg to 225 mg | 2 mg to 6 mg |
| 31A-g, 32A-g, 33A-g, 34A-g, and 35A-g | 550 mg to 650 mg | 175 mg to 225 mg | 175 mg to 225 mg | 5 mg to 10 mg |
| 31A-h, 32A-h, 33A-h, 34A-h, and 35A-h | 550 mg to 650 mg | 175 mg to 225 mg | 175 mg to 225 mg | 10 mg to 15 mg |
| 31A-i, 32A-i, 33A-i, 34A-i, and 35A-i | 575 mg to 625 mg | 175 mg to 225 mg | 175 mg to 225 mg | 0.1 mg to 15 mg |
| 31A-j, 32A-j, 33A-j, 34A-j, and 35A-j | 575 mg to 625 mg | 175 mg to 225 mg | 175 mg to 225 mg | 2 mg to 6 mg |
| 31A-k, 32A-k, 33A-k, 34A-k, and 35A-k | 575 mg to 625 mg | 175 mg to 225 mg | 175 mg to 225 mg | 5 mg to 10 mg |
| 31A-l, 32A-l, 33A-l, 34A-l, and 35A-l | 575 mg to 625 mg | 175 mg to 225 mg | 175 mg to 225 mg | 10 mg to 15 mg |
| 31A-m, 32A-m, 33A-m, 34A-m, and 35A-m | 600 mg | 200 mg | 200 mg | 0.1 mg to 15 mg |
| 31A-n, 32A-n, 33A-n, 34A-n, and 35A-n | 600 mg | 200 mg | 200 mg | 2 mg to 6 mg |
| 31A-o, 32A-o, 33A-o, 34A-o, and 35A-o | 600 mg | 200 mg | 200 mg | 5 mg to 10 mg |
| 31A-p, 32A-p, 33A-p, 34A-p, and 35A-p | 600 mg | 200 mg | 200 mg | 10 mg to 15 mg |
| 31A-q, 32A-q, 33A-q, 34A-q, and 35A-q | 600 mg | 200 mg | 200 mg | 4 mg |
| 31A-r, 32A-r, 33A-r, 34A-r, and 35A-r | 600 mg | 200 mg | 200 mg | 5 mg |
| 31A-s, 32A-s, 33A-s, 34A-s, and 35A-s | 600 mg | 200 mg | 200 mg | 6 mg |
| 31A-t, 32A-t, 33A-t, 34A-t, and 35A-t | 600 mg | 200 mg | 200 mg | 7 mg |
| 31A-u, 32A-u, 33A-u, 34A-u, and 35A-u | 600 mg | 200 mg | 200 mg | 8 mg |
| 31A-v, 32A-v, 33A-v, 34A-v, and 35A-v | 600 mg | 200 mg | 200 mg | 9 mg |
| 31A-w, 32A-w, 33A-w, 34A-w, and 35A-w | 600 mg | 200 mg | 200 mg | 10 mg |
| 31A-x, 32A-x, 33A-x, 34A-x, and 35A-x | 600 mg | 200 mg | 200 mg | 11 mg |
| 31A-y, 32A-y, 33A-y, 34A-y, and 35A-y | 600 mg | 200 mg | 200 mg | 12 mg |
| 31A-z, 32A-z, 33A-z, 34A-z, and 35A-z | 500 mg to 700 mg | 150 mg to 250 mg | 150 mg to 250 mg | 0.1 mg to 25.0 mg |
| 31A-aa, 32A-aa, 33A-aa, 34A-aa, and 35A-aa | 500 mg to 700 mg | 150 mg to 250 mg | 150 mg to 250 mg | 15 mg to 20 mg |
| 31A-ab, 32A-ab, 33A-ab, 34A-ab, and 35A-ab | 500 mg to 700 mg | 150 mg to 250 mg | 150 mg to 250 mg | 20 mg to 25 mg |
| 31A-ac, 32A-ac, 33A-ac, 34A-ac, and 35A-ac | 300 mg to 600 mg | 50 mg to 250 mg | 50 mg to 350 mg | 0.1 mg to 25.0 mg |
| 31A-ad, 32A-ad, 33A-ad, 34A-ad, and 35A-ad | 300 mg to 550 mg | 50 mg to 200 mg | 50 mg to 300 mg | 0.1 mg to 20.0 mg |
| 31A-ae, 32A-ae, 33A-ae, 34A-ae, and 35A-ae | 300 mg to 500 mg | 50 mg to 175 mg | 50 mg to 250 mg | 0.1 mg to 15.0 mg |

Following the pattern of the tables above, the table below serves as Tables 31B, 32B, 33B, 34B, and 35B and provides combinations of agents that can be used in the uses, methods, regimens, and pharmaceutical compositions herein. Each of the listed combinations of agents includes amounts of efavirenz emtricitabine, and TAF, and differs only in the TLR7 Modulating Compound included. In the separate tables the TLR7 Modulating Compound, or a pharmaceutically acceptable salt thereof (collectively, TLR7 MC), comprises a) a compound of Formula II in Table 31B, b) the compound of Example 4 in Table 32B, c) the compound of Example 49 in Table 33B, d) the compound of Example 119 in Table 34B, and e) the compound of Example 120 in Table 35B.

Tables 31B, 32B, 33B, 34B, and 35B

| Comp. Ex. | efavirenz | emtricitabine | TAF | TLR7 MC |
|---|---|---|---|---|
| 31B-a, 32B-a, 33B-a, 34B-a, and 35B-a | 500 mg to 700 mg | 150 mg to 250 mg | 15 mg to 35 mg | 0.1 mg to 15 mg |
| 31B-b, 32B-b, 33B-b, 34B-b, and 35B-b | 500 mg to 700 mg | 150 mg to 250 mg | 15 mg to 35 mg | 2 mg to 6 mg |
| 31B-c, 32B-c, 33B-c, 34B-c, and 35B-c | 500 mg to 700 mg | 150 mg to 250 mg | 15 mg to 35 mg | 5 mg to 10 mg |
| 31B-d, 32B-d, 33B-d, 34B-d, and 35B-d | 500 mg to 700 mg | 150 mg to 250 mg | 15 mg to 35 mg | 10 mg to 15 mg |
| 31B-e, 32B-e, 33B-e, 34B-e, and 35B-e | 550 mg to 650 mg | 175 mg to 225 mg | 20 mg to 30 mg | 0.1 mg to 15 mg |
| 31B-f, 32B-f, 33B-f, 34B-f, and 35B-f | 550 mg to 650 mg | 175 mg to 225 mg | 20 mg to 30 mg | 2 mg to 6 mg |
| 31B-g, 32B-g, 33B-g, 34B-g, and 35B-g | 550 mg to 650 mg | 175 mg to 225 mg | 20 mg to 30 mg | 5 mg to 10 mg |
| 31B-h, 32B-h, 33B-h, 34B-h, and 35B-h | 550 mg to 650 mg | 175 mg to 225 mg | 20 mg to 30 mg | 10 mg to 15 mg |
| 31B-i, 32B-i, 33B-i, 34B-i, and 35B-i | 575 mg to 625 mg | 175 mg to 225 mg | 20 mg to 30 mg | 0.1 mg to 15 mg |
| 31B-j, 32B-j, 33B-j, 34B-j, and 35B-j | 575 mg to 625 mg | 175 mg to 225 mg | 20 mg to 30 mg | 2 mg to 6 mg |
| 31B-k, 32B-k, 33B-k, 34B-k, and 35B-k | 575 mg to 625 mg | 175 mg to 225 mg | 20 mg to 30 mg | 5 mg to 10 mg |
| 31B-l, 32B-l, 33B-l, 34B-l, and 35B-l | 575 mg to 625 mg | 175 mg to 225 mg | 20 mg to 30 mg | 10 mg to 15 mg |
| 31B-m, 32B-m, 33B-m, 34B-m, and 35B-m | 600 mg | 200 mg | 25 mg | 0.1 mg to 15 mg |
| 31B-n, 32B-n, 33B-n, 34B-n, and 35B-n | 600 mg | 200 mg | 25 mg | 2 mg to 6 mg |
| 31B-o, 32B-o, 33B-o, 34B-o, and 35B-o | 600 mg | 200 mg | 25 mg | 5 mg to 10 mg |
| 31B-p, 32B-p, 33B-p, 34B-p, and 35B-p | 600 mg | 200 mg | 25 mg | 10 mg to 15 mg |
| 31B-q, 32B-q, 33B-q, 34B-q, and 35B-q | 600 mg | 200 mg | 25 mg | 4 mg |
| 31B-r, 32B-r, 33B-r, 34B-r, and 35B-r | 600 mg | 200 mg | 25 mg | 5 mg |
| 31B-s, 32B-s, 33B-s, 34B-s, and 35B-s | 600 mg | 200 mg | 25 mg | 6 mg |
| 31B-t, 32B-t, 33B-t, 34B-t, and 35B-t | 600 mg | 200 mg | 25 mg | 7 mg |
| 31B-u, 32B-u, 33B-u, 34B-u, and 35B-u | 600 mg | 200 mg | 25 mg | 8 mg |
| 31B-v, 32B-v, 33B-v, 34B-v, and 35B-v | 600 mg | 200 mg | 25 mg | 9 mg |
| 31B-w, 32B-w, 33B-w, 34B-w, and 35B-w | 600 mg | 200 mg | 25 mg | 10 mg |
| 31B-x, 32B-x, 33B-x, 34B-x, and 35B-x | 600 mg | 200 mg | 25 mg | 11 mg |
| 31B-y, 32B-y, 33B-y, 34B-y, and 35B-y | 600 mg | 200 mg | 25 mg | 12 mg |
| 31B-z, 32B-z, 33B-z, 34B-z, and 35B-z | 500 mg to 700 mg | 150 mg to 250 mg | 25 mg | 0.1 mg to 25.0 mg |
| 31B-aa, 32B-aa, 33B-aa, 34B-aa, and 35B-aa | 500 mg to 700 mg | 150 mg to 250 mg | 25 mg | 15 mg to 20 mg |
| 31B-ab, 32B-ab, 33B-ab, 34B-ab, and 35B-ab | 500 mg to 700 mg | 150 mg to 250 mg | 25 mg | 20 mg to 25 |
| 31B-ac, 32B-ac, 33B-ac, 34B-ac, and 35B-ac | 300 mg to 600 mg | 50 mg to 250 mg | 1 mg to 25 mg | 0.1 mg to 25.0 mg |
| 31B-ad, 32B-ad, 33B-ad, 34B-ad, and 35B-ad | 300 mg to 550 mg | 50 mg to 200 mg | 1 mg to 20 mg | 0.1 mg to 20.0 mg |
| 31B-ae, 32B-ae, 33B-ae, 34B-ae, and 35B-ae | 300 mg to 500 mg | 50 mg to 175 mg | 1 mg to 15 mg | 0.1 mg to 15.0 mg |

Combinations of Elvitegravir/Cobicistat/Emtricitabine/ TAF/TLR7 Modulators

Pharmaceutically effective amounts of the TLR7 modulating compounds, including those of Formula II, or a pharmaceutically acceptable salt thereof, as well as the compounds of Examples 4, 49, 119, 120, and 121, or a pharmaceutically acceptable salt thereof, can be combined with pharmaceutically effective amounts of elvitegravir, cobicistat, emtricitabine, and TAF for use in the methods of treatment discussed herein. For instance, as separate dosage forms, a pharmaceutically effective dose of a TLR7 modulating compound, or pharmaceutically acceptable salt thereof, may be combined in a treatment regimen of 150 mg elvitegravir, 150 mg cobicistat, 200 mg emtricitabine, and 300 mg tenofovir disoproxil fumarate, such as with a STRIBILD® tablet available from Gilead Sciences, Inc.

Also provided is a pharmaceutical composition comprising:
- a) a pharmaceutically effective amount of elvitegravir;
- b) a pharmaceutically effective amount of cobicistat;
- c) a pharmaceutically effective amount of emtricitabine;
- d) a pharmaceutically effective amount of tenofovir alafenamide (TAF), or a pharmaceutically acceptable salt thereof;
- e) a pharmaceutically effective amount of a TLR7 modulating compound, or a pharmaceutically acceptable salt thereof; and
- f) a pharmaceutically acceptable carrier or excipient.

Also provided is a pharmaceutical composition comprising:
- a) a pharmaceutically effective amount of elvitegravir;
- b) a pharmaceutically effective amount of cobicistat;
- c) a pharmaceutically effective amount of emtricitabine;
- d) a pharmaceutically effective amount of tenofovir alafenamide (TAF), or a pharmaceutically acceptable salt thereof;
- e) a pharmaceutically effective amount of a compound of Formula II, or a pharmaceutically acceptable salt thereof; and
- f) a pharmaceutically acceptable carrier or excipient.

Also provided are 19 separate pharmaceutical compositions, each comprising 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of a compound selected from one of the group of Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof. Each of the separate pharmaceutical compositions comprises one formula, for instance, one embodiment comprises 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of a compound of Formula III, or a pharmaceutically acceptable salt thereof, another comprises 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of a compound of Formula III(a), or a pharmaceutically acceptable salt thereof, etc.

Also provided are another group of separate pharmaceutical, each of the separate compositions comprising 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of a compound selected from the group of Examples 1 through 124. The first of the group of separate compositions comprises 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of the compound of Example 1, or a pharmaceutically acceptable salt thereof, the next separate composition comprises 1) a pharmaceutically effective amount of elvitegravir; 2) a pharmaceutically effective amount of emtricitabine; 3) a pharmaceutically effective amount of cobicistat; 4) a pharmaceutically effective amount of tenofovir alafenamide; 5) a pharmaceutically acceptable carrier or excipient; and 6) a pharmaceutically effective amount of the compound of Example 2, or a pharmaceutically acceptable salt thereof, etc.

Tables 36A, 37A, 38A, 39A, and 40A

Also provided are the specific pharmaceutical compositions and combinations comprising a pharmaceutically acceptable carrier or excipient and the individual pharmaceutically effective amounts of a) elvitegravir; b) emtricitabine; c) cobicistat; d) tenofovir alafenamide (TAF), and e) a pharmaceutically effective amount of a TLR7 Modulating Compound, or a pharmaceutically acceptable salt thereof (collectively "TLR7 MC").

Following the pattern of the tables above, the table below serves as Tables 36A, 37A, 38A, 39A, and 40A and provides combinations of agents that can be used in the uses, methods, regimens, and pharmaceutical compositions herein. Each of the listed combinations of agents includes amounts of elvitegravir, emtricitabine, cobicistat, and TAF, and differs only in the TLR7 Modulating Compound included. In the separate tables the TLR7 Modulating Compound, or a pharmaceutically acceptable salt thereof, comprises a) a compound of Formula II in Table 36A, b) the compound of Example 4 in Table 37A, c) the compound of Example 49 in Table 38A, d) the compound of Example 119 in Table 39A, and e) the compound of Example 120 in Table 40A.

| Comp. Ex. | elvitegravir | emtricitabine | cobicistat | TAF | TLR7 MC |
|---|---|---|---|---|---|
| 36A-a, 37A-a, 38A-a, 39A-a, and 40A-a | 100 mg to 200 mg | 150 mg to 250 mg | 100 mg to 200 mg | 5 mg to 50 mg | 0.1 mg to 15 mg |
| 36A-b, 37A-b, 38A-b, 39A-b, and 40A-b | 100 mg to 200 mg | 150 mg to 250 mg | 100 mg to 200 mg | 5 mg to 50 mg | 2 mg to 6 mg |

-continued

| Comp. Ex. | elvitegravir | emtricitabine | cobicistat | TAF | TLR7 MC |
|---|---|---|---|---|---|
| 36A-c, 37A-c, 38A-c, 39A-c, and 40A-c | 100 mg to 200 mg | 150 mg to 250 mg | 100 mg to 200 mg | 5 mg to 50 mg | 5 mg to 10 mg |
| 36A-d, 37A-d, 38A-d, 39A-d, and 40A-d | 100 mg to 200 mg | 150 mg to 250 mg | 100 mg to 200 mg | 5 mg to 50 mg | 10 mg to 15 mg |
| 36A-e, 37A-e, 38A-e, 39A-e, and 40A-e | 100 mg to 200 mg | 150 mg to 250 mg | 100 mg to 200 mg | 5 mg to 30 mg | 0.1 mg to 15 mg |
| 36A-f, 37A-f, 38A-f, 39A-f, and 40A-f | 100 mg to 200 mg | 150 mg to 250 mg | 100 mg to 200 mg | 5 mg to 30 mg | 2 mg to 6 mg |
| 36A-g, 37A-g, 38A-g, 39A-g, and 40A-g | 100 mg to 200 mg | 150 mg to 250 mg | 100 mg to 200 mg | 5 mg to 30 mg | 5 mg to 10 mg |
| 36A-h, 37A-h, 38A-h, 39A-h, and 40A-h | 100 mg to 200 mg | 150 mg to 250 mg | 100 mg to 200 mg | 5 mg to 30 mg | 10 mg to 15 mg |
| 36A-i, 37A-i, 38A-i, 39A-i, and 40A-i | 125 mg to 175 mg | 175 mg to 225 mg | 125 mg to 175 mg | 5 mg to 30 mg | 0.1 mg to 15 mg |
| 36A-j, 37A-j, 38A-j, 39A-j, and 40A-j | 125 mg to 175 mg | 175 mg to 225 mg | 125 mg to 175 mg | 5 mg to 30 mg | 2 mg to 6 mg |
| 36A-k, 37A-k, 38A-k, 39A-k, and 40A-k | 125 mg to 175 mg | 175 mg to 225 mg | 125 mg to 175 mg | 5 mg to 30 mg | 5 mg to 10 mg |
| 36A-l, 37A-l, 38A-l, 39A-l, and 40A-l | 125 mg to 175 mg | 175 mg to 225 mg | 125 mg to 175 mg | 5 mg to 30 mg | 10 mg to 15 mg |
| 36A-m, 37A-m, 38A-m, 39A-m, and 40A-m | 125 mg to 175 mg | 175 mg to 225 mg | 125 mg to 175 mg | 5 mg to 15 mg | 0.1 mg to 15 mg |
| 36A-n, 37A-n, 38A-n, 39A-n, and 40A-n | 125 mg to 175 mg | 175 mg to 225 mg | 125 mg to 175 mg | 5 mg to 15 mg | 2 mg to 6 mg |
| 36A-o, 37A-o, 38A-o, 39A-o, and 40A-o | 125 mg to 175 mg | 175 mg to 225 mg | 125 mg to 175 mg | 5 mg to 15 mg | 5 mg to 10 mg |
| 36A-p, 37A-p, 38A-p, 39A-p, and 40A-p | 125 mg to 175 mg | 175 mg to 225 mg | 125 mg to 175 mg | 5 mg to 15 mg | 10 mg to 15 mg |
| 36A-q, 37A-q, 38A-q, 39A-q, and 40A-q | 125 mg to 175 mg | 175 mg to 225 mg | 125 mg to 175 mg | 20 mg to 30 mg | 0.1 mg to 15 mg |
| 36A-r, 37A-r, 38A-r, 39A-r, and 40A-r | 125 mg to 175 mg | 175 mg to 225 mg | 125 mg to 175 mg | 20 mg to 30 mg | 2 mg to 6 mg |
| 36A-s, 37A-s, 38A-s, 39A-s, and 40A-s | 125 mg to 175 mg | 175 mg to 225 mg | 125 mg to 175 mg | 20 mg to 30 mg | 5 mg to 10 mg |
| 36A-t, 37A-t, 38A-t, 39A-t, and 40A-t | 125 mg to 175 mg | 175 mg to 225 mg | 125 mg to 175 mg | 20 mg to 30 mg | 10 mg to 15 mg |
| 36A-u, 37A-u, 38A-u, 39A-u, and 40A-u | 150 mg | 200 mg | 150 mg | 5 mg to 30 mg | 0.1 mg to 15 mg |
| 36A-v, 37A-v, 38A-v, 39A-v, and 40A-v | 150 mg | 200 mg | 150 mg | 5 mg to 30 mg | 2 mg to 6 mg |
| 36A-w, 37A-w, 38A-w, 39A-w, and 40A-w | 150 mg | 200 mg | 150 mg | 5 mg to 30 mg | 5 mg to 10 mg |
| 36A-x, 37A-x, 38A-x, 39A-x, and 40A-x | 150 mg | 200 mg | 150 mg | 5 mg to 30 mg | 10 mg to 15 mg |
| 36A-y, 37A-y, 38A-y, 39A-y, and 40A-y | 150 mg | 200 mg | 150 mg | 5 mg to 15 mg | 0.1 mg to 15 mg |
| 36A-z, 37A-z, 38A-z, 39A-z, and 40A-z | 150 mg | 200 mg | 150 mg | 5 mg to 15 mg | 2 mg to 6 mg |
| 36A-aa, 37A-aa, 38A-aa, 39A-aa, and 40A-aa | 150 mg | 200 mg | 150 mg | 5 mg to 15 mg | 5 mg to 10 mg |
| 36A-ab, 37A-ab, 38A-ab, 39A-ab, and 40A-ab | 150 mg | 200 mg | 150 mg | 5 mg to 15 mg | 10 mg to 15 mg |
| 36A-ac, 37A-ac, 38A-ac, 39A-ac, and 40A-ac | 150 mg | 200 mg | 150 mg | 20 mg to 30 mg | 0.1 mg to 15 mg |
| 36A-ad, 37A-ad, 38A-ad, 39A-ad, and 40A-ad | 150 mg | 200 mg | 150 mg | 20 mg to 30 mg | 2 mg to 6 mg |
| 36A-ae, 37A-ae, 38A-ae, 39A-ae, and 40A-ae | 150 mg | 200 mg | 150 mg | 20 mg to 30 mg | 5 mg to 10 mg |
| 36A-af, 37A-af, 38A-af, 39A-af, and 40A-of | 150 mg | 200 mg | 150 mg | 20 mg to 30 mg | 10 mg to 15 mg |
| 36A-ag, 37A-ag, 38A-ag, 39A-ag, and 40A-ag | 100 mg to 200 mg | 150 mg to 250 mg | 100 mg to 200 mg | 5 mg to 50 mg | 0.1 mg to 25.0 mg |
| 36A-ah, 37A-ah, 38A-ah, 39A-ah, and 40A-ah | 100 mg to 200 mg | 150 mg to 250 mg | 100 mg to 200 mg | 5 mg to 50 mg | 15 mg to 20 mg |
| 36A-ai, 37A-ai, 38A-ai, 39A-ai, and 40A-ai | 100 mg to 200 mg | 150 mg to 250 mg | 100 mg to 200 mg | 5 mg to 50 mg | 20 mg to 25 mg |
| 36A-aj, 37A-aj, 38A-aj, 39A-aj, and 40A-aj | 125 mg to 175 mg | 175 mg to 225 mg | 125 mg to 175 mg | 5 mg to 15 mg | 0.1 mg to 25.0 mg |
| 36A-ak, 37A-ak, 38A-ak, 39A-ak, and 40A-ak | 125 mg to 175 mg | 175 mg to 225 mg | 125 mg to 175 mg | 5 mg to 15 mg | 15 mg to 20 mg |
| 36A-al, 37A-al, 38A-al, 39A-al, and 40A-al | 125 mg to 175 mg | 175 mg to 225 mg | 125 mg to 175 mg | 5 mg to 15 mg | 20 mg to 25 mg |
| 36A-am, 37A-am, 38A-am, 39A-am, and 40A-am | 50 mg to 150 mg | 50 mg to 250 mg | 50 mg to 200 mg | 1 mg to 25 mg | 0.1 mg to 25.0 mg |
| 36A-an, 37A-an, 38A-an, 39A-an, and 40A-an | 50 mg to 125 mg | 50 mg to 200 mg | 50 mg to 150 mg | 1 mg to 20 mg | 0.1 mg to 20.0 mg |

| Comp. Ex. | elvitegravir | emtricitabine | cobicistat | TAF | TLR7 MC |
|---|---|---|---|---|---|
| 36A-ao, 37A-ao, 38A-ao, 39A-ao, and 40A-ao | 50 mg to 100 mg | 50 mg to 175 mg | 50 mg to 125 mg | 1 mg to 15 mg | 0.1 mg to 15.0 mg |

Also provided are pharmaceutical combinations and compositions comprising a pharmaceutically effective amount of a TLR7 modulating compound, a pharmaceutically effective amount of TAF, a pharmaceutically effective amount of emtricitabine, and a pharmaceutically effective amount of one or more antiviral agents selected from the group of:

non-nucleoside reverse transcriptase inhibitors, such as etravirine, delaviridine, efavirenz, and nevirapine, and pharmaceutically acceptable salts thereof;

nucleoside reverse transcriptase inhibitors, such as lamivudine, zidovudine, emtricitabine, abacavir, zalcitabine, TDF, and stavudine, and pharmaceutically acceptable salts thereof;

protease inhibitors, such as amprenavir, tipranavir, indinavir, saquinavir, lopinovir, ritonavir, fosamprenavir, darunivir, atazanavir, and nelfinavir, and pharmaceutically acceptable salts thereof;

CCR5 antagonists, such as maraviroc and enfuvirtide, and pharmaceutically acceptable salts thereof;

HIV integrase strand transfer inhibitors, such as raltegravir, and pharmaceutically acceptable salts thereof;

non-catalytic site integrase inhibitors, such as B1224436; and capsid inhibitors.

Within each of the pharmaceutical compositions listed herein which include the component "tenofovir alafenamide, or a pharmaceutically acceptable salt thereof" or "TAF" there is a further embodiment in which that component comprises tenofovir alafenamide fumarate in the amount indicated for "tenofovir alafenamide, or a pharmaceutically acceptable salt thereof" and all other components or elements are as listed for the specific composition. Within each of the pharmaceutical compositions listed herein which include the component "tenofovir alafenamide, or a pharmaceutically acceptable salt thereof" there is a further embodiment in which that component comprises tenofovir alafenamide hemifumarate in the amount indicated for "tenofovir alafenamide, or a pharmaceutically acceptable salt thereof" and all other components or elements are as listed for the specific composition.

Tables 36B, 37B, 38B, 39B, and 40B

Also provided are the specific pharmaceutical compositions and combinations comprising a pharmaceutically acceptable carrier or excipient and the individual pharmaceutically effective amounts of a) elvitegravir; b) emtricitabine; c) cobicistat; d) TDF, and e) a pharmaceutically effective amount of a TLR7 Modulating Compound or a pharmaceutically acceptable salt thereof (collectively "TLR7 MC").

Following the pattern of the tables above, the table below serves as Tables 36B, 37B, 38B, 39B, and 40B and provides combinations of agents that can be used in the uses, methods, regimens, and pharmaceutical compositions herein. Each of the listed combinations of agents includes amounts of elvitegravir, emtricitabine, TDF, and cobicistat, and differs only in the TLR7 Modulating Compound included. In the separate tables the TLR7 Modulating Compound, or a pharmaceutically acceptable salt thereof, comprises a) a compound of Formula II in Table 36B, b) the compound of Example 4 in Table 37B, c) the compound of Example 49 in Table 38B, d) the compound of Example 119 in Table 39B, and e) the compound of Example 120 in Table 40B.

| Comp. Ex. | elvitegravir | emtricitabine | cobicistat | TDF | TLR7 MC |
|---|---|---|---|---|---|
| 36B-a, 37B-a, 38B-a, 39B-a, and 40B-a | 100 mg to 200 mg | 150 mg to 250 mg | 100 mg to 200 mg | 250 mg to 350 mg | 0.1 mg to 15 mg |
| 36B-b, 37B-b, 38B-b, 39B-b, and 40B-b | 100 mg to 200 mg | 150 mg to 250 mg | 100 mg to 200 mg | 250 mg to 350 mg | 2 mg to 6 mg |
| 36B-c, 37B-c, 38B-c, 39B-c, and 40B-c | 100 mg to 200 mg | 150 mg to 250 mg | 100 mg to 200 mg | 250 mg to 350 mg | 5 mg to 10 mg |
| 36B-d, 37B-d, 38B-d, 39B-d, and 40B-d | 100 mg to 200 mg | 150 mg to 250 mg | 100 mg to 200 mg | 250 mg to 350 mg | 10 mg to 15 mg |
| 36B-e, 37B-e, 38B-e, 39B-e, and 40B-e | 100 mg to 200 mg | 150 mg to 250 mg | 100 mg to 200 mg | 275 mg to 325 mg | 0.1 mg to 15 mg |
| 36B-f, 37B-f, 38B-f, 39B-f, and 40B-f | 100 mg to 200 mg | 150 mg to 250 mg | 100 mg to 200 mg | 275 mg to 325 mg | 2 mg to 6 mg |
| 36B-g, 37B-g, 38B-g, 39B-g, and 40B-g | 100 mg to 200 mg | 150 mg to 250 mg | 100 mg to 200 mg | 275 mg to 325 mg | 5 mg to 10 mg |
| 36B-h, 37B-h, 38B-h, 39B-h, and 40B-h | 100 mg to 200 mg | 150 mg to 250 mg | 100 mg to 200 mg | 275 mg to 325 mg | 10 mg to 15 mg |
| 36B-i, 37B-i, 38B-i, 39B-i, and 40B-i | 125 mg to 175 mg | 175 mg to 225 mg | 125 mg to 175 mg | 275 mg to 325 mg | 0.1 mg to 15 mg |
| 36B-j, 37B-j, 38B-j, 39B-j, and 40B-j | 125 mg to 175 mg | 175 mg to 225 mg | 125 mg to 175 mg | 275 mg to 325 mg | 2 mg to 6 mg |
| 36B-k, 37B-k, 38B-k, 39B-k, and 40B-k | 125 mg to 175 mg | 175 mg to 225 mg | 125 mg to 175 mg | 275 mg to 325 mg | 5 mg to 10 mg |
| 36B-l, 37B-l, 38B-l, 39B-l, and 40B-l | 125 mg to 175 mg | 175 mg to 225 mg | 125 mg to 175 mg | 275 mg to 325 mg | 10 mg to 15 mg |
| 36B-m, 37B-m, 38B-m, 39B-m, and 40B-m | 125 mg to 175 mg | 175 mg to 225 mg | 125 mg to 175 mg | 275 mg to 325 mg | 15 mg to 20 mg |
| 36B-n, 37B-n, 38B-n, 39B-n, and 40B-n | 125 mg to 175 mg | 175 mg to 225 mg | 125 mg to 175 mg | 275 mg to 325 mg | 20 mg to 25 mg |
| 36B-o, 37B-o, 38B-o, 39B-o, and 40B-o | 150 mg | 200 mg | 150 mg | 275 mg to 325 mg | 0.1 mg to 15 mg |

-continued

| Comp. Ex. | elvitegravir | emtricitabine | cobicistat | TDF | TLR7 MC |
|---|---|---|---|---|---|
| 36B-p, 37B-p, 38B-p, 39B-p, and 40B-p | 150 mg | 200 mg | 150 mg | 275 mg to 325 mg | 2 mg to 6 mg |
| 36B-q, 37B-q, 38B-q, 39B-q, and 40B-q | 150 mg | 200 mg | 150 mg | 275 mg to 325 mg | 5 mg to 10 mg |
| 36B-r, 37B-r, 38B-r, 39B-r, and 40B-r | 150 mg | 200 mg | 150 mg | 275 mg to 325 mg | 10 mg to 15 mg |
| 36B-s, 37B-s, 38B-s, 39B-s, and 40B-s | 150 mg | 200 mg | 150 mg | 300 mg | 0.1 mg to 15 mg |
| 36B-t, 37B-t, 38B-t, 39B-t, and 40B-t | 150 mg | 200 mg | 150 mg | 300 mg | 2 mg to 6 mg |
| 36B-u, 37B-u, 38B-u, 39B-u, and 40B-u | 150 mg | 200 mg | 150 mg | 300 mg | 5 mg to 10 mg |
| 36B-v, 37B-v, 38B-v, 39B-v, and 40B-v | 150 mg | 200 mg | 150 mg | 300 mg | 10 mg to 15 mg |
| 36B-w, 37B-w, 38B-w, 39B-w, and 40B-w | 100 mg to 200 mg | 150 mg to 250 mg | 100 mg to 200 mg | 250 mg to 350 mg | 0.1 mg to 25.0 mg |
| 36B-x, 37B-x, 38B-x, 39B-x, and 40B-x | 100 mg to 200 mg | 150 mg to 250 mg | 100 mg to 200 mg | 250 mg to 350 mg | 15 mg to 20 mg |
| 36B-y, 37B-y, 38B-y, 39B-y, and 40B-y | 100 mg to 200 mg | 150 mg to 250 mg | 100 mg to 200 mg | 250 mg to 350 mg | 20 mg to 25 mg |
| 36B-z, 37B-z, 38B-z, 39B-z, and 40B-z | 125 mg to 175 mg | 175 mg to 225 mg | 125 mg to 175 mg | 150 mg to 300 mg | 0.1 mg to 25.0 mg |
| 36B-aa, 37B-aa, 38B-aa, 39B-aa, and 40B-aa | 50 mg to 150 mg | 50 mg to 250 mg | 50 mg to 200 mg | 150 mg to 250 mg | 0.1 mg to 25.0 mg |
| 36B-ab, 37B-ab, 38B-ab, 39B-ab, and 40B-ab | 50 mg to 125 mg | 50 mg to 200 mg | 50 mg to 150 mg | 150 mg to 200 mg | 0.1 mg to 20.0 mg |
| 36B-ac, 37B-ac, 38B-ac, 39B-ac, and 40B-ac | 50 mg to 100 mg | 50 mg to 175 mg | 50 mg to 125 mg | 100 mg to 150 mg | 0.1 mg to 15.0 mg |

Also provided are pharmaceutical combinations and compositions comprising a pharmaceutically effective amount of a TLR7 modulating compound, a pharmaceutically effective amount of TDF, a pharmaceutically effective amount of emtricitabine, and a pharmaceutically effective amount of one or more antiviral agents selected from the group of:

non-nucleoside reverse transcriptase inhibitors, such as etravirine, delaviridine, efavirenz, and nevirapine, and pharmaceutically acceptable salts thereof;

nucleoside reverse transcriptase inhibitors, such as lamivudine, zidovudine, emtricitabine, abacavir, zalcitabine, TAF, and stavudine, and pharmaceutically acceptable salts thereof;

protease inhibitors, such as amprenavir, tipranavir, indinavir, saquinavir, lopinovir, ritonavir, fosamprenavir, darunivir, atazanavir, and nelfinavir, and pharmaceutically acceptable salts thereof;

CCR5 antagonists, such as maraviroc and enfuvirtide, and pharmaceutically acceptable salts thereof;

HIV integrase strand transfer inhibitors, such as raltegravir, and pharmaceutically acceptable salts thereof;

non-catalytic site integrase inhibitors, such as B1224436; and capsid inhibitors.

Combination of Atazanavir Sulfate, Cobicistat, and a TLR7 Modulator

Pharmaceutically effective amounts of the TLR7 modulating compounds of Formula II, or a pharmaceutically acceptable salt thereof, as well as the compounds of Examples 119, 120, and 121, or a pharmaceutically acceptable salt thereof, can be combined with pharmaceutically effective amounts of atazanavir sulfate and cobicistat for use in the methods of treatment discussed herein. For instance, as separate dosage forms, a pharmaceutically effective dose of a TLR7 modulating compound, or pharmaceutically acceptable salt thereof, may be combined in a treatment regimen with a pharmaceutically effective dose of cobicistat and a REYATAZ® 150 mg, 200 mg, or 300 mg atazanavir sulfate capsule, which are available from Bristol-Meyers Squibb Co. As another example, a combined dosage unit, such as a tablet or capsule, comprising a pharmaceutically effective amount of cobicistat and a pharmaceutically effective amount of a TLR7 modulating compound, or pharmaceutically acceptable salt thereof, may be administered to a human in need thereof in coordination with administration of a pharmaceutically effective dose of atazanavir or atazanavir sulfate, such as seen in the 150 mg, 200 mg, or 300 mg REYATAZ® capsules.

Also provided is a pharmaceutical composition comprising:
  a) a pharmaceutically effective amount of atazanavir, or a pharmaceutically acceptable salt thereof;
  b) a pharmaceutically effective amount of cobicistat;
  c) a pharmaceutically effective amount of a compound which modulates TLR7 activity; and
  d) a pharmaceutically acceptable carrier or excipient.

Also provided is a pharmaceutical composition comprising:
  a) a pharmaceutically effective amount of atazanavir sulfate;
  b) a pharmaceutically effective amount of cobicistat;
  c) a pharmaceutically effective amount of a compound of Formula II or a pharmaceutically acceptable salt thereof; and
  d) a pharmaceutically acceptable carrier or excipient.

Also provided is a pharmaceutical composition comprising:
  a) a pharmaceutically effective amount of cobicistat;
  b) a pharmaceutically effective amount of a compound which modulates TLR7 activity; and
  c) a pharmaceutically acceptable carrier or excipient.

Also provided is a pharmaceutical composition comprising:
- a) a pharmaceutically effective amount of cobicistat;
- b) a pharmaceutically effective amount of a compound of Formula II or a pharmaceutically acceptable salt thereof; and
- c) a pharmaceutically acceptable carrier or excipient.

Also provided is a pharmaceutical composition comprising:
- d) a pharmaceutically effective amount of ritonavir;
- e) a pharmaceutically effective amount of a compound which modulates TLR7 activity; and
- f) a pharmaceutically acceptable carrier or excipient.

Also provided is a pharmaceutical composition comprising:
- d) a pharmaceutically effective amount of ritonavir;
- e) a pharmaceutically effective amount of a compound of Formula II or a pharmaceutically acceptable salt thereof; and
- f) a pharmaceutically acceptable carrier or excipient.

Also provided are 19 separate pharmaceutical compositions, each comprising 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of a compound selected from one of the group of Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III(f)(1), and Formula III(f)(2); or a pharmaceutically acceptable salt thereof. Each of the separate pharmaceutical compositions comprises one formula, for instance, one embodiment comprises 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of a compound selected from one of the group of Formula III, or a pharmaceutically acceptable salt thereof, another comprises 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of a compound selected from one of the group of Formula III(a), or a pharmaceutically acceptable salt thereof, etc.

Also provided are another group of separate pharmaceutical, each of the separate compositions comprises 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of a compound selected from the group of Examples 1 through 124, or a pharmaceutically acceptable salt thereof. The first of the group of separate compositions comprises 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of the compound of Example 1, or a pharmaceutically acceptable salt thereof, the next separate composition comprises 1) a pharmaceutically effective amount of atazanavir, or a pharmaceutically acceptable salt thereof; 2) a pharmaceutically effective amount of cobicistat; 3) a pharmaceutically acceptable carrier or excipient; and 4) a pharmaceutically effective amount of the compound of Example 2, or a pharmaceutically acceptable salt thereof, etc.

Pharmaceutical Composition Tables 41, 42, 43, 44, and 45

Also provided are the specific pharmaceutical combinations and compositions, wherein the designated compositions comprise a pharmaceutically acceptable carrier or excipient and the individual pharmaceutically effective amounts of a) atazanavir sulfate; b) cobicistat; and c) a pharmaceutically effective amount of a TLR7 modulating compound, or a pharmaceutically acceptable salt thereof (collectively "TLR7 MC").

Following the pattern of the tables above, the table below serves as Tables 41, 42, 43, 44, and 45 and provides combinations of agents that can be used in the uses, methods, regimens, and pharmaceutical compositions herein. Each of the listed combinations of agents includes amounts of emtricitabine, TDF, and atazanavir sulfate, and differs only in the TLR7 Modulating Compound included. In the separate tables the TLR7 Modulating Compound, or a pharmaceutically acceptable salt thereof, comprises a) a compound of Formula II in Table 41, b) the compound of Example 4 in Table 42, c) the compound of Example 49 in Table 43, d) the compound of Example 119 in Table 44, and e) the compound of Example 120 in Table 45.

Tables 41, 42, 43, 44, and 45

| Comp. Ex. | atazanavir sulfate | cobicistat | TLR7 MC |
|---|---|---|---|
| 41-a, 42-a, 43-a, 44-a, and 45-a | 250 mg to 350 mg | 100 mg to 200 mg | 0.1 mg to 15 mg |
| 41-b, 42-b, 43-b, 44-b, and 45-b | 250 mg to 350 mg | 100 mg to 200 mg | 2 mg to 6 mg |
| 41-c, 42-c, 43-c, 44-c, and 45-c | 250 mg to 350 mg | 100 mg to 200 mg | 5 mg to 10 mg |
| 41-d, 42-d, 43-d, 44-d, and 45-d | 250 mg to 350 mg | 100 mg to 200 mg | 10 mg to 15 mg |
| 41-e, 42-e, 43-e, 44-e, and 45-e | 275 mg to 325 mg | 125 mg to 175 mg | 0.1 mg to 15 mg |
| 41-f, 42-f, 43-f, 44-f, and 45-f | 275 mg to 325 mg | 125 mg to 175 mg | 2 mg to 6 mg |
| 41-g, 42-g, 43-g, 44-g, and 45-g | 275 mg to 325 mg | 125 mg to 175 mg | 5 mg to 10 mg |
| 41-h, 42-h, 43-h, 44-h, and 45-h | 275 mg to 325 mg | 125 mg to 175 mg | 10 mg to 15 mg |
| 41-i, 42-i, 43-i, 44-i, and 45-i | 290 mg to 310 mg | 140 mg to 160 mg | 0.1 mg to 15 mg |
| 41-j, 42-j, 43-j, 44-j, and 45-j | 290 mg to 310 mg | 140 mg to 160 mg | 2 mg to 6 mg |

-continued

| Comp. Ex. | atazanavir sulfate | cobicistat | TLR7 MC |
|---|---|---|---|
| 41-k, 42-k, 43-k, 44-k, and 45-k | 290 mg to 310 mg | 140 mg to 160 mg | 5 mg to 10 mg |
| 41-l, 42-l, 43-l, 44-l, and 45-l | 290 mg to 310 mg | 140 mg to 160 mg | 10 mg to 15 mg |
| 41-m, 42-m, 43-m, 44-m, and 45-m | 300 mg | 150 mg | 0.1 mg to 15 mg |
| 41-n, 42-n, 43-n, 44-n, and 45-n | 300 mg | 150 mg | 2 mg to 6 mg |
| 41-o, 42-o, 43-o, 44-o, and 45-o | 300 mg | 150 mg | 5 mg to 10 mg |
| 41-p, 42-p, 43-p, 44-p, and 45-p | 300 mg | 150 mg | 10 mg to 15 mg |
| 41-q, 42-q, 43-q, 44-q, and 45-q | 300 mg | 150 mg | 4 mg |
| 41-r, 42-r, 43-r, 44-r, and 45-r | 300 mg | 150 mg | 5 mg |
| 41-s, 42-s, 43-s, 44-s, and 45-s | 300 mg | 150 mg | 6 mg |
| 41-t, 42-t, 43-t, 44-t, and 45-t | 300 mg | 150 mg | 7 mg |
| 41-u, 42-u, 43-u, 44-u, and 45-u | 300 mg | 150 mg | 8 mg |
| 41-v, 42-v, 43-v, 44-v, and 45-v | 300 mg | 150 mg | 9 mg |
| 41-w, 42-w, 43-w, 44-w, and 45-w | 300 mg | 150 mg | 10 mg |
| 41-x, 42-x, 43-x, 44-x, and 45-x | 300 mg | 150 mg | 11 mg |
| 41-y, 42-y, 43-y, 44-y, and 45-y | 300 mg | 150 mg | 12 mg |
| 41-z, 42-z, 43-z, 44-z, and 45-z | 300 mg | 150 mg | 13 mg |
| 41-aa, 42-aa, 43-aa, 44-aa, and 45-aa | 300 mg | 150 mg | 14 mg |
| 41-ab, 42-ab, 43-ab, 44-ab, and 45-ab | 300 mg | 150 mg | 15 mg |
| 41-ac, 42-ac, 43-ac, 44-ac, and 45-ac | 150 mg to 250 mg | 100 mg to 200 mg | 0.1 mg to 15 mg |
| 41-ad, 42-ad, 43-ad, 44-ad, and 45-ad | 150 mg to 250 mg | 100 mg to 200 mg | 2 mg to 6 mg |
| 41-ae, 42-ae, 43-ae, 44-ae, and 45-ae | 150 mg to 250 mg | 100 mg to 200 mg | 5 mg to 10 mg |
| 41-af, 42-af, 43-af, 44-af, and 45-af | 150 mg to 250 mg | 100 mg to 200 mg | 10 mg to 15 mg |
| 41-ag, 42-ag, 43-ag, 44-ag, and 45-ag | 175 mg to 225 mg | 125 mg to 175 mg | 0.1 mg to 15 mg |
| 41-ah, 42-ah, 43-ah, 44-ah, and 45-ah | 175 mg to 225 mg | 125 mg to 175 mg | 2 mg to 6 mg |
| 41-ai, 42-ai, 43-ai, 44-ai, and 45-ai | 175 mg to 225 mg | 125 mg to 175 mg | 5 mg to 10 mg |
| 41-aj, 42-aj, 43-aj, 44-aj, and 45-aj | 175 mg to 225 mg | 125 mg to 175 mg | 10 mg to 15 mg |
| 41-ak, 42-ak, 43-ak, 44-ak, and 45-ak | 190 mg to 210 mg | 140 mg to 160 mg | 0.1 mg to 15 mg |
| 41-al, 42-al, 43-al, 44-al, and 45-al | 190 mg to 210 mg | 140 mg to 160 mg | 2 mg to 6 mg |
| 41-am, 42-am, 43-am, 44-am, and 45-am | 190 mg to 210 mg | 140 mg to 160 mg | 5 mg to 10 mg |
| 41-an, 42-an, 43-an, 44-an, and 45-an | 190 mg to 210 mg | 140 mg to 160 mg | 10 mg to 15 mg |
| 41-ao, 42-ao, 43-ao, 44-ao, and 45-ao | 200 mg | 150 mg | 0.1 mg to 15 mg |
| 41-ap, 42-ap, 43-ap, 44-ap, and 45-ap | 200 mg | 150 mg | 2 mg to 6 mg |
| 41-aq, 42-aq, 43-aq, 44-aq, and 45-aq | 200 mg | 150 mg | 5 mg to 10 mg |
| 41-ar, 42-ar, 43-ar, 44-ar, and 45-ar | 200 mg | 150 mg | 10 mg to 15 mg |
| 41-as, 42-as, 43-as, 44-as, and 45-as | 200 mg | 150 mg | 4 mg |
| 41-at, 42-at, 43-at, 44-at, and 45-at | 200 mg | 150 mg | 5 mg |
| 41-au, 42-au, 43-au, 44-au, and 45-au | 200 mg | 150 mg | 6 mg |
| 41-av, 42-av, 43-av, 44-av, and 45-av | 200 mg | 150 mg | 7 mg |

-continued

| Comp. Ex. | atazanavir sulfate | cobicistat | TLR7 MC |
|---|---|---|---|
| 41-aw, 42-aw, 43-aw, 44-aw, and 45-aw | 200 mg | 150 mg | 8 mg |
| 41-ax, 42-ax, 43-ax, 44-ax, and 45-ax | 200 mg | 150 mg | 9 mg |
| 41-ay, 42-ay, 43-ay, 44-ay, and 45-ay | 200 mg | 150 mg | 10 mg |
| 41-az, 42-az, 43-az, 44-az, and 45-az | 200 mg | 150 mg | 11 mg |
| 41-ba, 42-ba, 43-ba, 44-ba, and 45-ba | 200 mg | 150 mg | 12 mg |
| 41-bb, 42-bb, 43-bb, 44-bb, and 45-bb | 200 mg | 150 mg | 13 mg |
| 41-bc, 42-bc, 43-bc, 44-bc, and 45-bc | 200 mg | 150 mg | 14 mg |
| 41-bd, 42-bd, 43-bd, 44-bd, and 45-bd | 200 mg | 150 mg | 15 mg |
| 41-be, 42-be, 43-be, 44-be, and 45-be | 100 mg to 200 mg | 100 mg to 200 mg | 0.1 mg to 15 mg |
| 41-bf, 42-bf, 43-bf, 44-bf, and 45-bf | 100 mg to 200 mg | 100 mg to 200 mg | 2 mg to 6 mg |
| 41-bg, 42-bg, 43-bg, 44-bg, and 45-bg | 100 mg to 200 mg | 100 mg to 200 mg | 5 mg to 10 mg |
| 41-bh, 42-bh, 43-bh, 44-bh, and 45-bh | 100 mg to 200 mg | 100 mg to 200 mg | 10 mg to 15 mg |
| 41-bi, 42-bi, 43-bi, 44-bi, and 45-bi | 125 mg to 175 mg | 125 mg to 175 mg | 0.1 mg to 15 mg |
| 41-bj, 42-bj, 43-bj, 44-bj, and 45-bj | 125 mg to 175 mg | 125 mg to 175 mg | 2 mg to 6 mg |
| 41-bk, 42-bk, 43-bk, 44-bk, and 45-bk | 125 mg to 175 mg | 125 mg to 175 mg | 5 mg to 10 mg |
| 41-bl, 42-bl, 43-bl, 44-bl, and 45-bl | 125 mg to 175 mg | 125 mg to 175 mg | 10 mg to 15 mg |
| 41-bm, 42-bm, 43-bm, 44-bm, and 45-bm | 140 mg to 160 mg | 140 mg to 160 mg | 0.1 mg to 15 mg |
| 41-bn, 42-bn, 43-bn, 44-bn, and 45-bn | 140 mg to 160 mg | 140 mg to 160 mg | 2 mg to 6 mg |
| 41-bo, 42-bo, 43-bo, 44-bo, and 45-bo | 140 mg to 160 mg | 140 mg to 160 mg | 5 mg to 10 mg |
| 41-bp, 42-bp, 43-bp, 44-bp, and 45-bp | 140 mg to 160 mg | 140 mg to 160 mg | 10 mg to 15 mg |
| 41-bq, 42-bq, 43-bq, 44-bq, and 45-bq | 150 mg | 150 mg | 0.1 mg to 15 mg |
| 41-br, 42-br, 43-br, 44-br, and 45-br | 150 mg | 150 mg | 2 mg to 6 mg |
| 41-bs, 42-bs, 43-bs, 44-bs, and 45-bs | 150 mg | 150 mg | 5 mg to 10 mg |
| 41-bt, 42-bt, 43-bt, 44-bt, and 45-bt | 150 mg | 150 mg | 10 mg to 15 mg |
| 41-bu, 42-bu, 43-bu, 44-bu, and 45-bu | 150 mg | 150 mg | 4 mg |
| 41-bv, 42-bv, 43-bv, 44-bv, and 45-bv | 150 mg | 150 mg | 5 mg |
| 41-bw, 42-bw, 43-bw, 44-bw, and 45-bw | 150 mg | 150 mg | 6 mg |
| 41-bx, 42-bx, 43-bx, 44-bx, and 45-bx | 150 mg | 150 mg | 7 mg |
| 41-by, 42-by, 43-by, 44-by, and 45-by | 150 mg | 150 mg | 8 mg |
| 41-bz, 42-bz, 43-bz, 44-bz, and 45-bz | 150 mg | 150 mg | 9 mg |
| 41-ca, 42-ca, 43-ca, 44-ca, and 45-ca | 150 mg | 150 mg | 10 mg |
| 41-cb, 42-cb, 43-cb, 44-cb, and 45-cb | 150 mg | 150 mg | 11 mg |
| 41-cc, 42-cc, 43-cc, 44-cc, and 45-cc | 150 mg | 150 mg | 12 mg |
| 41-cd, 42-cd, 43-cd, 44-cd, and 45-cd | 150 mg | 150 mg | 13 mg |
| 41-ce, 42-ce, 43-ce, 44-ce, and 45-ce | 150 mg | 150 mg | 14 mg |
| 41-cf, 42-cf, 43-cf, 44-cf, and 45-cf | 150 mg | 150 mg | 15 mg |
| 41-cg, 42-cg, 43-cg, 44-cg, and 45-cg | 25 mg to 100 mg | 50 mg to 200 mg | 0.1 mg to 25.0 mg |

-continued

| Comp. Ex. | atazanavir sulfate | cobicistat | TLR7 MC |
|---|---|---|---|
| 41-ch, 42-ch, 43-ch, 44-ch, and 45-ch | 25 mg to 100 mg | 50 mg to 150 mg | 0.1 mg to 20.0 mg |
| 41-ci, 42-ci, 43-ci, 44-ci, and 45-ci | 25 mg to 100 mg | 50 mg to 125 mg | 0.1 mg to 15.0 mg |

Pharmaceutical Composition Tables 46 through 55

Also provided are the specific pharmaceutical compositions and combinations which comprises a pharmaceutically acceptable carrier or excipient and the individual pharmaceutically effective amounts of cobicistat or ritonavir and a pharmaceutically effective amount of a TLR7 Modulating Compound or a pharmaceutically acceptable salt thereof (collectively "TLR7 MC"), listed for each individual pharmaceutical composition.

Following the pattern of the tables above, the table below serves as Tables 46, 47, 48, 49, and 50 and provides combinations of agents that can be used in the uses, methods, regimens, and pharmaceutical compositions herein. Each of the listed combinations of agents includes amounts of cobicistat and differs only in the TLR7 Modulating Compound included. In the separate tables the TLR7 Modulating Compound, or a pharmaceutically acceptable salt thereof, comprises a) a compound of Formula II in Table 46, b) the compound of Example 4 in Table 47, c) the compound of Example 49 in Table 48, d) the compound of Example 119 in Table 49, and e) the compound of Example 120 in Table 50.

Tables 46, 47, 48, 49, and 50

| Comp. Ex. | cobicistat | TLR7 MC |
|---|---|---|
| 46-a, 47-a, 48-a, 49-a, and 50-a | 100 mg to 200 mg | 0.1 mg to 15 mg |
| 46-b, 47-b, 48-b, 49-b, and 50-b | 100 mg to 200 mg | 2 mg to 6 mg |
| 46-c, 47-c, 48-c, 49-c, and 50-c | 100 mg to 200 mg | 5 mg to 10 mg |
| 46-d, 47-d, 48-d, 49-d, and 50-d | 100 mg to 200 mg | 10 mg to 15 mg |
| 46-e, 47-e, 48-e, 49-e, and 50-e | 125 mg to 175 mg | 0.1 mg to 15 mg |
| 46-f, 47-f, 48-f, 49-f, and 50-f | 125 mg to 175 mg | 2 mg to 6 mg |
| 46-g, 47-g, 48-g, 49-g, and 50-g | 125 mg to 175 mg | 5 mg to 10 mg |
| 46-h, 47-h, 48-h, 49-h, and 50-h | 125 mg to 175 mg | 10 mg to 15 mg |
| 46-i, 47-i, 48-i, 49-i, and 50-i | 140 mg to 160 mg | 0.1 mg to 15 mg |
| 46-j, 47-j, 48-j, 49-j, and 50-j | 140 mg to 160 mg | 2 mg to 6 mg |
| 46-k, 47-k, 48-k, 49-k, and 50-k | 140 mg to 160 mg | 5 mg to 10 mg |
| 46-l, 47-l, 48-l, 49-l, and 50-l | 140 mg to 160 mg | 10 mg to 15 mg |
| 46-m, 47-m, 48-m, 49-m, and 50-m | 150 mg | 0.1 mg to 15 mg |
| 46-n, 47-n, 48-n, 49-n, and 50-n | 150 mg | 2 mg to 6 mg |
| 46-o, 47-o, 48-o, 49-o, and 50-o | 150 mg | 5 mg to 10 mg |
| 46-p, 47-p, 48-p, 49-p, and 50-p | 150 mg | 10 mg to 15 mg |
| 46-q, 47-q, 48-q, 49-q, and 50-q | 150 mg | 4 mg |
| 46-r, 47-r, 48-r, 49-r, and 50-r | 150 mg | 5 mg |
| 46-s, 47-s, 48-s, 49-s, and 50-s | 150 mg | 6 mg |
| 46-t, 47-t, 48-t, 49-t, and 50-t | 150 mg | 7 mg |
| 46-u, 47-u, 48-u, 49-u, and 50-u | 150 mg | 8 mg |
| 46-v, 47-v, 48-v, 49-v, and 50-v | 150 mg | 9 mg |
| 46-w, 47-w, 48-w, 49-w, and 50-w | 150 mg | 10 mg |
| 46-x, 47-x, 48-x, 49-x, and 50-x | 150 mg | 11 mg |
| 46-y, 47-y, 48-y, 49-y, and 50-y | 150 mg | 12 mg |
| 46-z, 47-z, 48-z, 49-z, and 50-z | 150 mg | 13 mg |
| 46-aa, 47-aa, 48-aa, 49-aa, and 50-aa | 150 mg | 14 mg |
| 46-ab, 47-ab, 48-ab, 49-ab, and 50-ab | 150 mg | 15 mg |
| 46-ac, 47-ac, 48-ac, 49-ac, and 50-ac | 50 mg to 150 mg | 0.1 mg to 25 mg |
| 46-ad, 47-ad, 48-ad, 49-ad, and 50-ad | 50 mg to 150 mg | 0.1 mg to 15 mg |
| 46-ae, 47-ae, 48-ae, 49-ae, and 50-ae | 50 mg to 150 mg | 2 mg to 6 mg |
| 46-af, 47-af, 48-af, 49-af, and 50-af | 50 mg to 150 mg | 5 mg to 10 mg |
| 46-ag, 47-ag, 48-ag, 49-ag, and 50-ag | 50 mg to 150 mg | 10 mg to 15 mg |

Following the pattern of the tables above, the table below serves as Tables 51, 52, 53, 54, and 55 and provides combinations of agents that can be used in the uses, methods, regimens, and pharmaceutical compositions herein. Each of the listed combinations of agents includes amounts of ritonavir and differs only in the TLR7 Modulating Compound included. In the separate tables the TLR7 Modulating Compound, or a pharmaceutically acceptable salt thereof (collectively "TLR7 MC"), comprises a) a compound of Formula II in Table 51, b) the compound of Example 4 in Table 52, c) the compound of Example 49 in Table 53, d) the compound of Example 119 in Table 54, and e) the compound of Example 120 in Table 55.

Tables 51, 52, 53, 54, and 55

| Comp. Ex. | ritonavir | TLR7 MC |
|---|---|---|
| 51-a, 52-a, 53-a, 54-a, and 55-a | 50 mg to 800 mg | 0.1 mg to 25 mg |
| 51-b, 52-b, 53-b, 54-b, and 55-b | 50 mg to 800 mg | 2 mg to 6 mg |
| 51-c, 52-c, 53-c, 54-c, and 55-c | 50 mg to 800 mg | 5 mg to 10 mg |
| 51-d, 52-d, 53-d, 54-d, and 55-d | 50 mg to 800 mg | 10 mg to 15 mg |
| 51-e, 52-e, 53-e, 54-e, and 55-e | 75 mg to 450 mg | 0.1 mg to 15 mg |
| 51-f, 52-f, 53-f, 54-f, and 55-f | 75 mg to 450 mg | 2 mg to 6 mg |
| 51-g, 52-g, 53-g, 54-g, and 55-g | 75 mg to 450 mg | 5 mg to 10 mg |
| 51-h, 52-h, 53-h, 54-h, and 55-h | 75 mg to 450 mg | 10 mg to 15 mg |
| 51-i, 52-i, 53-i, 54-i, and 55-i | 75 mg to 250 mg | 0.1 mg to 25 mg |
| 51-j, 52-j, 53-j, 54-j, and 55-j | 75 mg to 250 mg | 2 mg to 6 mg |
| 51-k, 52-k, 53-k, 54-k, and 55-k | 75 mg to 250 mg | 5 mg to 10 mg |
| 51-l, 52-l, 53-l, 54-l, and 55-l | 75 mg to 250 mg | 10 mg to 15 mg |
| 51-m, 52-m, 53-m, 54-m, and 55-m | 250 mg to 450 mg | 0.1 mg to 25 mg |
| 51-n, 52-n, 53-n, 54-n, and 55-n | 250 mg to 450 mg | 2 mg to 6 mg |
| 51-o, 52-o, 53-o, 54-o, and 55-o | 250 mg to 450 mg | 5 mg to 10 mg |
| 51-p, 52-p, 53-p, 54-p, and 55-p | 250 mg to 450 mg | 10 mg to 15 mg |

-continued

| Comp. Ex. | ritonavir | TLR7 MC |
|---|---|---|
| 51-q, 52-q, 53-q, 54-q, and 55-q | 100 mg | 0.1 mg to 25 mg |
| 51-r, 52-r, 53-r, 54-r, and 55-r | 100 mg | 2 mg to 6 mg |
| 51-s, 52-s, 53-s, 54-s, and 55-s | 100 mg | 5 mg to 10 mg |
| 51-t, 52-t, 53-t, 54-t, and 55-t | 100 mg | 10 mg to 15 mg |
| 51-u, 52-u, 53-u, 54-u, and 55-u | 50 mg to 150 mg | 4 mg |
| 51-v, 52-v, 53-v, 54-v, and 55-v | 50 mg to 150 mg | 5 mg |
| 51-w, 52-w, 53-w, 54-w, and 55-w | 50 mg to 150 mg | 6 mg |
| 51-x, 52-x, 53-x, 54-x, and 55-x | 50 mg to 150 mg | 7 mg |
| 51-y, 52-y, 53-y, 54-y, and 55-y | 50 mg to 150 mg | 8 mg |
| 51-z, 52-z, 53-z, 54-z, and 55-z | 50 mg to 150 mg | 9 mg |
| 51-aa, 52-aa, 53-aa, 54-aa, and 55-aa | 50 mg to 150 mg | 10 mg |
| 51-ab, 52-ab, 53-ab, 54-ab, and 55-ab | 50 mg to 150 mg | 11 mg |
| 51-ac, 52-ac, 53-ac, 54-ac, and 55-ac | 50 mg to 150 mg | 12 mg |
| 51-ad, 52-ad, 53-ad, 54-ad, and 55-ad | 50 mg to 150 mg | 13 mg |
| 51-ae, 52-ae, 53-ae, 54-ae, and 55-ae | 50 mg to 150 mg | 14 mg |
| 51-af, 52-af, 53-af, 54-af, and 55-af | 50 mg to 150 mg | 15 mg |
| 51-a, 52-a, 53-a, 54-a, and 55-a | 25 mg to 75 mg | 0.1 mg to 25 mg |
| 51-b, 52-b, 53-b, 54-b, and 55-b | 25 mg to 75 mg | 2 mg to 6 mg |
| 51-c, 52-c, 53-c, 54-c, and 55-c | 25 mg to 75 mg | 5 mg to 10 mg |
| 51-d, 52-d, 53-d, 54-d, and 55-d | 25 mg to 75 mg | 10 mg to 15 mg |

A pharmaceutically effective amount of a TLR7 modulating compound, including each of those described herein, can also be combined in dosing regimens and pharmaceutical compositions with a pharmaceutically effective amount of a protease inhibitor known in the art, or a pharmaceutically acceptable salt thereof.

Provided is a pharmaceutical composition comprising:
a) a pharmaceutically effective amount of a protease inhibitor;
b) a pharmaceutically effective amount of a TLR7 modulating compound; and
c) a pharmaceutically acceptable carrier or excipient.

For instance, combinations useful in pharmaceutical regimens and pharmaceutical compositions comprise:
a) a pharmaceutically effective amount of a protease inhibitor, or a pharmaceutically acceptable salt thereof, selected from the group of atazanavir, darunavir, indinavir, lopinavir, nelfinavir, saquinavir, tipranavir, fosamprenavir, ritonavir, amprenavir, and telaprevir; and
b) a pharmaceutically effective amount of a TLR7 modulating compound, or a pharmaceutically acceptable salt thereof, selected from the group of a compound of Formula II, Formula III, Formula III(a), Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III (c)(2), Formula III(d)(1), Formula III(d)(2), Formula III(e)(1), Formula III(e)(2), Formula III(f)(1), Formula III(f)(2), Compound Examples 1 through 124, including the compounds of Examples 4, 49, 119, 120, and 121, GSK2245035, Imiquimod, Resiquimod (R848), R-852 (R852A, PF-4878691), ANA773, 5-amino-7-hydroxy-3-((2R,3R,5S)-3-hydroxy-5-(hydroxymethyl)tetrahydrofuran-2-yl)thiazolo[4,5-d]pyrimidin-2(3H)-one (active metabolite of ANA773), AZD8848 (DSP3025), SM-360320, IMO-8400, CL097, CL075 (3M002), GARDIOUIMOD™ (1-(4-Amino-2-ethylaminomethylimidazo[4,5-c]quinolin-1-yl)-2-methylpropan-2-ol), Isatoribine, 6-amino-2-(butylamino)-7,9-dihydro-9-[(6-methyl-3-pyridinyl)methyl]-8H-purin-8-one (SM-276001), 852A (N-[4-(4-amino-2-ethyl-1H-imidazo[4,5-c]quinolin-1-yl)butyl] methanesulfonamide), 3M-854A and 3M-052, 5-(4-amino-2-methyl-1H-imidazo[4,5-c]quinolin-1-yl)-4,4-dimethylpentan-2-one (S-34240), and loxoribine;

wherein the separate pharmaceutical regimens comprise a pharmaceutically effective amount of each of the protease inhibitors in group a) above, individually, combined with a pharmaceutically effective amount of each TLR7 modulating compound, represented by a specific compound, agent, or formula of group b), individually, and the separate pharmaceutical compositions each comprise a pharmaceutically acceptable carrier or excipient, a pharmaceutically effective amount of each of the protease inhibitors in group a) above, individually, and a pharmaceutically effective amount of each TLR7 modulating compound, represented by a specific compound, agent, or formula of group b), individually. It is understood that the combinations of the eleven protease inhibitors in group a), individually, with the one hundred and forty one TLR7 modulating compounds of group b), represented by a specific compound, agent, or formula, provides 1771 separate combinations of one protease inhibitor and one TLR7 modulating compound each.

Examples of combinations of protease inhibitors and TLR7 modulating compounds for use in the methods and pharmaceutical compositions herein include those in Tables 57 through 66. Each of the combinations of a protease inhibitor and a TLR7 modulator listed in Tables 57 through 66, in combination with a pharmaceutically acceptable carrier or excipient, comprises an independent pharmaceutical composition.

TABLE 56

| Example | Protease Inhibitor | TLR7 Modulator |
|---|---|---|
| 56-a | Atazanavir - 100 mg to 500 mg | Formula II - 0.1 mg to 25 mg |
| 56-b | Atazanavir - 100 mg to 500 mg | Example 4 - 0.1 mg to 25 mg |
| 56-c | Atazanavir - 100 mg to 500 mg | Example 49 - 0.1 mg to 25 mg |
| 56-d | Atazanavir - 100 mg to 500 mg | Example 119 - 0.1 mg to 25 mg |
| 56-e | Atazanavir - 100 mg to 500 mg | Example 120 - 0.1 mg to 25 mg |
| 56-f | Atazanavir - 200 mg to 400 mg | Formula II - 0.1 mg to 15 mg |

TABLE 56-continued

| Example | Protease Inhibitor | TLR7 Modulator |
| --- | --- | --- |
| 56-g | Atazanavir - 200 mg to 400 mg | Example 4 - 0.1 mg to 15 mg |
| 56-h | Atazanavir - 200 mg to 400 mg | Example 49 - 0.1 mg to 15 mg |
| 56-i | Atazanavir - 200 mg to 400 mg | Example 119 - 0.1 mg to 15 mg |
| 56-j | Atazanavir - 200 mg to 400 mg | Example 120 - 0.1 mg to 15 mg |
| 56-k | Atazanavir - 200 mg to 400 mg | Formula II - 2 mg to 10 mg |
| 56-l | Atazanavir - 200 mg to 400 mg | Example 4 - 2 mg to 10 mg |
| 56-m | Atazanavir - 200 mg to 400 mg | Example 49 - 2 mg to 10 mg |
| 56-n | Atazanavir - 200 mg to 400 mg | Example 119 - 2 mg to 10 mg |
| 56-o | Atazanavir - 200 mg to 400 mg | Example 120 - 2 mg to 10 mg |
| 56-p | Atazanavir - 100 mg to 500 mg | ANA-773 - 200 mg to 2000 mg |
| 56-q | Atazanavir - 100 mg to 500 mg | GSK2245035 - 25 mg to 1000 mg |
| 56-r | Atazanavir - 100 mg to 500 mg | Imiquimod - 25 mg to 1000 mg |
| 56-s | Atazanavir - 100 mg to 500 mg | Imiquimod - 25 mg to 1000 mg |
| 56-t | Atazanavir - 100 mg to 500 mg | IMO8400 - 25 mg to 1000 mg |
| 56-u | Atazanavir - 100 mg to 500 mg | GSK2245035 - 25 mg to 1000 mg |
| 56-v | Atazanavir - 100 mg to 500 mg | CL075 - 1 mg to 100 mg |
| 56-w | Atazanavir - 100 mg to 500 mg | Gardiquimod - 25 mg to 1000 mg |
| 56x | Atazanavir - 100 mg to 500 mg | Loxoribine - 25 mg to 1000 mg |
| 56-y | Atazanavir - 300 mg | Formula II - 0.1 mg to 15 mg |
| 56-z | Atazanavir - 300 mg | Example 4 - 0.1 mg to 15 mg |
| 56-aa | Atazanavir - 300 mg | Example 49 - 0.1 mg to 15 mg |
| 56-ab | Atazanavir - 300 mg | Example 119 - 0.1 mg to 15 mg |
| 56-ac | Atazanavir - 300 mg | Example 120 - 0.1 mg to 15 mg |
| 56-ad | Atazanavir - 400 mg | Formula II - 0.1 mg to 15 mg |
| 56-ae | Atazanavir - 400 mg | Example 4 - 0.1 mg to 15 mg |
| 56-af | Atazanavir - 400 mg | Example 49 - 0.1 mg to 15 mg |
| 56-ag | Atazanavir - 400 mg | Example 119 - 0.1 mg to 15 mg |
| 56-ah | Atazanavir - 400 mg | Example 120 - 0.1 mg to 15 mg |

TABLE 57

| Example | Protease Inhibitor | TLR7 Modulator |
| --- | --- | --- |
| 57-a | darunavir - 50 mg to 1000 mg | Formula II - 0.1 mg to 25 mg |
| 57-b | darunavir - 50 mg to 1000 mg | Example 4 - 0.1 mg to 25 mg |
| 57-c | darunavir - 50 mg to 1000 mg | Example 49 - 0.1 mg to 25 mg |
| 57-d | darunavir - 50 mg to 1000 mg | Example 119 - 0.1 mg to 25 mg |
| 57-e | darunavir - 50 mg to 1000 mg | Example 120 - 0.1 mg to 25 mg |
| 57-f | darunavir - 50 mg to 800 mg | Formula II - 0.1 mg to 15 mg |
| 57-g | darunavir - 50 mg to 800 mg | Example 4 - 0.1 mg to 15 mg |
| 57-h | darunavir - 50 mg to 800 mg | Example 49 - 0.1 mg to 15 mg |
| 57-i | darunavir - 50 mg to 800 mg | Example 119 - 0.1 mg to 15 mg |
| 57-j | darunavir - 50 mg to 800 mg | Example 120 - 0.1 mg to 15 mg |
| 57-k | darunavir - 50 mg to 800 mg | Formula II - 2 mg to 10 mg |
| 57-l | darunavir - 50 mg to 800 mg | Example 4 - 2 mg to 10 mg |
| 57-m | darunavir - 50 mg to 800 mg | Example 49 - 2 mg to 10 mg |
| 57-n | darunavir - 50 mg to 800 mg | Example 119 - 2 mg to 10 mg |
| 57-o | darunavir - 50 mg to 800 mg | Example 120 - 2 mg to 10 mg |
| 57-p | darunavir - 50 mg to 800 mg | ANA-773 - 200 mg to 2000 mg |
| 57-q | darunavir - 50 mg to 800 mg | GSK2245035 - 25 mg to 1000 mg |
| 57-r | darunavir - 50 mg to 800 mg | Imiquimod - 25 mg to 1000 mg |
| 57-s | darunavir - 50 mg to 800 mg | Imiquimod - 25 mg to 1000 mg |
| 57-t | darunavir - 50 mg to 800 mg | IMO8400 - 25 mg to 1000 mg |
| 57-u | darunavir - 50 mg to 800 mg | GSK2245035 - 25 mg to 1000 mg |
| 57-v | darunavir - 50 mg to 800 mg | CL075 - 1 mg to 100 mg |
| 57-w | darunavir - 50 mg to 800 mg | Gardiquimod - 25 mg to 1000 mg |
| 57x | darunavir - 50 mg to 800 mg | Loxoribine - 25 mg to 1000 mg |
| 57-y | darunavir - 75 mg | Formula II - 0.1 mg to 15 mg |
| 57-z | darunavir - 75 mg | Example 4 - 0.1 mg to 15 mg |
| 57-aa | darunavir - 75 mg | Example 49 - 0.1 mg to 15 mg |
| 57-ab | darunavir - 75 mg | Example 119 - 0.1 mg to 15 mg |
| 57-ac | darunavir - 75 mg | Example 120 - 0.1 mg to 15 mg |
| 57-ad | darunavir - 150 mg | Formula II - 0.1 mg to 15 mg |
| 57-ae | darunavir - 150 mg | Example 4 - 0.1 mg to 15 mg |
| 57-af | darunavir - 150 mg | Example 49 - 0.1 mg to 15 mg |
| 57-ag | darunavir - 150 mg | Example 119 - 0.1 mg to 15 mg |
| 57-ah | darunavir - 150 mg | Example 120 - 0.1 mg to 15 mg |
| 57-ai | darunavir - 600 mg | Formula II - 0.1 mg to 15 mg |
| 57-aj | darunavir - 600 mg | Example 4 - 0.1 mg to 15 mg |
| 57-ak | darunavir - 600 mg | Example 49 - 0.1 mg to 15 mg |
| 57-al | darunavir - 600 mg | Example 119 - 0.1 mg to 15 mg |
| 57-am | darunavir - 600 mg | Example 120 - 0.1 mg to 15 mg |
| 57-an | darunavir - 800 mg | Formula II - 0.1 mg to 15 mg |
| 57-ao | darunavir - 800 mg | Example 4 - 0.1 mg to 15 mg |

TABLE 57-continued

| Example | Protease Inhibitor | TLR7 Modulator |
| --- | --- | --- |
| 57-ap | darunavir - 800 mg | Example 49 - 0.1 mg to 15 mg |
| 57-aq | darunavir - 800 mg | Example 119 - 0.1 mg to 15 mg |
| 57-ar | darunavir - 800 mg | Example 120 - 0.1 mg to 15 mg |

TABLE 58

| Example | Protease Inhibitor | TLR7 Modulator |
| --- | --- | --- |
| 58-a | indinavir - 100 mg to 1000 mg | Formula II - 0.1 mg to 25 mg |
| 58-b | indinavir - 100 mg to 1000 mg | Example 4 - 0.1 mg to 25 mg |
| 58-c | indinavir - 100 mg to 1000 mg | Example 49 - 0.1 mg to 25 mg |
| 58-d | indinavir - 100 mg to 1000 mg | Example 119 - 0.1 mg to 25 mg |
| 58-e | indinavir - 100 mg to 1000 mg | Example 120 - 0.1 mg to 25 mg |
| 58-f | indinavir - 100 mg to 1000 mg | Formula II - 0.1 mg to 15 mg |
| 58-g | indinavir - 100 mg to 1000 mg | Example 4 - 0.1 mg to 15 mg |
| 58-h | indinavir - 100 mg to 1000 mg | Example 49 - 0.1 mg to 15 mg |
| 58-i | indinavir - 100 mg to 1000 mg | Example 119 - 0.1 mg to 15 mg |
| 58-j | indinavir - 100 mg to 1000 mg | Example 120 - 0.1 mg to 15 mg |
| 58-k | indinavir - 200 mg to 800 mg | Formula II - 2 mg to 10 mg |
| 58-l | indinavir - 200 mg to 800 mg | Example 4 - 2 mg to 10 mg |
| 58-m | indinavir - 200 mg to 800 mg | Example 49 - 2 mg to 10 mg |
| 58-n | indinavir - 200 mg to 800 mg | Example 119 - 2 mg to 10 mg |
| 58-o | indinavir - 200 mg to 800 mg | Example 120 - 2 mg to 10 mg |
| 58-p | indinavir - 100 mg to 1000 mg | ANA-773 - 200 mg to 2000 mg |
| 58-q | indinavir - 100 mg to 1000 mg | GSK2245035 - 25 mg to 1000 mg |
| 58-r | indinavir - 100 mg to 1000 mg | Imiquimod - 25 mg to 1000 mg |
| 58-s | indinavir - 100 mg to 1000 mg | Imiquimod - 25 mg to 1000 mg |
| 58-t | indinavir - 100 mg to 1000 mg | IMO8400 - 25 mg to 1000 mg |
| 58-u | indinavir - 100 mg to 1000 mg | GSK2245035 - 25 mg to 1000 mg |
| 58-v | indinavir - 100 mg to 1000 mg | CL075 - 1 mg to 100 mg |
| 58-w | indinavir - 100 mg to 1000 mg | Gardiquimod - 25 mg to 1000 mg |
| 58x | indinavir - 100 mg to 1000 mg | Loxoribine - 25 mg to 1000 mg |
| 58-y | indinavir - 400 mg | Formula II - 0.1 mg to 15 mg |
| 58-z | indinavir - 400 mg | Example 4 - 0.1 mg to 15 mg |
| 58-aa | indinavir - 400 mg | Example 49 - 0.1 mg to 15 mg |
| 58-ab | indinavir - 400 mg | Example 119 - 0.1 mg to 15 mg |
| 58-ac | indinavir - 400 mg | Example 120 - 0.1 mg to 15 mg |
| 58-ad | indinavir - 800 mg | Formula II - 0.1 mg to 15 mg |
| 58-ae | indinavir - 800 mg | Example 4 - 0.1 mg to 15 mg |
| 58-af | indinavir - 800 mg | Example 49 - 0.1 mg to 15 mg |
| 58-ag | indinavir - 800 mg | Example 119 - 0.1 mg to 15 mg |
| 58-ah | indinavir - 800 mg | Example 120 - 0.1 mg to 15 mg |

TABLE 59

| Example | Protease Inhibitor | TLR7 Modulator |
| --- | --- | --- |
| 59-a | lopinavir - 100 mg to 1000 mg | Formula II - 0.1 mg to 25 mg |
| 59-b | lopinavir - 100 mg to 1000 mg | Example 4 - 0.1 mg to 25 mg |
| 59-c | lopinavir - 100 mg to 1000 mg | Example 49 - 0.1 mg to 25 mg |
| 59-d | lopinavir - 100 mg to 1000 mg | Example 119 - 0.1 mg to 25 mg |
| 59-e | lopinavir - 100 mg to 1000 mg | Example 120 - 0.1 mg to 25 mg |
| 59-f | lopinavir - 100 mg to 1000 mg | Formula II - 0.1 mg to 15 mg |
| 59-g | lopinavir - 100 mg to 1000 mg | Example 4 - 0.1 mg to 15 mg |
| 59-h | lopinavir - 100 mg to 1000 mg | Example 49 - 0.1 mg to 15 mg |
| 59-i | lopinavir - 100 mg to 1000 mg | Example 119 - 0.1 mg to 15 mg |
| 59-j | lopinavir - 100 mg to 1000 mg | Example 120 - 0.1 mg to 15 mg |
| 59-k | lopinavir - 200 mg to 800 mg | Formula II - 2 mg to 10 mg |
| 59-l | lopinavir - 200 mg to 800 mg | Example 4 - 2 mg to 10 mg |
| 59-m | lopinavir - 200 mg to 800 mg | Example 49 - 2 mg to 10 mg |
| 59-n | lopinavir - 200 mg to 800 mg | Example 119 - 2 mg to 10 mg |
| 59-o | lopinavir - 200 mg to 800 mg | Example 120 - 2 mg to 10 mg |
| 59-p | lopinavir - 100 mg to 1000 mg | ANA-773 - 200 mg to 2000 mg |
| 59-q | lopinavir - 100 mg to 1000 mg | GSK2245035 - 25 mg to 1000 mg |
| 59-r | lopinavir - 100 mg to 1000 mg | Imiquimod - 25 mg to 1000 mg |
| 59-s | lopinavir - 100 mg to 1000 mg | Imiquimod - 25 mg to 1000 mg |
| 59-t | lopinavir - 100 mg to 1000 mg | IMO8400 - 25 mg to 1000 mg |
| 59-u | lopinavir - 100 mg to 1000 mg | GSK2245035 - 25 mg to 1000 mg |
| 59-v | lopinavir - 100 mg to 1000 mg | CL075 - 1 mg to 100 mg |

TABLE 59-continued

| Example | Protease Inhibitor | TLR7 Modulator |
| --- | --- | --- |
| 59-w | lopinavir - 100 mg to 1000 mg | Gardiquimod - 25 mg to 1000 mg |
| 59x | lopinavir - 100 mg to 1000 mg | Loxoribine - 25 mg to 1000 mg |
| 59-y | lopinavir - 200 mg | Formula II - 0.1 mg to 15 mg |
| 59-z | lopinavir - 200 mg | Example 4 - 0.1 mg to 15 mg |
| 59-aa | lopinavir - 200 mg | Example 49 - 0.1 mg to 15 mg |
| 59-ab | lopinavir - 200 mg | Example 119 - 0.1 mg to 15 mg |
| 59-ac | lopinavir - 200 mg | Example 120 - 0.1 mg to 15 mg |
| 59-ad | lopinavir - 400 mg | Formula II - 0.1 mg to 15 mg |
| 59-ae | lopinavir - 400 mg | Example 4 - 0.1 mg to 15 mg |
| 59-af | lopinavir - 400 mg | Example 49 - 0.1 mg to 15 mg |
| 59-ag | lopinavir - 400 mg | Example 119 - 0.1 mg to 15 mg |
| 59-ah | lopinavir - 400 mg | Example 120 - 0.1 mg to 15 mg |
| 59-ai | lopinavir - 800 mg | Formula II - 0.1 mg to 15 mg |
| 59-aj | lopinavir - 800 mg | Example 4 - 0.1 mg to 15 mg |
| 59-ak | lopinavir - 800 mg | Example 49 - 0.1 mg to 15 mg |
| 59-al | lopinavir - 800 mg | Example 119 - 0.1 mg to 15 mg |
| 59-am | lopinavir - 800 mg | Example 120 - 0.1 mg to 15 mg |

TABLE 60

| Example | Protease Inhibitor | TLR7 Modulator |
| --- | --- | --- |
| 60-a | nelfinavir - 100 mg to 2500 mg | Formula II - 0.1 mg to 25 mg |
| 60-b | nelfinavir - 100 mg to 2500 mg | Example 4 - 0.1 mg to 25 mg |
| 60-c | nelfinavir - 100 mg to 2500 mg | Example 49 - 0.1 mg to 25 mg |
| 60-d | nelfinavir - 100 mg to 2500 mg | Example 119 - 0.1 mg to 25 mg |
| 60-e | nelfinavir - 100 mg to 2500 mg | Example 120 - 0.1 mg to 25 mg |
| 60-f | nelfinavir - 250 mg to 2500 mg | Formula II - 0.1 mg to 15 mg |
| 60-g | nelfinavir - 250 mg to 2500 mg | Example 4 - 0.1 mg to 15 mg |
| 60-h | nelfinavir - 250 mg to 2500 mg | Example 49 - 0.1 mg to 15 mg |
| 60-i | nelfinavir - 250 mg to 2500 mg | Example 119 - 0.1 mg to 15 mg |
| 60-j | nelfinavir - 250 mg to 2500 mg | Example 120 - 0.1 mg to 15 mg |
| 60-k | nelfinavir - 250 mg to 2500 mg | Formula II - 2 mg to 10 mg |
| 60-l | nelfinavir - 250 mg to 2500 mg | Example 4 - 2 mg to 10 mg |
| 60-m | nelfinavir - 250 mg to 2500 mg | Example 49 - 2 mg to 10 mg |
| 60-n | nelfinavir - 250 mg to 2500 mg | Example 119 - 2 mg to 10 mg |
| 60-o | nelfinavir - 250 mg to 2500 mg | Example 120 - 2 mg to 10 mg |
| 60-p | nelfinavir - 250 mg to 2500 mg | ANA-773 - 200 mg to 2000 mg |
| 60-q | nelfinavir - 250 mg to 2500 mg | GSK2245035 - 25 mg to 1000 mg |
| 60-r | nelfinavir - 250 mg to 2500 mg | Imiquimod - 25 mg to 1000 mg |
| 60-s | nelfinavir - 250 mg to 2500 mg | Imiquimod - 25 mg to 1000 mg |
| 60-t | nelfinavir - 250 mg to 2500 mg | IMO8400 - 25 mg to 1000 mg |
| 60-u | nelfinavir - 250 mg to 2500 mg | GSK2245035 - 25 mg to 1000 mg |
| 60-v | nelfinavir - 250 mg to 2500 mg | CL075 - 1 mg to 100 mg |
| 60-w | nelfinavir - 250 mg to 2500 mg | Gardiquimod - 25 mg to 1000 mg |
| 60x | nelfinavir - 250 mg to 2500 mg | Loxoribine - 25 mg to 1000 mg |
| 60-y | nelfinavir - 250 mg | Formula II - 0.1 mg to 15 mg |
| 60-z | nelfinavir - 250 mg | Example 4 - 0.1 mg to 15 mg |
| 60-aa | nelfinavir - 250 mg | Example 49 - 0.1 mg to 15 mg |
| 60-ab | nelfinavir - 250 mg | Example 119 - 0.1 mg to 15 mg |
| 60-ac | nelfinavir - 250 mg | Example 120 - 0.1 mg to 15 mg |
| 60-ad | nelfinavir - 625 mg | Formula II - 0.1 mg to 15 mg |
| 60-ae | nelfinavir - 625 mg | Example 4 - 0.1 mg to 15 mg |
| 60-af | nelfinavir - 625 mg | Example 49 - 0.1 mg to 15 mg |
| 60-ag | nelfinavir - 625 mg | Example 119 - 0.1 mg to 15 mg |
| 60-ah | nelfinavir - 625 mg | Example 120 - 0.1 mg to 15 mg |

TABLE 61

| Example | Protease Inhibitor | TLR7 Modulator |
| --- | --- | --- |
| 61-a | saquinavir - 200 mg to 1500 mg | Formula II - 0.1 mg to 25 mg |
| 61-b | saquinavir - 200 mg to 1500 mg | Example 4 - 0.1 mg to 25 mg |
| 61-c | saquinavir - 200 mg to 1500 mg | Example 49 - 0.1 mg to 25 mg |
| 61-d | saquinavir - 200 mg to 1500 mg | Example 119 - 0.1 mg to 25 mg |
| 61-e | saquinavir - 200 mg to 1500 mg | Example 120 - 0.1 mg to 25 mg |
| 61-f | saquinavir - 500 mg to 1000 mg | Formula II - 0.1 mg to 15 mg |
| 61-g | saquinavir - 500 mg to 1000 mg | Example 4 - 0.1 mg to 15 mg |
| 61-h | saquinavir - 500 mg to 1000 mg | Example 49 - 0.1 mg to 15 mg |

TABLE 61-continued

| Example | Protease Inhibitor | TLR7 Modulator |
| --- | --- | --- |
| 61-i | saquinavir - 500 mg to 1000 mg | Example 119 - 0.1 mg to 15 mg |
| 61-j | saquinavir - 500 mg to 1000 mg | Example 120 - 0.1 mg to 15 mg |
| 61-k | saquinavir - 500 mg to 1000 mg | Formula II - 2 mg to 10 mg |
| 61-l | saquinavir - 500 mg to 1000 mg | Example 4 - 2 mg to 10 mg |
| 61-m | saquinavir - 500 mg to 1000 mg | Example 49 - 2 mg to 10 mg |
| 61-n | saquinavir - 500 mg to 1000 mg | Example 119 - 2 mg to 10 mg |
| 61-o | saquinavir - 500 mg to 1000 mg | Example 120 - 2 mg to 10 mg |
| 61-p | saquinavir - 200 mg to 1500 mg | ANA-773 - 200 mg to 2000 mg |
| 61-q | saquinavir - 200 mg to 1500 mg | GSK2245035 - 25 mg to 1000 mg |
| 61-r | saquinavir - 200 mg to 1500 mg | Imiquimod - 25 mg to 1000 mg |
| 61-s | saquinavir - 200 mg to 1500 mg | Imiquimod - 25 mg to 1000 mg |
| 61-t | saquinavir - 200 mg to 1500 mg | IMO8400 - 25 mg to 1000 mg |
| 61-u | saquinavir - 200 mg to 1500 mg | GSK2245035 - 25 mg to 1000 mg |
| 61-v | saquinavir - 200 mg to 1500 mg | CL075 - 1 mg to 100 mg |
| 61-w | saquinavir - 200 mg to 1500 mg | Gardiquimod - 25 mg to 1000 mg |
| 61x | saquinavir - 200 mg to 1500 mg | Loxoribine - 25 mg to 1000 mg |
| 61-y | saquinavir - 200 mg | Formula II - 0.1 mg to 15 mg |
| 61-z | saquinavir - 200 mg | Example 4 - 0.1 mg to 15 mg |
| 61-aa | saquinavir - 200 mg | Example 49 - 0.1 mg to 15 mg |
| 61-ab | saquinavir - 200 mg | Example 119 - 0.1 mg to 15 mg |
| 61-ac | saquinavir - 200 mg | Example 120 - 0.1 mg to 15 mg |
| 61-ad | saquinavir - 500 mg | Formula II - 0.1 mg to 15 mg |
| 61-ae | saquinavir - 500 mg | Example 4 - 0.1 mg to 15 mg |
| 61-af | saquinavir - 500 mg | Example 49 - 0.1 mg to 15 mg |
| 61-aq | saquinavir - 500 mg | Example 119 - 0.1 mg to 15 mg |
| 61-ah | saquinavir - 500 mg | Example 120 - 0.1 mg to 15 mg |

TABLE 62

| Example | Protease Inhibitor | TLR7 Modulator |
| --- | --- | --- |
| 62-a | tipranavir - 50 mg to 500 mg | Formula II - 0.1 mg to 25 mg |
| 62-b | tipranavir - 50 mg to 500 mg | Example 4 - 0.1 mg to 25 mg |
| 62-c | tipranavir - 50 mg to 500 mg | Example 49 - 0.1 mg to 25 mg |
| 62-d | tipranavir - 50 mg to 500 mg | Example 119 - 0.1 mg to 25 mg |
| 62-e | tipranavir - 50 mg to 500 mg | Example 120 - 0.1 mg to 25 mg |
| 62-f | saquinavir - 100 mg to 500 mg | Formula II - 0.1 mg to 15 mg |
| 62-q | saquinavir - 100 mg to 500 mg | Example 4 - 0.1 mg to 15 mg |
| 62-h | saquinavir - 100 mg to 500 mg | Example 49 - 0.1 mg to 15 mg |
| 62-i | saquinavir - 100 mg to 500 mg | Example 119 - 0.1 mg to 15 mg |
| 62-j | saquinavir - 100 mg to 500 mg | Example 120 - 0.1 mg to 15 mg |
| 62-k | saquinavir - 100 mg to 500 mg | Formula II - 2 mg to 10 mg |
| 62-l | saquinavir - 100 mg to 500 mg | Example 4 - 2 mg to 10 mg |
| 62-m | saquinavir - 100 mg to 500 mg | Example 49 - 2 mg to 10 mg |
| 62-n | saquinavir - 100 mg to 500 mg | Example 119 - 2 mg to 10 mg |
| 62-o | saquinavir - 100 mg to 500 mg | Example 120 - 2 mg to 10 mg |
| 62-p | tipranavir - 50 mg to 500 mg | ANA-773 - 200 mg to 2000 mg |
| 62-q | tipranavir - 50 mg to 500 mg | GSK2245035 - 25 mg to 1000 mg |
| 62-r | tipranavir - 50 mg to 500 mg | Imiquimod - 25 mg to 1000 mg |
| 62-s | tipranavir - 50 mg to 500 mg | Imiquimod - 25 mg to 1000 mg |
| 62-t | tipranavir - 50 mg to 500 mg | IMO8400 - 25 mg to 1000 mg |
| 62-u | tipranavir - 50 mg to 500 mg | GSK2245035 - 25 mg to 1000 mg |
| 62-v | tipranavir - 50 mg to 500 mg | CL075 - 1 mg to 100 mg |
| 62-w | tipranavir - 50 mg to 500 mg | Gardiquimod - 25 mg to 1000 mg |
| 62x | tipranavir - 50 mg to 500 mg | Loxoribine - 25 mg to 1000 mg |
| 62-y | tipranavir - 100 mg | Formula II - 0.1 mg to 15 mg |
| 62-z | tipranavir - 100 mg | Example 4 - 0.1 mg to 15 mg |
| 62-aa | tipranavir - 100 mg | Example 49 - 0.1 mg to 15 mg |
| 62-ab | tipranavir - 100 mg | Example 119 - 0.1 mg to 15 mg |
| 62-ac | tipranavir - 100 mg | Example 120 - 0.1 mg to 15 mg |
| 62-ad | tipranavir - 250 mg | Formula II - 0.1 mg to 15 mg |
| 62-ae | tipranavir - 250 mg | Example 4 - 0.1 mg to 15 mg |
| 62-af | tipranavir - 250 mg | Example 49 - 0.1 mg to 15 mg |
| 62-ag | tipranavir - 250 mg | Example 119 - 0.1 mg to 15 mg |
| 62-ah | tipranavir - 250 mg | Example 120 - 0.1 mg to 15 mg |

TABLE 63

| Example | Protease Inhibitor | TLR7 Modulator |
| --- | --- | --- |
| 63-a | fosamprenavir - 500 mg to 1500 mg | Formula II - 0.1 mg to 25 mg |
| 63-b | fosamprenavir - 500 mg to 1500 mg | Example 4 - 0.1 mg to 25 mg |
| 63-c | fosamprenavir - 500 mg to 1500 mg | Example 49 - 0.1 mg to 25 mg |
| 63-d | fosamprenavir - 500 mg to 1500 mg | Example 119 - 0.1 mg to 25 mg |
| 63-e | fosamprenavir - 500 mg to 1500 mg | Example 120 - 0.1 mg to 25 mg |
| 63-f | fosamprenavir - 500 mg to 1500 mg | Formula II - 0.1 mg to 15 mg |
| 63-g | fosamprenavir - 500 mg to 1500 mg | Example 4 - 0.1 mg to 15 mg |
| 63-h | fosamprenavir - 500 mg to 1500 mg | Example 49 - 0.1 mg to 15 mg |
| 63-i | fosamprenavir - 500 mg to 1500 mg | Example 119 - 0.1 mg to 15 mg |
| 63-j | fosamprenavir - 500 mg to 1500 mg | Example 120 - 0.1 mg to 15 mg |
| 63-k | fosamprenavir - 500 mg to 1500 mg | Formula II - 2 mg to 10 mg |
| 63-l | fosamprenavir - 500 mg to 1500 mg | Example 4 - 2 mg to 10 mg |
| 63-m | fosamprenavir - 500 mg to 1500 mg | Example 49 - 2 mg to 10 mg |
| 63-n | fosamprenavir - 500 mg to 1500 mg | Example 119 - 2 mg to 10 mg |
| 63-o | fosamprenavir - 500 mg to 1500 mg | Example 120 - 2 mg to 10 mg |
| 63-p | fosamprenavir - 500 mg to 1500 mg | ANA-773 - 200 mg to 2000 mg |
| 63-q | fosamprenavir - 500 mg to 1500 mg | GSK2245035 - 25 mg to 1000 mg |
| 63-r | fosamprenavir - 500 mg to 1500 mg | Imiquimod - 25 mg to 1000 mg |
| 63-s | fosamprenavir - 500 mg to 1500 mg | Imiquimod - 25 mg to 1000 mg |
| 63-t | fosamprenavir - 500 mg to 1500 mg | IMO8400 - 25 mg to 1000 mg |
| 63-u | fosamprenavir - 500 mg to 1500 mg | GSK2245035 - 25 mg to 1000 mg |
| 63-v | fosamprenavir - 500 mg to 1500 mg | CL075 - 1 mg to 100 mg |
| 63-w | fosamprenavir - 500 mg to 1500 mg | Gardiquimod - 25 mg to 1000 mg |
| 63x | fosamprenavir - 500 mg to 1500 mg | Loxoribine - 25 mg to 1000 mg |
| 63-y | fosamprenavir - 700 mg | Formula II - 0.1 mg to 15 mg |
| 63-z | fosamprenavir - 700 mg | Example 4 - 0.1 mg to 15 mg |
| 63-aa | fosamprenavir - 700 mg | Example 49 - 0.1 mg to 15 mg |
| 63-ab | fosamprenavir - 700 mg | Example 119 - 0.1 mg to 15 mg |
| 63-ac | fosamprenavir - 700 mg | Example 120 - 0.1 mg to 15 mg |
| 63-ad | fosamprenavir - 500 mg | Formula II - 0.1 mg to 15 mg |
| 63-ae | fosamprenavir - 500 mg | Example 4 - 0.1 mg to 15 mg |
| 63-af | fosamprenavir - 500 mg | Example 49 - 0.1 mg to 15 mg |
| 63-ag | fosamprenavir - 500 mg | Example 119 - 0.1 mg to 15 mg |
| 63-ah | fosamprenavir - 500 mg | Example 120 - 0.1 mg to 15 mg |

TABLE 64

| Example | Protease Inhibitor | TLR7 Modulator |
| --- | --- | --- |
| 64-a | ritonavir - 100 mg to 1000 mg | Formula II - 0.1 mg to 25 mg |
| 64-b | ritonavir - 100 mg to 1000 mg | Example 4 - 0.1 mg to 25 mg |
| 64-c | ritonavir - 100 mg to 1000 mg | Example 49 - 0.1 mg to 25 mg |
| 64-d | ritonavir - 100 mg to 1000 mg | Example 119 - 0.1 mg to 25 mg |
| 64-e | ritonavir - 100 mg to 1000 mg | Example 120 - 0.1 mg to 25 mg |
| 64-f | ritonavir - 100 mg to 1000 mg | Formula II - 0.1 mg to 15 mg |
| 64-g | ritonavir - 100 mg to 1000 mg | Example 4 - 0.1 mg to 15 mg |
| 64-h | ritonavir - 100 mg to 1000 mg | Example 49 - 0.1 mg to 15 mg |
| 64-i | ritonavir - 100 mg to 1000 mg | Example 119 - 0.1 mg to 15 mg |
| 64-j | ritonavir - 100 mg to 1000 mg | Example 120 - 0.1 mg to 15 mg |
| 64-k | ritonavir - 100 mg to 1000 mg | Formula II - 2 mg to 10 mg |
| 64-l | ritonavir - 100 mg to 1000 mg | Example 4 - 2 mg to 10 mg |
| 64-m | ritonavir - 100 mg to 1000 mg | Example 49 - 2 mg to 10 mg |
| 64-n | ritonavir - 100 mg to 1000 mg | Example 119 - 2 mg to 10 mg |
| 64-o | ritonavir - 100 mg to 1000 mg | Example 120 - 2 mg to 10 mg |
| 64-p | ritonavir - 100 mg to 1000 mg | ANA-773 - 200 mg to 2000 mg |
| 64-q | ritonavir - 100 mg to 1000 mg | GSK2245035 - 25 mg to 1000 mg |
| 64-r | ritonavir - 100 mg to 1000 mg | Imiquimod - 25 mg to 1000 mg |
| 64-s | ritonavir - 100 mg to 1000 mg | Imiquimod - 25 mg to 1000 mg |
| 64-t | ritonavir - 100 mg to 1000 mg | IMO8400 - 25 mg to 1000 mg |
| 64-u | ritonavir - 100 mg to 1000 mg | GSK2245035 - 25 mg to 1000 mg |
| 64-v | ritonavir - 100 mg to 1000 mg | CL075 - 1 mg to 100 mg |
| 64-w | ritonavir - 100 mg to 1000 mg | Gardiquimod - 25 mg to 1000 mg |
| 64x | ritonavir - 100 mg to 1000 mg | Loxoribine - 25 mg to 1000 mg |
| 64-y | ritonavir - 200 mg to 600 mg | Formula II - 0.1 mg to 15 mg |
| 64-z | ritonavir - 200 mg to 600 mg | Example 4 - 0.1 mg to 15 mg |
| 64-aa | ritonavir - 200 mg to 600 mg | Example 49 - 0.1 mg to 15 mg |
| 64-ab | ritonavir - 200 mg to 600 mg | Example 119 - 0.1 mg to 15 mg |
| 64-ac | ritonavir - 200 mg to 600 mg | Example 120 - 0.1 mg to 15 mg |
| 64-ad | ritonavir - 50 mg | Formula II - 0.1 mg to 15 mg |
| 64-ae | ritonavir - 50 mg | Example 4 - 0.1 mg to 15 mg |
| 64-af | ritonavir - 50 mg | Example 49 - 0.1 mg to 15 mg |
| 64-ag | ritonavir - 50 mg | Example 119 - 0.1 mg to 15 mg |
| 64-ah | ritonavir - 50 mg | Example 120 - 0.1 mg to 15 mg |
| 64-ai | ritonavir - 100 mg | Formula II - 0.1 mg to 15 mg |

TABLE 64-continued

| Example | Protease Inhibitor | TLR7 Modulator |
| --- | --- | --- |
| 64-aj | ritonavir - 100 mg | Example 4 - 0.1 mg to 15 mg |
| 64-ak | ritonavir - 100 mg | Example 49 - 0.1 mg to 15 mg |
| 64-al | ritonavir - 100 mg | Example 119 - 0.1 mg to 15 mg |
| 64-am | ritonavir - 100 mg | Example 120 - 0.1 mg to 15 mg |

TABLE 65

| Example | Protease Inhibitor | TLR7 Modulator |
| --- | --- | --- |
| 65-a | amprenavir - 100 mg to 1500 mg | Formula II - 0.1 mg to 25 mg |
| 65-b | amprenavir - 100 mg to 1500 mg | Example 4 - 0.1 mg to 25 mg |
| 65-c | amprenavir - 100 mg to 1500 mg | Example 49 - 0.1 mg to 25 mg |
| 65-d | amprenavir - 100 mg to 1500 mg | Example 119 - 0.1 mg to 25 mg |
| 65-e | amprenavir - 100 mg to 1500 mg | Example 120 - 0.1 mg to 25 mg |
| 65-f | amprenavir - 100 mg to 1500 mg | Formula II - 0.1 mg to 15 mg |
| 65-g | amprenavir - 100 mg to 1500 mg | Example 4 - 0.1 mg to 15 mg |
| 65-h | amprenavir - 100 mg to 1500 mg | Example 49 - 0.1 mg to 15 mg |
| 65-i | amprenavir - 100 mg to 1500 mg | Example 119 - 0.1 mg to 15 mg |
| 65-j | amprenavir - 100 mg to 1500 mg | Example 120 - 0.1 mg to 15 mg |
| 65-k | amprenavir - 100 mg to 1500 mg | Formula II - 2 mg to 10 mg |
| 65-l | amprenavir - 100 mg to 1500 mg | Example 4 - 2 mg to 10 mg |
| 65-m | amprenavir - 100 mg to 1500 mg | Example 49 - 2 mg to 10 mg |
| 65-n | amprenavir - 100 mg to 1500 mg | Example 119 - 2 mg to 10 mg |
| 65-o | amprenavir - 100 mg to 1500 mg | Example 120 - 2 mg to 10 mg |
| 65-p | amprenavir - 100 mg to 1500 mg | ANA-773 - 200 mg to 2000 mg |
| 65-q | amprenavir - 100 mg to 1500 mg | GSK2245035 - 25 mg to 1000 mg |
| 65-r | amprenavir - 100 mg to 1500 mg | Imiquimod - 25 mg to 1000 mg |
| 65-s | amprenavir - 100 mg to 1500 mg | Imiquimod - 25 mg to 1000 mg |
| 65-t | amprenavir - 100 mg to 1500 mg | IMO8400 - 25 mg to 1000 mg |
| 65-u | amprenavir - 100 mg to 1500 mg | GSK2245035 - 25 mg to 1000 mg |
| 65-v | amprenavir - 100 mg to 1500 mg | CL075 - 1 mg to 100 mg |
| 65-w | amprenavir - 100 mg to 1500 mg | Gardiquimod - 25 mg to 1000 mg |
| 65x | amprenavir - 100 mg to 1500 mg | Loxoribine - 25 mg to 1000 mg |
| 65-y | amprenavir - 500 mg to 1300 mg | Formula II - 0.1 mg to 15 mg |
| 65-z | amprenavir - 500 mg to 1300 mg | Example 4 - 0.1 mg to 15 mg |
| 65-aa | amprenavir - 500 mg to 1300 mg | Example 49 - 0.1 mg to 15 mg |
| 65-ab | amprenavir - 500 mg to 1300 mg | Example 119 - 0.1 mg to 15 mg |
| 65-ac | amprenavir - 500 mg to 1300 mg | Example 120 - 0.1 mg to 15 mg |
| 65-ad | amprenavir - 100 mg | Formula II - 0.1 mg to 15 mg |
| 65-ae | amprenavir - 100 mg | Example 4 - 0.1 mg to 15 mg |
| 65-af | amprenavir - 100 mg | Example 49 - 0.1 mg to 15 mg |
| 65-ag | amprenavir - 100 mg | Example 119 - 0.1 mg to 15 mg |
| 65-ah | amprenavir - 100 mg | Example 120 - 0.1 mg to 15 mg |
| 65-ai | amprenavir - 150 mg | Formula II - 0.1 mg to 15 mg |
| 65-aj | amprenavir - 150 mg | Example 4 - 0.1 mg to 15 mg |
| 65-ak | amprenavir - 150 mg | Example 49 - 0.1 mg to 15 mg |
| 65-al | amprenavir - 150 mg | Example 119 - 0.1 mg to 15 mg |
| 65-am | amprenavir - 150 mg | Example 120 - 0.1 mg to 15 mg |

Another embodiment comprises a kit comprising a pharmaceutically effective amount of an antiviral agent, or a pharmaceutically acceptable salt thereof, a pharmaceutically effective amount of a TLR7 modulating compound, or a pharmaceutically acceptable salt thereof, and directions for the administration of the antiviral agent and the TLR7 modulating compound. A further embodiment comprises the kit just described wherein the antiviral agent and the TLR7 modulating compound are present in the same pharmaceutical composition. Another embodiment comprises the kit just described wherein the antiviral agent and the TLR7 modulating compound are present in separate pharmaceutical compositions.

A series of embodiments is provided within the description of each kit herein wherein the TLR7 modulating compound is selected from those of Formula II, Formula III, Formula III(a), Formula III(b), Formula III(c), Formula III(d), Formula III(e), Formula III(f), Formula III(a)(1), Formula III(a)(2), Formula III(b)(1), Formula III(b)(2), Formula III(c)(1), Formula III(c)(2), Formula III(d)(1), Formula III(d)(2), Formula III(e)(1), Formula III(e)(2), Formula III (f)(1), and Formula III(f)(2), or a compound selected from Examples 1 through 124, including each of the compounds of Examples 4, 49, 119, and 120; or a pharmaceutically acceptable salt thereof, as well as each of the other TLR7 modulating compounds referenced herein.

Each of the kits described herein may further comprise a container and a label or a package insert on or associated with the container. The term "package insert" refers to instructions customarily included in commercial packages of therapeutic products providing relevant information, such as indications, usage, dosages, administration, contraindications and/or warnings associated with the therapeutic products.

Separate embodiments also comprise individual kits each comprising pharmaceutical compositions comprising the pharmaceutically effective amounts of the one or more antiviral agents and the TLR7 modulator described for each of the individual combinations listed in Tables 1A through 65, and directions for their administration. It is understood that each listed combination appears in a separate kit. A further set of separate embodiments comprises the kits just described wherein the one or more antiviral agents and the TLR7 modulating compound are present in the same pharmaceutical composition. Another set of embodiments comprises the kits just described wherein the one or more antiviral agents of each combination are in one pharmaceutical composition and the TLR7 modulating compound is present in a separate pharmaceutical composition. Another set of embodiments for those combinations with three or more antiviral agents comprises the kits just described wherein two or more antiviral agents of each combination are in one pharmaceutical composition, at least one antiviral agent is in a separate pharmaceutical composition, and the TLR7 modulating compound is present in another separate pharmaceutical composition. A further set of embodiments comprises the kits just described wherein each of the antiviral agents of each combination are in a separate pharmaceutical composition, with one antiviral agent per composition, and the TLR7 modulating compound is present in another separate pharmaceutical composition.

Also provided are separate embodiments comprising the use of the pharmaceutically effective amounts of each of the antiviral compounds and TLR7 modulating compounds in each of individual combinations listed in Tables 1A through 65 for use in the treatment of HIV in a human. It is understood that each individual combination in the tables represents a separate embodiment for use in the treatment of an HIV infection in a human. Also provided are separate embodiments comprising the use of the pharmaceutically effective amounts of each of the antiviral compounds and TLR7 modulating compounds in each of individual combinations in the Tables listed above for:
 a) use in treating an HIV infection in a virologically suppressed human;
 b) use in inducing HIV of inducing HIV gene expression in a human infected with HIV;
 c) use in inducing HIV gene expression in a human infected with HIV wherein active HIV gene expression in the human has been suppressed by administration of antiretroviral therapy;
 d) use in inducing HIV gene expression in a latent HIV reservoir in a human infected with HIV;
 e) use in enhancing HIV gene expression in HIV infected cells in a human infected with HIV;
 f) use in lowering the chronic set point of HIV viral load in a human infected with HIV;
 g) use in inducing transient HIV-1 viremia in a virologically suppressed human infected with HIV-1;
 h) use in reducing HIV viremia in a human infected with HIV;
 i) use in enhancing immune cell activity and increasing HIV gene expression in a human infected with HIV;
 j) use in enhancing the efficacy of an antiviral agent in a human infected with HIV;
 k) use in inducing transient HIV-1 viremia in a virologically suppressed human infected with HIV-1;
 l) use in enhancing the efficacy of an HIV vaccine; and
 m) use in eliminating an HIV infection in a human.

Also provided are separate embodiments comprising the use of the pharmaceutically effective amounts of each of the antiviral compounds and TLR7 modulating compounds in each of individual combinations in the Tables listed above for the manufacture of a medicament for:
 a) treating an HIV infection in a virologically suppressed human;
 b) inducing HIV of inducing HIV gene expression in a human infected with HIV;
 c) inducing HIV gene expression in a human infected with HIV wherein active HIV gene expression in the human has been suppressed by administration of antiretroviral therapy;
 d) inducing HIV gene expression in a latent HIV reservoir in a human infected with HIV;
 e) enhancing HIV gene expression in HIV infected cells in a human infected with HIV;
 f) lowering the chronic set point of HIV viral load in a human infected with HIV;
 g) inducing transient HIV-1 viremia in a virologically suppressed human infected with HIV-1;
 h) reducing HIV viremia in a human infected with HIV;
 i) enhancing immune cell activity and increasing HIV gene expression in a human infected with HIV;
 j) enhancing the efficacy of an antiviral agent in a human infected with HIV;
 k) use in inducing transient HIV-1 viremia in a virologically suppressed human infected with HIV-1;
 l) enhancing the efficacy of an HIV vaccine; and
 m) eliminating an HIV infection in a human.

Further separate embodiments for each of the kits described herein comprises the individual kit as described wherein
 a) each of the pharmaceutical compositions comprising the one or more antiviral agents and the TLR7 modulator are each provided for daily dosing;
 b) each of the pharmaceutical compositions comprising antiviral agents are provided for once daily administration and the pharmaceutical composition comprising the TLR7 modulator are provided for less than daily administration; and
 c) each of the pharmaceutical compositions comprising antiviral agents are provided for once or twice daily administration and the pharmaceutical composition comprising the TLR7 modulator are provided for less than daily administration.

For each of the kits in which the pharmaceutical compositions comprising antiviral agents are provided for once or twice daily administration and the pharmaceutical composition comprising the TLR7 modulator are provided for less than daily administration, the pharmaceutical composition comprising the TLR7 modulator may be for administration every other day or every $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, or $30^{th}$ day. Another embodiment for each of such kits comprises:
 a) a number of daily dose compositions, such as an oral tablet or capsule, each daily dose composition comprising a pharmaceutically effective amount of at least one antiviral agent;
 b) a number of less than daily dose compositions, such as an oral tablet or capsule, each daily dose composition comprising a pharmaceutically effective amount of at least one antiviral agent and a pharmaceutically effective amount of a TLR7 modulator; and
 c) directions for the administration of the daily dose compositions and the less than daily dose compositions.

It is understood that in such kits there would be an equal number of daily dose compositions and less than daily dose compositions in kits wherein the TLR7 modulator is intended for every other day administration, there would be twice as many daily dose compositions as less than daily dose compositions in kits wherein the TLR7 modulator is intended for every third day administration, etc. Such kits may further include means for containing the compositions for scheduled administration, such as a cycle pack or a blister pack into which the individual compositions are contained in separate sections according to the order of their scheduled administration.

Also provided is a kit comprising:
a) a pharmaceutically effective amount of a TLR7 modulating compound;
b) a pharmaceutically effective amount of an HIV antibody; and
c) directions for the administration of the TLR7 modulating compound and the HIV antibody.

Also provided is a kit comprising:
a) a pharmaceutically effective amount of a TLR7 modulating compound;
b) a pharmaceutically effective amount of an HIV vaccine; and
c) directions for the administration of the TLR7 modulating compound and the HIV vaccine.

Also provided is a kit comprising:
a) a pharmaceutically effective amount of a TLR7 modulating compound;
b) a pharmaceutically effective amount of a latency reversing agent; and
c) directions for the administration of the TLR7 modulating compound and the latency reversing agent.

Provided are separate embodiments comprising:
the use of a TLR7 modulating compound and an antiretroviral agent, or a pharmaceutically acceptable salt thereof, in the preparation of a medicament for treating an HIV infection in a human;
the use of a TLR7 modulating compound of Formula II and an antiretroviral agent, or a pharmaceutically acceptable salt thereof, in the preparation of a medicament for treating an HIV infection in a human;
the use of a compound of Example 4 and an antiretroviral agent, or a pharmaceutically acceptable salt thereof, in the preparation of a medicament for treating an HIV infection in a human;
the use of a compound of Example 49 and an antiretroviral agent, or a pharmaceutically acceptable salt thereof, in the preparation of a medicament for treating an HIV infection in a human;
the use of a compound of Example 119 and an antiretroviral agent, or a pharmaceutically acceptable salt thereof, in the preparation of a medicament for treating an HIV infection in a human;
the use of a compound of Example 120 and an antiretroviral agent, or a pharmaceutically acceptable salt thereof, in the preparation of a medicament for treating an HIV infection in a human; and
the use of a compound of Example 121 and an antiretroviral agent, or a pharmaceutically acceptable salt thereof, in the preparation of a medicament for treating an HIV infection in a human.

Also provided are separate embodiments comprising:
the use of a TLR7 modulating compound and a latency-reversing agent, or a pharmaceutically acceptable salt thereof, in the preparation of a medicament for treating an HIV infection in a human;
the use of a TLR7 modulating compound of Formula II and a latency-reversing agent, or a pharmaceutically acceptable salt thereof, in the preparation of a medicament for treating an HIV infection in a human;
the use of a compound of Example 4 and a latency-reversing agent, or a pharmaceutically acceptable salt thereof, in the preparation of a medicament for treating an HIV infection in a human;
the use of a compound of Example 49 and a latency-reversing agent, or a pharmaceutically acceptable salt thereof, in the preparation of a medicament for treating an HIV infection in a human;
the use of a compound of Example 119 and a latency-reversing agent, or a pharmaceutically acceptable salt thereof, in the preparation of a medicament for treating an HIV infection in a human;
the use of a compound of Example 120 and a latency-reversing agent, or a pharmaceutically acceptable salt thereof, in the preparation of a medicament for treating an HIV infection in a human; and
the use of a compound of Example 121 and a latency-reversing agent, or a pharmaceutically acceptable salt thereof, in the preparation of a medicament for treating an HIV infection in a human.

Provided are separate embodiments comprising:
the use of a TLR7 modulating compound, or a pharmaceutically acceptable salt thereof, in the preparation of a medicament for enhancing the efficacy of an antiviral agent;
the use of a TLR7 modulating compound of Formula II, or a pharmaceutically acceptable salt thereof, in the preparation of a medicament for enhancing the efficacy of an antiviral agent;
the use of a compound of Example 4, or a pharmaceutically acceptable salt thereof, in the preparation of a medicament for enhancing the efficacy of an antiviral agent;
the use of a compound of Example 49, or a pharmaceutically acceptable salt thereof, in the preparation of a medicament for enhancing the efficacy of an antiviral agent;
the use of a compound of Example 119, or a pharmaceutically acceptable salt thereof, in the preparation of a medicament for enhancing the efficacy of an antiviral agent;
the use of a compound of Example 120, or a pharmaceutically acceptable salt thereof, in the preparation of a medicament for enhancing the efficacy of an antiviral agent; and
the use of a compound of Example 121, or a pharmaceutically acceptable salt thereof, in the preparation of a medicament for enhancing the efficacy of an antiviral agent.

Provided are separate embodiments comprising:
the use of a TLR7 modulating compound, or a pharmaceutically acceptable salt thereof, in the preparation of a medicament for enhancing the efficacy of an HIV vaccine;
the use of a TLR7 modulating compound of Formula II, or a pharmaceutically acceptable salt thereof, in the preparation of a medicament for enhancing the efficacy of an HIV vaccine;
the use of a compound of Example 4, or a pharmaceutically acceptable salt thereof, in the preparation of a medicament for enhancing the efficacy of an HIV vaccine;
the use of a compound of Example 49, or a pharmaceutically acceptable salt thereof, in the preparation of a medicament for enhancing the efficacy of an HIV vaccine;

the use of a compound of Example 119, or a pharmaceutically acceptable salt thereof, in the preparation of a medicament for enhancing the efficacy of an HIV vaccine;
the use of a compound of Example 120, or a pharmaceutically acceptable salt thereof, in the preparation of a medicament for enhancing the efficacy of an HIV vaccine; and
the use of a compound of Example 121, or a pharmaceutically acceptable salt thereof, in the preparation of a medicament for enhancing the efficacy of an HIV vaccine.

Provided are separate embodiments comprising:
the use of a TLR7 modulating compound, or a pharmaceutically acceptable salt thereof, in the preparation of a medicament for eliminating an HIV infection in a human;
the use of a TLR7 modulating compound of Formula II, or a pharmaceutically acceptable salt thereof, in the preparation of a medicament for eliminating an HIV infection in a human;
the use of a compound of Example 4, or a pharmaceutically acceptable salt thereof, in the preparation of a medicament for eliminating an HIV infection in a human;
the use of a compound of Example 49, or a pharmaceutically acceptable salt thereof, in the preparation of a medicament for eliminating an HIV infection in a human;
the use of a compound of Example 119, or a pharmaceutically acceptable salt thereof, in the preparation of a medicament for eliminating an HIV infection in a human;
the use of a compound of Example 120, or a pharmaceutically acceptable salt thereof, in the preparation of a medicament for eliminating an HIV infection in a human; and
the use of a compound of Example 121, or a pharmaceutically acceptable salt thereof, in the preparation of a medicament for eliminating an HIV infection in a human.

Provided are separate embodiments comprising:
the use of a TLR7 modulating compound, or a pharmaceutically acceptable salt thereof, in the preparation of a medicament for inducing HIV gene expression in a human infected with HIV;
the use of a TLR7 modulating compound of Formula II, or a pharmaceutically acceptable salt thereof, in the preparation of a medicament for inducing HIV gene expression in a human infected with HIV;
the use of a compound of Example 4, or a pharmaceutically acceptable salt thereof, in the preparation of a medicament for inducing HIV gene expression in a human infected with HIV;
the use of a compound of Example 49, or a pharmaceutically acceptable salt thereof, in the preparation of a medicament for inducing HIV gene expression in a human infected with HIV;
the use of a compound of Example 119, or a pharmaceutically acceptable salt thereof, in the preparation of a medicament for inducing HIV gene expression in a human infected with HIV;
the use of a compound of Example 120, or a pharmaceutically acceptable salt thereof, in the preparation of a medicament for inducing HIV gene expression in a human infected with HIV; and
the use of a compound of Example 121, or a pharmaceutically acceptable salt thereof, in the preparation of a medicament for inducing HIV gene expression in a human infected with HIV.

Provided are separate embodiments comprising:
the use of a TLR7 modulating compound, or a pharmaceutically acceptable salt thereof, in the preparation of a medicament for enhancing HIV gene expression in HIV infected cells in a human infected with HIV;
the use of a TLR7 modulating compound of Formula II, or a pharmaceutically acceptable salt thereof, in the preparation of a medicament for enhancing HIV gene expression in HIV infected cells in a human infected with HIV;
the use of a compound of Example 4, or a pharmaceutically acceptable salt thereof, in the preparation of a medicament for enhancing HIV gene expression in HIV infected cells in a human infected with HIV;
the use of a compound of Example 49, or a pharmaceutically acceptable salt thereof, in the preparation of a medicament for enhancing HIV gene expression in HIV infected cells in a human infected with HIV;
the use of a compound of Example 119, or a pharmaceutically acceptable salt thereof, in the preparation of a medicament for enhancing HIV gene expression in HIV infected cells in a human infected with HIV;
the use of a compound of Example 120, or a pharmaceutically acceptable salt thereof, in the preparation of a medicament for enhancing HIV gene expression in HIV infected cells in a human infected with HIV; and
the use of a compound of Example 121, or a pharmaceutically acceptable salt thereof, in the preparation of a medicament for enhancing HIV gene expression in HIV infected cells in a human infected with HIV.

Provided are separate embodiments comprising:
the use of a TLR7 modulating compound, or a pharmaceutically acceptable salt thereof, in the preparation of a medicament for inducing transient HIV-1 viremia in a virologically suppressed human infected with HIV-1;
the use of a TLR7 modulating compound of Formula II, or a pharmaceutically acceptable salt thereof, in the preparation of a medicament inducing transient HIV-1 viremia in a virologically suppressed human infected with HIV-1;
the use of a compound of Example 4, or a pharmaceutically acceptable salt thereof, in the preparation of a medicament for inducing transient HIV-1 viremia in a virologically suppressed human infected with HIV-1;
the use of a compound of Example 49, or a pharmaceutically acceptable salt thereof, in the preparation of a medicament for inducing transient HIV-1 viremia in a virologically suppressed human infected with HIV-1;
the use of a compound of Example 119, or a pharmaceutically acceptable salt thereof, in the preparation of a medicament for inducing transient HIV-1 viremia in a virologically suppressed human infected with HIV-1;
the use of a compound of Example 120, or a pharmaceutically acceptable salt thereof, in the preparation of a medicament for inducing transient HIV-1 viremia in a virologically suppressed human infected with HIV-1; and
the use of a compound of Example 121, or a pharmaceutically acceptable salt thereof, in the preparation of a medicament for inducing transient HIV-1 viremia in a virologically suppressed human infected with HIV-1.

Provided are separate embodiments comprising:

the use of a TLR7 modulating compound, or a pharmaceutically acceptable salt thereof, in the preparation of a medicament for the treatment of an HIV-1 infection in a virologically suppressed human infected with HIV-1;

the use of a TLR7 modulating compound of Formula II, or a pharmaceutically acceptable salt thereof, in the preparation of a medicament for the treatment of an HIV-1 infection in a virologically suppressed human infected with HIV-1;

the use of a compound of Example 4, or a pharmaceutically acceptable salt thereof, in the preparation of a medicament the treatment of an HIV-1 infection in a virologically suppressed human infected with HIV-1;

the use of a compound of Example 49, or a pharmaceutically acceptable salt thereof, in the preparation of a medicament for the treatment of an HIV-1 infection in a virologically suppressed human infected with HIV-1;

the use of a compound of Example 119, or a pharmaceutically acceptable salt thereof, in the preparation of a medicament for the treatment of an HIV-1 infection in a virologically suppressed human infected with HIV-1;

the use of a compound of Example 120, or a pharmaceutically acceptable salt thereof, in the preparation of a medicament for the treatment of an HIV-1 infection in a virologically suppressed human infected with HIV-1; and the use of a compound of Example 121, or a pharmaceutically acceptable salt thereof, in the preparation of a medicament for the treatment of an HIV-1 infection in a virologically suppressed human infected with HIV-1.

Also provided is the use of a pharmaceutically effective amount of a TLR7 modulating compound, or a pharmaceutically acceptable salt thereof, for inhibiting HIV replication in a human infected with an HIV virus. Also provided is the use of a pharmaceutically effective amount of a TLR7 modulating compound of Formula II, or a pharmaceutically acceptable salt thereof, for inhibiting HIV replication in a human infected with an HIV virus. Also provided is the use of a pharmaceutically effective amount of a TLR7 modulating compound of Example 4, or a pharmaceutically acceptable salt thereof, for inhibiting HIV replication in a human infected with an HIV virus. Also provided is the use of a pharmaceutically effective amount of a TLR7 modulating compound of Example 49, or a pharmaceutically acceptable salt thereof, for inhibiting HIV replication in a human infected with an HIV virus. Also provided is the use of a pharmaceutically effective amount of a TLR7 modulating compound of Example 119, or a pharmaceutically acceptable salt thereof, for inhibiting HIV replication in a human infected with an HIV virus. Also provided is the use of a pharmaceutically effective amount of a TLR7 modulating compound of Example 120, or a pharmaceutically acceptable salt thereof, for inhibiting HIV replication in a human infected with an HIV virus. Also provided is the use of a pharmaceutically effective amount of a TLR7 modulating compound of Example 121, or a pharmaceutically acceptable salt thereof, for inhibiting HIV replication in a human infected with an HIV virus. Also provided are the use separate uses of a pharmaceutically effective amount of a TLR7 modulating compound selected from Examples 1-124 herein, or a pharmaceutically acceptable salt thereof, for inhibiting HIV replication in a human infected with an HIV virus.

Also provided is the use of a pharmaceutically effective amount of a TLR7 modulating compound, or a pharmaceutically acceptable salt thereof, as a research tool for inhibiting HIV replication. Also provided is the use of a pharmaceutically effective amount of a TLR7 modulating compound of Formula II, or a pharmaceutically acceptable salt thereof, as a research tool for inhibiting HIV replication. Also provided is the use of a pharmaceutically effective amount of a TLR7 modulating compound of Example 4, or a pharmaceutically acceptable salt thereof, as a research tool for inhibiting HIV replication. Also provided is the use of a pharmaceutically effective amount of a TLR7 modulating compound of Example 49, or a pharmaceutically acceptable salt thereof, as a research tool for inhibiting HIV replication. Also provided is the use of a pharmaceutically effective amount of a TLR7 modulating compound of Example 119, or a pharmaceutically acceptable salt thereof, as a research tool for inhibiting HIV replication. Also provided is the use of a pharmaceutically effective amount of a TLR7 modulating compound of Example 120, or a pharmaceutically acceptable salt thereof, as a research tool for inhibiting HIV replication. Also provided is the use of a pharmaceutically effective amount of a TLR7 modulating compound of Example 121, or a pharmaceutically acceptable salt thereof, as a research tool for inhibiting HIV replication. Also provided are the use separate uses of a pharmaceutically effective amount of a TLR7 modulating compound selected from Examples 1-124 herein, or a pharmaceutically acceptable salt thereof, as a research tool for inhibiting HIV replication.

Also provided is the use of a pharmaceutically effective amount of a TLR7 modulating compound, or a pharmaceutically acceptable salt thereof, for treating an HIV infection in a human in need thereof.

Also provided is the use of a pharmaceutically effective amount of a TLR7 modulating compound, or a pharmaceutically acceptable salt thereof, in combination with a pharmaceutically effective amount of a combination antiretroviral therapy regimen, for treating an HIV infection in a human in need thereof.

Also provided is the use of a pharmaceutically effective amount of a TLR7 modulating compound, or a pharmaceutically acceptable salt thereof, in combination with a pharmaceutically effective amount of a combination antiretroviral therapy regimen, for treating an HIV infection in a human in need thereof, wherein the combination antiretroviral therapy regimen is sufficient to lower the level of HIV detected in the human's blood or plasma from a first level to a second level, wherein the first level is at a concentration greater than the second level.

Also provided is the use of a pharmaceutically effective amount of a TLR7 modulating compound, or a pharmaceutically acceptable salt thereof, in combination with a pharmaceutically effective amount of an HIV antibody, for treating an HIV infection in a human in need thereof Also provided is the use of a pharmaceutically effective amount of a TLR7 modulating compound, or a pharmaceutically acceptable salt thereof, in combination with a pharmaceutically effective amount of a combination antiretroviral therapy regimen, for treating an HIV infection in a virologically suppressed human infected with HIV-1, wherein the combination antiretroviral therapy regimen is sufficient to lower the level of HIV detected in the human's blood or plasma from a first level to a second level, wherein the first level is at a concentration greater than the second level.

Also provided is the use of a pharmaceutically effective amount of a TLR7 modulating compound, or a pharmaceutically acceptable salt thereof, for inducing HIV gene expression in a human infected with HIV wherein active HIV gene expression in the human has been suppressed by administration of antiretroviral therapy.

Also provided is the use of a pharmaceutically effective amount of a TLR7 modulating compound, or a pharmaceutically acceptable salt thereof, for lowering the chronic set point of HIV viral load in a human infected with HIV.

Also provided is the use of a pharmaceutically effective amount of a TLR7 modulating compound, or a pharmaceutically acceptable salt thereof, for inducing transient HIV-1 viremia in a virologically suppressed human infected with HIV-1.

Also provided is the use of a pharmaceutically effective amount of a TLR7 modulating compound, or a pharmaceutically acceptable salt thereof, for enhancing the efficacy of a pharmaceutically effective amount of an antiviral agent in a human infected with HIV.

Also provided is the use of a pharmaceutically effective amount of a TLR7 modulating compound, or a pharmaceutically acceptable salt thereof, for enhancing the efficacy of an HIV vaccine.

Also provided is the use of a pharmaceutically effective amount of a TLR7 modulating compound, or a pharmaceutically acceptable salt thereof, for eliminating an HIV infection in a human.

Also provided is the use of a pharmaceutically effective amount of a TLR7 modulating compound, or a pharmaceutically acceptable salt thereof, for eliminating an HIV infection in a human, wherein the human is receiving a pharmaceutically effective amount of a combination antiretroviral therapy Also provided is the use of a pharmaceutically effective amount of a TLR7 modulating compound, or a pharmaceutically acceptable salt thereof, in combination with a pharmaceutically effective amount of a combination antiretroviral therapy regimen, for eliminating an HIV infection in a human in need thereof, wherein the combination antiretroviral therapy regimen is sufficient to lower the level of HIV detected in the human's blood or plasma from a first level to a second level, wherein the first level is at a concentration greater than the second level.

Also provided is the use of a pharmaceutically effective amount of a TLR7 modulating compound, or a pharmaceutically acceptable salt thereof, in combination with a pharmaceutically effective amount of an HIV antibody, for eliminating an HIV infection in a human in need thereof.

Also provided is the use of a pharmaceutically effective amount of a TLR7 modulating compound, or a pharmaceutically acceptable salt thereof, in combination with a pharmaceutically effective amount of an HIV vaccine, for eliminating an HIV infection in a human in need thereof.

Biological Examples

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

EXAMPLES

Example 201

Formulation of Example 4

A sterile formulation of Example 4 suitable for oral dosing was prepared. Initially, a vehicle solution was prepared by dissolving propyl gallate in 0.001N HCl (pH 3.0) to obtain a final concentration of propyl gallate of 0.005% (w/v). Three solution formulations the compound of Example 4 were prepared by dissolving a sufficient amount of the compound of Example 4 in the 0.005% propyl gallate vehicle solution, to arrive at final concentrations of 0.1 mg/mL, 0.2 mg/mL, and 0.3 mg/mL Compound 4. These compositions were frozen at −20° C. until time of use.

Example 202 cART Formulation

A cART formulation containing 20 mg/mL tenofovir (TFV, GMP grade), 50 mg/mL emtricitabine (FTC, GMP grade), and 2.5 mg/mL dolutegravir (DTG, 95% purity) was prepared in a solvent containing a final concentration of 25% (v/v) polyethylene glycol 400 (PEG-400, Spectrum Chemical New Brunswick, N.J.), 15% (w/v) Captisol (Ligand Pharmaceuticals, LA Jolla, Calif.) and 0.075N sodium hydroxide (NaOH, Spectrum Chemical, New Brunswick, N.J.) in water. This formulation was prepared by mixing DTG stock solution (10 mg/mL of DTG in PEG-400), TFV and FTC stock solution (80 mg/mL of TFV and 200 mg/mL of FTC in 0.3 N NaOH), and 30% (w/w) captosil solution at a 1:1:2 (v:v:v) ratio. The final solution was clear with a pH~6. It was sterile filtered, then aliquoted into sterile glass and frozen at −20° C. until used.

Example 203

TLR7 Modulating Compound in SIV+ Viremic Rhesus at Chronic Set Point

Five chronically infected, SIV+ rhesus macaques were either treated with the compound of Example 4 (n=3 animals) or with dosing vehicle (placebo, n=2 animals) in a multiple-dose, dose escalation, placebo controlled study. The macaques were infected with simian immunodeficiency virus for sufficient period of time to establish a chronic set point (i.e., a state of persistent viremia, i.e., post-peak viremia where host immunological control of virus replication is established, although this does not lead to complete viral suppression) prior to dosing with the compound of Example 4. The animals were not administered combination antiretroviral therapy during any part of the study.

The animals were dosed once weekly by oral gavage (via nasogastric tube) with either the compound of Example 4 or placebo. Three animals were administered the compound of Example 4, prepared as described in Example 201. The first week, 1 mL/kg of the 0.1 mg/mL formulation was administered, corresponding to a dose of 0.1 mg/kg. The second week, 1 mL/kg of the 0.2 mg/mL formulation was administered, corresponding to a dose of 0.2 mg/kg. On weeks three through five, 1 mL/kg of the 0.3 mg/mL formulation was administered, corresponding to a dose of 0.3 mg/kg.

Each week, two animals (placebo group) were administered the dosing vehicle as described in Example 201 at 1 mL/kg.

Figure 2:
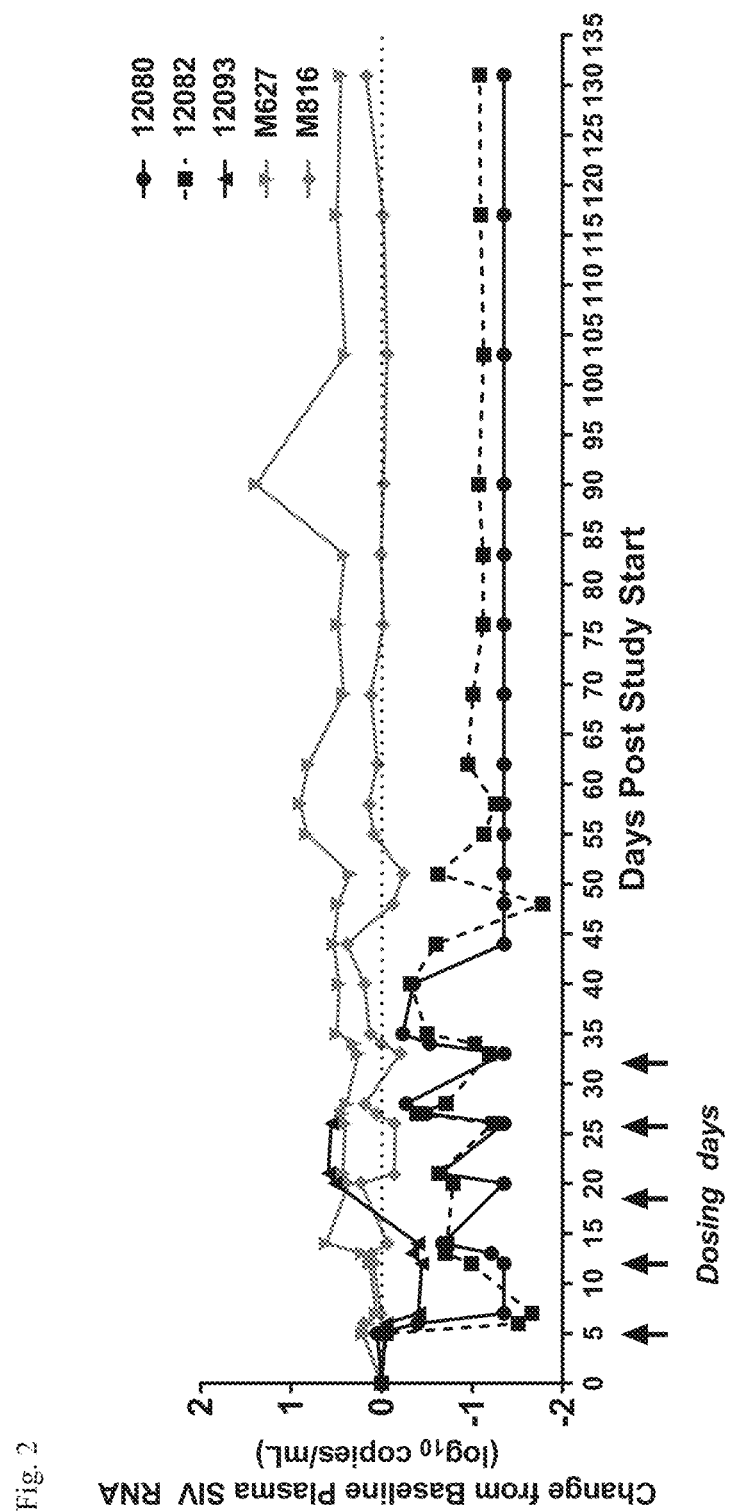
FIG. 2 depicts the change in viral load from baseline (day 0) for each study day in the SIV⁺ rhesus macaques study.

Each formulation of Example 201 or dosing vehicle only (placebo) was used fresh and thawed to room temperature prior to dosing. Plasma viral loads (expressed as SIV RNA copies per mL of plasma) were determined by quantitative RT-PCR of the SIV RNA measuring the gag gene transcripts at various times throughout the study for animals administered the compound of Example 4 and the placebo animals. The data are shown in FIGS. 1 and 2. FIG. 1 depicts the absolute viral load for each animal for each study day. FIG. 2 depicts the change in viral load from baseline (day 0) for each study day. In FIGS. 1 and 2, the dark black data points correspond to data from animals dosed with the compound of Example 4 while the shaded gray data points correspond to data from animals dosed with the placebo.

In FIGS. 1 and 2, dosing days are shown by the arrows on the horizontal x-axis relative to start of administration of the compound of Example 4.

As shown in FIG. 2, three of the three animals administered the compound of Example 4, experienced a decrease in viral load ranging from approximately 0.4 to 1.8 $\log_{10}$ immediately following the first dose. This amount of decrease in plasma viral load was not observed in animals administered the placebo. The animal that initiated the study with the highest viral load exhibited a decrease in viral load following dosing (FIG. 2). However, this animal was removed from the study prior to being administered the fourth and fifth dose due to SIV-related symptoms.

The animal that initiated the study with the lowest viral load (lowest chronic set point) maintained a plasma viral load that was undetectable (<50 RNA copies/mL) for at least 100 days following the last dose of the compound of Example 4 as shown in FIG. 1. In a second animal dosed with the compound of Example 4 there was also a sustained decrease in viral load set point by approximately 1 log order compared to pre-dose ($\log_{10}$ RNA copies) that was maintained at least 100 days following the last dose (FIG. 2). Together, the data shown in FIG. 1 and FIG. 2 demonstrate there was a decrease in plasma viral load after the first dose of study compound, followed by cyclic viral increases with subsequent doses, and sustained maintenance of a new and lower chronic viral set point as compared to pre-administration of the compound of Example 4.

Example 204

TLR7 Modulating Compound in cART Treated SIV⁺ Viremic Rhesus with Undetectable Plasma Viremia A group of 10 Indian rhesus macaques (*Macaca mulatta*) were treated with the compound of Example 4 or dosing vehicle of Example 201 (placebo group) in a multiple dose, dose escalation study. The macaques were infected with simian immunodeficiency virus (SIVmac251) by repeat low-dose rectal mucosal challenge. Beginning on day 65 post-infection, after establishment of peak viremia and an early viral chronic set point, the animals were treated with a the cART by sub-cutaneous injection at 1 mL/kg, the administration of which was for approximately one year. During the time of cART administration plasma viral loads decreased to undetectable levels (SIV gag RNA<50 copies/mL) by Day 168 post-infection, and were maintained for approximately 5 months prior to administration of the compound of Example 4 by use of daily cART. In addition, animals were maintained on the same cART regimen when dosed with the compound of Example 4. The amount of antiretrovirals administered to each animal, on a daily basis, in the cART formulation were 20 mg/kg tenofovir, 50 mg/kg emtricitibine (FTC), and 2.5 mg/kg dolutegravir. The animals were administered cART daily from approximately day 65 post-infection, through viral suppression and administration of the compound of Example 4 until approximately two weeks post-last dose of the compound from Example 4 at which time cART was stopped to monitor plasma viral load rebound kinetics.

Beginning on Day 317 post-infection, the animals were dosed once every other week with either the compound of Example 4 or dosing vehicle of Example 201 (placebo group). Four animals were dosed with the compound of Example 4, prepared as described in Example 201. The first week, 1 mL/kg of the 0.1 mg/mL formulation was dosed, corresponding to a dose of 0.1 mg/kg. The third week, 1 mL/kg of the 0.2 mg/mL formulation was dosed, corresponding to a dose of 0.2 mg/kg. On weeks five through thirteen, 1 mL/kg of the 0.3 mg/mL formulation was dosed, corresponding to a dose of 0.3 mg/kg (seven doses in total). The other six animals were controls, of which three were given seven doses of saline by oral gavage once every two weeks; the other three animals were left untreated. Approximately two weeks following the last dose of the compound of Example 4, cART was stopped in the three saline-dosed placebo animals and the four animals who had received the compound of Example 4. Approximately one month later, cART was stopped in the three untreated control animals. Following cART cessation viral loads were monitored for a period of six months.

Each formulation of the compound of Example 4 or dosing vehicle of Example 201 was thawed at room temperature prior to dosing. Animals were dosed by oral gavage via nasogastric tube.

Plasma viral loads (expressed as SIV RNA copies per mL of plasma) were determined by quantitative RT-PCR of the SIV RNA measuring the gag gene transcripts at various times throughout the study. Viral loads for animals administered the compound of Example 4 and placebo group are shown in Table 1 and in FIG. 3. Viral loads for each animal for each study day relative to time of administration of the first dose of the compound of Example 4 are depicted in FIG. 3; dosing days are shown by the arrows on the horizontal x-axis.

Figure 3:
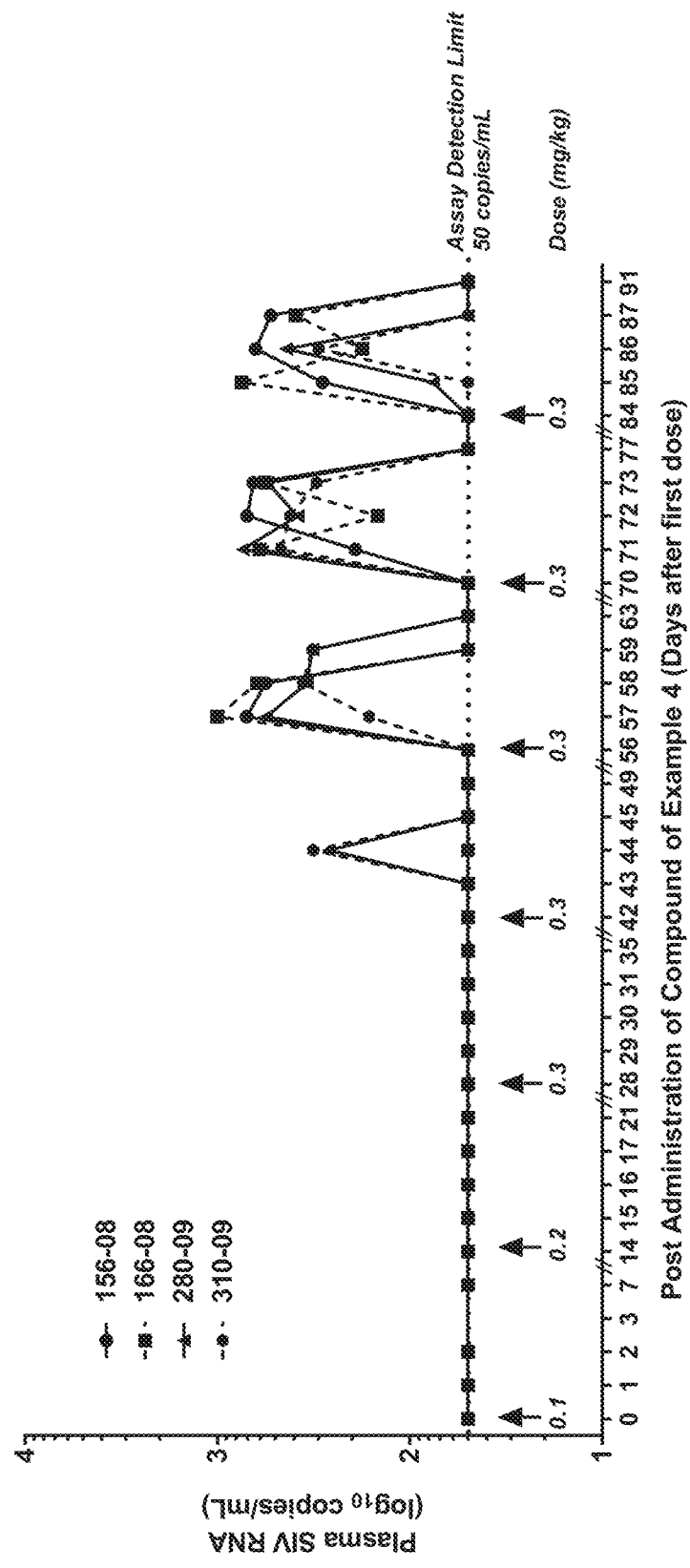
FIG. 3 depicts the absolute viral load for each animal for each study day in the SIV⁺ rhesus macaques study.
Figure 4:
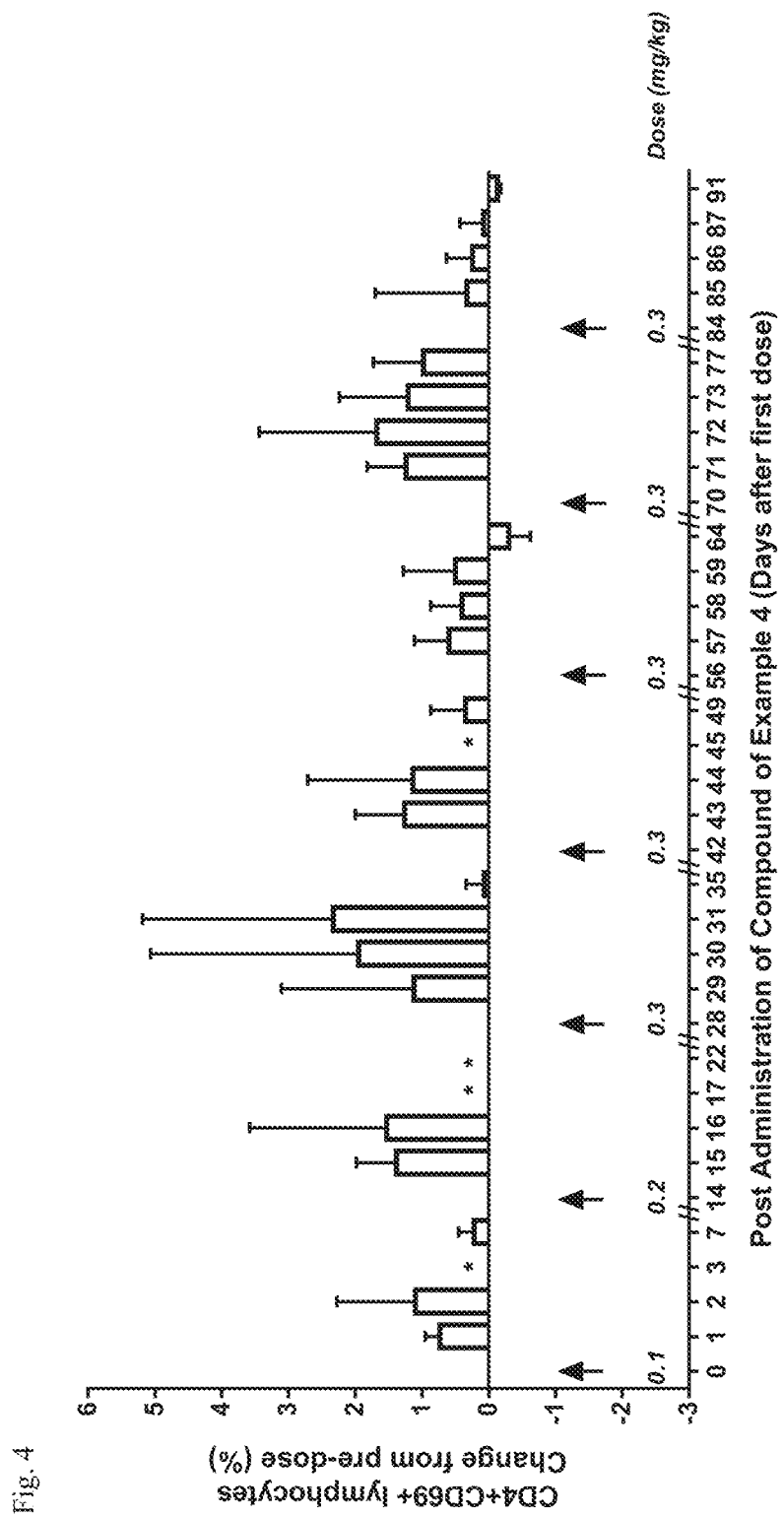
FIG. 4 depicts the CD8+ T-lymphocyte activation induced by dosing the compound of Example 4 in the SIV⁺ rhesus macaques study.
Figure 5:
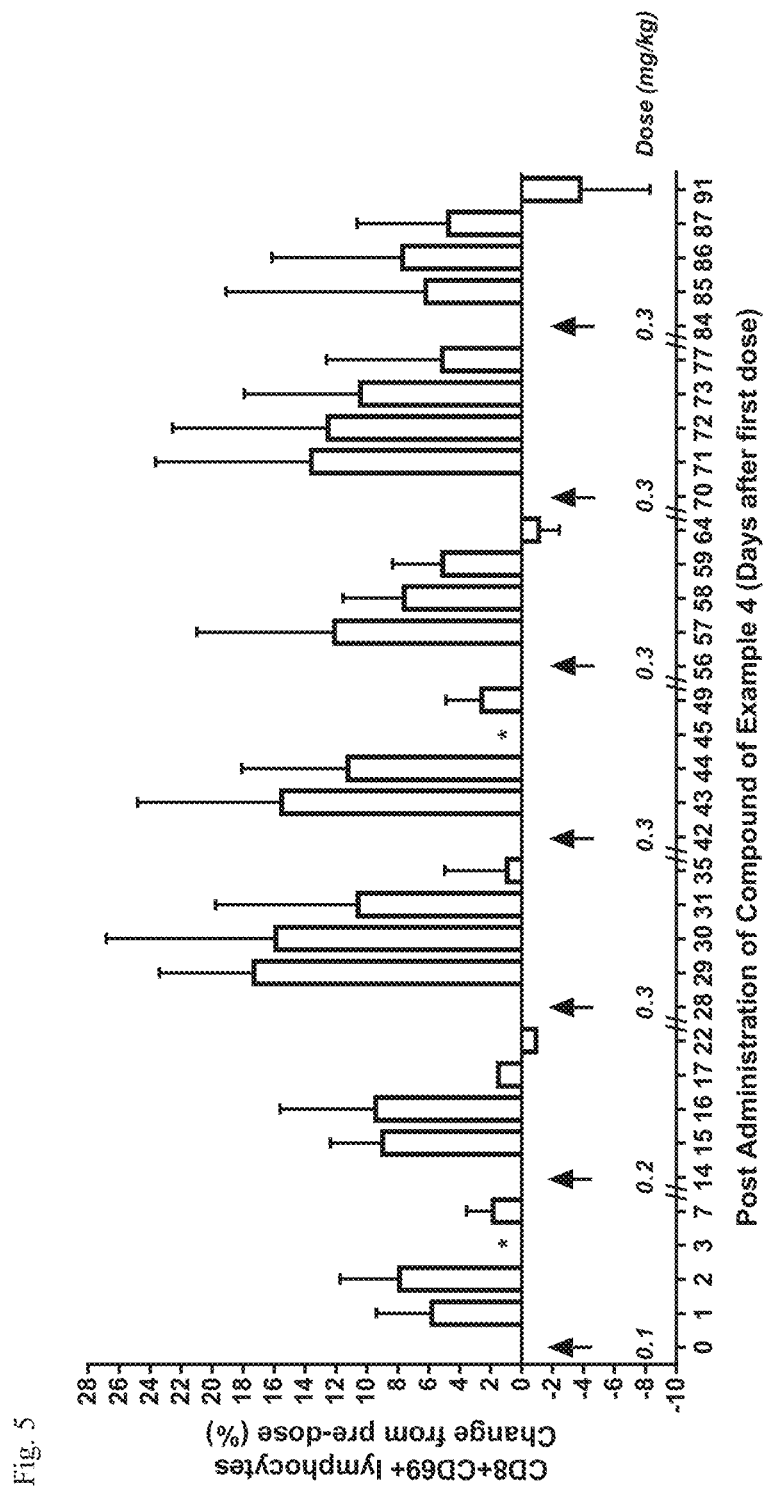
FIG. 5 depicts NK cell activation induced by dosing the compound of Example 4 in the SIV⁺ rhesus macaques study.
Figure 6:
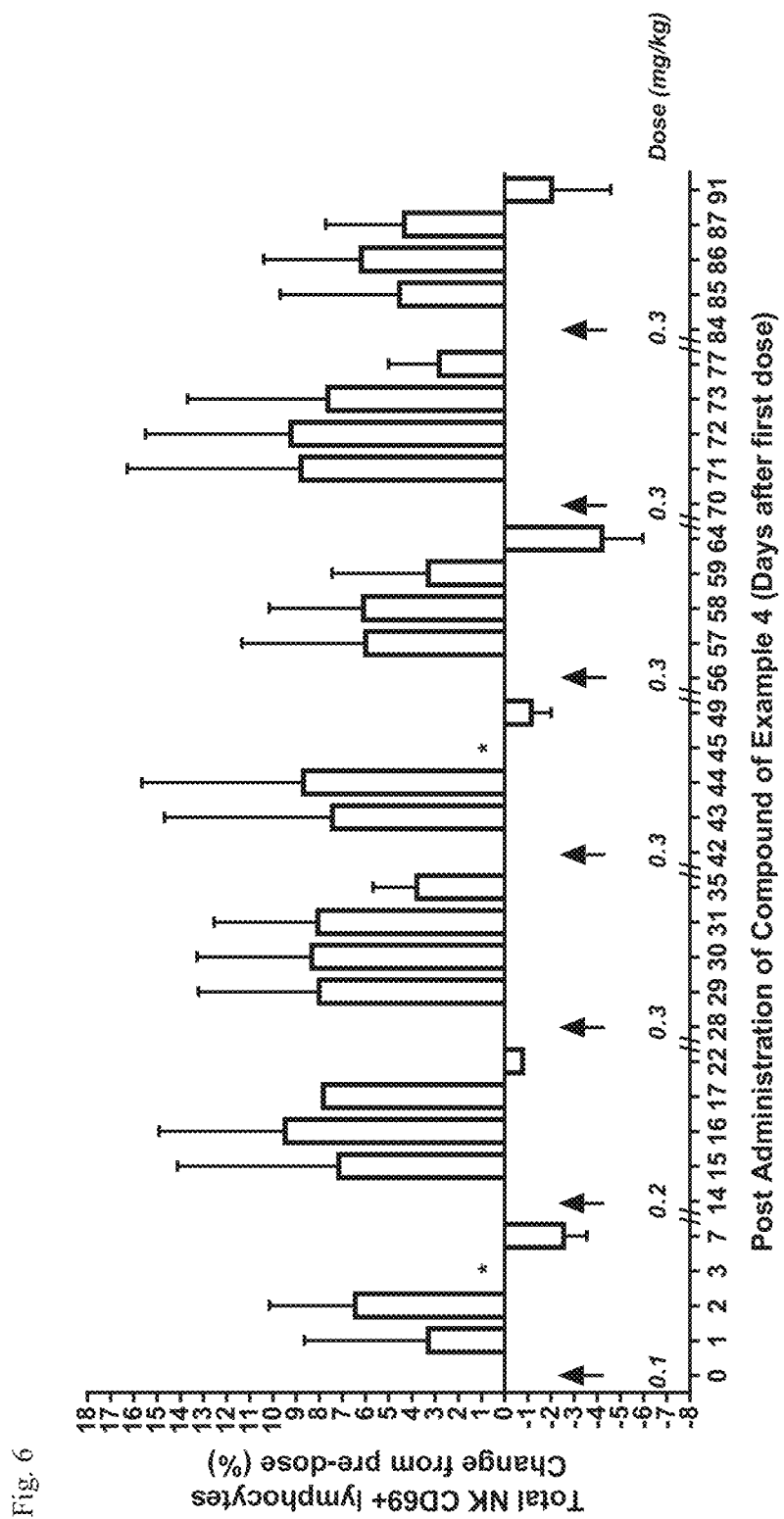
FIG. 6 depicts change in activated CD4 lymphocytes by dosing of the compound of Example 4 in SIV+ Rhesus Macaques on cART.

As shown in Table 1 and FIG. 3, detectable plasma virus was observed in the animals administered the compound of Example 4 approximately 24-72 hours after each of the last three doses of study drug (at 0.3 mg/kg). In each case, the virus levels returned to baseline (<50 copies per mL) prior to administration of the following dose. Virus levels remained undetectable for a total of 13 days after the last dose of the compound of Example 4. While the data are not shown in FIG. 3, in the three saline-dosed placebo animals and untreated control animals there was no detectable change in plasma virus expression during the dosing period and the animals maintained SIV RNA<50 copies/mL.

TABLE 1

Plasma Virus Levels from Dosing the Compound of Example 4 in SIV+ Rhesus Macaques on cART (Doses 4-7)

Plasma SIV RNA (copies/mL)
The Compound of Example 4 at 0.3 mg/kg

| Animal | Pre | 1 | 2 | 3 | 7 | Pre | 1 | 2 | 3 | 7 |
|---|---|---|---|---|---|---|---|---|---|---|
| | Time point (Days post-dose) Dose 4 | | | | | Time point (Days post-dose) Dose 5 | | | | |
| 156-08 | <50 | <50 | <50 | <50 | <50 | <50 | 706 | 563 | <50 | <50 |
| 166-08 | <50 | <50 | <50 | <50 | <50 | <50 | 1005 | 623 | <50 | <50 |
| 280-09 | <50 | <50 | 264 | <50 | <50 | <50 | 561 | 344 | 322 | <50 |
| 310-09 | <50 | <50 | 319 | <50 | <50 | <50 | 163 | 361 | 322 | <50 |
| | Time point (Days post-dose) Dose 6 | | | | | Time point (Days post-dose) Dose 7 | | | | |
| 156-08 | <50 | 193 | 701 | 650 | <50 | <50 | 285 | 634 | 530 | <50 |
| 166-08 | <50 | 605 | 147 | 567 | <50 | <50 | 750 | 177 | 394 | <50 |
| 280-09 | <50 | 741 | 383 | 551 | <50 | <50 | 76 | 440 | <50 | <50 |
| 310-09 | <50 | 468 | 421 | 305 | <50 | <50 | 50 | 299 | <50 | <50 |

The data from this portion of the dose-escalation study demonstrates that the compound of Example 4 reproducibly induced transient plasma viremia in the presence of cART followed by a return to full plasma SIV RNA suppression. The transient increases in detectable plasma virus occurred after 4 to 5 doses of the compound of Example 4 administered orally once every 14 days.

After two weeks following the last dose of study drug, cART therapy was also stopped in all dosed (placebo dosed included) animals. In the untreated control group of animals, cART was stopped 30 days later. Table 2 denotes the average viral load chronic set point from day 42-81 following cessation of cART for each of the animals in the study. As shown in Table 2, all animals experienced plasma viral rebound within 7 to 14 days after cART cessation. However, when comparing the pre-cART plasma SIV RNA chronic set point to the post-cART cessation chronic set point within the animals administered the compound of Example 4 this was approximately ~0.5 $\log_{10}$ lower (mean change for all animals treated with the compound of Example 4) than the change observed in those animals in the placebo group (mean change for all animals administered dosing vehicle of Example 201).

TABLE 2

Plasma Virus Chronic Set Point Changes by the Compound of Example 4 Dosing in SIV+ Rhesus Macaques (Pre-cART and Post-cART Cessation)

Plasma SIV RNA

| Animal ID | Treatment | Chronic Set Point Day 42-63 Pre-cART (copy/mL) | Chronic Set Point Day 42-81 Post-cART Cessation (copy/mL) | Change in Chronic Set Point ($-\log_{10}$ copy/mL) | Mean Change in Chronic Set Point ($-\log_{10}$ copy/mL) | p-value Compound of Example 4 dosed group versus placebo |
|---|---|---|---|---|---|---|
| 156-08 | Example 4 | 237,667 | 3,553 | −1.83 | −1.26 | 0.076 |
| 166-08 | Example 4 | 76,833 | 10,062 | −0.88 | | |
| 280-09 | Example 4 | 156,333 | 20,146 | −0.89 | | |
| 310-09 | Example 4 | 666,333 | 24,527 | −1.43 | | |
| 205-08 | Saline | 100,300 | 14,114 | −0.85 | −0.70 | |
| 267-08 | Saline | 285,500 | 103,036 | −0.44 | | |
| 105-09 | Saline | 3,273,333 | 418,279 | −0.89 | | |
| 234-09 | Untreated | 1,735,333 | 285,364 | −0.78 | | |
| 322-09 | Untreated | 84,429 | 8,504 | −1.00 | | |
| 374-09 | Untreated | 358,405 | 109,653 | −0.51 | | |

Example 205

Proviral SIV DNA Measurements in Peripheral Blood Mononuclear Cells (PBMCs), Lymph Node, and Colon A whole blood sample, an inguinal lymph node sample, and a colon pinch biopsy sample were taken from the animals dosed with the compound of Example 4 and from the animals dosed with the vehicle of Example 201 (placebo group) in the study described in Example 204. These samples were taken prior to initiation of dosing and two weeks after the last dose; all samples were taken while animals were on cART. Total DNA was isolated from each sample using commercially available blood and tissue DNA extraction kits. Proviral SIV DNA levels were measured by quantitative PCR (qPCR) using probe-primer sets specific to the SIV gag gene and normalization for cellular input by measuring the glyceraldehyde 3-phosphate dehydrogenase (GAPDH) gene levels. In comparing proviral SIV DNA amounts in the pre- and post-treatment PBMC, inguinal lymph node, and colon samples within each animal, there was a clear decrease in proviral DNA content for three of four animals treated with the compound of Example 4 across all tissues. In one of the compound treated animals (166-08), there was only a noted decrease in the proviral DNA content in the PBMCs, a minor increase in lymph node, and a minor decrease in the colon. In the vehicle-dosed placebo control animals, however, there were slight to moderate increases in two of three animals in proviral SIV DNA in the PBMC and colon samples, and relatively stable levels in lymph node samples.

TABLE 3

Proviral SIV DNA in PBMCs, Lymph Node and Colon from SIV+ Rhesus Macaques on cART

| | PBMC | | Lymph node | | Colon | |
|---|---|---|---|---|---|---|
| Animal | Pre | Post | Pre | Post | Pre | Post |
| | SIV DNA from Animals Treated with the Compound of Example 4 (copies/$10^6$ cells) | | | | | |
| 156-08 | 120 | 3 | 130 | 3 | 110 | 3 |
| 166-08 | 150 | 100 | 270 | 280 | 230 | 210 |
| 280-09 | 68 | 34 | 31 | 3 | 80 | 3 |
| 310-09 | 160 | 89 | 210 | 84 | 150 | 3 |

TABLE 3-continued

Proviral SIV DNA in PBMCs, Lymph Node and Colon from SIV+ Rhesus Macaques on cART

| Animal | PBMC | | Lymph node | | Colon | |
|---|---|---|---|---|---|---|
| | Pre | Post | Pre | Post | Pre | Post |
| SIV DNA from Animals Treated with the Dosing Vehicle of Example 201 (copies/$10^6$ cells) | | | | | | |
| 205-08 | 62 | 130 | 120 | 155 | 100 | 130 |
| 267-08 | 110 | 110 | 220 | 180 | 180 | 160 |
| 105-09 | 160 | 180 | 170 | 170 | 200 | 220 |

Example 206

Peripheral Lymphocyte Activation

During the course of treatment with the compound of Example 4 as described in Example 204, peripheral lymphocyte activation was monitored in the groups dosed with the compound of Example 4 or the dosing vehicle of Example 201 (placebo), by measuring the expression of the early activation marker CD69 on various lymphocyte subsets by flow cytometry methodology. This methodology was used to quantify the percentage of immune cell subsets expressing the early activation marker. Standard data acquisition techniques were employed on a flow cytometer and by the use of antibodies conjugated to fluorescent molecules where the antibodies recognize rhesus macaque cell surface proteins on various immune cell subsets. In animals dosed with the compound of Example 4, whole blood samples were collected for each dose at various time points both at pre- and post-administration of compound. Total PBMCs were stained in the whole blood samples using antibodies that were chosen to be reactive to rhesus CD3, CD4, CD8, NKG2A, CD16 and CD56, each conjugated to different fluorescent probes to delineate CD3+CD4+CD8− lymphocytes, CD3+CD4−CD8+ lymphocytes and CD3-CD8+ NKG2A+CD16+ CD56+ NK cells. The flow cytometry data presented herein are from animals treated with the compound of Example 4.

Peripheral CD4 lymphocytes (CD3+CD4+CD8−) demonstrated transient activation in response to the compound of Example 4 dosing based on expression of the early activation marker CD69. The percent change from pre-dose levels in cells expressing CD69 increased at 24 to 72 hours post-dose and returned back to near pre-dose levels one week after dosing. The percent change in of peripheral activated CD4 lymphocytes also increased in magnitude based on dose of the compound of Example 4). At the dose of 0.1 mg/kg Example 4, the mean maximum percent change in CD69 expression at any time point on CD4 lymphocytes was 1.1% (pre-dose range 0.5-1.7%), at a dose of 0.2 mg/kg the mean maximum percent change was 1.5% (pre-dose range 0.5-2%), and at the first dose of 0.3 mg/kg the mean maximum percent change was 2.3% (pre-dose range 0.6-2.5%). However, all subsequent doses did not achieve similar levels of peripheral CD4 lymphocyte activation; mean maximum percent change in CD69 expression was 1.7%.

Peripheral CD8 lymphocytes (CD3+CD8+CD4−) also demonstrated transient activation in response to dosing with the compound of Example 4, based on the expression of CD69. The percent changes from pre-dose levels in CD8 lymphocytes expressing CD69 increased at 24 to 72 hours post-dose and returned back to near pre-dose levels one week after dosing. The percent change in peripheral activated CD8 lymphocytes also increased in magnitude based on dose of the compound of Example 4. At the dose of 0.1 mg/kg the mean maximum percent change in CD69 expression at any time point on CD8 lymphocytes was 7.8% (pre-dose range 3.3-12.6%), at a dose of 0.2 mg/kg the mean maximum percent change was 9.5% (pre-dose range 3.0-15.7%), and at the first dose of 0.3 mg/kg the mean maximum percent change was 17.3% (pre-dose range 5.0-14.4%). However, all subsequent 0.3 mg/kg doses did not achieve similar levels of peripheral CD8 lymphocyte activation; mean maximum percent change in CD69 expression was 15.5%.

Total peripheral NK cells (CD3-CD8+ NKG2A+CD16+ CD56+, which included CD16 low/high and CD56 low/high) also demonstrated transient activation in response to dosing with the compound of Example 4, based on the expression of CD69. The percent changes from pre-dose levels in NK cells expressing CD69 increased by 24 to 72 hours post-dose and generally returned back to or slightly below pre-dose levels one week after dosing. The percent change in peripheral activated NK cells only slightly increased in magnitude based on dose of the compound of Example 4. At the dose of 0.1 mg/kg the mean maximum percent change in CD69 expression at any time point on NK cells was 6.5% (pre-dose range 89-95%), at a dose of 0.2 mg/kg the mean maximum percent change was 9.5% (pre-dose range 83-95%), at the first dose of 0.3 mg/kg the mean maximum expression was 8.3% (pre-dose range 84-95%), and at the second dose of 0.3 mg/kg the mean maximum expression was 8.7% (pre-dose range 82-97%). All subsequent 0.3 mg/kg doses achieved similar levels of peripheral NK cell activation; mean maximum percent change in CD69 expression ranged from 6.1 to 9.2%.

Conclusion

The compound of Example 4 is able to induce transient expression of plasma SIV in the rhesus macaque model of HIV-1 infection. The compound of Example 4 reduced the amount of proviral SIV DNA content in PBMCs, inguinal lymph node, and colon tissue which are markers for reduction of the viral reservoir. Further, administration with the compound of Example 4 produced an immunological response that was measureable in the absence of cART, as demonstrated by the lower plasma virus chronic set point (post-cART cessation) after the administration of the compound.

In Vitro Testing

The in vitro testing of the compounds disclosed herein are designed to show similar activation of immune cells in total PBMC cultures from virally suppressed HIV-1 infected donors. Both molecules can also induce HIV-1 replication in cultures of resting PBMCs obtained from virologically suppressed HIV-1 infected patients. In addition, both molecules show direct antiviral affects in cultures of activated PBMCs exogenously infected with HIV-1.

Example 207

In Vitro Lymphocyte Subset Activation in PBMC Cultures from Healthy and HIV-1 Infected Donors Total PBMC cultures were derived from Ficoll-purified buffy coats obtained from healthy human donors or leukapheresis samples obtained from HIV-1 infected donors (HIV-1 infected donors were patients on cART and virally suppressed HIV RNA<50 copies/mL for 1 year). Total PBMC cultures were treated with various concentrations of the identified TLR7 modulating compounds (Compounds of Example 4 and Example 49) for 24 hours. At the end of the incubation period, total PBMC were harvested and stained with antibodies conjugated to specific fluorophores to delineate human CD4 lymphocytes (CD3+CD4+CD8−) or CD8 lymphocytes (CD3+CD8+CD4−) and co-expressing the early activation marker CD69. Cells were analyzed by flow cytometry and data collected on an LSR FortessaX20 instrument (BD Biosciences).

The tested TLR7 modulating compounds were able to induce lymphocyte activation in vitro, specifically to cause activation of CD4+ and CD8+ lymphocytes. The maximum percentage of cells activated was similar for both compounds within each donor.

TABLE 4

Percent Induction of CD69 on CD4+ Lymphocytes in PBMC Cultures from HIV-1 Infected Donors Induced by TLR7 Modulating Compounds
Percent Increase in CD69 Expression on CD3 + CD4+ Lymphocytes

| Donor ID | Untreated Background (%) | Example 4 Maximum Expression (Actual %) | Example 49 Maximum Expression (Actual %) | Example 4 Maximum Expression Background Subtracted (%) | Example 49 Maximum Expression Background Subtracted (%) | Example 4 Mean Maximum Expression Background Subtracted (%) | Example 49 Mean Maximum Expression Background Subtracted (%) |
|---|---|---|---|---|---|---|---|
| 120 | 38 | 57 | 59 | 19 | 21 | 22 | 22 |
| 121 | 20 | 41 | 39 | 21 | 20 | | |
| 122 | 1.5 | 26 | 24 | 25 | 23 | | |
| 123 | 0.8 | 24 | 25 | 24 | 24 | | |

TABLE 5

Percent Induction of CD69 on CD8+ Lymphocytes in PBMC Cultures from Healthy and HIV-1 Infected Donors by TLR7 Modulating Compounds
Percent Increase in CD69 Expression on CD3 + CD8+ Lymphocytes

| Donor ID | Untreated Background (%) | Example 4 Maximum Expression (Actual %) | Example 49 Maximum Expression (Actual %) | Example 4 Maximum Expression Background Subtracted (%) | Example 49 Maximum Expression Background Subtracted (%) | Example 4 Mean Maximum Expression Background Subtracted (%) | Example 49 Mean Maximum Expression Background Subtracted (%) |
|---|---|---|---|---|---|---|---|
| 120 | 25 | 60 | 55 | 36 | 31 | 32 | 31 |
| 121 | 15 | 44 | 43 | 30 | 29 | | |
| 122 | 2 | 35 | 35 | 33 | 33 | | |
| 123 | 2 | 32 | 32 | 30 | 30 | | |

Example 208

Induced HIV-1 Expression in PBMC Cultures from HIV-1 Infected Donors on cART Treated with TLR7 Modulating Compounds To assess the ability to activate HIV-1 expression in total PBMC cultures, Ficoll-purified leukapheresis samples obtained from HIV-1 infected donors (HIV-1 infected donors were patients on cART and virally suppressed HIV RNA<50 copies/mL for ≥1 year) were tested. Isolated PBMCs were treated with various concentrations (0.1, 1, and 10 µM) of the TLR7 modulating compounds (compounds of Example 4 and Example 49) or dimethyl sulfoxide (DMSO) treated (vehicle control) for 4 to 5 days. The cultures were maintained in the presence of antivirals (elvitegravir and efavirenz at 100 nM each) to prevent viral spread and amplification in order to measure initial virus production (latency reversal) created by the TLR7 modulating compounds. At the end of the incubation period cell-free culture supernatants were harvested and HIV-1 RNA levels were quantified by the COBAS® AmpliPrep/COBAS® TaqMan HIV-1 Test, v2.0 (Roche).

In the absence of any other activation stimuli, treatment with the TLR7 modulating compounds induced the HIV-1 expression in PBMC cultures from all donors tested (Table 6). Two-fold or higher activation over the DMSO control was observed in cultures from 4 of 6, 3 of 6, and 1 of 4 patients following the treatment with the compound of Example 49 at concentrations of 0.1, 1, and 10 µM, respectively. A similar frequency of response was observed following treatment with the compound of Example 4. Two-fold or higher induction of HIV-1 expression was observed in 6 out of 6 donors with at least one TLR-7 agonist (n=2 donors) or both agonists (n=4 donors). Without wishing to be bound by a particular theory it is thought that the lack of consistent dose responsive viral expression to either agonist within the concentration ranges tested across the tested donors may result from a combined net effect induced by the dual capability of the TLR7 modulating compounds to induce virus expression and exert an antiviral effect. While the antiviral effect of the TLR7 modulating compounds was not directly measured in Example 208, other data presented from Example 207 and Example 209 demonstrate these potential antiviral activities. Both of these biological activities may manifest at different compound concentrations in a donor-dependent manner, resulting in the variation in TLR7 modulating compound concentrations at which HIV-1 activation can occur. Overall, these data demonstrate the in vitro induction of HIV-1 expression by the TLR7 modulating agents.

TABLE 6

Induction of HIV-1 Expression in PBMC Cultures Derived from HIV-1 Infected Donors on cART by TLR7 Modulating Compounds

| | Fold HIV-1 Induction [a] | | | | | |
|---|---|---|---|---|---|---|
| | Example 49 Treated (µM) | | | Example 4 Treated (µM) | | |
| Donor ID | 0.1 | 1 | 10 | 0.1 | 1 | 10 |
| 122 | 1.5 | 2.4 | n.d.[b] | 2.9 | 5.7 | n.d. |
| 124 | 3.0 | 1.5 | 1.3 | 1.0 | 1.4 | 5.1 |
| 125 | 1.5 | 9.9 | 3.0 | 1.0 | 1.0 | 1.1 |
| 126 | 2.0 | 2.0 | 1.0 | 2.1 | 2.9 | 2.9 |
| 127 | 1.8 | 1.6 | 1.0 | 2.7 | 2.1 | 3.8 |
| 128 | 6.6 | 3.9 | n.d. | 4.1 | 0.3 | n.d. |
| Geometric Mean | 2.3 | 2.8 | 1.4 | 2.0 | 1.6 | 3.9 |
| Donors with ≥2-fold HIV-1 induction | 3 of 6 | 4 of 6 | 1 of 4 | 4 of 6 | 3 of 6 | 3 of 4 |

[a] Fold induction expressed as a ratio of HIV-1 RNA copies detected in cell culture supernatants from agonist and DMSO treated wells. Mean fold activation from three independent wells for each donor and each condition.
[b] not determined Tables 7, 8, 9, 10 and 11. Induction of HIV-1 Expression in PBMC Cultures Derived from HIV-1 Infected Donors on cART Using the method described above in Example 208, HIV-1 expression in PBMC cultures derived from four additional HIV-1 infected donors on cART were tested in the presence of the compounds of Examples 4, 29, 120, 121, 122, 123, 124, resiquimod, and imiquimod.

TABLE 7

| | Fold HIV-1 Induction [a] | | | | | |
|---|---|---|---|---|---|---|
| | Example 49 (GS-9620) Treatment (μM) | | | Example 4 Treatment (μM) | | |
| Donor ID | 0.01 | 0.156 | 2.5 | 0.01 | 0.156 | 2.5 |
| 152 | 19.2 | 23.2 | 28.8 | 6.3 | 2.9 | 4.1 |
| 153 | 11.2 | 4.7 | 12.0 | 3.1 | 5.3 | 8.3 |
| 154 | 1.1 | 5.0 | 3.6 | 3.0 | 7.2 | 3.2 |
| 155 | 1.1 | 3.8 | 6.4 | 6.0 | 7.4 | 2.3 |
| Geometric Mean | 4.0 | 6.7 | 9.4 | 4.3 | 5.3 | 4.0 |
| Donors with ≥2-fold HIV-1 Induction | 2 of 4 | 4 of 4 | 4 of 4 | 4 of 4 | 4 of 4 | 4 of 4 |

TABLE 8

| | Fold HIV-1 Induction [a] | | | | | |
|---|---|---|---|---|---|---|
| | Example 120 Treatment (μM) | | | Example 121 Treatment (μM) | | |
| Donor ID | 0.01 | 0.156 | 2.5 | 0.01 | 0.156 | 2.5 |
| 152 | 7.2 | 8.1 | 2.0 | 2.0 | 4.0 | 3.5 |
| 153 | 2.3 | 2.5 | 6.6 | 0.7 | 0.8 | 2.3 |
| 154 | 3.8 | 7.7 | 5.8 | 2.0 | 5.0 | 4.4 |
| 155 | 3.6 | 5.7 | 3.4 | 1.1 | 0.2 | 2.1 |
| Geometric Mean | 3.9 | 5.5 | 4.0 | 1.3 | 1.3 | 2.9 |
| Donors with ≥2-fold HIV-1 Induction | 4 of 4 | 4 of 4 | 4 of 4 | 2 of 4 | 2 of 4 | 4 of 4 |

TABLE 9

| | Fold HIV-1 Induction [a] | | | | | |
|---|---|---|---|---|---|---|
| | Example 122 Treatment (μM) | | | Resiquimod (R848) Treatment (μM) | | |
| Donor ID | 0.01 | 0.156 | 2.5 | 0.01 | 0.156 | 2.5 |
| 152 | 14.0 | 31.2 | 16.9 | 5.4 | 21.4 | 10.3 |
| 153 | 16.0 | 4.4 | 8.2 | 5.4 | 7.5 | 10.0 |
| 154 | 0.4 | 0.8 | 2.0 | 9.3 | 2.5 | 4.2 |
| 155 | 6.8 | 5.0 | 8.4 | 2.3 | 5.7 | 6.9 |
| Geometric Mean | 5.0 | 4.8 | 6.9 | 5.0 | 6.9 | 7.4 |
| Donors with ≥2-fold HIV-1 Induction | 3 of 4 | 3 of 4 | 4 of 4 | 4 of 4 | 4 of 4 | 4 of 4 |

TABLE 10

| | Fold HIV-1 Induction [a] | | | | | |
|---|---|---|---|---|---|---|
| | Imiquimod Treatment (μM) | | | Example 123 (R-852A) Treatment (μM) | | |
| Donor ID | 0.01 | 0.156 | 2.5 | 0.01 | 0.156 | 2.5 |
| 152 | 5.8 | 6.6 | 10.0 | 6.4 | 7.2 | 6.6 |
| 153 | 2.7 | 6.0 | 10.7 | 4.7 | 6.2 | 5.4 |
| 154 | 5.5 | 4.8 | 10.0 | 1.6 | 7.2 | 5.8 |
| 155 | 3.8 | 4.4 | 0.5 | 0.3 | 0.4 | 3.3 |
| Geometric Mean | 4.3 | 5.4 | 4.8 | 1.9 | 3.4 | 5.1 |
| Donors with ≥2-fold HIV-1 Induction | 4 of 4 | 4 of 4 | 3 of 4 | 2 of 4 | 3 of 4 | 4 of 4 |

TABLE 11

| | Fold HIV-1 Induction [a] Example 124 Treatment (μM) | | |
|---|---|---|---|
| Donor ID | 0.01 | 0.156 | 2.5 |
| 152 | 1.2 | 0.7 | 1.8 |
| 153 | 4.5 | 4.3 | 3.2 |
| 154 | 8.0 | 9.6 | 5.8 |
| 155 | 4.4 | 0.4 | 0.2 |
| Geometric Mean | 3.7 | 1.8 | 1.6 |
| Donors with ≥2-fold HIV-1 Induction | 3 of 4 | 2 of 4 | 2 of 4 |

[a] Fold induction expressed as a ratio of HIV-1 RNA copies detected in culture supernatants from TLR7 agonist treated and DMSO treated wells, values in bold indicate ≥2-fold induction. Supernatants were collected on Day 4. Mean fold induction from three independent wells for each donor and each condition. For Table 2 data, PBMCs were added to pre-plated compounds and immediately transferred to an incubator. This method was adopted to minimize the potential for processing and handling effects on the cells. For Table 1 data, PBMCs were added to plates and then compounds were added subsequently before the plates were transferred to an incubator.

Example 209

Antiviral Activity on In Vitro HIV-1 Infected PBMC Cultures by TLR7 Modulating Compounds Antiretroviral activity was assessed by testing the TLR7 modulating compounds (Compounds of Example 4 and Example 49) in total human PBMC cultures that were first treated with mitogen (phytohemogglutinin A) for two days prior to infection with HIV-1$_{BaL}$. Infected cells were cultured in the presence of interleukin-2 and various concentrations of the TLR7 modulating compounds or the nucleoside analog HIV-1 reverse transcriptase inhibitor azidothymidine (AZT, positive control) for six days. At the end of the incubation period, cell-free culture supernatants were harvested and antiviral activity determined by measuring production of HIV-1 Gag p24 by commercially available ELISA kits. The TLR7 modulating compounds showed potent and concentration-dependent antiretroviral activity in each of the eight donor cultures tested, with a mean EC$_{50}$ of 170 nM and 33 nM, respectively (12). The data demonstrate that the TLR7 modulating compounds both have HIV-1 antiviral activity in this assay system.

TABLE 12

Antiviral Activity in HIV-1 Infected PBMC
Cultures by TLR7 Modulating Compounds

|  | Example 49 | Example 4 | AZT |
|---|---|---|---|
| Mean EC$_{50}$ (nM)$^a$ | 170 ± 240 | 33 ± 35 | 10 ± 8 |
| Range EC$_{50}$ (nM) | 4 to 691 | 0.8 to 81 | 1.7 to 29 |

$^a$Mean ± SD values obtained from at least 8 independent donors

Example 210

Activation of HIV by Example 49 Ex Vivo in PBMCs

Figure 7:
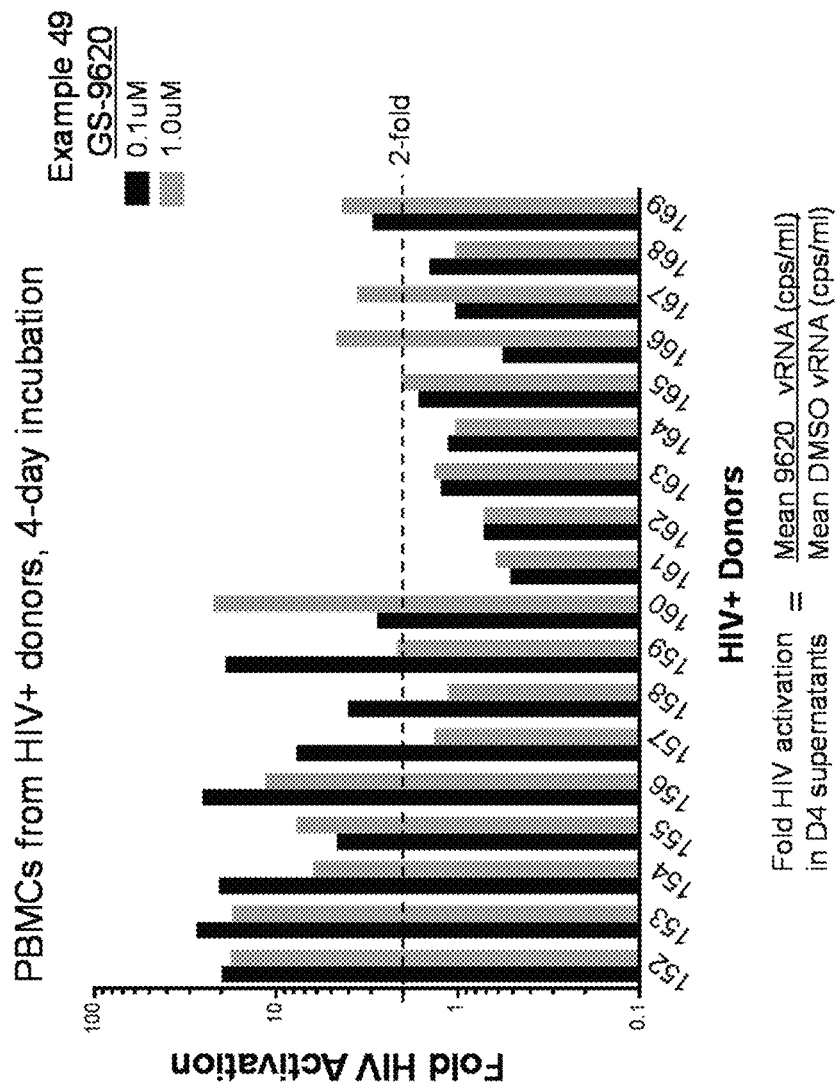
FIG. 7 depicts activation of HIV by the compound of Example 49 ex vivo in PBMCs from HIV+ patients on cART.

PBMCs from 18 HIV-infected donors (Donor IDs 152-169) on suppressive cART were isolated, as described previously in Materials and Methods (PBMC Isolation), and immediately added to tissue culture plates pre-equilibrated at 37° C. with media containing DMSO or the compound of Example 49 (GS-9620) at 0.1 uM or 1.0 uM. At day 4 after treatment, cell-free culture supernatants were collected and HIV viral RNA was quantitated using the automated COBAS® AmpliPrep/COBAS® TaqMan® HIV-1 Test, v2.0 system (Roche Diagnostics, Indianapolis, Ind.), as described previously in Materials and Methods (HIV-1 Activation Assay). Geometric mean fold HIV activations from three independent wells for each donor and each condition were expressed as a ratio of HIV-1 RNA copies/ml detected in culture supernatants from TLR7 agonist treated and DMSO treated wells. Fold HIV activation values were plotted using GraphPad Prism software (GraphPad, San Diego, Calif.) and can be seen in FIG. 7. The dashed line indicates 2-fold induction.

TABLE 13

|  | GS-9620 | | |
|---|---|---|---|
| N = 18 | 100 nM | 1,000 nM | 100 and/or 1,000 nM |
| N (%) with ≥2-fold activation | 10 (56) | 11 (61) | 13 (72) |
| Fold range | 2.7-26.6 | 2.0-21.5 | 2.0-26.6 |
| Fold geometric mean | 9.3 | 6.5 | 9.1 |

Example 211

Induction of Cytokines/Chemokines by Example 49 Ex Vivo

PBMCs from HIV-infected donors on suppressive cART were isolated, as described previously, and immediately added to tissue culture plates pre-equilibrated at 37° C. with media containing DMSO or the compound of Example 49 (GS-9620) at concentrations from 0.1 nM or 10.0 uM. At day 2 after treatment, cell-free culture supernatants were collected and frozen at −80C for subsequent analysis. Frozen supernatants were thawed at room temperature, and the cytokines and chemokines indicated were quantitated with a custom multiplexed xMAP Luminex® assay following the manufacturer's instructions (Thermo Fisher Scientific Inc., Grand Island, N.Y., custom-designed kit).

| GS-9620 fold induced vs. DMSO control | Cytokine |
|---|---|
| >100-fold | IFNα, IFNω, IL-1 RA, IL-6, IL-10, IP-10, I-TAC, MIP-1α, MIP-1β, MCP-1 |
| 10- to 100-fold | IFNγ, IL-8, IL-29, GROα, IL-1β, TNFα, |
| 2- to 10-fold | IL-2, IL-12, IL-15, IL-21, IL-23(p19), RANTES, TRAIL, Granzyme B, SDF-1α |
| <2-fold | BAFF, IFNβ, IL-4, IL-5, IL-12 (p70), IL-13, IL-17, IL-18, IL-27, IL-31, SCD40L, TNFS10, MMP-1 |

Example 212

Maximal HIV Activation by Example 49 is Dependent on IFNα/β Receptor Signaling

Figure 8:
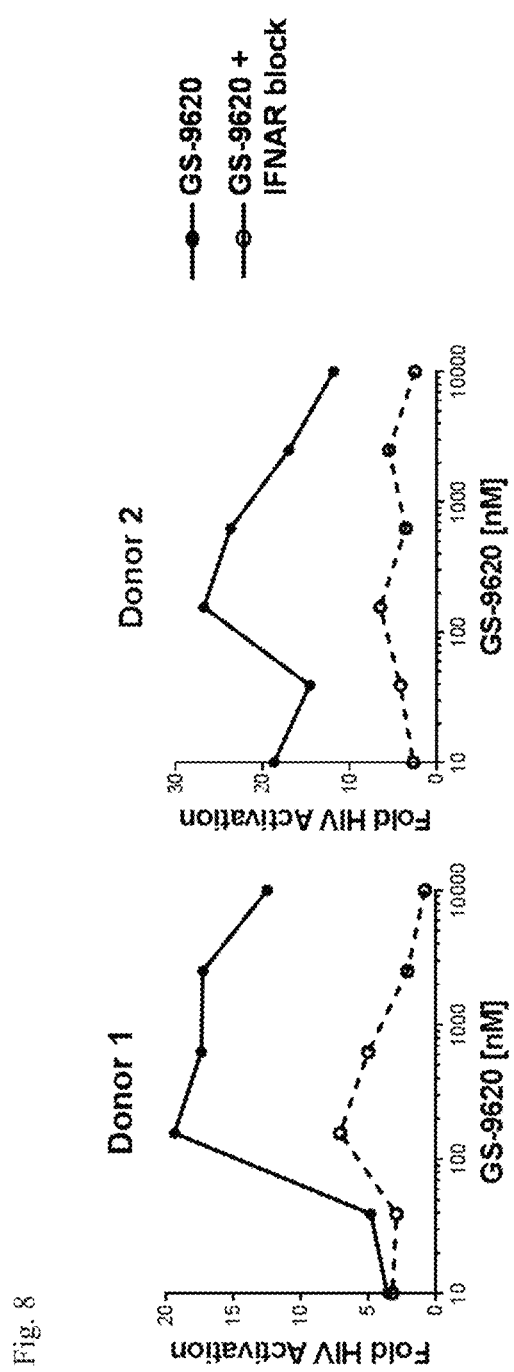
FIG. 8 depicts maximal HIV activation by the compound of Example 49 is dependent on IFNα/β signaling.

PBMCs from HIV-infected donors on suppressive cART were isolated, as before, and treated with the compound of Example 49 (GS-9620) at the doses indicated (10 nM to 10 uM) in the presence or absence of a mouse monoclonal antibody (clone MMHAR-2) against the human Interferon α/β receptor chain 2 (PBL Assay Science, Piscataway, N.J., Cat #21385-1) used at 1:500 dilution. At day 4 after treatment, cell-free culture supernatant was collected and HIV viral RNA was quantitated using the AmliPrep/COBAS® TaqMan® assay. Fold HIV activation in PBMCs from two HIV-infected donors treated with the compound of Example 49 alone and in combination with the anti-IFNα/β mAB (IFNAR block) is depicted in FIG. 8. An 85% mean maximal reduction was seen in 4 donors (p<0.05, paired t-test).

Example 213

Activation of HIV by Recombinant IFNα Ex Vivo

Figure 9:
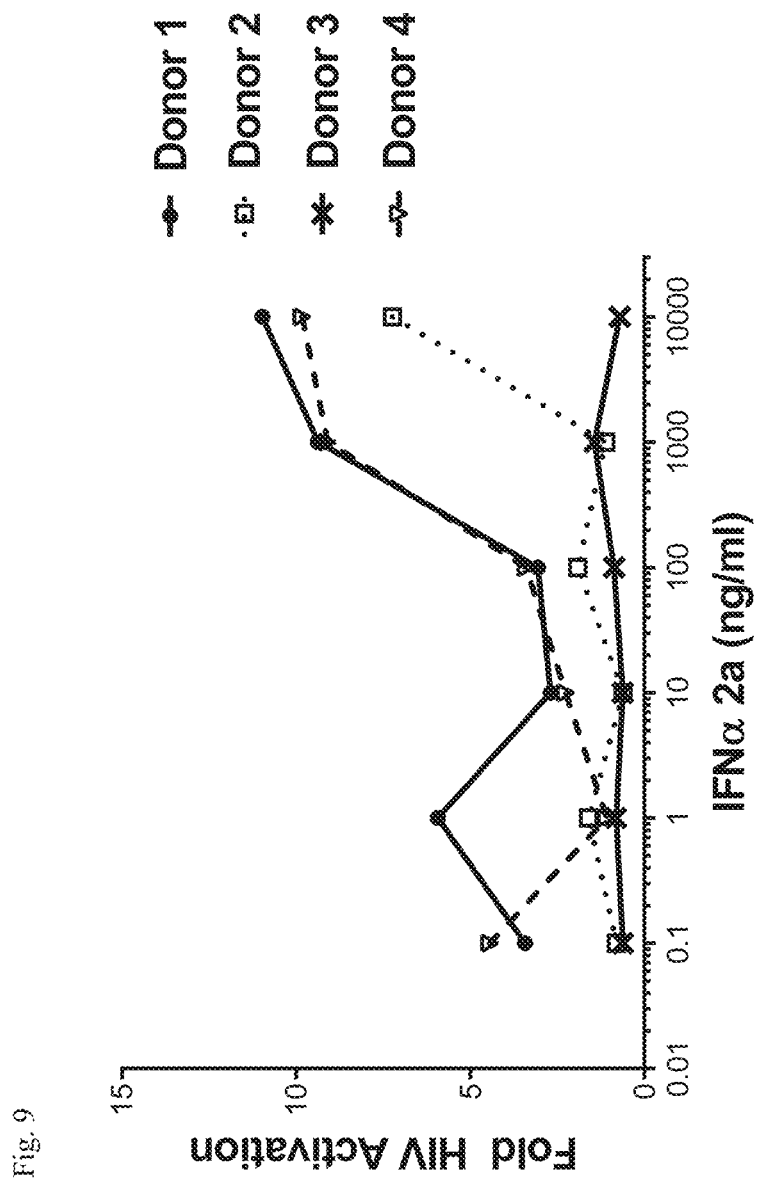
FIG. 9 depicts activation of HIV by recombinant IFNα ex vivo.

PBMCs from HIV-infected donors on suppressive cART were isolated, as before, and treated with human interferon alpha 2a (PBL Assay Science, Piscataway, N.J., Cat #11100-1) at the concentrations indicated. At day 4 after treatment, cell-free culture supernatant was collected and HIV viral RNA was quantitated using the AmliPrep/COBAS® TaqMan® assay. Fold HIV activation for four donors is depicted in FIG. 9.

Example 214

Correlation of HIV Activation

Figure 10:
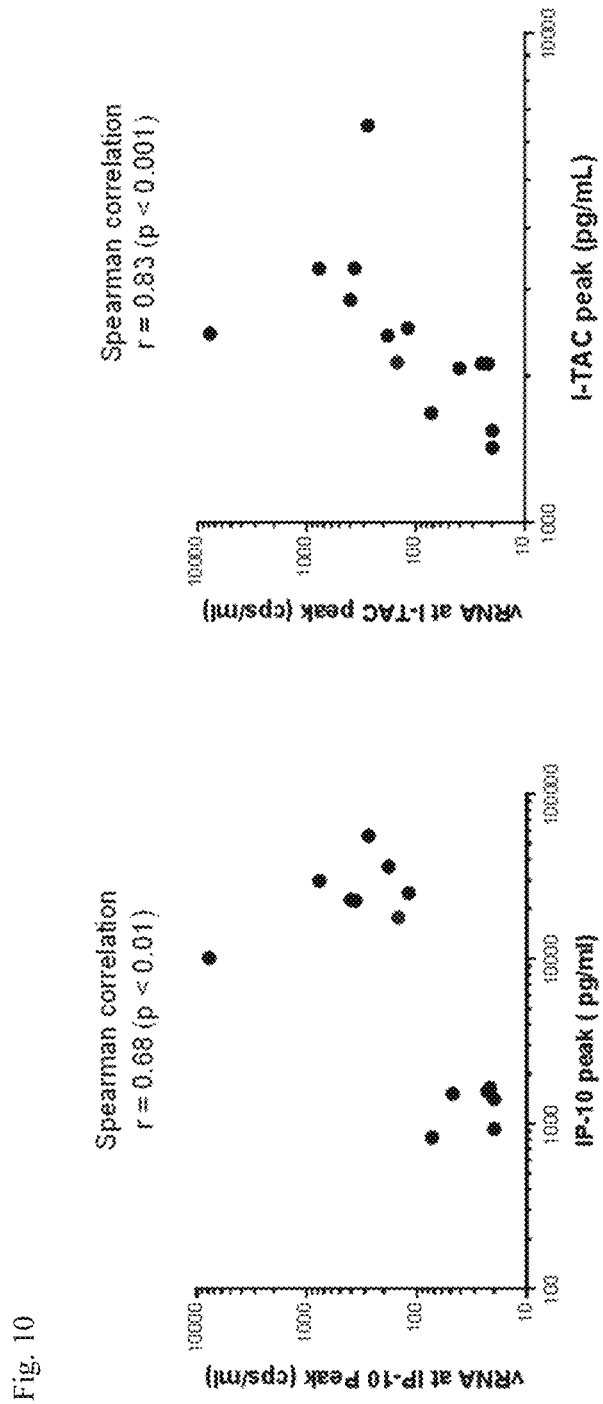
FIG. 10 depicts the correlation of HIV activation indicated by vRNA levels plotted at the concentration of Example 49 that induced peak IP-10 or I-TAC levels.

PBMCs from 14 HIV-infected donors (Donor IDs 152-165) on suppressive cART were isolated, as described previously, and immediately added to tissue culture plates pre-equilibrated at 37 C with media containing DMSO or the compound of Example 49 (GS-9620) from 0.1 nM or 10.0 uM. At day 2 after treatment, cell-free culture supernatants were collected and frozen at −80° C. for subsequent analysis. Frozen supernatants were thawed at room temperature, and the cytokines and chemokines indicated were quantitated with a custom Luminex® kit, as previously described. At day 4 after treatment, cell-free culture supernatants were collected and HIV viral RNA was quantitated using the automated COBAS® AmpliPrep/COBAS® TaqMan® HIV-1 Test, v2.0 system (Roche Diagnostics, Indianapolis, Ind.). To generate scatter plots, levels of HIV-1 vRNA that were induced at the concentration of GS-9620 that induced peak IP-10 (CXCL10) or I-TAC (CXCL11) levels were plotted as a single data point for each donor. Graphs were generated and Spearman's rank order correlation r and p values were calculated using GraphPad Prism software (GraphPad, San Diego, Calif.), as noted in FIG. 10.

Example 215

Reduction of HIV Induction

Figure 11:
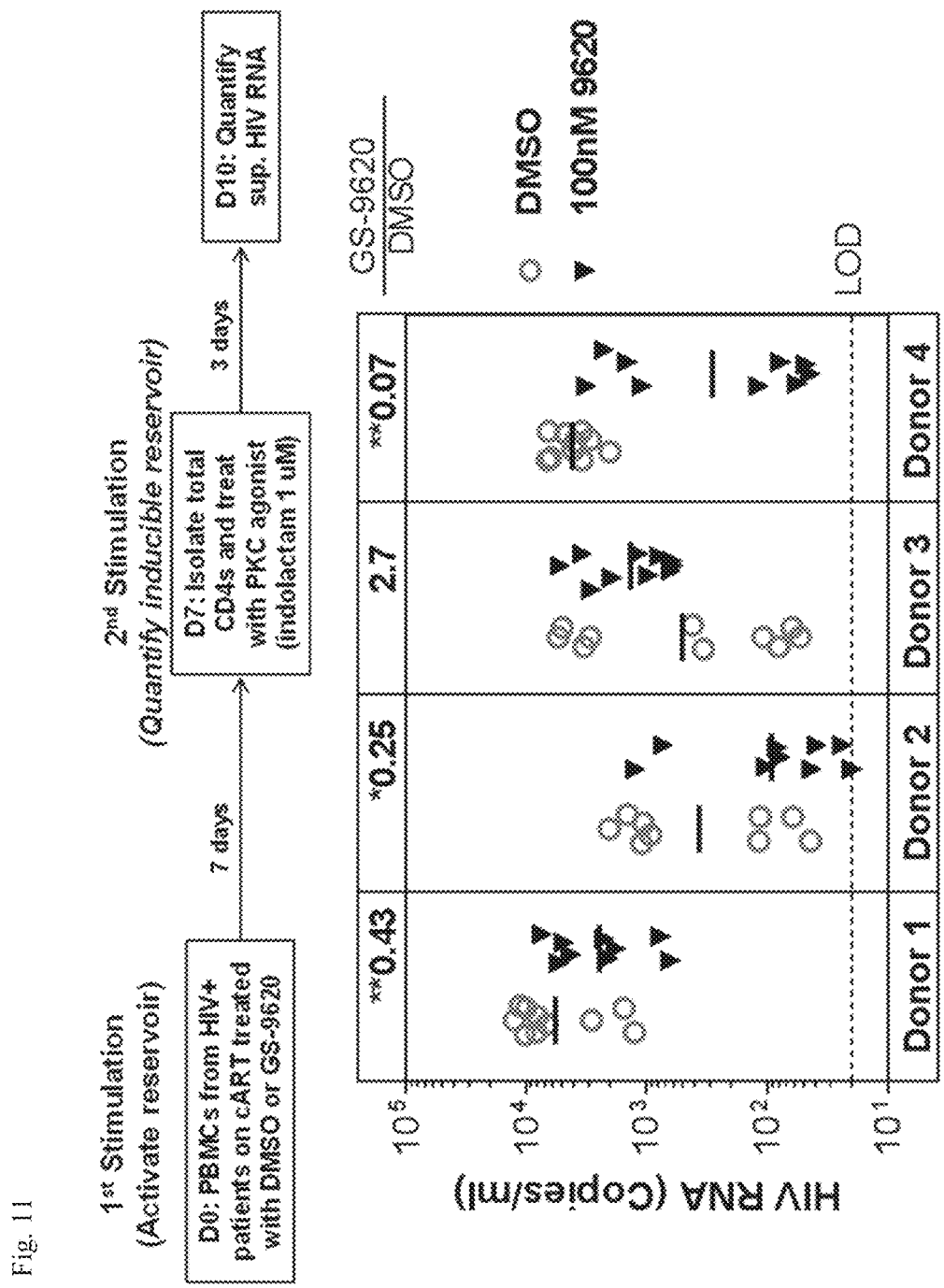
FIG. 11 depicts HIV induction in PBMCs treated with Example 4 or DMSO and subsequent stimulation with a PKC agonist (indolactam).

PBMCs from 4 HIV-infected donors (Donor IDs 141-144) on suppressive cART were isolated, as described previously, and treated with DMSO or the compound of Example 49 (GS-9620) at 0.1 uM. At day 7 after treatment, non-adherent cells were collected and total CD4 T cells were isolated using the EASYEP™ Human T Cell Enrichment Kit (STEMCELL Technologies Inc., Vancouver, BC). CD4 T cells were then stimulated with the protein kinase C (PKC) agonist indolactam at 1 uM for 3 additional days, at which time cell-free culture supernatants were collected and HIV viral RNA was quantitated using the automated COBAS® AmpliPrep/COBAS® TaqMan® HIV-1 Test, v2.0 system (Roche Diagnostics, Indianapolis, Ind.). HIV-1 RNA copies/ml were plotted for each donor for DMSO and GS-9620 treatment GraphPad Prism software (GraphPad, San Diego, Calif.), and statistically significant differences were indicated (*$p<0.05$, **$p<0.01$ paired t-test), as seen in FIG. 11.

Example 216

Induction of HIV-Specific Polyfunctional CD8 T Cells by Example 49 Ex Vivo

Figure 12:
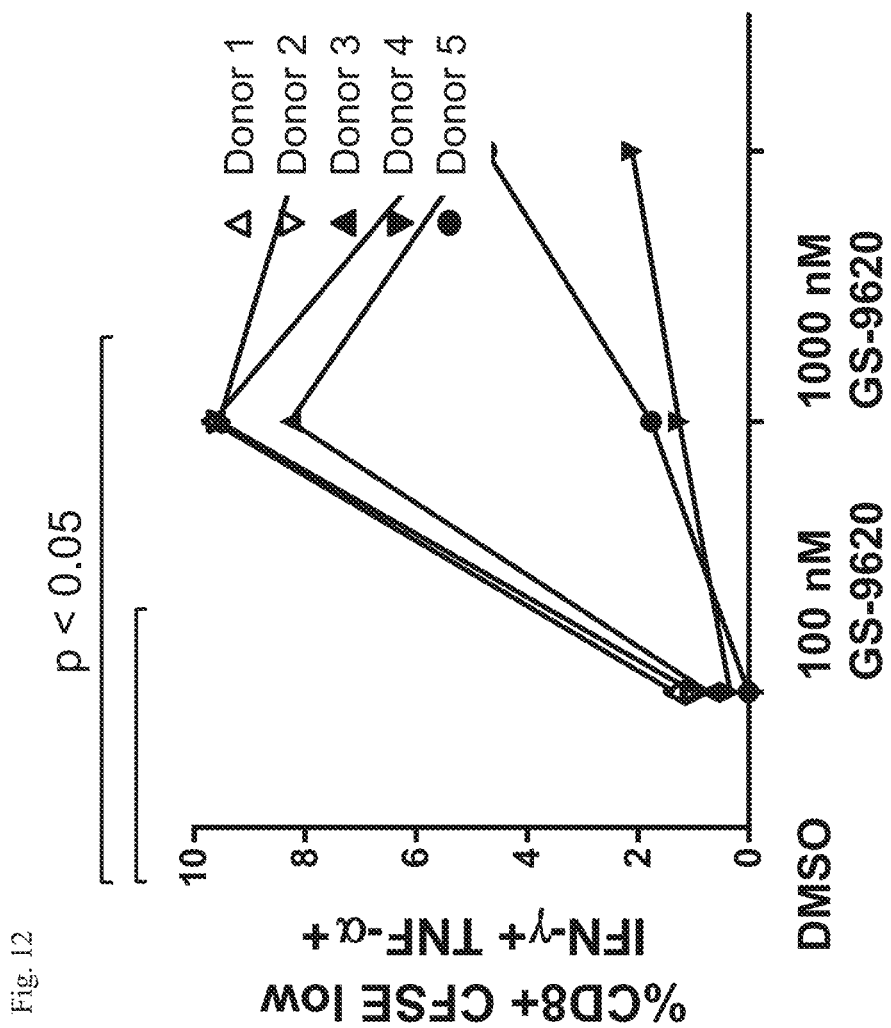
FIG. 12 depicts increased levels of proliferation in CD8 cells treated with Example 49.

PBMCs from 5 HIV-infected donors (Donor IDs 178-180 and 182-183) on suppressive cART were isolated, as described previously, and stained with carboxyfluorescein succinimiyl ester (CFSE). PBMC cultures were treated with DMSO or the compound of Example 49 (GS-9620) at 0.1 or 1 uM. Cultures were incubated at 37° C. for 2 days and treated with 500 ng/ml 15-mer peptide pools derived from overlapping HIV gag, pol, nef, and env consensus peptides (JPT Peptide Technologies GmbH). Cells were incubated at 37° C. for 8 days. Cultures were split into duplicate sets and stained in dulbecco's phosphate buffered saline (DPBS) with LIVE/DEAD Fixable Aqua Dead Cell Stain (Life Technologies). The immune recall response was performed as follows. One culture set was treated with the same HIV peptide pools and the other set was treated with 500 ng/ml CMV/EBV/Flu/Tetanus (CEFT) peptides (JPT Peptide Technologies GmbH). After one hour at 37° C., cultures were treated with 0.7 μl GolgiStop (BD Biosciences) containing monensin and 1 μl GolgiPlug (BD Biosciences) containing brefeldin A. Cultures were incubated for 3 additional hours at 37° C. and stained for 15 minutes with anti-CD4-v450, anti-CD3-AlexaFlour 700, and anti CD8-APC-H7 (BD Biosciences). Cultures were fixed with IC Fixation Buffer (eBioscience) and permeabilized with Permeabilization Buffer (eBioscience). Anti-IFN-gamma-APC and anti-TNFalpha-PerCP-Cy5.5 (BD Biosciences) were used to stain intracellular cytokine production. FACS was performed on a LSR Fortessa (BD Biosciences) and data analysis was done with FlowJo software (TreeStar). Response to CEFT peptides were subtracted from the response seen with HIV peptides. Data was plotted and statistical analysis was done with GraphPad Prism software (GraphPad). Treatment with Example 49 at 0.1 uM increased the mean level of polyfunctional proliferating CD8 T cells (CFSE low, IFNg+, TNFa+) by 9.0-fold compared to treatment with DMSO ($p<0.05$; Student's unpaired, two-tailed t-test). Treatment with Example 49 at 1 uM increased the mean level of polyfunctional proliferating CD8 T cells (CFSE low, IFNg+, TNFa+) by 7.5-fold compared to treatment with DMSO ($p<0.005$; Student's unpaired, two-tailed t-test), as depicted in FIG. 12.

Example 217

Figure 13:
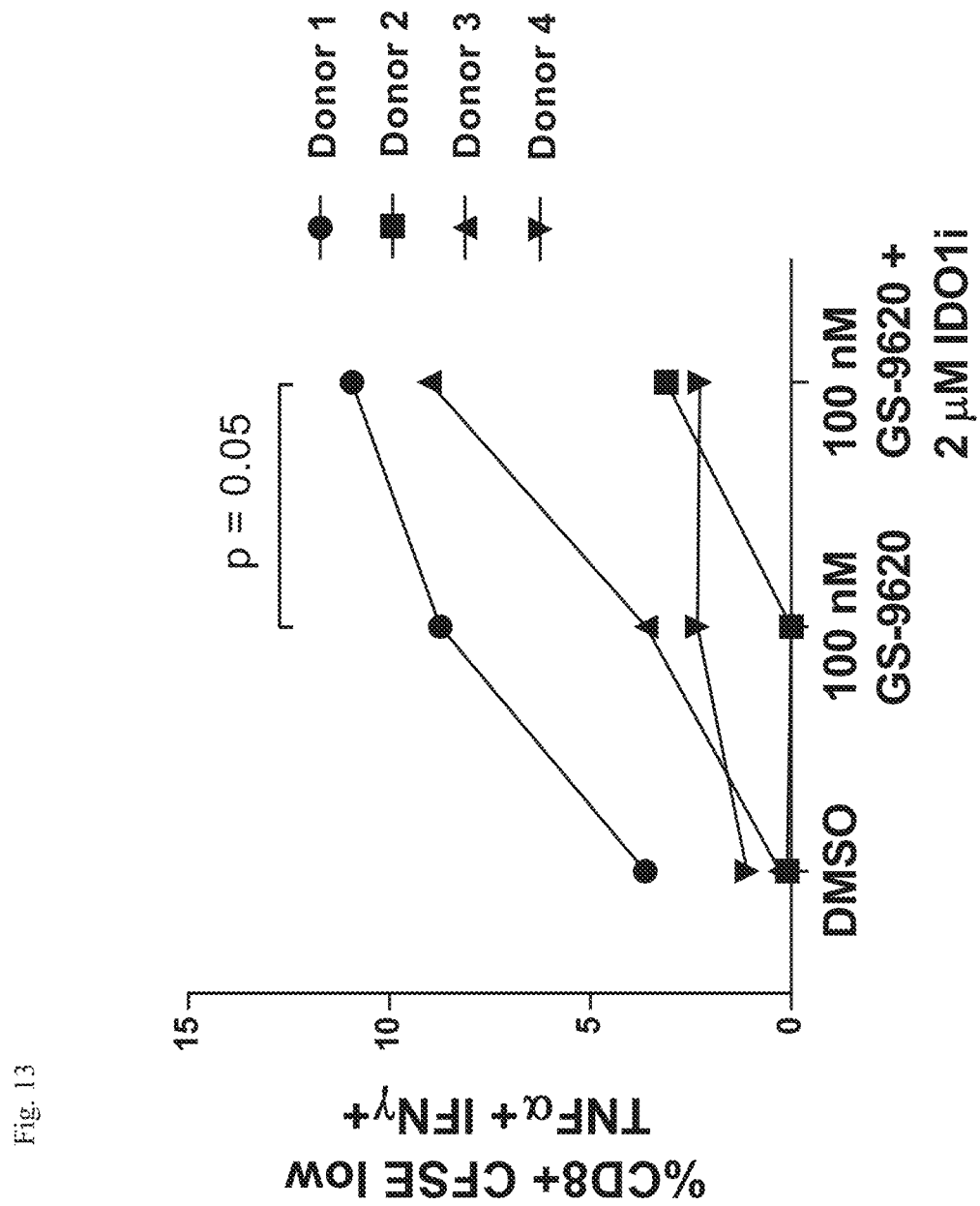
FIG. 13 depicts increased levels of proliferation in CD8 cells treated with Example 49 and an IDO1 inhibitor.

Enhanced Induction of HIV-Specific Polyfunctional CD8 T Cells by a Combination of Example 49 and an Indoleamine 2,3-Dioxygenase (IDO, IDO1) Inhibitor PBMCs from 4 HIV-infected donors (Donor IDs 180-183) on suppressive cART were isolated, as described previously, stained with CFSE, and treated with 500 ng/ml 15-mer peptide pools derived from overlapping HIV gag, pol, nef, and env consensus peptides (JPT Peptide Technologies GmbH). PBMC cultures were treated with DMSO or the compound of Example 49 (GS-9620) at 0.1 uM. In some cultures treated with Example 49, the IDO1 small molecule inhibitor, INCB024360, was combined at 2 μM. Cells were incubated at 37° C. for 8 days, then split into duplicate sets and stained in DPBS with LIVE/DEAD Fixable Aqua Dead Cell Stain (Life Technologies). The immune recall response was performed as previously described. FACS was performed on a LSR Fortessa (BD Biosciences) and data analysis was done with FlowJo software (TreeStar). Data was plotted and statistical analysis was done with GraphPad Prism software (GraphPad). Treatment with Example 49 increased the mean level of polyfunctional proliferating CD8 T cells (CFSE low, IFNg+, TNFa+) by 2.9-fold compared to treatment with DMSO. In this context, inhibition of IDO1 by INCB024360 further increased the mean level of polyfunctional proliferating CD8 T cells by 70% ($p=0.05$; TLR7 only vs. TLR7+IDO1 using the Student's paired, one-tailed t-test), as depicted in FIG. 13.

Example 218

Enhanced Killing of HIV-Infected CD4 T Cells by a Combination of Example 49 and the HIV Antibody PGT121

PBMCs from 2 healthy donors (AllCells: Donor IDs A4593, A4596, A4606) were isolated, as described previously. PBMCs were treated with DMSO or with the compound of Example 49 (GS-9620) at 0.1 uM or 1 uM in replicate culture sets of 8 for 5 days. In parallel, total CD4 T cells were isolated from each donors' PBMCs using the EasySep Human CD4+ T cell Enrichment Kit (Stemcell Technologies). CD4 T cells were infected in bulk with the HIV-1 clinical isolate HT593 (NIH AIDS Reagent Program) using 50-100 ng p24/million CD4 T cells by spinfecting at 1200×g for 2 hours. HIV-infected CD4 T cells were incubated for 5 days at 37° C. in RPMI plus 10% FBS with 30 U/mL IL-2 (Invitrogen). After 5 days in culture, HIV-infected CD4 T cells were washed, counted, and added to PBMCs from the autologous donor at a ratio of 20 PBMCs to 1 CD4 T cell (20:1). To each co-culture replicate, HIV antibody PGT121 (Gilead Sciences, Inc.) was added at concentrations from 6.7e-5 nM to 6.7e2 nM. Co-cultures were incubated with or without HIV antibody for 1 day at 37° C.

Figure 14:
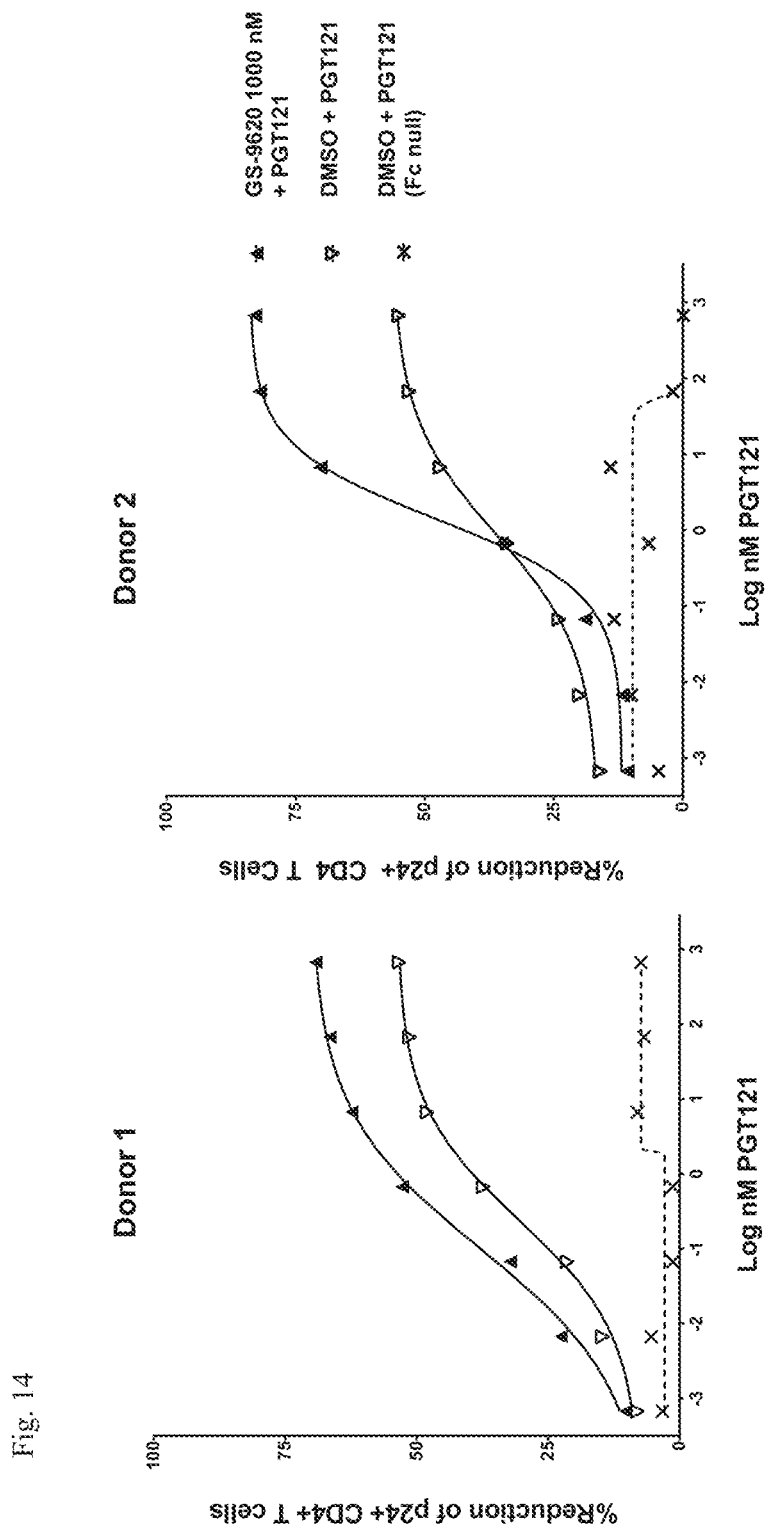
FIG. 14 depicts enhanced killing of HIV-infected CD4 cells treated with Example 49 and PGT121.

Co-cultures were collected and stained with live/dead Fixable Aqua Dead Cell Stain (Invitrogen) and PE-Cy7-labeled antibody to CD4 (BD Biosciences). Cells were fixed and permeabilized, as described previously, and stained with PE labeled antibody to HIV Gag protein p24 (Beckman Coulter). FACS was performed on a LSR Fortessa (BD Biosciences) and data analysis was done with FlowJo software (TreeStar). Data was plotted and statistical analysis was done with GraphPad Prism software (GraphPad). Killing of HIV-infected CD4 T cells was calculated as a reduction of CD4+p24+ T cells at each PGT121 concentration relative to cultures without PGT121. For the DMSO-treated cultures combined with PGT121, maximal killing was 30% or 40%, and the area under the curve (AUC), an integrative measure of killing potency and maximal killing, was 99 or 108 respectively. Relative to DMSO controls, treatment with Example 49 (GS-9620) at 0.1 uM increased the maximal killing by 30% or 38% and increased the AUC by 32% or 52% respectively. Relative to DMSO controls, treatment with Example 49 (GS-9620) at 1 uM increased the maximal killing by 50% or 48% and increased the AUC by 52% or 73% respectively, as depicted in FIG. 14.

We claim:

1. A method of treating an HIV infection in a human in need thereof, the method comprising
    (a) administering to the human a pharmaceutically effective amount of a combination antiretroviral therapy regimen sufficient to lower the level of HIV detected in the human's blood or plasma to less than 50 copies of HIV-1 RNA per mL, thereby providing a virologically suppressed human;
    (b) administering to the viroloically suppressed human a pharmaceutically effective amount of a TLR7 modulating compound having the formula

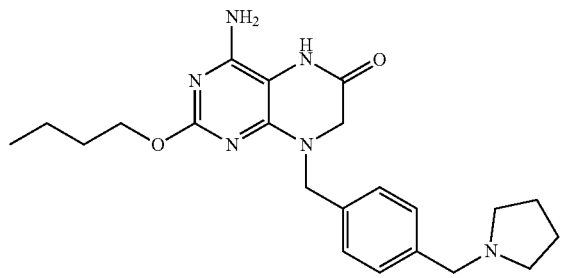

or

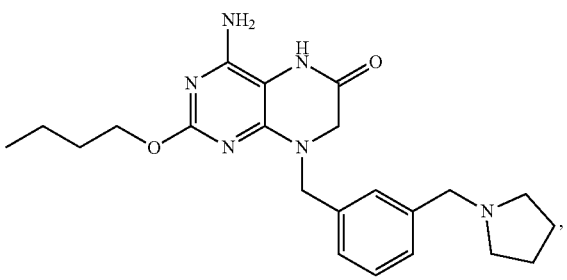

or a pharmaceutically acceptable salt thereof; and
    (c) administering to the virologically suppressed human a pharmaceutically effective amount of broadly neutralizing HIV antibody PGT121,
    thereby treating the HIV infection.

2. The method of claim 1, wherein the TLR7 modulating compound is a compound of the formula:

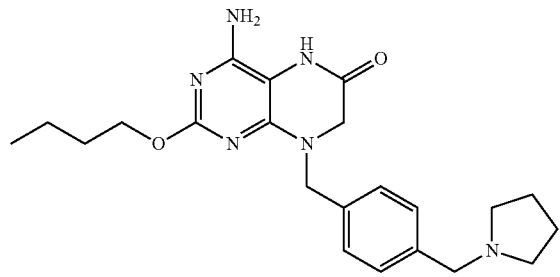 [SMILES: CCCCOc1nc(N)c2c(n1)N(Cc1ccc(CN3CCCC3)cc1)CC(=O)N2]

or a pharmaceutically acceptable salt thereof.

3. The method of claim 1, wherein the TLR7 modulating compound is a compound of the formula:

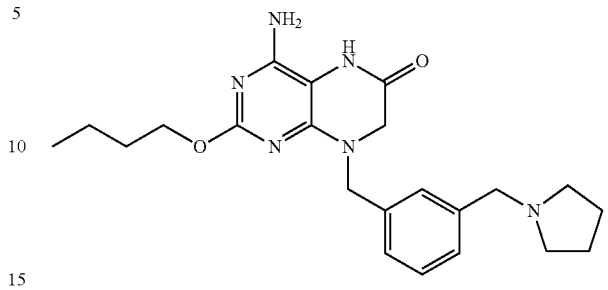

or a pharmaceutically acceptable salt thereof.

4. The method of claim 1, wherein the combination antiretroviral therapy regimen comprises one or more agents selected from the group consisting of raltegravir, elvitegravir, soltegravir, GSK 1265744, dolutegravir, didanosine, tenofovir disoproxil fumarate, tenofovir alafenamide, emtricitabine, lamivudine, stavudine, zidovudine, abacavir, elvucitabine, CMX-157, festinavir, nevirapine, efavirenz, etravirine, rilpivirine, fosdevirine, MK-1439, lersivirine, atazanavir, darunavir, indinavir, lopinavir, nelfinavir, saquinavir, tipranavir, fosamprenavir, maraviroc, enfuvirtide, BMS-663068, bevirimat, cobicistat, and ritonavir; or a pharmaceutically acceptable salt thereof.

5. The method of claim 1, wherein the measurable viral load in the viroloically suppressed human is less than 20 copies of HIV-1 RNA per mL.

6. The method of claim 1, further comprising the step of administering to the viroloically suppressed human a pharmaceutically effective amount of a latency-reversing agent.

7. A method of treating an HIV infection in a human in need thereof, the method comprising
    (a) administering to the human a pharmaceutically effective amount of a combination antiretroviral therapy regimen sufficient to lower the level of HIV detected in the human's blood or plasma to less than 50 copies of HIV-1 RNA per mL, thereby providing a viroloically suppressed human;
    (b) administering to the virologically suppressed human a pharmaceutically effective amount of
    a TLR7 modulating compound having the formula

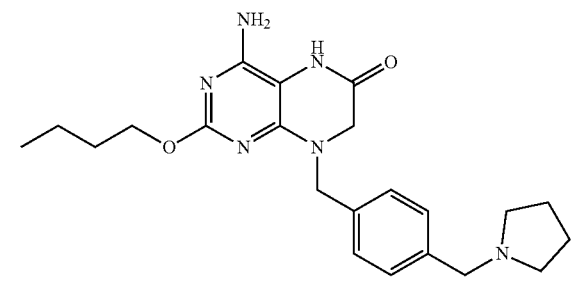

or

-continued

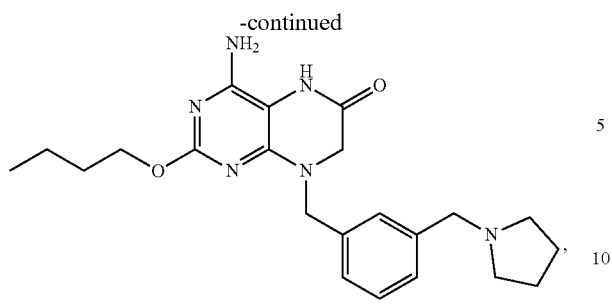

or a pharmaceutically acceptable salt thereof;
- (c) administering to the virologically suppressed human a pharmaceutically effective amount of broadly neutralizing HIV antibody PGT 121; and
- (d) administering to the virologically suppressed human a pharmaceutically effective amount of an HIV vaccine, thereby treating the HIV infection.

8. The method of claim 7, wherein the HIV vaccine is developed from Adenoviridae, Poxviridae, Herpesviridae, Adeno-associated viruses, rubella poliovirus, Venezuelan equine encephalitis virus, lentivirus or Sendai vectors.

9. The method of claim 7, wherein the HIV vaccine comprises an Ad26 vector or a Modified Vaccinia Ankara (MVA) vector.

* * * * *

UNITED STATES PATENT AND TRADEMARK OFFICE
CERTIFICATE OF CORRECTION

| | |
|---|---|
| PATENT NO. | : 11,116,774 B2 |
| APPLICATION NO. | : 14/795676 |
| DATED | : September 14, 2021 |
| INVENTOR(S) | : Geleziunas et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 123 days.

Signed and Sealed this
Twenty-first Day of February, 2023

*Katherine Kelly Vidal*

Katherine Kelly Vidal
*Director of the United States Patent and Trademark Office*